US011396525B2

(12) United States Patent
Robichaud et al.

(10) Patent No.: US 11,396,525 B2
(45) Date of Patent: Jul. 26, 2022

(54) C17, C20, AND C21 SUBSTITUTED NEUROACTIVE STEROIDS AND THEIR METHODS OF USE

(71) Applicant: Sage Therapeutics, Inc., Cambridge, MA (US)

(72) Inventors: Albert Jean Robichaud, Boston, MA (US); Gabriel Martinez Botella, Wayland, MA (US); Boyd L. Harrison, Princeton Junction, NJ (US); Francesco G. Salituro, Marlborough, MA (US); Andrew Griffin, L'lle Bizard (CA); Maria Jesus Blanco-Pillado, Arlington, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/316,853

(22) PCT Filed: Jul. 11, 2017

(86) PCT No.: PCT/US2017/041600
§ 371 (c)(1),
(2) Date: Jan. 10, 2019

(87) PCT Pub. No.: WO2018/013613
PCT Pub. Date: Jan. 18, 2018

(65) Prior Publication Data
US 2019/0248831 A1    Aug. 15, 2019

Related U.S. Application Data

(60) Provisional application No. 62/424,083, filed on Nov. 18, 2016, provisional application No. 62/360,847, filed on Jul. 11, 2016, provisional application No. 62/360,813, filed on Jul. 11, 2016.

(51) Int. Cl.
| C07J 41/00 | (2006.01) |
| C07J 1/00 | (2006.01) |
| C07J 43/00 | (2006.01) |
| C07J 9/00 | (2006.01) |
| C07J 7/00 | (2006.01) |
| C07J 17/00 | (2006.01) |
| A61P 25/20 | (2006.01) |
| A61P 25/28 | (2006.01) |
| A61P 25/18 | (2006.01) |
| A61P 5/00 | (2006.01) |
| A61P 25/08 | (2006.01) |

(52) U.S. Cl.
CPC ............ *C07J 41/0005* (2013.01); *A61P 5/00* (2018.01); *A61P 25/08* (2018.01); *A61P 25/18* (2018.01); *A61P 25/20* (2018.01); *A61P 25/28* (2018.01); *C07J 1/0029* (2013.01); *C07J 1/0081* (2013.01); *C07J 1/0085* (2013.01); *C07J 7/002* (2013.01); *C07J 9/00* (2013.01); *C07J 17/00* (2013.01); *C07J 41/005* (2013.01); *C07J 41/0011* (2013.01); *C07J 41/0066* (2013.01); *C07J 41/0094* (2013.01); *C07J 43/003* (2013.01)

(58) Field of Classification Search
CPC .............................. C07J 41/011; C07J 41/0066
See application file for complete search history.

(56) References Cited

U.S. PATENT DOCUMENTS

| 2,856,415 A | 10/1958 | Mihina |
| 3,169,134 A | 2/1965 | Klimstra et al. |
| 3,206,459 A | 9/1965 | Cross |
| 3,580,937 A | 5/1971 | Campbell et al. |
| 3,943,124 A | 3/1976 | Phillipps et al. |
| 3,983,111 A | 9/1976 | Phillipps et al. |
| 3,998,829 A | 12/1976 | Phillips et al. |
| 4,029,777 A | 6/1977 | Engelfried et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |

(Continued)

FOREIGN PATENT DOCUMENTS

| CA | 2831054 A1 | 12/2013 |
| CN | 1190404 A | 8/1998 |

(Continued)

OTHER PUBLICATIONS

Morrow. Pharmacology and Therapeutics, 2007, 116, 1-6. (Year: 2007).*
Seljeset. Advances in Pharmacology, 2015, 72, 165-187. (Year: 2015).*
Reddy. Trends in Pharmacological Sciences, 2016, 37(7), 343-361. (Year: 2016).*
Wong. Journal of Affective Disorders, 2016, 203, 84-100. (Year: 2016).*
Holt. Journal of Medicinal Chemistry, 1990, 33, 943-950. (Year: 1990).*
Rowland (Schizophrenia Bulletin, 2013, 39(5), 1096-1104 (Year: 2013).*

(Continued)

*Primary Examiner* — Noble E Jarrell
(74) *Attorney, Agent, or Firm* — Honigman LLP; Kathryn D. Doyle; Jonathan P. O'Brien

(57) ABSTRACT

Described herein are neuroactive steroids or a pharmaceutically acceptable salt thereof. Such compounds are envisioned, in certain embodiments, to behave as GABA modulators. Also provided are pharmaceutical compositions comprising a compound described herein and methods of use and treatment, e.g., such as for inducing sedation and/or anesthesia.

15 Claims, No Drawings

(56) References Cited

U.S. PATENT DOCUMENTS

| | | |
|---|---|---|
| 6,277,838 B1 | 8/2001 | Upasani et al. |
| 6,717,002 B2 | 4/2004 | Yano et al. |
| 6,780,853 B1 | 8/2004 | Upasani et al. |
| 6,844,456 B2 | 1/2005 | Covey |
| 7,064,116 B2 | 6/2006 | Calogeropoulou et al. |
| 7,067,507 B2 * | 6/2006 | Pulley ............... A61P 43/00 514/183 |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0249120 A1 | 9/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |
| 2018/0071315 A1 | 3/2018 | Cashman et al. |
| 2019/0160078 A1 | 5/2019 | Masuoka et al. |
| 2019/0177358 A1 | 6/2019 | Martinez Botella et al. |
| 2019/0337975 A1 | 11/2019 | Bryson et al. |

FOREIGN PATENT DOCUMENTS

| | | |
|---|---|---|
| CN | 101412742 A | 4/2009 |
| CN | 101624414 A | 1/2010 |
| CN | 104136452 A | 11/2014 |
| CN | 108727453 A | 11/2018 |
| DE | 2330342 A1 | 1/1974 |
| DE | 2526373 A1 | 12/1976 |
| DE | 2700267 A1 | 7/1977 |
| DE | 2632677 A1 | 1/1978 |
| EP | 0104489 A1 | 4/1984 |
| EP | 0656365 A1 | 6/1995 |
| EP | 1038880 A2 | 9/2000 |
| FR | 1994 M | 9/1963 |
| GB | 1380246 A | 1/1975 |
| GB | 1430942 A | 4/1976 |
| GB | 1494097 A | 12/1977 |
| GB | 1538869 A | 1/1979 |
| GB | 1570394 A | 7/1980 |
| GB | 1581234 A | 12/1980 |
| GB | 1581235 A | 12/1980 |
| RU | 2194712 C2 | 12/2002 |
| RU | 2243232 C2 | 12/2004 |
| RU | 2010100334 A | 7/2011 |
| RU | 2675855 C2 | 12/2018 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | WO 94/27608 * | 12/1994 |
| WO | 1995021617 A1 | 8/1995 |
| WO | 1996003421 A1 | 2/1996 |
| WO | 1996016076 A1 | 5/1996 |
| WO | 9640043 A2 | 12/1996 |
| WO | 9805337 A1 | 2/1998 |
| WO | 0066614 A1 | 11/2000 |
| WO | WO 2004085457 * | 10/2004 |
| WO | 2005051972 A1 | 6/2005 |
| WO | 2005105822 A2 | 11/2005 |
| WO | 2006037016 A2 | 4/2006 |
| WO | 2006131392 A1 | 12/2006 |
| WO | 2008151745 A1 | 12/2008 |
| WO | 2008157460 A1 | 12/2008 |
| WO | 2010003391 A2 | 1/2010 |
| WO | 2010054158 A2 | 5/2010 |
| WO | 2010107815 A1 | 9/2010 |
| WO | 2012013816 A1 | 2/2012 |
| WO | 2012083090 A2 | 6/2012 |
| WO | 2012109752 A1 | 8/2012 |
| WO | 2012110010 A1 | 8/2012 |
| WO | 2012116290 A2 | 8/2012 |
| WO | 2013019711 A2 | 2/2013 |
| WO | 2013036835 A1 | 3/2013 |
| WO | 2013056181 A1 | 4/2013 |
| WO | 2013188792 A2 | 12/2013 |
| WO | 2013192097 A1 | 12/2013 |
| WO | 2014058736 A1 | 4/2014 |
| WO | 2014071449 A1 | 5/2014 |
| WO | 2014100228 A1 | 6/2014 |
| WO | 2014108808 A2 | 7/2014 |
| WO | 2014122480 A1 | 8/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016036724 A1 | 3/2016 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016131414 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019018119 A1 | 1/2019 |
| WO | 2019045121 A1 | 3/2019 |
| WO | 2019051264 A1 | 3/2019 |
| WO | 2019094724 A1 | 5/2019 |

OTHER PUBLICATIONS

Fatemi (Journal of Autism and Developmental Disorders, 2009, 39, 223-230 (Year: 2009).*

Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

(56) References Cited

OTHER PUBLICATIONS

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.
Heard et al., "Steroids. VII. Preparation of of androstan-3(b)-ol-7-one from from dehydroisoandrosterone", Journal of Biological Chemistry, 1946, vol. 165, pp. 677-685.
Hewett et al., "Amino steroids Part III. 2- and 3-Amino-5a-androstanes", Journal of the Chemical Society, 1968, vol. 9, pp. 1134-1140.
Hill et al., "Pholochemische Reaktionen. 32 Milleilung. UV-Bestrahlung von gesattigten und bela,gamma- ngesalligten, homoal-lylisch konjugierten steroidaldehyden", Helvetica Chimica Acta, 1946, vol. 49, No. 1, pp. 292-311.
Hogenkamp et al., "Pharmacological profile of a 17b-heteroaryl-substituted neuroactive steroid", Psychopharmacology, vol. 231, (2014), pp. 3517-3524.
Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.
Hu et al., "Neurosteroid analogues. Part 5. Enantiomers of neuroactive steroids and benz[e]indenes: total synthesis,18 electrophysiological effects on GABAA receptor function and anesthetic actions in tadpoles", J. Chem. Soc. Perkin Trans 1, 1997, pp. 3665-3671.
Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.
Im et al., "Studies on the Mechanism of Interactions between Anesthetic Steroids and y-Aminobutyric AcidA Receptors", Molecular Pharmacology (1990), 37(3), pp. 429-434.
International Search Report and Written Opinion for Corresponding International Application No. PCT/CN2014/078820 dated Feb. 27, 2015.
International Search Report and Written Opinion for Corresponding International Application No. PCT/CN2015/080216 dated Aug. 3, 2015.
International Search Report and Written Opinion for Corresponding International Application No. PCT/CN2015/095765 dated Mar. 4, 2016.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for Corresponding International Application No. PCT/US2018/050012 dated Dec. 7, 2018.
International Search Report and Written Opinion for Corresponding International Application No. PCT/US2018/051048 dated Jan. 11, 2019.
International Search Report and Written Opinion for Corresponding International Application No. PCT/US2018/064546 dated Apr. 9, 2019.
International Search Report and Written Opinion for Corresponding International Application No. PCT/US2019/036848 dated Aug. 22, 2019.
International Search Report and Written Opinion for Corresponding International Application No. PCT/US2019/055926 dated Jan. 14, 2020.
International Search Report and Written Opinion for Corresponding International Application No. PCT/US2019/057195 dated Jan. 22, 2020.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report and Written Opinion for International Application No. PCT/US2018/067277 dated May 24, 2019.
International Search Report and Written Opinion for International Application No. PCT/US2018/067306 dated May 28, 2019.
International Search Report and Written Opinion for International Application No. PCT/US2019/013315 dated Jun. 14, 2019.
International Search Report for International Application No. PCT/US2012/060136 dated Mar. 27, 2013.
Itoh et al., "On the acid-catalyzed d-homoannulation of pregnanetriol 20-sulfate and its c-20 isomeric sulfate", Chemical and Pharmaceutical Bulletin. 1994, vol. 42, No. 9, pp. 1736-1744.
Jiang et al., "Neurosteroid analogues. 9. Conformationally constrained pregnanes: structure-activity studies of 13,24-cyclo-18, 21-dinorcholane analogues of the GABA modulatory and anesthetic steroids (3a,5a)- and (3a,5a)-3-hydroxypregnan-20-one", Journal of Medicinal Chemistry, 2003, vol. 46, pp. 5334-5348.
Jungmann et al., "7-Keto-5b-ätiansäure-Derivate. über Gallensäuren und verwandte Stoffe, 51. Mitteilung [Bile acids and related substances. LI. 7-0xo-5. beta.-etianic acid derivatives]", Helvetica Chimica Acta, vol. 41, No. 5, (1958), pp. 1206-1233.
Kaji et al., "Synthesis of 3-epi-6, 7- dideoxyxestobergsterol A", Chem. & Pharm. Bulletin, 2000, vol. 48, No. 10, pp. 1480-1483.
Kanes et al., "A multiple-ascending dose study of the neuroactive steroid Sage-217", Biological Psychiatry, vol. 81, No. 10, 2017, pp. S347.
Adams et al., "The estrogenic activity and enzymic oxidation of 17b-estradiol-17a-d1", Steroids, Elsevier Science Publishers, (1965), pp. 75-84.

(56) References Cited

OTHER PUBLICATIONS

Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Anonymous: "Archive History for NCT03000530", Aug. 4, 2017, Retrieved from the Internet: <URL:https://www.clinicaltrials.gov/ct2/his>tory/NCT03000530?V-_6=View#StudyPageTop; [retrieved on Nov. 20, 2018].
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs," Bioorganic & Medicinal Chemistry Letters 20:6680-6684 (2010).
Berge et al., J. Pharmaceutical Sciences, 1977, vol. 66, pp. 1-19.
Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp. A-J.
CAS Registry No. 1040410-23-8 [Database Registry in STN]; STN Entry Date: Aug. 12, 2008; Chemical Name: 1-((3S,8R,9S,10S,13S,14S,17S)-3-hydroxy-10,13-dimethyl-2,3,4,5,8,9,10,11,12,13,14,15,16,17-tetradecahydro-1H-cyclopenta[a]phenanthren-17-yl)ethan-1-one.
CAS Registry No. 162882-77-1 [Database Registry in STN]; STN Entry Date: May 11, 1995; Chemical Name: (3a,5b)-3-Hydroxy-3-methyl-19-norpregnan-20-one.
CAS Registry No. 162883-68-3 [Database Registry in STN]; STN Entry Date: May 11, 1995; Chemical Name: 19-Norpregnan-20-one, 3-hydroxy-3-methyl-, (3a,5a)-.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chen et al., "The mechanism investigation in substitution of 21-bromo-3a-hydroxy-3b-methoxymethyl-5a-pregnan-20-one with nucleophiles", Steroids, vol. 71, (2006), pp. 942-948.
Chodounska et al., "Epalons: Synthesis of 3a, 7a-Dihydroxy-5a-Pregnan-20-One", Collection Symposium Series, vol. 33, No. 10, (1998), pp. 1543-1548.
D'hulst et al., "Expression of the GABAergic system in animal models for fragile X syndrome and fragile X associated tremor/ataxia syndrome (FXTAS)", Brain Research, 2008, vol. 1253, pp. 176-183.

Database CAPLUS in STN, Acc. No. 1995:986323, Upasani et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Database Medline, US National Library of Medicine, Bethesda, MD, 1984, Welling: "Intentions affecting drug absorption", Database accession No. NLM6388952, abstract.
Deluca et al., "Synthesis of 3b-Hydroxy[21-14C] -5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, p. IX.
Durán et al., "Synthesis of 6-thia analogs of the natural neurosteroid allopregnanolone", Tetrahedron, Elsevier Science Publishers, 2006, vol. 62, No. 20, pp. 4762-4768.
Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.
Eimon et al., "Brain activity patterns in high-throughput electrophysiology screen predict both drug efficacies and side effects", Nature Communications, (2018) 9:219, pp. 1-14.
Evers et al., "A Synthetic 18-Norsteroid Distinguishes Between Two Neuroactive Steroid Binding Sites on GABAA Receptors", Journal of Pharmacology and Experimental Therapeutics, 2010, vol. 333, No. 2, pp. 404-413.
Extended European Search Report for application PCT/CN2014075593 dated Aug. 26, 2016.
Extended European Search Report for application PCT/CN2014075594 dated Aug. 26, 2016.
Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799.
Fesik et al., "Geometric Requirements for Membrane Perturbation and Anesthetic Activity", Molecular Pharmacology, 1985, vol. 27, pp. 624-629.
Galofre et al., "GABAA receptor and cell membrane potential as functional endpoints in cultured neurons to evaluate chemicals for human acute toxicity", Neurotoxicology and Teratology, (2009), vol. 32, pp. 52-61.
Gasior et al., "Neuroactive steroids: potential therapeutic use in neurological and psychiatric disorders", Trends in Pharmacological Science, (1999), vol. 20, No. 3, pp. 107-112.
Gottesmann, "GABA Mechanisms and Sleep", Neuroscience, (2002), vol. 111, No. 2, pp. 231-239.
Green et al., "The nonfeminizing enantiomer of 17b-estradiol exerts protective effects in neuronal cultures and a rat model of cerebral ischemia", Endocrinology, 2001, vol. 142, pp. 400-406.
Guardia et al., "GABAergic and Glutamatergic Modulation in Binge Eating: Therapeutic Approach", Current pharmaceuticaldesign, 2011, vol. 17, No. 14, pp. 1396-1409.
Gunduz-Bruce et al.,"Sage-217 in Major Depressive Disorder: A Multicenter, Randomized, Double-Blind, Phase 2 Placebo-Controlled Trial", European Nueuropsychopharmacology, vol. 29, 2019, pp. S59-S-60, Abstract.
Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.
Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.

(56) References Cited

OTHER PUBLICATIONS

Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.
Gyermek et al., "Steroids, CCCX. 1 Structure-Activity Relationship of Some Steroidal Hypnotic Agents", Journal of Medicinal Chemistry, 1968, vol. 11, No. 1, pp. 117-125.
Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 1548-4556.
Han et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.
Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.
Hawkins et al., "The synthetic neuroactive steroid SGE-516 reduces seizure burden and improves survival in a Dravet syndrome mouse model", Science Reports, (2017), pp. 1-8.
Kanes et al., "A single-ascending dose study of the neuroactive steroid Sage-217", Biological Psychiatry, vol. 81, No. 10, 2017, pp. S31.
Kasai et al., "Neurosteroid analogues: synthesis of 6-aza-allopregnanolone", Tetrahedron, Elsevier Science Publishers, 2005, vol. 61, No. 9, pp. 2269-2278.
Katona et al., "Neurosteroid analogues. 12. Potent enhancement of GABA-mediated chloride currents at GABAA receptors by ent-androgens", European Journal of Medicinal Chemistry, 2008, vol. 43, No. 1, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol— (A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lehmann et al., "Schweinegallensäuren Der Abbau von Hyocholsäure zu Pregnanderivaten", vol. 32, No. 3-4, (1966), pp. 217-224.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Mariangela et al., "The influence of neuroactive steroid lipophilicity on gabaa receptor modulation: Evidence for a low-affinity interaction", Journal of Neurophysiology, 2009, vol. 102, No. 2, pp. 1254-1264.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.

Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Möhler, "The GABA system in anxiety and depression and its therapeutic potential", Neuropharmacology, (2012) 62; pp. 42-53.
Nicoletti et al., "Synthesis and GABAA receptor activity of 6-oxa-analogs of neurosteroids", Steroids, Elsevier Science Publishers 2000, vol. 65, No. 6, pp. 349-356.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem CID: 70249446, [database online], created Dec. 1, 2012 [retrieved on Mar. 21, 2018]. Retrieved from the National Center for Biotechnology Information, PubChem Compound Database, using internet URL: <https://pubchem.ncbi.nlm.nih.gov/compound/70249446>.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Qian et al., "The efficient and enantiospecific total synthesis of cyclopenta[b]phenanthrenes structurally related to neurosteroids". Adv. Syn. & Cata., 2010, vol. 352, Nos. 11-12, pp. 2057-2061.
Rogawski et al., "Neuroactive Steroids for the Treatment of Status Epilepticus", Epilepsia (2013), vol. 54, No. 6, pp. 93-98.
Rongone et al., "In vivo metabolism of d-homotestosterone", Steroids, vol. 1, No. 6, 1963, pp. 664-669.
Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.
Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.
Rychnovsky et al., "Synthesis of ent-cholesterol, the unnatural enantiomer", Journal of Organic Chemistry, 1992, vol. 57, No. 9, pp. 2732-2736.

(56) References Cited

OTHER PUBLICATIONS

Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fflf35-fc4c-4eb2-9456-3228ec891a59; [retrieved on Dec. 21, 2018].

Santaniello & Caspi, "Reduction of certain steroidal 19-sulfonic esters with metal hydrides", J. of Ster. Biochem, 1976, vol. 7, No. 3, pp. 223-227.

Saporito et al., "Intravenously Administered Ganaxolone Blocks Diazepam-Resistant Lithium-Pilocarpine-Induced Status Epilepticus in Rats: Comparison with Allopregnanolone", Journal of Pharmacology Exp. Ther. 2019, 368(3), pp. 326-327.

Sarett., "A new method for the preparation of 17(alpha)-hydroxy-20-ketopregnanes", J. Am. Chem. Soc., 1948, vol. 70, pp. 1454-1458.

Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.

Shen et al., "Microbial aromatization of 19-hydroxymethylepidehydroandrosterone acetate by Corynebacterium simplex", Huaxue Xuebao, 1983, vol. 41, No. 5, pp. 473-474.

Shu et al., "Characteristics of concatemeric GABM receptors containing alpha4/d subunits expressed in Xenopus pocytes" British Journal of Pharmacology (2012) 165, 2228-2243.

Shu et al., "Photodynamic effects of steroid-conjugated fluorophores on gabaa receptors", Molecular Pharmacology, 2009, vol. 76, No. 4, pp. 754-765.

Slavíková et al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.

Spiegel et al., "Use of Nonaqueous Solvents in Parenteral Products", Journal of Pharmaceutical Sciences, 1963, vol. 52, No. 10, pp. 917-927.

Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.

Stastna et al., "Neurosteroid Analogues. 16. A New Explanation for the Lack of Anesthetic Effects in D16—Alphaxalone and Identification of a D17(20) Analogue with Potent Anesthetic Activity", Journal of Medicinal Chemistry, 2011, vol. 54, No. 11, pp. 3926-3934.

Stastna et al., "Stereoselectivity of sodium borohydride reduction of saturated steroidal ketones utilizing conditions of Luche reduction", Steroids, 2010, vol. 75, No. 10, pp. 721-725.

Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.

Stastna et al., "The use of symmetry in enantioselective synthesis: Four pairs of chrysene enantiomers prepared from 19-nortestosterone", Org. Biomol. Chem., 2011, vol. 9, pp. 4685-4694.

Sunöl et al., "Activity of b-nor analogues of neurosteroids on the gabaa receptor in primary neuronal cultures", Journal of Medicinal Chemistry, 2006, vol. 49, No. 11, pp. 3225-3234.

Supplemental European Search Report, European Patent Application No. 14826212.4, dated Feb. 16, 2017.

Suthoff et al., "Assessment of Health-Related Quality of Life by the SF36V2 in a Phase 2, Randomized Placebo-Controlled Trial of the GABA A Receptor Positive Allosteric Modulator Sage-217 in Major Depressive Disorder", Value in Health, vol. 21, No. Suppl. 3, 2018, Abstract.

Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.

Upasani et al., "3a-Hydroxy-3β-(phenylethynyl)-5β-pregnan-20-ones: Synthesis and Pharmacological Activity of Neuroactive Steroids with High Affinity for GABAA Receptors", J. Med. Chem. (1997) vol. 40, No. 1, pp. 73-84.

Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.

Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.

Vanover et al., "Response-Rate Suppression in Operant Paradigm as Predictor of Soporific Potency in Rats and dentification of Three Novel Sedative-Hypnotic Neuroactive Steroids", The Journal of Pharmacology and Experimental Therapeutics, (1999), vol. 291, No. 3, pp. 1317-1323.

Veleiro et al., "Structure-activity relationships of neuroactive steroids acting on the gabaa receptor", Current Medicinal Chemistry, 2009, vol. 16, No. 4, pp. 455-472.

Veleiro et al., "Synthesis and GABAA Receptor Acitivity of a6, 19-Oxido Analogue of Pregnanolone", Bioorganic & Medicinal Chemistry Letters, (2003), vol. 13, pp. 343-345.

Welling, "Interactions affecting drug absorption", Clinical Pharmacokinetics, vol. 9, No. 5, Sep. 1984 (Sep. 1984), pp. 404-434.

Wicha et al., "Transformations of steroidal neopentyl systems. II. Migration of acetate from the 3beta- to the 19-hydroxyl in delta 5 and A/B-trans steroids", Canadian Journal of Chemistry, 1967, vol. 45, No. 7, pp. 707-711.

Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.

Wicha et al., "Transformations of steroidal neopentyl systems. V. Synthesis and proof of the configuration of 19amethyl-19 5-alcohols", Journal of the Chemical Society [Section] C: Organic, 1969, vol. 6, pp. 947-951.

Wicha et al., "Transformations of steroidal neopentyl systems. VI. Intramolecular Claisen condensation of 19R-acetoxy- 19A-methyl-3-ones of the 5alpha series", Tetrahedron, 1969, vol. 25, No. 17, pp. 3961-3968.

Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19—oxo-5alpha-analogs", Journal of Organic Chemistry, 1973, vol. 38 No. 7, pp. 1280-1283.

Wu, "A New Classification of Prodrugs: Regulatory Perspectives", Pharmaceuticals, 2009, vol. 2, pp. 77-81.

Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.

Zonana et al., "The Neurobiology of Postpartum Depression", CNS Spectrums, (2005), pp. 792-799, 805.

Zorumski et al., "Enantioselective Modulation of GABAergic Synaptic Transmission by Steroids and Benz[dindenes in Hippocampal Microcultures", Synapse, (1998), vol. 29, pp. 162-171.

Sedley, W., et al., "Human Auditory Cortex Neurochemistry Reflects the Presence and Severity of Tinnitus", J Neuroscience, Nov. 4, 2015; 35(44): pp. 14822-8.

Allinger, N. L. et al., "Conformational analysis. XL. Configuration of 3-bromo-3-methylcholestane and the conformational equilibrium in 1-bromo-1-methylcyclohexane." Tetrahedron, 1965, 21(3), 603-6.

CAS Registry No. 896717-08-1; STN Entry Date Jul. 28, 2006.

CAS Registry No. 1018787-30-8; STN Entry Date May 1, 2008.

(56) References Cited

OTHER PUBLICATIONS

Templeton, J. F. et al, "Stereoselective reduction of C-2 substituted steroid C-3 ketones with lithium tris-(R,S-1,2-dimethylpropyl)-borohydride and sodium borohydride." Steroids, 1986, 48(5-6), 339-46.

* cited by examiner

C17, C20, AND C21 SUBSTITUTED NEUROACTIVE STEROIDS AND THEIR METHODS OF USE

CROSS-REFERENCE TO RELATED APPLICATIONS

The present application is a U.S. National Phase Application under 35 U.S.C. § 371 of International Application PCT/US2017/041600, filed Jul. 11, 2017, which claims priority to U.S. Ser. No. 62/360,813 filed Jul. 11, 2016, U.S. Ser. No. 62/360,847 filed Jul. 11, 2016, and U.S. Ser. No. 62/424,083 filed Nov. 18, 2016, which are incorporated herein by reference.

BACKGROUND

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately –70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization, e.g., a change of potential from –70 mV to –50 mV. This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains at least one distinct site for interaction with neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

Compounds as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

In an aspect, provided herein is a compound of the Formula (I):

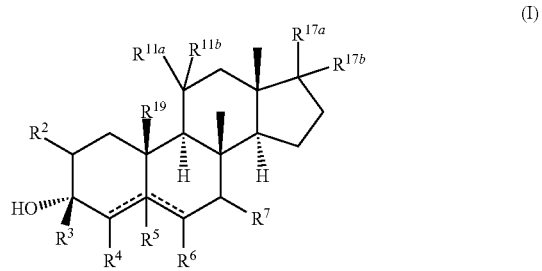

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —S(=O)$R^{A2}$, —$SO_2R^{A2}$, or —S(=O)$_2$ $OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)—; $R^3$ is alkyl, alkenyl, carbocyclyl, heterocyclyl, aryl, or heteroaryl; each of $R^{17a}$ and $R^{17b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —N($R^{A1}$)$_2$, —NHC(=O)$R^{A1}$, —S(=O)$R^{A2}$, —$SO_2R^{A2}$, or —S(=O)$_2OR^{A1}$, wherein at least one of $R^{17a}$ and $R^{17b}$ is not hydrogen; $R^{19}$ is hydrogen or alkyl (e.g., unsubstituted alkyl or substituted alkyl (e.g., —C($R^C$)$_2$ $OR^{A1}$, wherein $R^C$ is hydrogen or alkyl)); $R^5$ is absent or hydrogen; and ═══ represents a single or double bond, wherein when one ═══ is a double bond, the other ═══ is a single bond and $R^5$ is absent.

In some embodiments, $R^{19}$ is hydrogen or alkyl. In some embodiments, $R^{19}$ is unsubstituted alkyl. In some embodiments, $R^{19}$ is substituted alkyl. In some embodiments, $R^{19}$ is —$CH_2OH$, —$CH_2OCH_3$, —$CH_2OCH_2CH_3$, or —$CH_2OCH(CH_3)_2$.

In some embodiments, $R^2$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^2$ is hydrogen, halogen, alkyl, or $-OR^{A1}$. In some embodiments, $R^2$ is hydrogen.

In some embodiments, $R^3$ is alkyl, alkenyl, carbocyclyl, heterocyclyl, aryl, or heteroaryl. In some embodiments, $R^3$ is alkyl (e.g., substituted or unsubstituted alkyl). In some embodiments, $R^3$ is methyl and ethyl (e.g., substituted or unsubstituted alkyl).

In some embodiments, $R^4$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^4$ is hydrogen, halogen, alkyl, or $-OR^{A1}$. In some embodiments, $R^4$ is hydrogen.

In some embodiments, ==== represents a single bond and $R^5$ is hydrogen. In some embodiments, $R^5$ is absent, and ==== represents a single or double bond, wherein when one ==== is a double bond, the other ==== is a single bond.

In some embodiments, $R^6$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^6$ is hydrogen, halogen, alkyl, or $-OR^{A1}$. In some embodiments, $R^6$ is hydrogen.

In some embodiments, $R^7$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^7$ is hydrogen, halogen, alkyl, or $-OR^{A1}$. In some embodiments, $R^7$ is hydrogen.

In some embodiments, $R^{11a}$ is hydrogen, halogen, alkyl, carbocyclyl, heterocyclyl, aryl, heteroaryl, $-OR^{A1}$, $-SR^{A1}$, $-N(R^{A1})_2$, or $R^{11a}$ and $R^{11b}$ together with the carbon atom to which they are attached form $-C(=O)-$. In some embodiments, $R^{11a}$ is hydrogen, halogen, alkyl, or $-OR^{A1}$. In some embodiments, $R^{11a}$ and $R^{11b}$ together with the carbon atom to which they are attached form $-C(=O)-$. In some embodiments, $R^{11a}$ and $R^{11b}$ are hydrogen.

In some embodiments, each of $R^2$, $R^4$, $R^6$, $R^7$, $R^{11a}$, and $R^{11b}$ is independently hydrogen, halogen, alkyl, carbocyclyl, heterocyclyl, aryl, heteroaryl, $-OR^{A1}$, $-SR^{A1}$, or $-N(R^{A1})_2$. In some embodiments, each of $R^2$, $R^4$, $R^6$, $R^7$, $R^{11a}$, and $R^{11b}$ is independently hydrogen, halogen, alkyl, or $-OR^{A1}$. In some embodiments, $R^2$, $R^4$, $R^6$, $R^7$, $R^{11a}$, and $R^{11b}$ are hydrogen.

In some embodiments, each of $R^{7a}$ and $R^{17b}$ is independently hydrogen, halogen, cyano, nitro, alkyl, alkenyl, alkynyl, carbocyclyl, heterocyclyl, $-SR^{A1}$, $-N(R^{A1})_2$, $-NHC(=O)R^{A1}$, $-S(=O)R^{A2}$, $-SO_2R^{A2}$, or $-S(=O)_2OR^{A1}$, wherein at least one of $R^{17a}$ and $R^{17b}$ is not hydrogen. In some embodiments, each of $R^{17a}$ and $R^{17b}$ is independently hydrogen, halogen, nitro, alkyl, alkenyl, alkynyl, carbocyclyl, heterocyclyl, $-SR^{A1}$, $-N(R^{A1})_2$, $-NHC(=O)R^{A1}$, $-S(=O)R^{A2}$, $-SO_2R^{A2}$, or $-S(=O)_2OR^{A1}$, wherein at least one of $R^{17a}$ and $R^{17b}$ is not hydrogen.

In some embodiments, $R^{17a}$ is halogen, cyano, nitro, alkyl, carbocyclyl, heterocyclyl, $-OR^{A1}$, $-SR^{A1}$, $-N(R^{A1})_2$, $-NHC(=O)R^{A1}$, $-S(=O)R^{A2}$, or $-SO_2R^{A2}$. In some embodiments, $R^{17a}$ is halogen, nitro, alkyl, carbocyclyl, heterocyclyl, $-OR^{A1}$, $-SR^{A1}$, $-N(R^{A1})_2$, $-NHC(=O)R^{A1}$, $-S(=O)R^{A2}$, or $-SO_2R^{A2}$. In some embodiments, $R^{17a}$ is halogen, cyano, nitro, alkyl, $-OR^{A1}$, $-SR^{A1}$u, or $-N(R^{A1})_2$.

In an aspect, provided herein is a compound of the Formula (II):

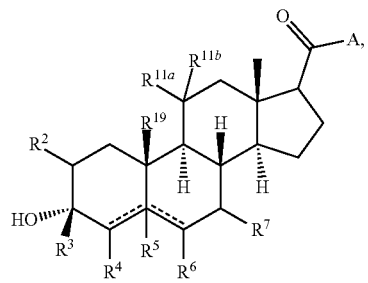

(II)

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, $-OR^{A1}$, $-SR^{A1}$, $-N(R^{A1})_2$, $-NHC(=O)R^{A1}$, $-NHC(=O)OR^{A1}$, $-S(=O)R^{A2}$, $-SO_2R^{A2}$, or $-S(=O)_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{1b}$ together with the carbon atom to which they are attached form a carbocyclyl, heterocyclyl, or $-C(=O)-$ group; $R^3$ is hydrogen, alkyl, alkenyl, carbocyclyl, heterocyclyl, aryl, or heteroaryl; A is alkyl, alkenyl, alkynyl, carbocyclyl, heterocyclyl, $-OR^{A1}$, $-SR^{A1}$, or $-N(R^{A1})_2$; $R^{19}$ is hydrogen or alkyl (e.g., unsubstituted alkyl (e.g., $-CH_3$) or substituted alkyl (e.g., $-C(R^C)_2OR^{A1}$, wherein $R^C$ is hydrogen or alkyl)); $R^5$ is absent or hydrogen; and ==== represents a single or double bond, wherein when one ==== is a double bond, the other ==== is a single bond and $R^5$ is absent.

In some embodiments, A is hydrogen, alkyl, alkenyl, alkynyl, carbocyclyl, heterocyclyl, or $-OR^{A1}$.

In some embodiments, $R^{19}$ is hydrogen. In some embodiments, $R^{19}$ is alkyl (e.g., substituted or unsubstituted alkyl). In some embodiments, $R^{19}$ is $-CH_3$ or $-CH_2CH_3$. In some embodiments, $R^{19}$ is $-C(R^C)_2OR^{A1}$. In some embodiments, $R^{19}$ is $-CH_2OH$, $-CH_2OCH_3$, $-CH_2OCH_2CH_3$, or $-CH_2OCH(CH_3)_2$.

In some embodiments, $R^2$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^2$ is hydrogen, halogen, alkyl, or $-OR^{A1}$. In some embodiments, $R^2$ is hydrogen.

In some embodiments, $R^3$ is alkyl (e.g., substituted or unsubstituted alkyl). In some embodiments, $R^3$ is methyl and ethyl (e.g., substituted or unsubstituted methyl, substituted or unsubstituted ethyl).

In some embodiments, $R^4$ is hydrogen, halogen, alkyl, carbocyclyl, heterocyclyl, aryl, heteroaryl, $-OR^{A1}$, $-SR^{A1}$, or $-N(R^{A1})_2$. In some embodiments, $R^4$ is hydrogen, halogen, alkyl, or $-OR^{A1}$. In some embodiments, $R^4$ is hydrogen.

In some embodiments, ==== represents a single bond and $R^5$ is hydrogen. In some embodiments, $R^5$ is absent, and ==== represents a single or double bond, wherein when one ==== is a double bond, the other ==== is a single bond.

In some embodiments, $R^6$ is hydrogen, halogen, alkyl, carbocyclyl, heterocyclyl, aryl, heteroaryl, $—OR^{A1}$, $—SR^{A1}$, or $—N(R^{A1})_2$. In some embodiments, $R^6$ is hydrogen, halogen, alkyl, or $—OR^{A1}$. In some embodiments, $R^6$ is hydrogen.

In some embodiments, $R^7$ is hydrogen, halogen, alkyl, carbocyclyl, heterocyclyl, aryl, heteroaryl, $—OR^{A1}$, $—SR^{A1}$, or $—N(R^{A1})_2$. In some embodiments, $R^7$ is hydrogen, halogen, alkyl, or $—OR^{A1}$. In some embodiments, $R^7$ is hydrogen.

In some embodiments, $R^{11a}$ is hydrogen, halogen, alkyl, carbocyclyl, heterocyclyl, aryl, heteroaryl, $—OR^{A1}$, $—SR^{A1}$, $—N(R^{A1})_2$, or $R^{11a}$ and $R^{11b}$ together with the carbon atom to which they are attached form $—C(=O)—$. In some embodiments, $R^{11a}$ is hydrogen, halogen, alkyl, or $—OR^{A1}$. In some embodiments, $R^{11a}$ and $R^{11b}$ together with the carbon atom to which they are attached form $—C(=O)—$. In some embodiments, $R^{11a}$ and $R^{11b}$ are hydrogen.

In some embodiments, each of $R^2$, $R^4$, $R^6$, $R^7$, $R^{1a}$, and $R^{11b}$ is independently hydrogen, halogen, alkyl, carbocyclyl, heterocyclyl, aryl, heteroaryl, $—OR^{A1}$, $—SR^{A1}$, or $—N(R^{A1})_2$. In some embodiments, each of $R^2$, $R^4$, $R^6$, $R^7$, $R^{11a}$, and $R^{11b}$ is hydrogen, halogen, alkyl, or $—OR^{A1}$. In some embodiments, each of $R^2$, $R^4$, $R^6$, $R^7$, $R^{11a}$, and $R^{11b}$ is hydrogen.

In some embodiments, the compound of Formula (II) is a compound of the Formula (II-a) or (II-b):

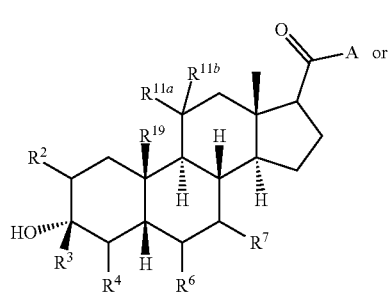

(II-a)

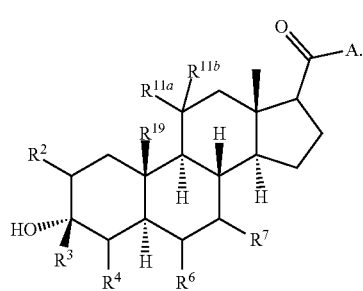

(II-b)

In some embodiments, the compound of Formula (II) is a compound of the Formula (II-c):

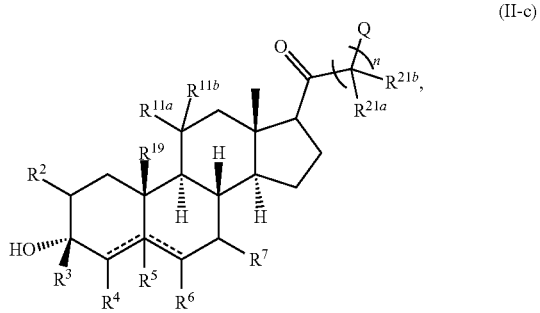

(II-c)

wherein:
each of $R^{21a}$ and $R^{21b}$ is independently hydrogen, halogen, cyano, nitro, alkyl, alkenyl, alkynyl, carbocyclyl, heterocyclyl, aryl, heteroaryl, $—OR^{A1}$, $—SR^{A1}$, $—N(R^{A1})_2$, $—NHC(=O)R^{A1}$, $—NHC(=O)OR^{A1}$, $—S(=O)R^{A2}$, $—SO_2R^{A2}$, or $—S(=O)_2OR^{A}$; or $R^{21a}$ and $R^{21b}$ together with the carbon atom to which they are attached form a carbocyclyl, heterocyclyl, or $—C(=O)—$ group; Q is hydrogen, halogen, cyano, nitro, alkyl, alkenyl, alkynyl, carbocyclyl, heterocyclyl, aryl, heteroaryl, $—OR^{A1}$, $—SR^{A1}$, or $—N(R^{A1})_2$; and n is an integer selected from 1, 2, and 3.

In some embodiments, the compound of Formula (II) is a compound of the Formula (II-d):

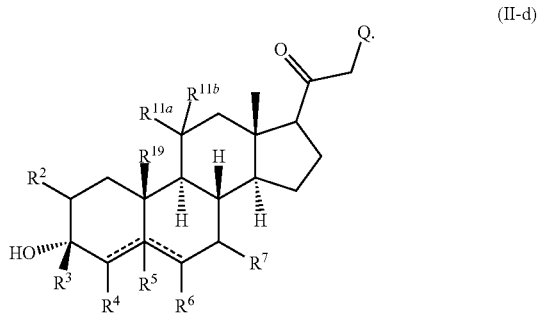

(II-d)

In an aspect, provided herein is a compound of the Formula (III):

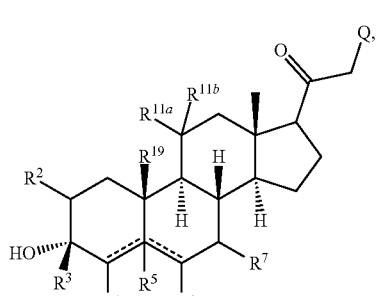

(III)

wherein:
or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —OR$^{A1}$, —SR$^{A}$—, —N(R$^{A1}$)$_2$, —NHC(=O)R$^{A1}$, —NHC(=O)OR$^{A1}$, —S(=O)R$^{A2}$, —SO$_2$R$^{A2}$, or —S(=O)$_2$OR$^{A1}$, wherein each instance of R$^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two R$^{A1}$ groups are joined to form an heterocyclic or heteroaryl ring; and R$^{A2}$ is alkyl, alkenyl, alkynyl, carbocyclyl, heterocyclyl, aryl, or heteroaryl; or R$^{11a}$ and R$^{11b}$ together with the carbon atom to which they are attached form a carbocyclyl, heterocyclyl, or —C(=O)— group; Q is hydrogen, halogen, cyano, nitro, alkyl, alkenyl, alkynyl, —OR$^{A1}$, —SR$^{A1}$, or —N(R$^{A1}$)$_2$; R$^{19}$ is unsubstituted alkyl; R$^5$ is absent or hydrogen; and ===== represents a single or double bond, wherein when one ===== is a double bond, the other ===== is a single bond and R$^5$ is absent.

In an aspect, provided herein is a compound of the Formula (IV):

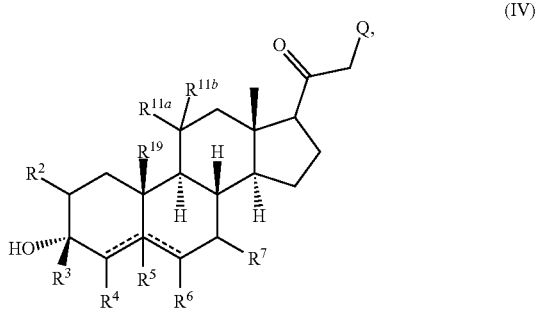

(IV)

or a pharmaceutically acceptable salt thereof, wherein: each of R$^2$, R$^4$, R$^6$, R$^7$, R$^{11a}$, and R$^{11b}$ is independently hydrogen, halogen, cyano, nitro, alkyl, alkenyl, alkynyl, carbocyclyl, heterocyclyl, aryl, heteroaryl, —OR$^{A1}$, —SR$^{A1}$, —N(R$^{A1}$)$_2$, —NHC(=O)R$^{A1}$, —NHC(=O)OR$^{A1}$, —S(=O)R$^{A2}$, —SO$_2$R$^{A2}$, or —S(=O)$_2$OR$^{A1}$, wherein each instance of R$^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two R$^{A1}$ groups are joined to form an heterocyclic or heteroaryl ring; and R$^{A2}$ is alkyl, alkenyl, alkynyl, carbocyclyl, heterocyclyl, aryl, or heteroaryl; or R$^{11a}$ and R$^{1b}$ together with the carbon atom to which they are attached form a carbocyclyl, heterocyclyl, or —C(=O)— group; R$^3$ is alkyl, alkenyl, carbocyclyl, heterocyclyl, aryl, or heteroaryl; Q is halogen, cyano, nitro, heterocyclyl linked through a C atom, aryl, heteroaryl linked through a C atom, —O-alkenyl, —O-alkynyl, —SR$^{A1}$, —N(R$^{A1}$)$_2$, —NHC(=O)R$^{A1}$, —NHC(=O)OR$^{A1}$, —S(=O)R$^{A2}$, —SO$_2$R$^{A2}$, or —S(=O)$_2$OR$^{A1}$; R$^{19}$ is C(R$^C$)$_2$OR$^{A1}$, wherein R$^C$ is hydrogen or alkyl; R$^5$ is absent or hydrogen; and ===== represents a single or double bond, wherein when one ===== is a double bond, the other ===== is a single bond and R$^5$ is absent.

In an aspect, provided herein is a compound of the Formula (I):

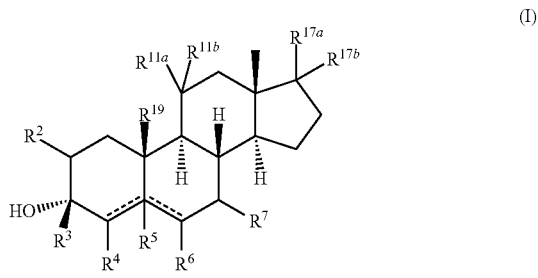

(I)

or a pharmaceutically acceptable salt thereof, wherein: each of R$^2$, R$^4$, R$^6$, R$^7$, R$^{11a}$, and R$^{11b}$ is independently hydrogen, halogen, cyano, nitro, alkyl, alkenyl, alkynyl, carbocyclyl, heterocyclyl, aryl, heteroaryl, —OR$^{A1}$, —SR$^{A1}$, —N(R$^{A1}$)$_2$, —NHC(=O)R$^{A1}$, —S(=O)R$^{A2}$, —SO$_2$R$^{A2}$, or —S(=O)$_2$OR$^{A1}$, wherein each instance of R$^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two R$^{A1}$ groups are joined to form an heterocyclic or heteroaryl ring; and R$^{A2}$ is alkyl, alkenyl, alkynyl, carbocyclyl, heterocyclyl, aryl, or heteroaryl; or R$^{11a}$ and R$^{11b}$ together with the carbon atom to which they are attached form a carbocyclyl, heterocyclyl, or —C(=O)—; R$^3$ is hydrogen, alkyl, alkenyl, carbocyclyl, heterocyclyl, aryl, or heteroaryl; each of R$^{17a}$ and R$^{17b}$ is independently hydrogen, halogen, cyano, nitro, alkyl, alkenyl, alkynyl, carbocyclyl, heterocyclyl, aryl, heteroaryl, —OR$^{A1}$, —SR$^{A1}$, —N(R$^{A1}$)$_2$, —NHC(=O)R$^{A1}$, —S(=O)R$^{A2}$, —SO$_2$R$^{A2}$, or —S(=O)$_2$OR$^{A1}$, wherein at least one of R$^{17a}$ and R$^{17b}$ is not hydrogen; R$^{19}$ is hydrogen or alkyl (e.g., unsubstituted alkyl or substituted alkyl (e.g., —C(R$^C$)$_2$OR$^{A1}$, wherein R$^C$ is hydrogen or alkyl)); R$^5$ is absent or hydrogen; and ===== represents a single or double bond, wherein when one ===== is a double bond, the other ===== is a single bond and R$^5$ is absent.

In some embodiments, R$^{19}$ is hydrogen or alkyl. In some embodiments, R$^{19}$ is unsubstituted alkyl. In some embodiments, R$^{19}$ is substituted alkyl. In some embodiments, R$^{19}$ is —CH$_2$OH, —CH$_2$OCH$_3$, —CH$_2$OCH$_2$CH$_3$, or —CH$_2$OCH(CH$_3$)$_2$.

In some embodiments, R$^2$ is hydrogen, halogen, alkyl, carbocyclyl, heterocyclyl, aryl, heteroaryl, —OR$^{A1}$, —SR$^{A1}$, or —N(R$^{A1}$)$_2$. In some embodiments, R$^2$ is hydrogen, halogen, alkyl, or —OR$^{A1}$. In some embodiments, R$^2$ is hydrogen.

In some embodiments, R$^3$ is alkyl, alkenyl, carbocyclyl, heterocyclyl, aryl, or heteroaryl. In some embodiments, R$^3$ is alkyl (e.g., substituted or unsubstituted alkyl), alkenyl, carbocyclyl, heterocyclyl, aryl, or heteroaryl. In some embodiments, R$^3$ is methyl and ethyl (e.g., substituted or unsubstituted alkyl).

In some embodiments, R$^4$ is hydrogen, halogen, alkyl, carbocyclyl, heterocyclyl, aryl, heteroaryl, —OR$^{A1}$, —SR$^{A1}$, or —N(R$^{A1}$)$_2$. In some embodiments, R$^4$ is hydrogen, halogen, alkyl, or —OR$^{A1}$. In some embodiments, R$^4$ is hydrogen.

In some embodiments, ===== represents a single bond and R$^5$ is hydrogen. In some embodiments, R$^5$ is absent, and ===== represents a single or double bond, wherein when one ===== is a double bond, the other ===== is a single bond.

In some embodiments, R⁶ is hydrogen, halogen, alkyl, carbocyclyl, heterocyclyl, aryl, heteroaryl, —OR^A1, —SR^A1, or —N(R^A1)₂. In some embodiments, R⁶ is hydrogen, halogen, alkyl, or —OR^A1. In some embodiments, R⁶ is hydrogen.

In some embodiments, R⁷ is hydrogen, halogen, alkyl, carbocyclyl, heterocyclyl, aryl, heteroaryl, —OR^A1, —SR^A1, or —N(R^A1)₂. In some embodiments, R⁷ is hydrogen, halogen, alkyl, or —OR^A1. In some embodiments, R⁷ is hydrogen.

In some embodiments, R^11a is hydrogen, halogen, alkyl, carbocyclyl, heterocyclyl, aryl, heteroaryl, —OR^A1, —SR^A1, —N(R^A1)₂, or R^11a and R^11b together with the carbon atom to which they are attached form —C(=O)—. In some embodiments, R^11a is hydrogen, halogen, alkyl, or —OR^A1. In some embodiments, R^11a and R^11b together with the carbon atom to which they are attached form —C(=O)—. In some embodiments, R^11a and R^11b are hydrogen.

In some embodiments, each of R², R⁴, R⁶, R⁷, R^11a, and R^11b is independently hydrogen, halogen, alkyl, carbocyclyl, heterocyclyl, aryl, heteroaryl, —OR^A1, —SR^A1, or —N(R^A1)₂. In some embodiments, each of R², R⁴, R⁶, R⁷, R^11a, and R^11b is independently hydrogen, halogen, alkyl, or —OR^A1. In some embodiments, R², R⁴, R⁶, R⁷, R^11a, and R^11b are hydrogen.

In some embodiments, each of R^17a and R^17b is independently hydrogen, halogen, cyano, nitro, alkyl, alkenyl, alkynyl, carbocyclyl, heterocyclyl, —SR^A1, —N(R^A1)₂, —NHC(=O)R^A1—S(=O)R^A2, —SO₂R^A2, or —S(=O)₂OR^A1, wherein at least one of R^17a and R^17b is not hydrogen. In some embodiments, each of R^17a and R^17b is independently hydrogen, halogen, nitro, alkyl, alkenyl, alkynyl, carbocyclyl, heterocyclyl, —SR^A1, —N(R^A1)₂, —NHC(=O)R^A1—S(=O)R^A2, —SO₂R^A2, or —S(=O)₂OR^A1, wherein at least one of R^17a and R^17b is not hydrogen.

In some embodiments, R^17a is halogen, cyano, nitro, alkyl, carbocyclyl, heterocyclyl, —OR^A1, —SR^A1, —N(R^A1)₂, —NHC(=O)R^A1, —S(=O)R^A2, or —SO₂R^A2. In some embodiments, R^17a is halogen, nitro, alkyl, carbocyclyl, heterocyclyl, —OR^A1, —SR^A1, —N(R^A1)₂, —NHC(=O)R^A1, —S(=O)R^A2, or —SO₂R^A2. In some embodiments, R^17a is halogen, cyano, nitro, alkyl, —OR^A1, —SR^A1, or —N(R^A1)₂.

In some embodiments, the compound is:

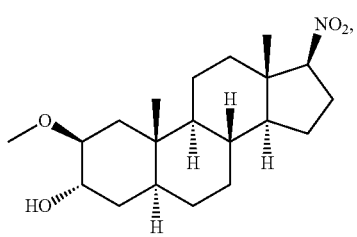

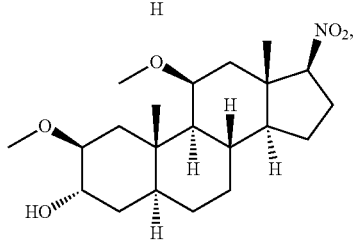

-continued

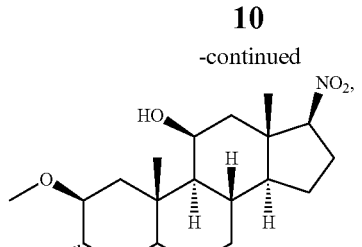

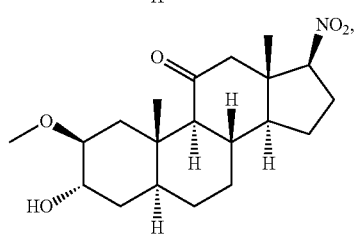

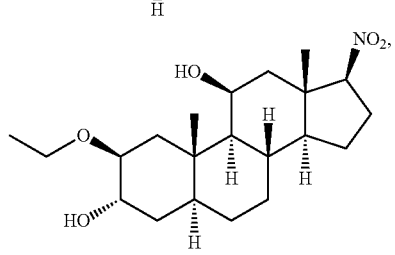

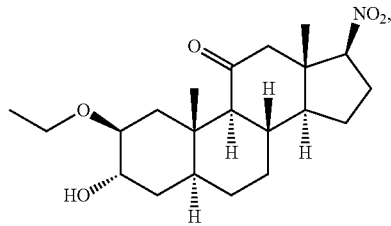

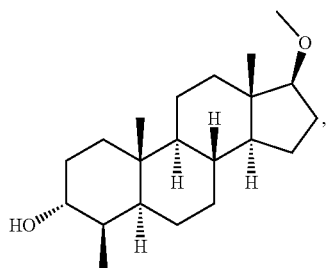

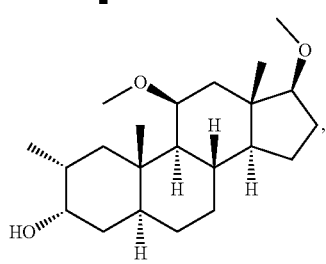

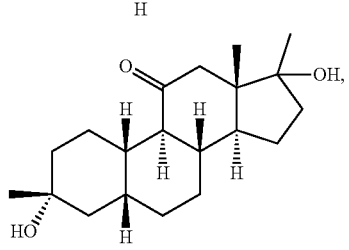

or a pharmaceutically acceptable salt thereof.

In an aspect, provided herein is a compound of the Formula (II):

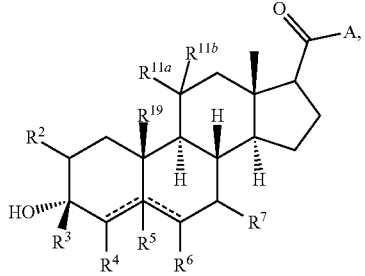

(II)

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{41}$, —$SR^{41}$, —$N(R^{41})_2$, —NHC(=O)$R^{41}$, —NHC(=O)$OR^{41}$, —S(=O)$R^{42}$, —$SO_2R^{42}$, or —S(=O)$_2OR^{41}$, wherein each instance of $R^{41}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an heterocyclic or heteroaryl ring; and $R^{42}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; $R^3$ is hydrogen, alkyl, alkenyl, carbocyclyl, heterocyclyl, aryl, or heteroaryl; A is alkyl, alkenyl, alkynyl, carbocyclyl, heterocyclyl, —$OR^{41}$, —$SR^{41}$, or —$N(R^{41})_2$; $R^{19}$ is hydrogen or alkyl (e.g., unsubstituted alkyl (e.g., —$CH_3$) or substituted alkyl (e.g., —$C(R^C)_2OR^{41}$, wherein $R^C$ is hydrogen or alkyl)); $R^5$ is absent or hydrogen; and
==== represents a single or double bond, wherein when one ==== is a double bond, the other ==== is a single bond and $R^5$ is absent.

In some embodiments, A is hydrogen, alkyl, alkenyl, alkynyl, carbocyclyl, heterocyclyl, or —$OR^{41}$.

In some embodiments, $R^{19}$ is hydrogen. In some embodiments, $R^{19}$ is alkyl (e.g., substituted or unsubstituted alkyl). In some embodiments, $R^{19}$ is —$CH_3$ or —$CH_2CH_3$. In some embodiments, $R^{19}$ is —$C(R^C)_2OR^{41}$. In some embodiments, $R^{19}$ is —$CH_2OH$, —$CH_2OCH_3$, —$CH_2OCH_2CH_3$, or —$CH_2OCH(CH_3)_2$.

In some embodiments, $R^2$ is hydrogen, halogen, alkyl, carbocyclyl, heterocyclyl, aryl, heteroaryl, —$OR^{41}$, —$SR^{41}$, or —$N(R^{41})_2$. In some embodiments, $R^2$ is hydrogen, halogen, alkyl, or —$OR^{41}$. In some embodiments, $R^2$ is hydrogen.

In some embodiments, $R^3$ is alkyl (e.g., substituted or unsubstituted alkyl). In some embodiments, $R^3$ is methyl and ethyl (e.g., substituted or unsubstituted methyl, substituted or unsubstituted ethyl).

In some embodiments, $R^4$ is hydrogen, halogen, alkyl, carbocyclyl, heterocyclyl, aryl, heteroaryl, —$OR^{41}$, —$SR^{41}$, or —$N(R^{41})_2$. In some embodiments, $R^4$ is hydrogen, halogen, alkyl, or —$OR^{41}$. In some embodiments, $R^4$ is hydrogen.

In some embodiments, ==== represents a single bond and $R^5$ is hydrogen. In some embodiments, $R^5$ is absent, and ==== represents a single or double bond, wherein when one ==== is a double bond, the other ==== is a single bond.

In some embodiments, $R^6$ is hydrogen, halogen, alkyl, carbocyclyl, heterocyclyl, aryl, heteroaryl, —$OR^{41}$, —$SR^{41}$, or —$N(R^{41})_2$. In some embodiments, $R^6$ is hydrogen, halogen, alkyl, or —$OR^{41}$. In some embodiments, $R^6$ is hydrogen.

In some embodiments, $R^7$ is hydrogen, halogen, alkyl, carbocyclyl, heterocyclyl, aryl, heteroaryl, —$OR^{41}$, —$SR^{41}$, or —$N(R^{41})_2$. In some embodiments, $R^7$ is hydrogen, halogen, alkyl, or —$OR^{41}$. In some embodiments, $R^7$ is hydrogen.

In some embodiments, $R^{11a}$ is hydrogen, halogen, alkyl, carbocyclyl, heterocyclyl, aryl, heteroaryl, —$OR^{41}$, —$SR^{41}$, —$N(R^{41})_2$, or $R^{11a}$ and $R^{11b}$ together with the carbon atom to which they are attached form —C(=O)—. In some embodiments, $R^{11a}$ is hydrogen, halogen, alkyl, or —$OR^{41}$. In some embodiments, $R^{11a}$ and $R^{11b}$ together with the carbon atom to which they are attached form —C(=O)—. In some embodiments, $R^{11a}$ and $R^{11b}$ are hydrogen.

In some embodiments, each of $R^2$, $R^4$, $R^6$, $R^7$, $R^{11a}$, and $R^{11b}$ is independently hydrogen, halogen, alkyl, carbocyclyl, heterocyclyl, aryl, heteroaryl, —$OR^{41}$, —$SR^{41}$, or —$N(R^{41})_2$. In some embodiments, each of $R^2$, $R^4$, $R^6$, $R^7$, $R^{11a}$, and $R^{11b}$ is hydrogen, halogen, alkyl, or —$OR^{41}$. In some embodiments, each of $R^2$, $R^4$, $R^6$, $R^7$, $R^{11a}$, and $R^{11b}$ is hydrogen.

In some embodiments, the compound of Formula (II) is a compound of the Formula (II-a) or (II-b):

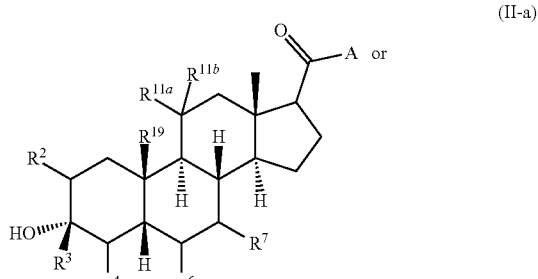

(II-a)

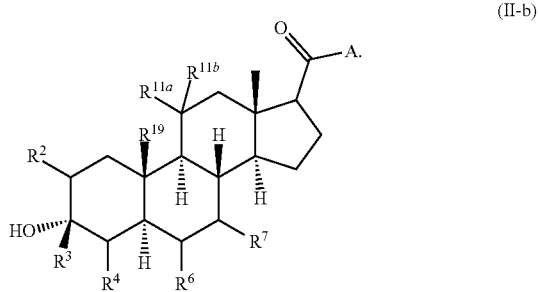

(II-b)

In some embodiments, the compound of Formula (I) is a compound of the Formula (II-c):

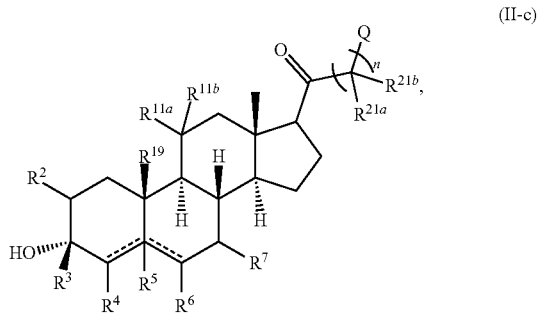

(II-c)

wherein:

each of $R^{21a}$ and $R^{21b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)$OR^{A1}$, —S(=O)$R^{A2}$, —$SO_2R^{A2}$, or —S(=O)$_2OR^{A1}$; or $R^{21a}$ and $R^{21b}$ together with the carbon atom to which they are attached form a carbocyclyl, heterocyclyl, or —C(=O)— group; Q is hydrogen, halogen, cyano, nitro, alkyl, alkenyl, alkynyl, carbocyclyl, heterocyclyl, aryl, heteroaryl, —$OR^{A1}$, —$SR^{A1}$, or —$N(R^{A1})_2$; and n is an integer selected from 1, 2, and 3.

In some embodiments, the compound of Formula (II) is a compound of the Formula (II-d):

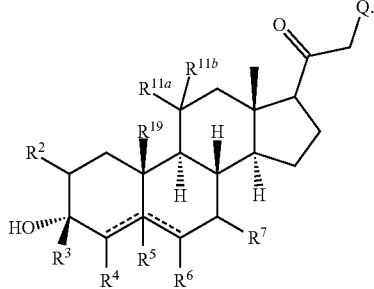

(II-d)

In an aspect, provided herein is a compound of the Formula (III-a):

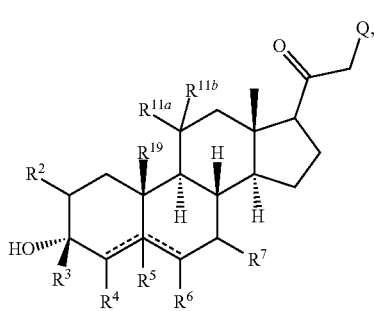

(III-a)

wherein:

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)$OR^{A1}$, —S(=O)$R^{A2}$, —$SO_2R^{A2}$, or —S(=O)$_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; Q is hydrogen, halogen, cyano, nitro, alkyl, alkenyl, alkynyl, —$OR^{A1}$, —$SR^{A1}$, or —$N(R^{A1})_2$; $R^{19}$ is unsubstituted alkyl; $R^5$ is absent or hydrogen; and ==== represents a single or double bond, wherein when one ==== is a double bond, the other ==== is a single bond and $R^5$ is absent.

In an aspect, provided herein is a compound of the Formula (III-b):

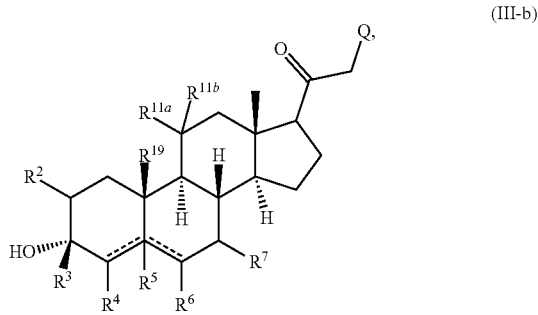

(III-b)

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)$OR^{A1}$, —S(=O)$R^{A2}$, —$SO_2R^{A2}$, or —S(=O)$_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; $R^3$ is alkyl, alkenyl, carbocyclyl, heterocyclyl, aryl, or heteroaryl; Q is halogen, cyano, nitro, heterocyclyl linked through a C atom, aryl, heteroaryl linked through a C atom, —O-alkenyl, —O-alkynyl, —$SR^{A1}$, —$N(R^{A1})_2$, —NHC(=O)$R^{A1}$, —NHC(=O)$OR^{A1}$, —S(=O)$R^{A2}$, —$SO_2R^{A2}$, or —S(=O)$_2OR^{A1}$; $R^{19}$ is —$C(R^C)_2OR^{A1}$, wherein $R^C$ is hydrogen or alkyl; $R^5$ is absent or hydrogen; and ==== represents a single or double bond, wherein when one ==== is a double bond, the other ==== is a single bond and $R^5$ is absent.

In an aspect, provided herein is a compound of Formula (1-A):

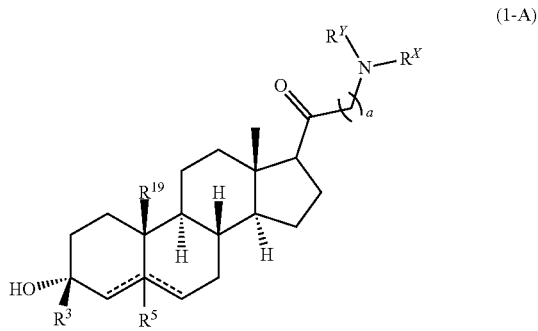

(1-A)

or a pharmaceutically acceptable salt thereof, wherein: $R^3$ is alkyl, alkenyl, carbocyclyl, heterocyclyl, aryl, or heteroaryl; each of $R^X$ and $R^Y$ is independently hydrogen, aryl, or alkyl, or $R^X$ and $R^Y$ are joined together to form a 3-10 membered heterocyclic ring; $R^{19}$ is hydrogen or alkyl (e.g., unsubstituted alkyl or substituted alkyl (e.g., —$C(R^C)_2OR^{A1}$, wherein $R^C$ is hydrogen or alkyl)); $R^5$ is absent or hydrogen; ==== represents a single or double bond, wherein when one ==== is a double bond, the other ==== is a single bond and $R^5$ is absent; and a is 0 or 1; provided that $R^X$ and $R^Y$ are joined together to form a 3-8 membered heterocyclic ring only when a is 0.

In some embodiments, $R^X$ and $R^Y$ are not both hydrogen. In some embodiments, $R^3$ is alkyl. In some embodiments, $R^{19}$ is hydrogen.

In some embodiments, the compound is a compound of Formula (1-A-1)

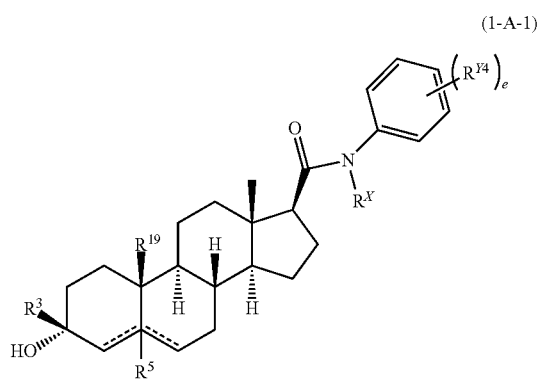

(1-A-1)

wherein each instance of $R^{Y4}$ is independently alkyl, cyano, or halo; and e is 0, 1, 2, 3, 4, or 5.

In some embodiments, each instance of $R^{Y4}$ is independently hydrogen, —$CH_3$, —CN, or —F. In some embodiments, e is 3. In some embodiments, $R^X$ is hydrogen. In some embodiments, each instance of $R^{Y4}$ is independently hydrogen, —$CH_3$, —CN, or —F, $R^X$ is hydrogen, and e is 3. In some embodiments, each instance of $R^{Y4}$ is independently hydrogen, —$CH_3$, —CN, or —F, $R^X$ is hydrogen, and e is 2. In some embodiments, e is 1. In some embodiments, $R^{Y4}$ is —F. In some embodiments, $R^{Y4}$ is —F and e is 1.

In some embodiments, the compound is a compound of Formula (1-A-2)

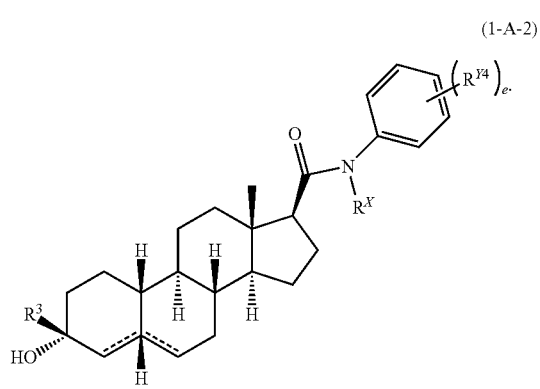

(1-A-2)

In some embodiments, each instance of $R^{Y4}$ is independently hydrogen, —$CH_3$, —CN, or —F. In some embodiments, e is 3. In some embodiments, $R^X$ is hydrogen. In some embodiments, each instance of $R^{Y4}$ is independently hydrogen, —$CH_3$, —CN, or —F, $R^X$ is hydrogen, and e is 3. In some embodiments, each instance of $R^{Y4}$ is independently hydrogen, —$CH_3$, —CN, or —F, $R^X$ is hydrogen, and e is 2. In some embodiments, e is 1. In some embodiments, $R^{Y4}$ is —F.

In some embodiments, the compound is a compound of Formula (1-A-3)

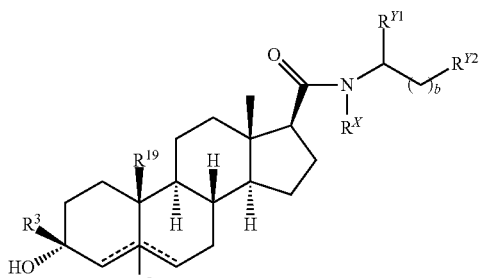

(1-A-3)

wherein each of $R^{Y1}$ and $R^{Y2}$ is independently alkyl, cycloalkyl, heterocycyl, aryl, or heteroaryl; and b=0, 1, 2, 3.

In some embodiments, $R^{Y1}$ and $R^{Y2}$ are not both —CH$(CH_3)_2$.

In some embodiments, the compound is a compound of Formula (1-A-4)

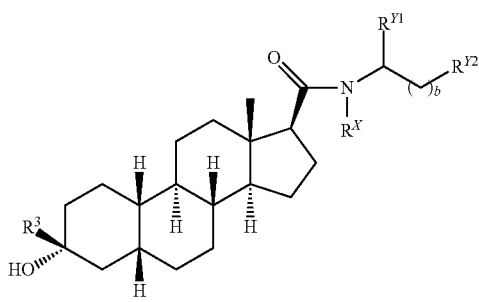

(1-A-4)

In some embodiments, $R^{Y1}$ is hydrogen, —$CH_3$, or —$CH_2CH_3$, —$CH(CH_3)_2$, or cycloalkyl. In some embodiments, $R^3$ is —$CH_3$, —$CF_3$, —$CH_2OCH_3$, —$CH_2OCH_2CH_3$. In some embodiments, $R^{Y2}$ is heteocyclyl, aryl, or heteroaryl. In some embodiments, $R^{Y2}$ is aryl substituted with 0-5 occurrences of —$CH_3$, —CN, —F, —$CF_3$, or combinations thereof or heteroaryl substituted with 0-5 occurrences of —$CH_3$, —CN, —F, —$CF_3$.

In some embodiments, $R^{Y2}$ is aryl substituted with 0-5 occurrences of —$CH_3$, —CN, —F, —$CF_3$, or $R^X$ is hydrogen, —$CH_3$, or —$CH_2CH_3$. In some embodiments, $R^{Y2}$ is aryl substituted with 0-5 occurrences of —$CH_3$, —CN, —F, —$CF_3$.

In some embodiments, the compound is a compound of Formula (1-A-5)

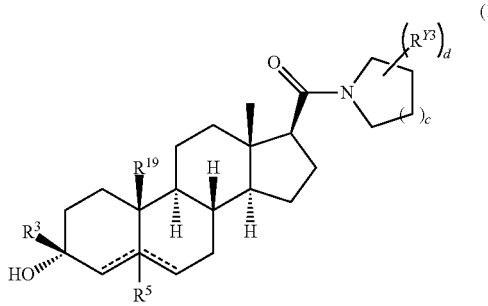

(1-A-5)

wherein each occurrence of $R^{Y3}$ is aryl or heteroaryl, or two $R^{Y3}$ groups are joined together to form a 6-10 membered ring; c is 0, 1, 2, or 3; and d is 0, 1, 2, or 3.

In some embodiments, the compound is a compound of Formula (1-A-6)

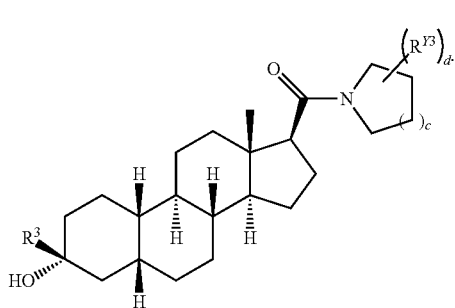
(1-A-6)

In some embodiments, if d is 2, then two $R^{Y3}$ groups are joined together to form aryl. In some embodiments, $R^{Y2}$ is aryl substituted with 0-5 occurrences of —CH₃, —CN, —F, —CF₃. In some embodiments, the compound is a compound of Formula (1-A-7) or Formula (1-A-8)

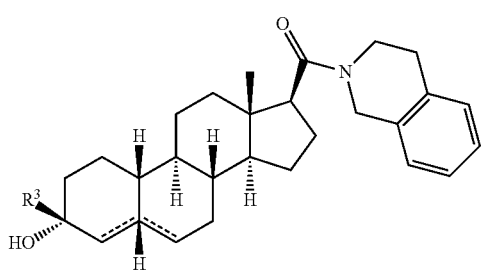
(1-A-7)

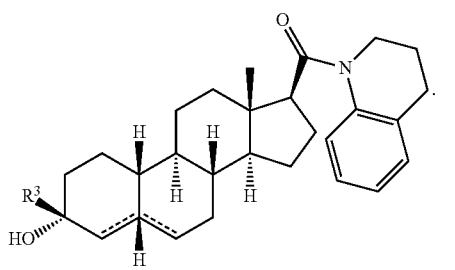
(1-A-8)

In some embodiments, $R^{Y2}$ is aryl substituted with 0-5 occurrences of —CH₃, —CN, —F, —CF₃, or $R^3$ is —CH₃, —CF₃, —CH₂OCH₃, —CH₂OCH₂CH₃.

In an aspect, provided herein is a compound of Formula (2-A),

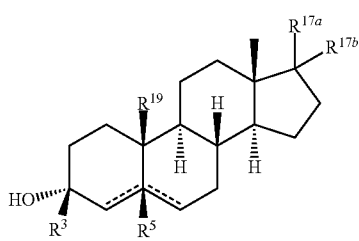
(2-A)

or a pharmaceutically acceptable salt thereof, wherein $R^3$ is —CH₃, —CF₃, —CH₂OCH₃, —CH₂OCH₂CH₃; $R^{19}$ is hydrogen, —CH₃, or —CH₂OR$^{41}$, wherein R$^{41}$ is optionally substituted alkyl; $R^3$ is —CH₃, —CF₃, —CH₂OCH₃, —CH₂OCH₂CH₃; $R^{17a}$ is —NR$^{A2}$R$^{A3}$, —N(R1)C(O)R$^{A2}$, —N(R1)SO₂R$^{A2}$, —OR$^{A3}$, cycloalkyl, heterocyclyl, aryl, or heteroaryl, wherein each of R$^{A2}$ and R$^{A3}$ is independently hydrogen, carbocyclyl, heterocyclyl, aryl, heteroaryl, or —OR$^{A4}$, wherein R$^{A4}$ is hydrogen or alkyl; or $R^{17a}$ is

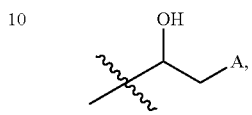

wherein A is oxazolyl or thiazolyl; $R^{17a}$ is hydrogen, hydroxyl, alkyl, or alkoxy; and ==== represents a single or double bond, wherein when one ==== is a double bond, the other ==== is a single bond and $R^5$ is absent; provided that: when $R^{17a}$ is oxazolyl or

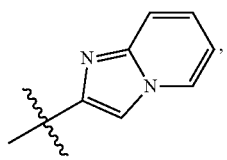 [SMILES: *c1cn2ccccc2n1]

then $R^{17b}$ is not hydrogen, or when $R^{17a}$ is heterocyclyl, then $R^{19}$ is hydrogen, or when $R^{17a}$ is —OR$^{A4}$, then $R^{19}$ is hydrogen.

In some embodiments, $R^{17a}$ is —NR$^{A2}$R$^{A3}$, —N(R1)C(O)R$^{A2}$, —N(R1)SO₂R$^{A2}$. In some embodiments, $R^{17a}$ is aryl, heteroaryl, cycloalkyl, or heterocyclyl. In some embodiments, $R^{19}$ is hydrogen. In some embodiments, $R^{17a}$ is heteroaryl. In some embodiments, $R^{17a}$ is heteroaryl and $R^{19}$ is hydrogen. In some embodiments, $R^{17a}$ is pyridyl and $R^{19}$ is hydrogen.

In an aspect, provided herein is a compound of Formula (3-A)

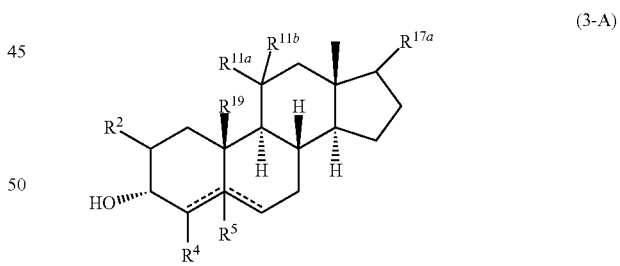
(3-A)

or a pharmaceutically acceptable salt thereof, wherein $R^{19}$ is hydrogen or alkyl; $R^{17a}$ is nitro or alkoxy (e.g., —OCH₃); each of $R^2$, $R^4$, $R^{11a}$, or $R^{11b}$ is independently hydrogen, alkyl, or alkoxy, or $R^{11a}$ and $R^{11b}$ are joined together to form oxo; ==== represents a single or double bond, wherein when one ==== is a double bond, the other ==== is a single bond and $R^5$ is absent; and $R^5$ is absent or hydrogen as determined by valency; provided that, when $R^2$, $R^{11a}$, and $R^{11b}$ are hydrogen, then $R^4$ is alkyl, or when $R^4$, $R^{11a}$, and $R^{11b}$ are hydrogen, then $R^2$ is alkyl, or when $R^4$ is hydrogen, then $R^2$ is —OH or alkoxy, $R^{11a}$ is hydrogen, and $R^{11b}$ is —OH or alkoxy, or $R^2$ is —OH or alkoxy and $R^{11a}$ and $R^{11b}$ are joined together to form oxo.

In some embodiments, $R^4$ is hydrogen, $R^2$ is —OH or alkoxy, $R^{11a}$ is hydrogen, and $R^{11b}$ is —OH or alkoxy. In some embodiments, $R^4$ is hydrogen, $R^2$ is —OH or alkoxy, and $R^{11a}$ and $R^{11b}$ are joined together to form oxo. In some embodiments, $R^{17a}$ is nitro. In some embodiments, $R^{17a}$ is alkoxy. In some embodiments, $R^{17a}$ is methoxy and $R^2$ is methyl.

In an aspect, also provided herein are compounds described in Table 1 or pharmaceutically acceptable salts thereof.

In an aspect, provided herein is a pharmaceutical composition comprising a compound described herein (e.g., a compound of the Formula (I), Formula (II), Formula (III), or Formula (IV), Formula (1-A), Formula (2-A), or Formula (3-A)) and a pharmaceutically acceptable excipient.

In an aspect, provided herein is a method of inducing sedation and/or anesthesia in a subject, comprising administering to the subject an effective amount of a compound described herein (e.g., a compound of the Formula (I), Formula (II), Formula (III), or Formula (IV), Formula (1-A), Formula (2-A), or Formula (3-A)), or a pharmaceutically acceptable salt thereof.

In an aspect, provided herein is a method of administering an effective amount of a compound, a pharmaceutically acceptable salt thereof, or pharmaceutical composition of a compound described herein (e.g., a compound of the Formula (I), Formula (II), Formula (III), or Formula (IV), Formula (1-A), Formula (2-A), or Formula (3-A)), to a subject in need thereof, wherein the subject experiences sedation and/or anesthesia within two hours of administration. In some embodiments, the subject experiences sedation and/or anesthesia within one hour of administration. In some embodiments, the subject experiences sedation and/or anesthesia instantaneously. In some embodiments, the compound is administered by intravenous administration. In some embodiments, the compound is administered chronically.

In some embodiments, the subject is a mammal. In some embodiments, the subject is a human.

In some embodiments, the compound is administered in combination with another therapeutic agent.

In an aspect, provided herein is a method for treating seizure in a subject, comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating epilepsy or status epilepticus in a subject, the method comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating a neuroendocrine disorder or dysfunction in a subject, comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating a neurodegenerative disease or disorder in a subject, comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating a movement disorder or tremor in a subject, comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating a mood disorder or anxiety disorder in a subject, comprising administering to the subject an effective amount of a compound described herein (e.g., a compound of the Formula (I), Formula (II), Formula (III), or Formula (IV), Formula (1-A), Formula (2-A), or Formula (3-A)).

In an aspect, provided herein is a method for treating disorders related to GABA function in a subject in need thereof, the method comprising administering to the subject a therapeutically effective amount of a compound, a pharmaceutically acceptable salt thereof, or pharmaceutical composition of a compound described herein (e.g., a compound of the Formula (I), Formula (II), Formula (III), or Formula (IV), Formula (1-A), Formula (2-A), or Formula (3-A)).

In an aspect, provided herein is a kit comprising a solid composition comprising a compound described herein (e.g., a compound of the Formula (I), Formula (II), Formula (III), or Formula (IV), Formula (1-A), Formula (2-A), or Formula (3-A)) and a sterile diluent.

Thus, in another aspect, provided are methods of treating a CNS-related disorder in a subject in need thereof, comprising administering to the subject an effective amount of a compound as described herein (e.g., a compound of the Formula (I), Formula (II), Formula (III), or Formula (IV), Formula (1-A), Formula (2-A), or Formula (3-A)). In certain embodiments, the CNS-related disorder is selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In certain embodiments, the compound is administered orally, subcutaneously, intravenously, or intramuscularly. In certain embodiments, the compound is administered chronically. In certain embodiments, the compound is administered continuously, e.g., by continuous intravenous infusion.

In some embodiments, the subject is a subject with Rett syndrome, Fragile X syndrome, or Angelman syndrome.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

The absolute configuration of an asymmetric center can be determined using methods known to one skilled in the art. In some embodiments, the absolute configuration of an asymmetric center in a compound can be elucidated from the X-ray single-crystal structure of the compound. In some embodiments, the absolute configuration of an asymmetric center elucidated by the X-ray crystal structure of a compound can be used to infer the absolute configuration of a corresponding asymmetric center in another compound obtained from the same or similar synthetic methodologies. In some embodiments, absolute configuration of an asymmetric center can be determined using nuclear Overhauser effect (NOE) experiments via nuclear magnetic resonance (NMR) spectroscopy.

In some embodiments, an asymmetric center of known absolute configuration can be introduced into a compound with a chiral reactant, e.g., a chiral amine. In some embodiments, an asymmetric center of known absolute configuration can be introduced into a compound with a reaction methodology, e.g., by a reductive amination.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 8 carbon atoms ("$C_{1-8}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 8 carbon atoms ("$C_{2-8}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-3}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 8 carbon atoms ("$C_{2-8}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Aryl groups include, but are not limited to, phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

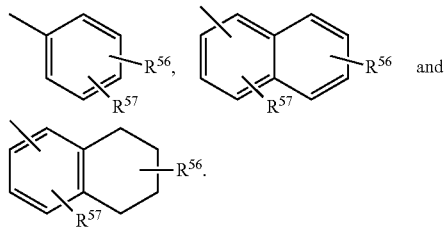

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}$ $SOR^{59}$ $NR^{58}SO_2R^{59}$, COOalkyl, COOaryl, $CONR^{58}R^{59}$, $CONR^{58}$ $OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

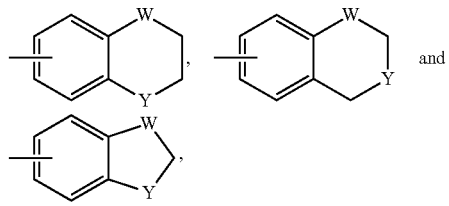

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Halo" or "halogen," independently or as part of another substituent, mean, unless otherwise stated, a fluorine (F), chlorine (Cl), bromine (Br), or iodine (I) atom. The term "halide" by itself or as part of another substituent, refers to a fluoride, chloride, bromide, or iodide atom. In certain embodiments, the halo group is either fluorine or chlorine.

"Haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Hydroxy" or "hydroxyl," independently or as part of another substituent, mean, unless otherwise stated, a —OH group.

Hydroxyalkyl" or "hydroxylalkyl" can include alkyl structures that are substituted with one or more hydroxyl groups.

"Heteroaryl" refers to a radical of a 5-10 membered monocyclic or bicyclic 4n+2 aromatic ring system (e.g., having 6 or ☐ ☐ ☐ ☐ ☐ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following formulae:

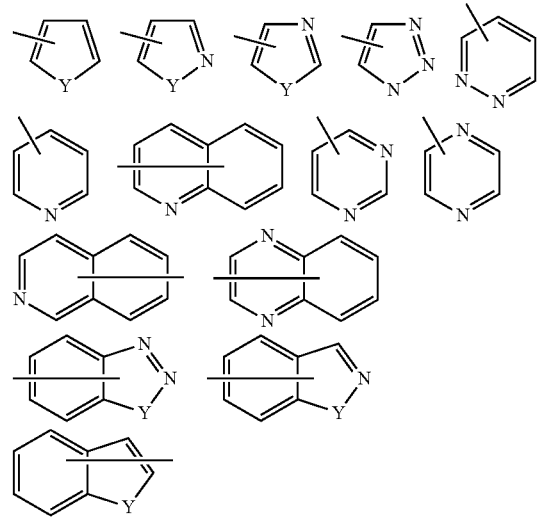

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_5$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

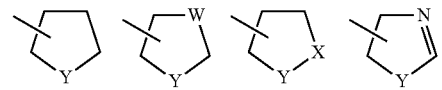

-continued

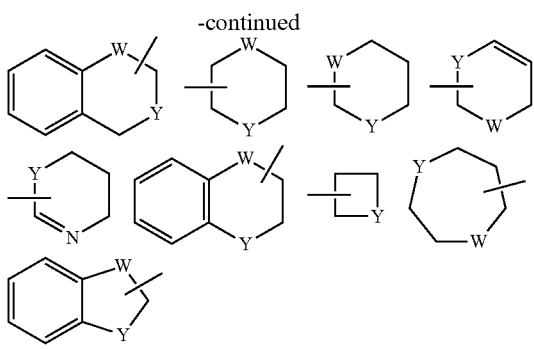

wherein each W is selected from CR$^{67}$, C(R$^{67}$)$_2$, NR$^{67}$, O, and S; and each Y is selected from NR$^{67}$, O, and S; and R$^{67}$ is independently hydrogen, C$_1$-C$_8$ alkyl, C$_3$-C$_{10}$ cycloalkyl, 4-10 membered heterocyclyl, C$_6$-C$_{10}$ aryl, and 5-10-membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (e.g., amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R$^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)C$_1$-C$_8$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents hydrogen or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_{3-10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl, and benzylcarbonyl. In certain embodiments, R$^{28}$ is C$_1$-C$_8$ alkyl, substituted with halo or hydroxy; C$_3$-C$_{10}$ cycloalkyl, 4-10-membered heterocyclyl, C$_6$-C$_{10}$ aryl, arylalkyl, 5-10-membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e., with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxy, nitro, thioalkoxy, thioaryloxy, thiol, alkyl-S(O)—, aryl-S(O)—, alkyl-S(O)$_2$— and aryl-S(O)$_2$—. Exemplary "substituted alkoxy" groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo" refers to =O.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_{3-8}$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents hydrogen or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —N$_3$.

"Carbamoyl" or "amido" refers to the radical —C(O)NH$_2$.

"Substituted carbamoyl" or "substituted amido" refers to the radical —C(O)N(R$^{62}$)$_2$ wherein each R$^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{62}$ is not a hydrogen. In certain embodiments, R$^{62}$ is selected from H, C$_1$-C$_8$ alkyl, C$_3$-C$_{10}$ cycloalkyl, 4-10 membered heterocyclyl, C$_6$-C$_{10}$ aryl, and 5-10 membered heteroaryl; or C$_1$-C$_8$ alkyl substituted with halo or hydroxy; or C$_3$-C$_{10}$ cycloalkyl, 4-10 membered heterocyclyl, C$_6$-C$_{10}$ aryl, or 5-10 membered heteroaryl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; provided that at least one R$^{62}$ is other than H.

"Carboxy" refers to the radical —C(O)OH.

"Cyano" refers to the radical —CN.

"Nitro" refers to the radical —NO$_2$.

"Ethenyl" refers to substituted or unsubstituted —(C=C)—. "Ethylene" refers to substituted or unsubstituted —(C—C)—. "Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{C}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_1$-$C_{10}$ alkyl, $C_1$-$C_{10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_1$ alkyl)$_2^+$X$^-$, —NH$_2$(C$_{1-6}$ alkyl)$^+$X, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14-membered heteroaryl, or two $R^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)OR$^{aa}$, —C(=O)N(R$^{cc}$)$_2$, —S(=O)$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)R$^{aa}$), which include, but are not limited to, formamide and acetamide; carbamate groups (e.g., —C(=O)OR$^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2$R$^{aa}$), which include, but are not limited to, p-toluenesulfonamide (Ts), methanesulfonamide (Ms), and N-[2-(trimethylsilyl)ethoxy]methylamine (SEM).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

As used herein, the term "modulation" refers to the inhibition or potentiation of GABA receptor function. A "modulator" (e.g., a modulator compound) may be, for example, an agonist, partial agonist, antagonist, or partial antagonist of the GABA receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

Provided herein are compounds (e.g., compound of Formula (I)), pharmaceutical compositions, and their methods of use to treat a disease or disorder as described herein.

Compounds

Compounds described herein are generally designed to modulate GABA function, and therefore to act as neuroactive steroids for the treatment and prevention of CNS-related conditions in a subject. Modulation, as used herein, refers to the inhibition or potentiation of GABA receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In an aspect, provided herein is a compound of the Formula (I):

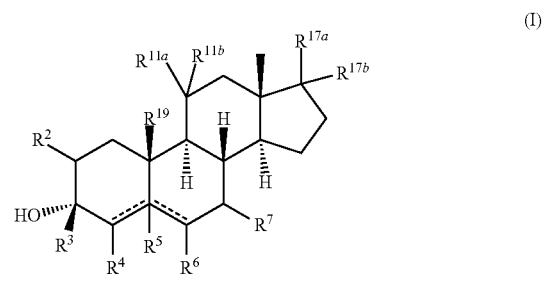

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{41}$, —$SR^{41}$, —$N(R^4)_2$, —$NHC(=O)R^4)R$, —$S(=O)R^{42}$, —$SO_2R^{42}$, or —$S(=O)_2 OR^{41}$, wherein each instance of $R^{41}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an heterocyclic or heteroaryl ring; and $R^{42}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —$C(=O)$—; $R^3$ is hydrogen, alkyl, alkenyl, carbocyclyl, heterocyclyl, aryl, or heteroaryl; each of $R^{17a}$ and $R^{17b}$ is independently hydrogen, halogen, cyano, nitro, alkyl, alkenyl, alkynyl, carbocyclyl, heterocyclyl, aryl, heteroaryl, —$OR^{41}$, —$SR^{41}$, —$N(R^{41})_2$, —$NHC(=O)R^{41}$, —$S(=O)R^{42}$, —$SO_2R^{42}$, or —$S(=O)_2R^{41}$, wherein at least one of R$^{17a}$ and R$^{17b}$ is not hydrogen; R$^{19}$ is hydrogen or alkyl (e.g., unsubstituted alkyl or substituted alkyl (e.g., —C(R$^C$)$_2$OR$^{41}$, wherein R$^C$ is hydrogen or alkyl)); R$^5$ is absent or hydrogen; and ==== represents a single or double bond, wherein when one ==== is a double bond, the other ==== is a single bond and R$^5$ is absent.

In some embodiments, R$^{19}$ is hydrogen or alkyl. In some embodiments, R$^{19}$ is unsubstituted alkyl. In some embodiments, R$^{19}$ is substituted alkyl. In some embodiments, R$^{19}$ is —CH$_2$OH, —CH$_2$OCH$_3$, —CH$_2$OCH$_2$CH$_3$, or —CH$_2$OCH(CH$_3$)$_2$.

In some embodiments, R$^2$ is hydrogen, halogen, alkyl, carbocyclyl, heterocyclyl, aryl, heteroaryl, —OR$^{41}$, —SR$^{41}$, or —N(R$^{41}$)$_2$. In some embodiments, R$^2$ is hydrogen, halogen, alkyl, or —OR$^{41}$. In some embodiments, R$^2$ is hydrogen.

In some embodiments, R$^3$ is alkyl, alkenyl, carbocyclyl, heterocyclyl, aryl, or heteroaryl. In some embodiments, R$^3$ is alkyl (e.g., substituted or unsubstituted alkyl), alkenyl, carbocyclyl, heterocyclyl, aryl, or heteroaryl. In some embodiments, R$^3$ is methyl and ethyl (e.g., substituted or unsubstituted alkyl).

In some embodiments, R$^4$ is hydrogen, halogen, alkyl, carbocyclyl, heterocyclyl, aryl, heteroaryl, —OR$^{41}$, —SR$^{41}$, or —N(R$^{41}$)$_2$. In some embodiments, R$^4$ is hydrogen, halogen, alkyl, or —OR$^{41}$. In some embodiments, R$^4$ is hydrogen.

In some embodiments, ==== represents a single bond and R$^5$ is hydrogen. In some embodiments, R$^5$ is absent, and ==== represents a single or double bond, wherein when one ==== is a double bond, the other ==== is a single bond.

In some embodiments, R$^6$ is hydrogen, halogen, alkyl, carbocyclyl, heterocyclyl, aryl, heteroaryl, —OR$^{41}$, —SR$^{41}$, or —N(R$^{41}$)$_2$. In some embodiments, R$^6$ is hydrogen, halogen, alkyl, or —OR$^{41}$. In some embodiments, R$^6$ is hydrogen.

In some embodiments, R$^7$ is hydrogen, halogen, alkyl, carbocyclyl, heterocyclyl, aryl, heteroaryl, —OR$^{41}$, —SR$^{41}$, or —N(R$^{41}$)$_2$. In some embodiments, R$^7$ is hydrogen, halogen, alkyl, or —OR$^{41}$. In some embodiments, R$^7$ is hydrogen.

In some embodiments, R$^{11a}$ is hydrogen, halogen, alkyl, carbocyclyl, heterocyclyl, aryl, heteroaryl, —OR$^{41}$, —SR$^{41}$, —N(R$^A$)$_2$, or R$^{11a}$ and R$^{11b}$ together with the carbon atom to which they are attached form —C(=O)—. In some embodiments, R$^{11a}$ is hydrogen, halogen, alkyl, or —OR$^{41}$. In some embodiments, R$^{11a}$ and R$^{11b}$ together with the carbon atom to which they are attached form —C(=O)—. In some embodiments, R$^{11a}$ and R$^{11b}$ are hydrogen.

In some embodiments, each of R$^2$, R$^4$, R$^6$, R$^7$, R$^{11a}$, and R$^{11b}$ is independently hydrogen, halogen, alkyl, carbocyclyl, heterocyclyl, aryl, heteroaryl, —OR$^{41}$, —SR$^{41}$, or —N(R$^{41}$)$_2$. In some embodiments, each of R$^2$, R$^4$, R$^6$, R$^7$, R$^{11a}$, and R$^{11b}$ is independently hydrogen, halogen, alkyl, or —OR$^{41}$. In some embodiments, R$^2$, R$^4$, R$^6$, R$^7$, R$^{11a}$, and R$^{11b}$ are hydrogen.

In some embodiments, each of R$^{17a}$ and R$^{17b}$ is independently hydrogen, halogen, cyano, nitro, alkyl, alkenyl, alkynyl, carbocyclyl, heterocyclyl, —SR$^{41}$, —N(R$^{41}$)$_2$, —NHC(=O)R$^{41}$—S(=O)R$^{42}$, —SO$_2$R$^{42}$ or —S(=O)$_2$OR$^{41}$, wherein at least one of R$^{17a}$ and R$^{17b}$ is not hydrogen. In some embodiments, each of R$^{17a}$ and R$^{17b}$ is independently hydrogen, halogen, nitro, alkyl, alkenyl, alkynyl, carbocyclyl, heterocyclyl, —SR$^{41}$, —N(R$^{41}$)$_2$, —NHC(=O)R$^{41}$—S(=O)R$^{42}$, —SO$_2$R$^{42}$, or —S(=O)$_2$OR$^{41}$, wherein at least one of R$^{17a}$ and R$^{17b}$ is not hydrogen.

In some embodiments, R$^{17a}$ is halogen, cyano, nitro, alkyl, carbocyclyl, heterocyclyl, —OR$^{41}$, —SR$^{41}$, —N(R$^{41}$)$_2$, —NHC(=O)R$^{41}$, —S(=O)R$^{42}$, or —SO$_2$R$^{42}$. In some embodiments, R$^{17a}$ is halogen, nitro, alkyl, carbocyclyl, heterocyclyl, —OR$^{41}$, —SR$^{41}$, —N(R$^{41}$)$_2$, —NHC(=O)R$^{41}$, —S(=O)R$^{42}$, or —SO$_2$R$^{42}$. In some embodiments, R$^{17a}$ is halogen, cyano, nitro, alkyl, —OR$^{41}$, —SR$^{41}$, or —N(R$^{41}$)$_2$.

In some embodiments, the compound is:

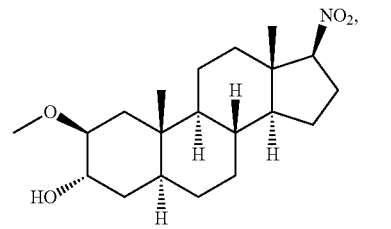

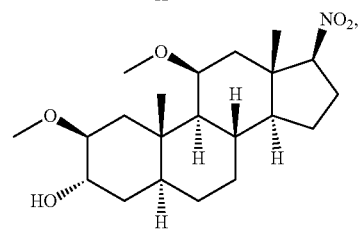

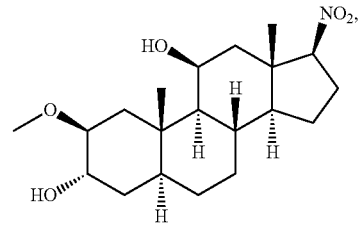

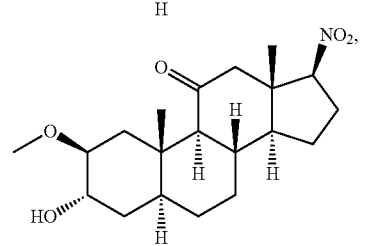

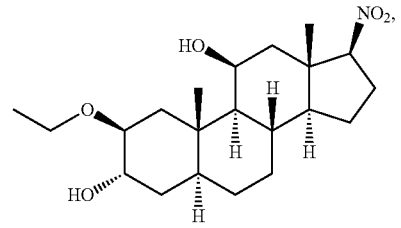

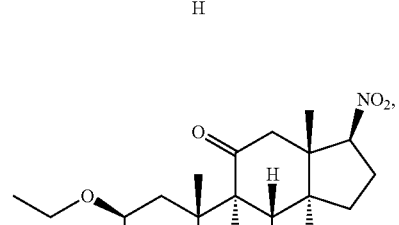

-continued

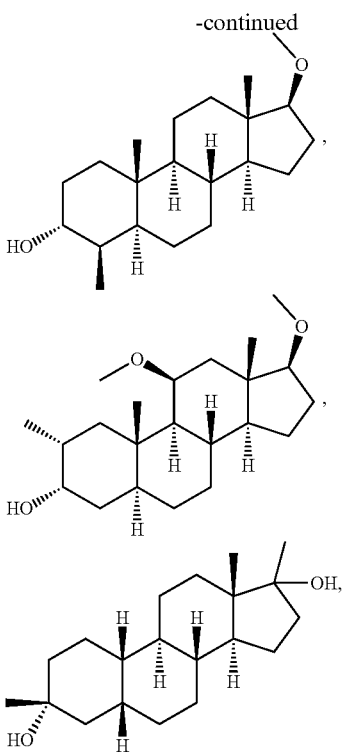

or a pharmaceutically acceptable salt thereof.

In an aspect, provided herein is a compound of the Formula (II):

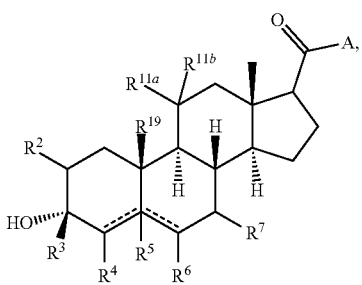

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{41}$, —$SR^{41}$, —$N(R^{41})_2$, —NHC(=O)$R^{41}$, —NHC(=O)O$R^{41}$, —S(=O)$R^{42}$, —$SO_2R^{42}$, or —S(=O)$_2OR^{41}$, wherein each instance of $R^{41}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an heterocyclic or heteroaryl ring; and $R^{42}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; $R^3$ is hydrogen, alkyl, alkenyl, carbocyclyl, heterocyclyl, aryl, or heteroaryl; A is alkyl, alkenyl, alkynyl, carbocyclyl, heterocyclyl, —$OR^{41}$, —$SR^{41}$, or —$N(R^{41})_2$; $R^{19}$ is hydrogen or alkyl (e.g., unsubstituted alkyl (e.g., —$CH_3$) or substituted alkyl (e.g., —$C(R^C)_2OR^{41}$, wherein $R^C$ is hydrogen or alkyl)); $R^5$ is absent or hydrogen; and ==== represents a single or double bond, wherein when one ==== is a double bond, the other ==== is a single bond and $R^5$ is absent.

In some embodiments, A is hydrogen, alkyl, alkenyl, alkynyl, carbocyclyl, heterocyclyl, or —$OR^{41}$.

In some embodiments, $R^{19}$ is hydrogen. In some embodiments, $R^{19}$ is alkyl (e.g., substituted or unsubstituted alkyl). In some embodiments, $R^{19}$ is —$CH_3$ or —$CH_2CH_3$. In some embodiments, $R^{19}$ is —$C(R^C)_2OR^{41}$. In some embodiments, $R^{19}$ is —$CH_2OH$, —$CH_2OCH_3$, —$CH_2OCH_2CH_3$, or —$CH_2OCH(CH_3)_2$.

In some embodiments, $R^2$ is hydrogen, halogen, alkyl, carbocyclyl, heterocyclyl, aryl, heteroaryl, —$OR^{41}$, —$SR^{41}$, or —$N(R^{41})_2$. In some embodiments, $R^2$ is hydrogen, halogen, alkyl, or —$OR^{41}$. In some embodiments, $R^2$ is hydrogen.

In some embodiments, $R^3$ is alkyl (e.g., substituted or unsubstituted alkyl). In some embodiments, $R^3$ is methyl and ethyl (e.g., substituted or unsubstituted methyl, substituted or unsubstituted ethyl).

In some embodiments, $R^4$ is hydrogen, halogen, alkyl, carbocyclyl, heterocyclyl, aryl, heteroaryl, —$OR^{41}$, —$SR^{41}$, or —$N(R^{41})_2$. In some embodiments, $R^4$ is hydrogen, halogen, alkyl, or —$OR^{41}$. In some embodiments, $R^4$ is hydrogen.

In some embodiments, ==== represents a single bond and $R^5$ is hydrogen. In some embodiments, $R^5$ is absent, and ==== represents a single or double bond, wherein when one ==== is a double bond, the other ==== is a single bond.

In some embodiments, $R^6$ is hydrogen, halogen, alkyl, carbocyclyl, heterocyclyl, aryl, heteroaryl, —$OR^{41}$, —$SR^{41}$, or —$N(R^{41})_2$. In some embodiments, $R^6$ is hydrogen, halogen, alkyl, or —$OR^{41}$. In some embodiments, $R^6$ is hydrogen.

In some embodiments, $R^7$ is hydrogen, halogen, alkyl, carbocyclyl, heterocyclyl, aryl, heteroaryl, —$OR^{41}$, —$SR^{41}$, or —$N(R^{41})_2$. In some embodiments, $R^7$ is hydrogen, halogen, alkyl, or —$OR^{41}$. In some embodiments, $R^7$ is hydrogen.

In some embodiments, $R^{11a}$ is hydrogen, halogen, alkyl, carbocyclyl, heterocyclyl, aryl, heteroaryl, —$OR^{41}$, —$SR^{41}$, —$N(R^{41})_2$, or $R^{11a}$ and $R^{11b}$ together with the carbon atom to which they are attached form —C(=O)—. In some embodiments, $R^{11a}$ is hydrogen, halogen, alkyl, or —$OR^{41}$. In some embodiments, $R^{11a}$ and $R^{11b}$ together with the carbon atom to which they are attached form —C(=O)—. In some embodiments, $R^{11a}$ and $R^{11b}$ are hydrogen.

In some embodiments, each of $R^2$, $R^4$, $R^6$, $R^7$, $R^{11a}$, and $R^{11b}$ is independently hydrogen, halogen, alkyl, carbocyclyl, heterocyclyl, aryl, heteroaryl, —$OR^{41}$, —$SR^{41}$, or —$N(R^{41})_2$. In some embodiments, each of $R^2$, $R^4$, $R^6$, $R^7$, $R^{11a}$, and $R^{11b}$ is hydrogen, halogen, alkyl, or —$OR^{41}$. In some embodiments, each of $R^2$, $R^4$, $R^6$, $R^7$, $R^{11a}$, and $R^{11b}$ is hydrogen.

In some embodiments, the compound of Formula (II) is a compound of the Formula (II-a) or (II-b):

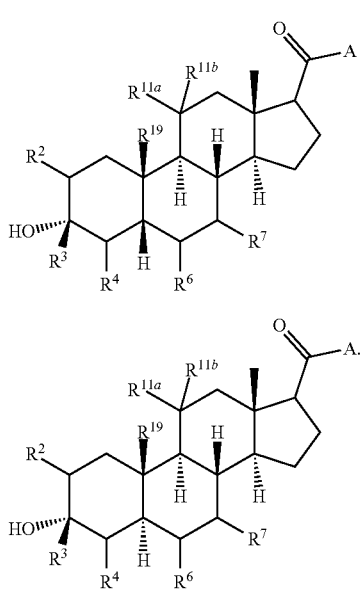

In some embodiments, the compound of Formula (I) is a compound of the Formula (II-c):

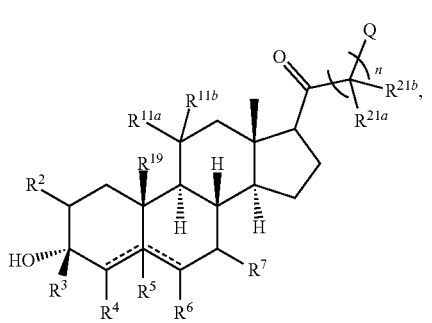

wherein:
each of $R^{21a}$ and $R^{21b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)O$R^{A1}$, —S(=O)$R^{A2}$, —SO$_2R^{A2}$, or —S(=O)$_2OR^{A1}$; or $R^{21a}$ and $R^{21b}$ together with the carbon atom to which they are attached form a carbocyclyl, heterocyclyl, or —C(=O)— group; Q is hydrogen, halogen, cyano, nitro, alkyl, alkenyl, alkynyl, carbocyclyl, heterocyclyl, aryl, heteroaryl, —$OR^{A1}$, —$SR^{A1}$, or —$N(R^{A1})_2$; and n is an integer selected from 1, 2, and 3.

In some embodiments, the compound of Formula (II) is a compound of the Formula (II-d):

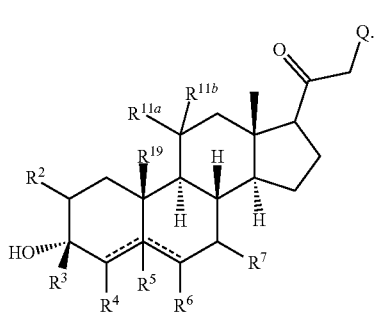

In an aspect, provided herein is a compound of the Formula (III-a):

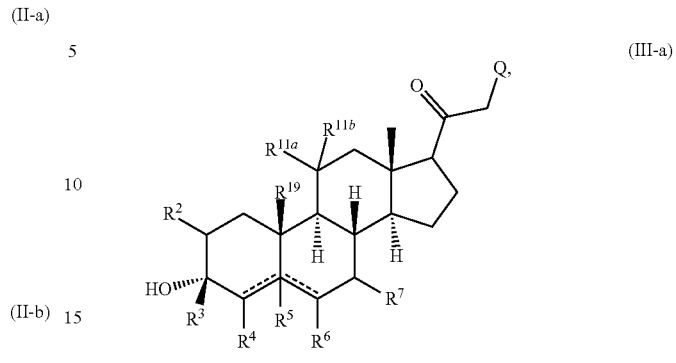

wherein:
or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)O$R^{A1}$, —S(=O)$R^{A2}$, —SO$_2R^{A2}$, or —S(=O)$_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an heterocyclic or heteroaryl ring; and $R^{A2}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; Q is hydrogen, halogen, cyano, nitro, alkyl, alkenyl, alkynyl, —$OR^{A1}$, —$SR^{A1}$, or —$N(R^{A1})_2$; $R^{19}$ is unsubstituted alkyl; $R^5$ is absent or hydrogen; and ==== represents a single or double bond, wherein when one ==== is a double bond, the other ==== is a single bond and $R^5$ is absent.

In an aspect, provided herein is a compound of the Formula (III-b):

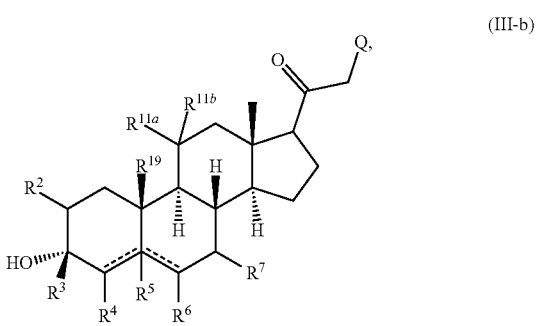

or a pharmaceutically acceptable salt thereof, wherein: each of $R^2$, $R^4$, $R^6$, $R^7$, $R^{11a}$, and $R^{11b}$ is independently hydrogen, halogen, cyano, nitro, alkyl, alkenyl, alkynyl, carbocyclyl, heterocyclyl, aryl, heteroaryl, —$OR^{A1}$, —$SR^{A1}$, —$N(R^{A1})_2$, —NHC(=O)$R^{A1}$, —NHC(=O)O$R^{A1}$, —S(=O)$R^{A2}$, —SO$_2R^{A2}$, or —S(=O)$_2OR^{A1}$, wherein each instance of $R^{A1}$ is independently hydrogen, alkyl, alkenyl, alkynyl, carbocyclyl, heterocyclyl, aryl, heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an heterocyclic or heteroaryl ring; and $R^{42}$ is alkyl, alkenyl, alkynyl, carbocyclyl, heterocyclyl, aryl, or heteroaryl; or $R^{11a}$ and $R^{11b}$ together with the carbon atom to which they are attached form a carbocyclyl, heterocyclyl, or —C(=O)— group; $R^3$ is alkyl, alkenyl, carbocyclyl, heterocyclyl, aryl, or heteroaryl; Q is halogen, cyano, nitro, heterocyclyl linked through a C atom, aryl, heteroaryl linked through a C atom, —O-alkenyl, —O-alkynyl, —$SR^{41}$, —$N(R^{41})_2$, —$NHC(=O)R^{41}$, —$NHC(=O)OR^{41}$, —$S(O)R^{42}$, —$SO_2R^{42}$, or —$S(=O)_2OR^{41}$; $R^{19}$ is —$C(R^C)_2OR^{41}$, wherein $R^C$ is hydrogen or alkyl; $R^5$ is absent or hydrogen; and ===== represents a single or double bond, wherein when one ===== is a double bond, the other ===== is a single bond and $R^5$ is absent.

In an aspect, provided herein is a compound of Formula (1-A):

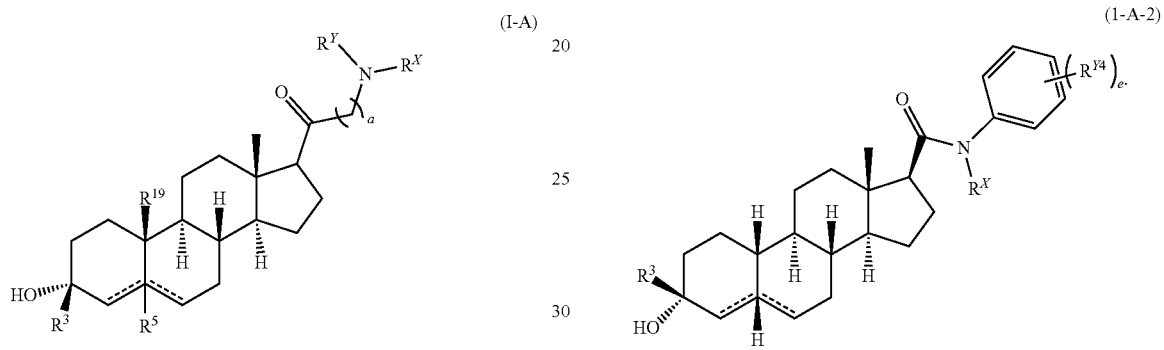

(I-A)

or a pharmaceutically acceptable salt thereof, wherein: $R^3$ is alkyl, alkenyl, carbocyclyl, heterocyclyl, aryl, or heteroaryl; each of $R^X$ and $R^Y$ is independently hydrogen, aryl, or alkyl, or
$R^X$ and $R^Y$ are joined together to form a 3-10 membered heterocyclic ring; $R^{19}$ is hydrogen or alkyl (e.g., unsubstituted alkyl or substituted alkyl (e.g., —$C(R^C)_2OR^{41}$, wherein $R^C$ is hydrogen or alkyl)); $R^5$ is absent or hydrogen; ===== represents a single or double bond, wherein when one ===== is a double bond, the other ===== is a single bond and $R^5$ is absent; and a is 0 or 1; provided that $R^X$ and $R^Y$ are joined together to form a 3-8 membered heterocyclic ring only when a is 0.

In some embodiments, $R^X$ and $R^Y$ are not both hydrogen. In some embodiments, $R^3$ is alkyl. In some embodiments, $R^{19}$ is hydrogen.

In some embodiments, the compound is a compound of Formula (1-A-1)

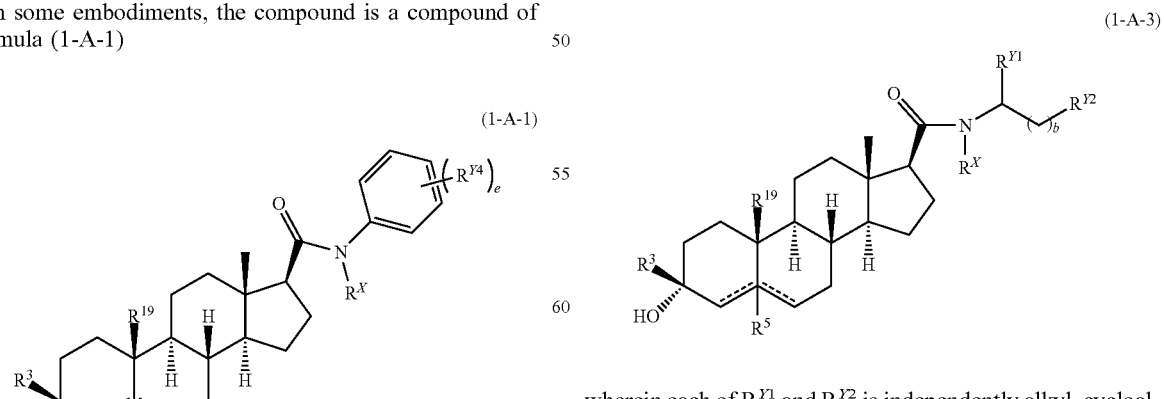

(1-A-1)

wherein each instance of $R^{Y4}$ is independently alkyl, cyano, or halo; and e is 0, 1, 2, 3, 4, or 5.

In some embodiments, each instance of $R^{Y4}$ is independently hydrogen, —$CH_3$, —CN, or —F. In some embodiments, e is 3. In some embodiments, $R^X$ is hydrogen. In some embodiments, each instance of $R^{Y4}$ is independently hydrogen, —$CH_3$, —CN, or —F, $R^X$ is hydrogen, and e is 3. In some embodiments, each instance of $R^{Y4}$ is independently hydrogen, —$CH_3$, —CN, or —F, $R^X$ is hydrogen, and e is 2. In some embodiments, e is 1. In some embodiments, $R^{Y4}$ is —F. In some embodiments, $R^{Y4}$ is —F and e is 1.

In some embodiments, the compound is a compound of Formula (1-A-2)

(1-A-2)

In some embodiments, each instance of $R^{Y4}$ is independently hydrogen, —$CH_3$, —CN, or —F. In some embodiments, e is 3. In some embodiments, $R^X$ is hydrogen. In some embodiments, each instance of $R^{Y4}$ is independently hydrogen, —$CH_3$, —CN, or —F, $R^X$ is hydrogen, and e is 3. In some embodiments, each instance of $R^{Y4}$ is independently hydrogen, —$CH_3$, —CN, or —F, $R^X$ is hydrogen, and e is 2. In some embodiments, e is 1. In some embodiments, $R^{Y4}$ is —F.

In some embodiments, the compound is a compound of Formula (1-A-3)

(1-A-3)

wherein each of $R^{Y1}$ and $R^{Y2}$ is independently alkyl, cycloalkyl, heterocycyl, aryl, or heteroaryl; and b=0, 1, 2, 3.

In some embodiments, $R^{Y1}$ and $R^{Y2}$ are not both —CH$(CH_3)_2$.

In some embodiments, the compound is a compound of Formula (1-A-4)

(1-A-4)

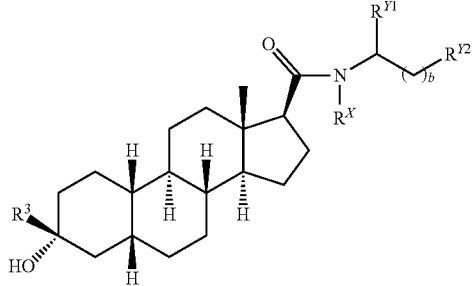

In some embodiments, $R^{Y1}$ is hydrogen, —CH₃, or —CH₂CH₃, —CH(CH₃)₂, or cycloalkyl. In some embodiments, $R^3$ is —CH₃, —CF₃, —CH₂OCH₃, —CH₂OCH₂CH₃. In some embodiments, $R^{Y2}$ is heteocyclyl, aryl, or heteroaryl. In some embodiments, $R^{Y2}$ is aryl substituted with 0-5 occurrences of —CH₃, —CN, —F, —CF₃, or combinations thereof or heteroaryl substituted with 0-5 occurrences of —CH₃, —CN, —F, —CF₃.

In some embodiments, $R^{Y2}$ is aryl substituted with 0-5 occurrences of —CH₃, —CN, —F, —CF₃, or $R^X$ is hydrogen, —CH₃, or —CH₂CH₃. In some embodiments, $R^{Y2}$ is aryl substituted with 0-5 occurrences of —CH₃, —CN, —F, —CF₃.

In some embodiments, the compound is a compound of Formula (1-A-5)

(1-A-5)

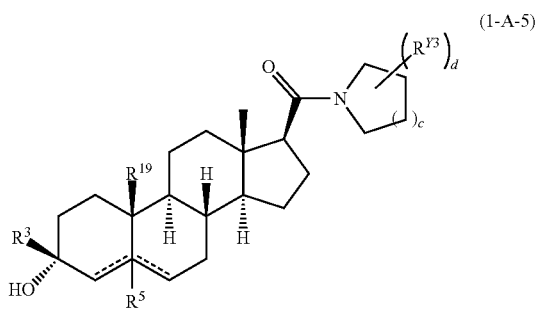

wherein each occurrence of $R^{Y3}$ is aryl or heteroaryl, or two $R^{Y3}$ groups are joined together to form a 6-10 membered ring;

c is 0, 1, 2, or 3; and
d is 0, 1, 2, or 3.

In some embodiments, the compound is a compound of Formula (1-A-6)

(1-A-6)

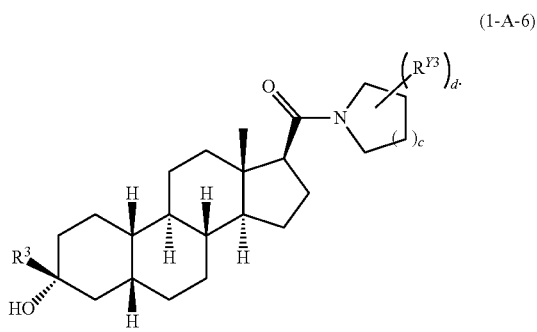

In some embodiments, if d is 2, then two $R^{Y3}$ groups are joined together to form aryl. In some embodiments, $R^{Y2}$ is aryl substituted with 0-5 occurrences of —CH₃, —CN, —F, —CF₃. In some embodiments, the compound is a compound of Formula (1-A-7) or Formula (1-A-8)

(1-A-7)

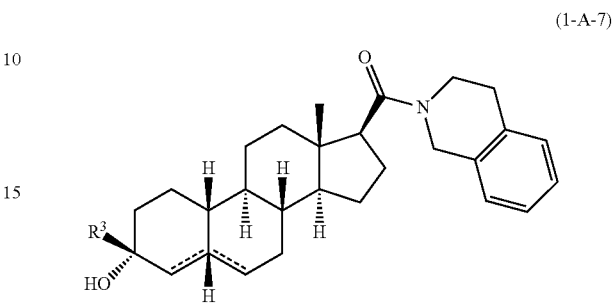

(1-A-8)

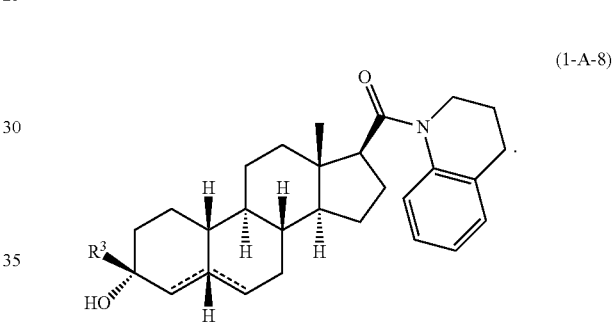

In some embodiments, $R^{Y2}$ is aryl substituted with 0-5 occurrences of —CH₃, —CN, —F, —CF₃, or $R^3$ is —CH₃, —CF₃, —CH₂OCH₃, —CH₂OCH₂CH₃.

In an aspect, provided herein is a compound of Formula (2-A), (2-A)

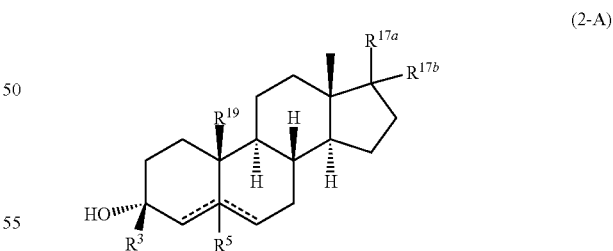

or a pharmaceutically acceptable salt thereof, wherein $R^3$ is —CH₃, —CF₃, —CH₂OCH₃, —CH₂OCH₂CH₃; $R^{19}$ is hydrogen, —CH₃, or —CH₂OR$^{41}$, wherein $R^{41}$ is optionally substituted alkyl; $R^3$ is —CH₃, —CF₃, —CH₂OCH₃, —CH₂OCH₂CH₃; $R^{17a}$ is —NR$^{42}$R$^{43}$, —N(R1)C(O)R$^{42}$, —N(R1)SO₂R$^{42}$, —OR$^{43}$, cycloalkyl, heterocyclyl, aryl, or heteroaryl, wherein each of $R^{42}$ and $R^{43}$ is independently hydrogen, carbocyclyl, heterocyclyl, aryl, heteroaryl, or —OR$^{44}$, wherein $R^{44}$ is hydrogen or alkyl; or $R^{17A}$ is

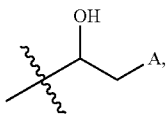

wherein A is oxazolyl or thiazolyl; $R^{17b}$ is hydrogen, hydroxyl, alkyl, or alkoxy; and ==== represents a single or double bond, wherein when one ==== is a double bond, the other ==== is a single bond and $R^5$ is absent; provided that: when $R^{17a}$ is oxazolyl or

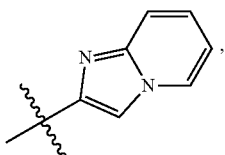 [SMILES: *c1cn2ccccc2n1]

then $R^{17b}$ is not hydrogen, or when $R^{17a}$ is heterocyclyl, then $R^{19}$ is hydrogen, or when $R^{17a}$ is —$OR^{44}$, then $R^{19}$ is hydrogen.

In some embodiments, $R^{17a}$ is —$NR^{42}R^{43}$, —$N(R1)C(O)R^{42}$, —$N(R1)SO_2R^{42}$. In some embodiments, $R^{17a}$ is aryl, heteroaryl, cycloalkyl, or heterocyclyl. In some embodiments, $R^{19}$ is hydrogen. In some embodiments, $R^{17a}$ is heteroaryl. In some embodiments, $R^{17a}$ is heteroaryl and $R^{19}$ is hydrogen. In some embodiments, $R^{17a}$ is pyridyl and $R^{19}$ is hydrogen.

In an aspect, provided herein is a compound of Formula (3-A)

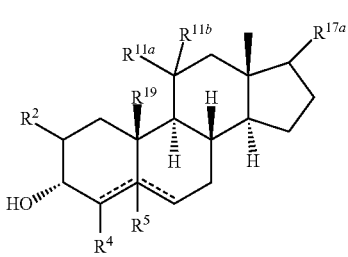

or a pharmaceutically acceptable salt thereof, wherein $R^{19}$ is hydrogen or alkyl; $R^{17a}$ is nitro or alkoxy (e.g., —$OCH_3$); each of $R^2$, $R^4$, $R^{11a}$, or $R^{11b}$ is independently hydrogen, alkyl, or alkoxy, or $R^{11a}$ and $R^{11b}$ are joined together to form oxo; ==== represents a single or double bond, wherein when one ==== is a double bond, the other ==== is a single bond and $R^5$ is absent; and $R^5$ is absent or hydrogen as determined by valency; provided that, when $R^2$, $R^{11a}$, and $R^{11b}$ are hydrogen, then $R^4$ is alkyl, or when $R^4$, $R^{11a}$, and $R^{11b}$ are hydrogen, then $R^2$ is alkyl, or when $R^4$ is hydrogen, then $R^2$ is —OH or alkoxy, $R^{11a}$ is hydrogen, and $R^{11b}$ is —OH or alkoxy, or $R^2$ is —OH or alkoxy and $R^{11a}$ and $R^{11b}$ are joined together to form oxo.

In some embodiments, $R^4$ is hydrogen, $R^2$ is —OH or alkoxy, $R^{11a}$ is hydrogen, and $R^{11b}$ is —OH or alkoxy. In some embodiments, $R^4$ is hydrogen, $R^2$ is —OH or alkoxy, and $R^{11a}$ and $R^{11b}$ are joined together to form oxo. In some embodiments, $R^{17a}$ is nitro. In some embodiments, $R^{17a}$ is alkoxy. In some embodiments, $R^{17a}$ is methoxy and $R^2$ is methyl.

Additionally provided herein are compounds shown in Table 1 below or a pharmaceutically acceptable salt thereof.

TABLE 1

Exemplary compounds of the invention.

| Structure | Compound Number |
|---|---|
| (structure) | 1 |
| (structure) | 2 |

TABLE 1-continued

Exemplary compounds of the invention.

| Structure | Compound Number |
|---|---|
| 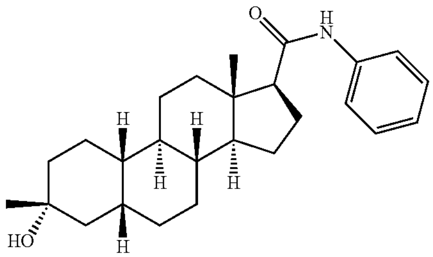 | 3 |
| 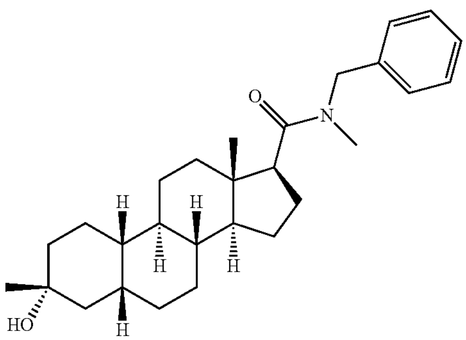 | 4 |
| 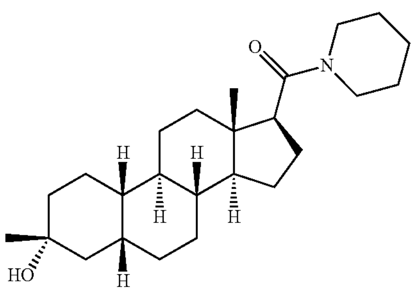 | 5 |
| 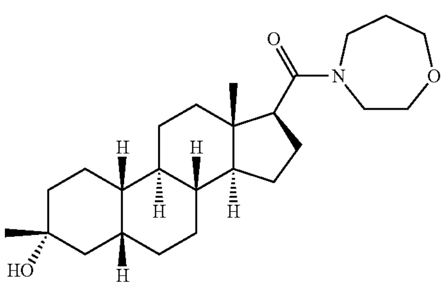 | 6 |
| 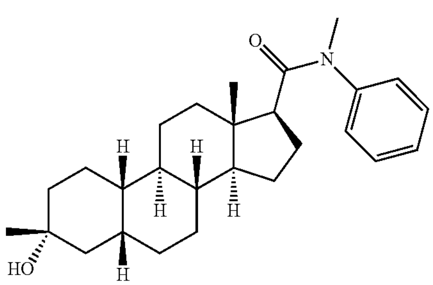 | 7 |

TABLE 1-continued

Exemplary compounds of the invention.

| Structure | Compound Number |
|---|---|
| 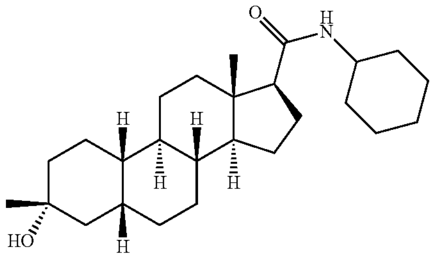 | 8 |
| 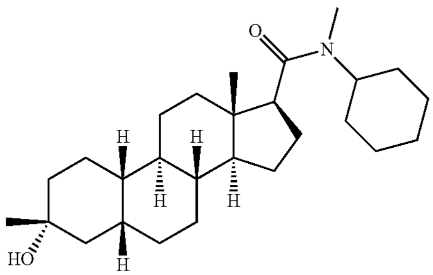 | 9 |
| 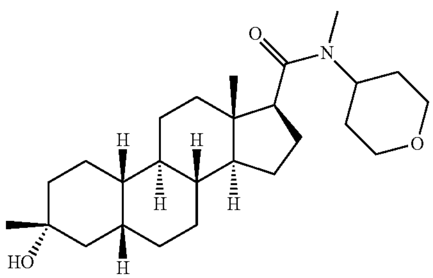 | 10 |
| 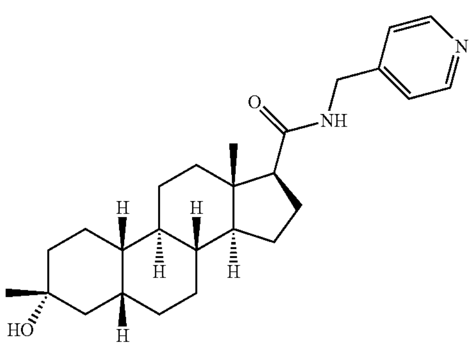 | 11 |
| 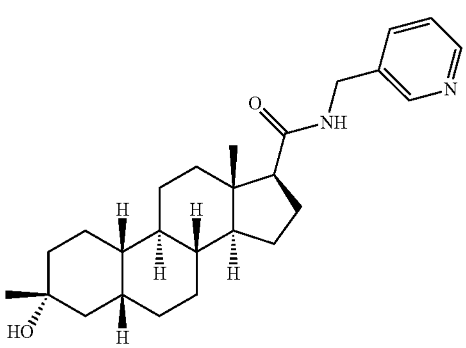 | 12 |

TABLE 1-continued

Exemplary compounds of the invention.

| Structure | Compound Number |
|---|---|
| 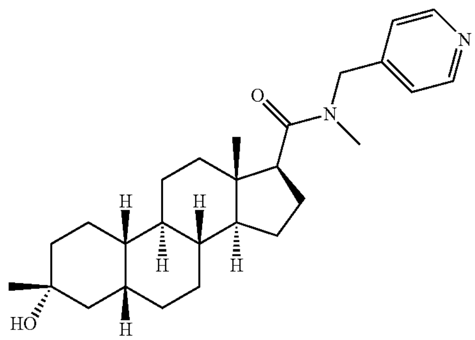 | 13 |
| 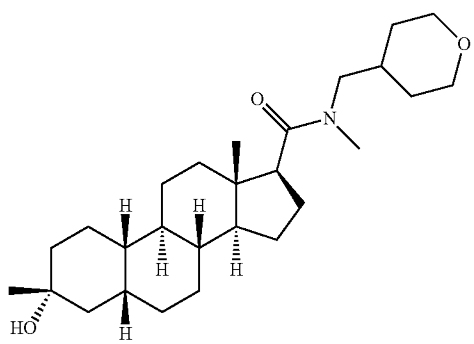 | 14 |
| 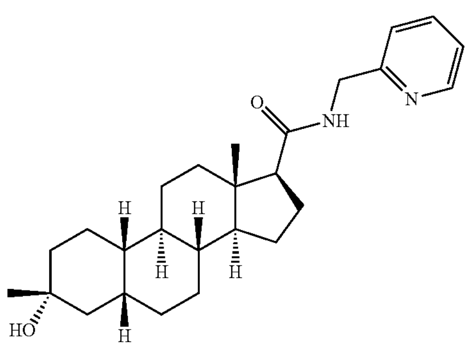 | 15 |
| 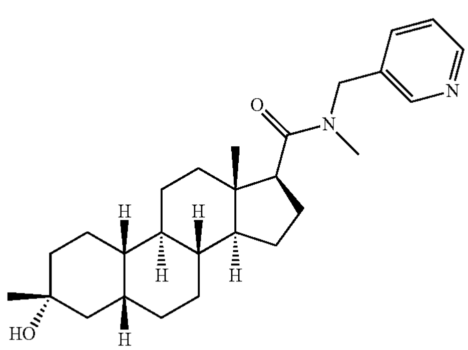 | 16 |

TABLE 1-continued

Exemplary compounds of the invention.

| Structure | Compound Number |
|---|---|
| 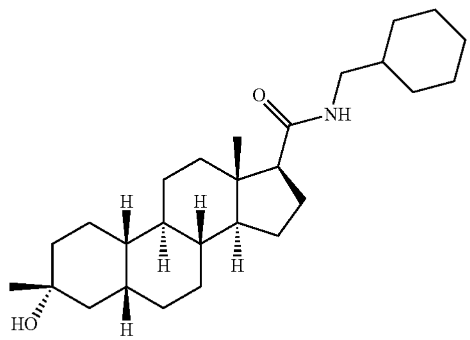 | 17 |
| 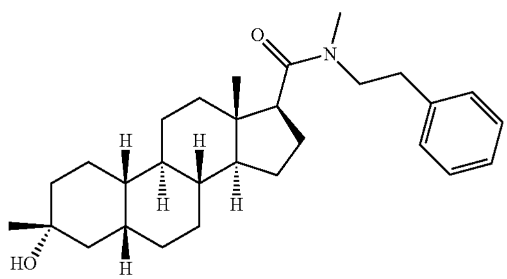 | 18 |
| 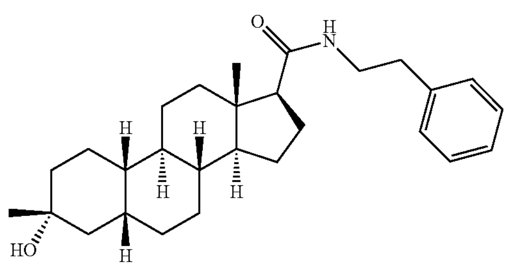 | 19 |
| 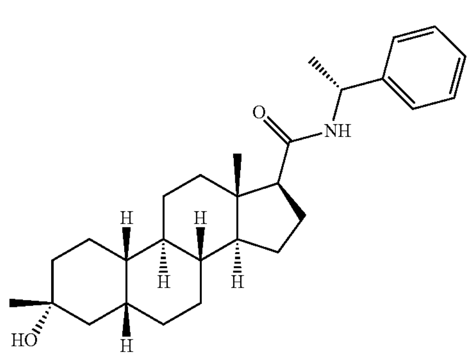 | 20 |

TABLE 1-continued

Exemplary compounds of the invention.

| Structure | Compound Number |
|---|---|
| 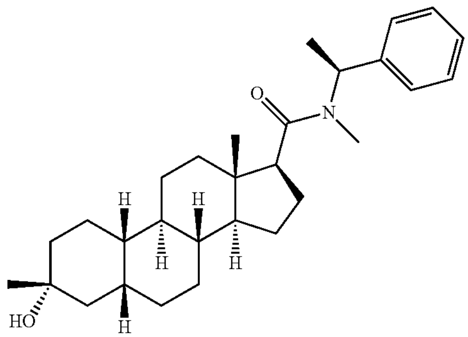 | 21 |
| 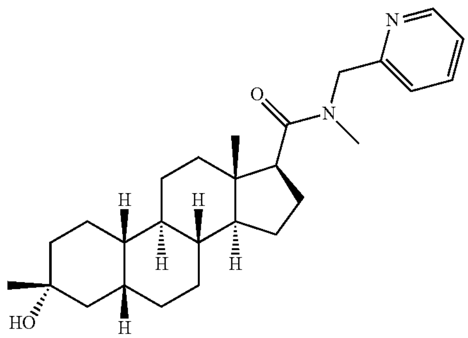 | 22 |
| 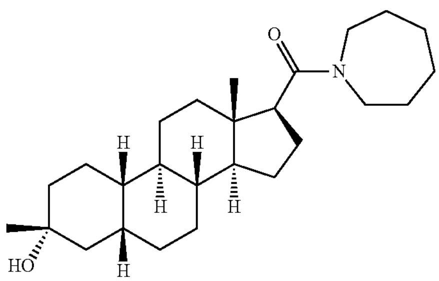 | 23 |
| 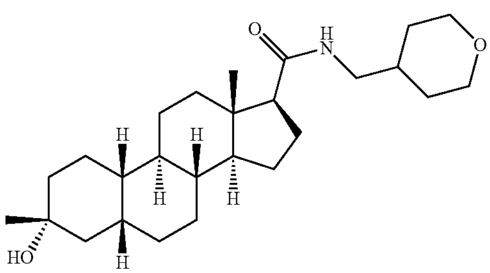 | 24 |
| 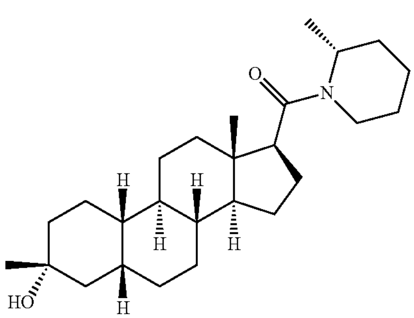 | 25 |

TABLE 1-continued

Exemplary compounds of the invention.

| Structure | Compound Number |
|---|---|
| 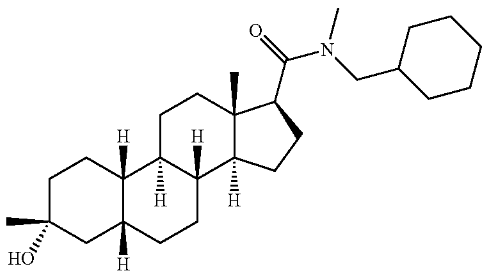 | 26 |
| 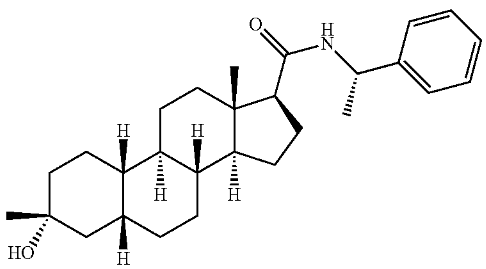 | 27 |
| 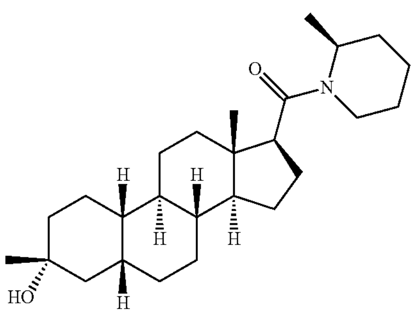 | 28 |
| 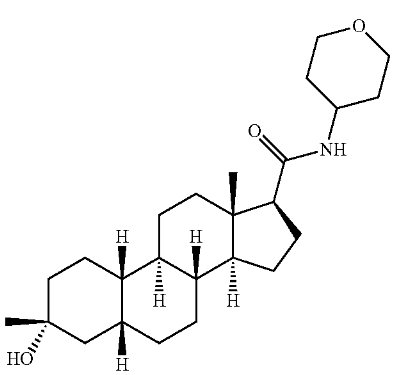 | 29 |

TABLE 1-continued

Exemplary compounds of the invention.

| Structure | Compound Number |
|---|---|
| 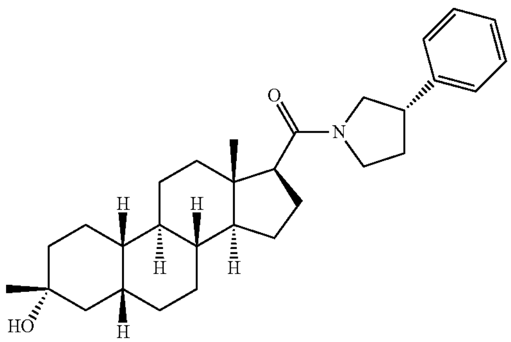 | 30 |
| 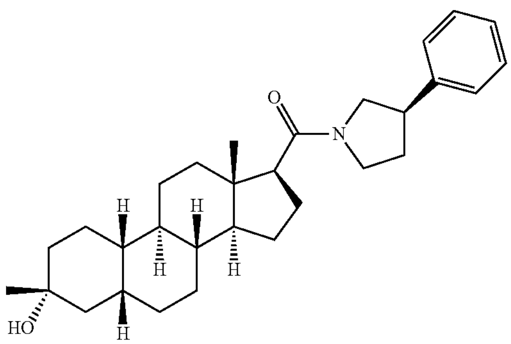 | 31 |
| 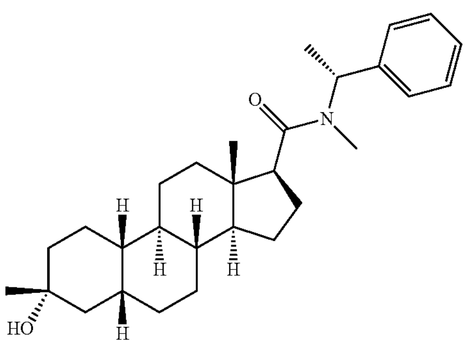 | 32 |
| 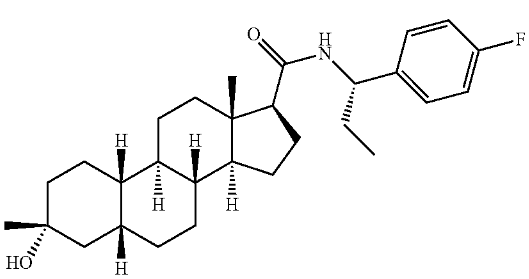 | 33 |

TABLE 1-continued
Exemplary compounds of the invention.
| Structure | Compound Number |
|---|---|
| 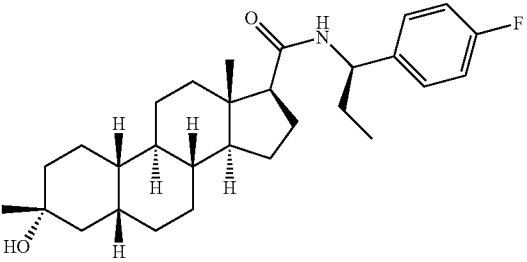 | 34 |
| 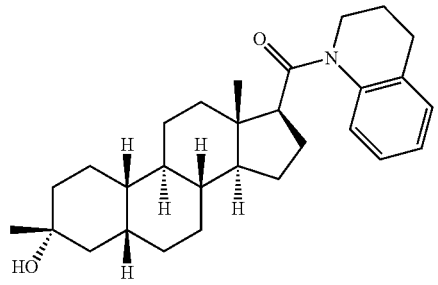 | 35 |
| 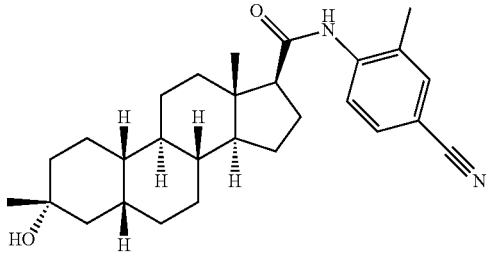 | 36 |
| 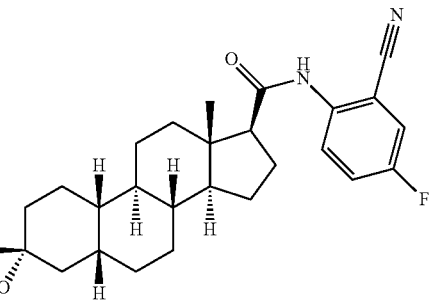 | 37 |
| 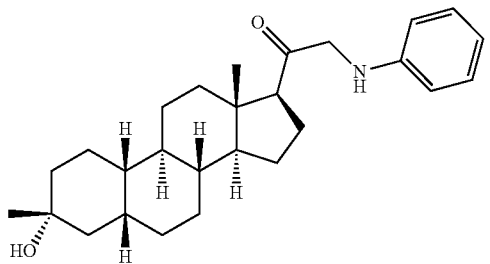 | 38 |

TABLE 1-continued

Exemplary compounds of the invention.

| Structure | Compound Number |
|---|---|
| 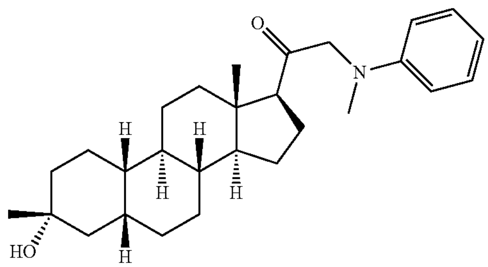 | 39 |
| 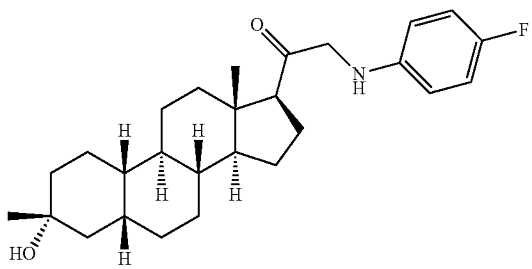 | 40 |
| 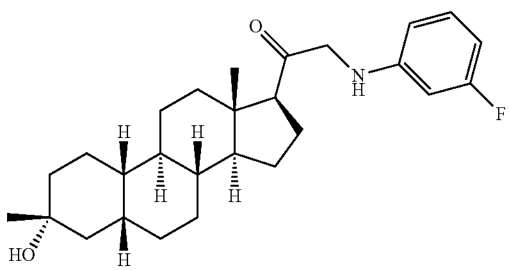 | 41 |
| 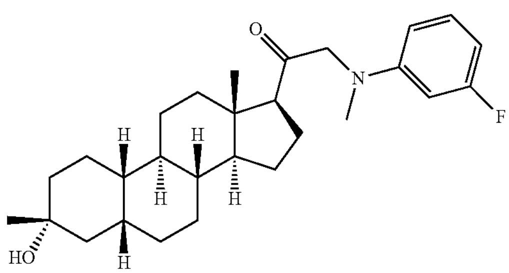 | 42 |
| 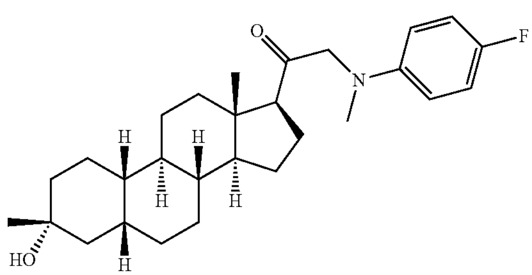 | 43 |

TABLE 1-continued

Exemplary compounds of the invention.

| Structure | Compound Number |
|---|---|
| 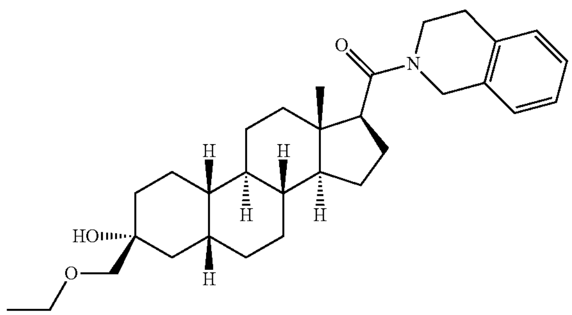 | 44 |
| 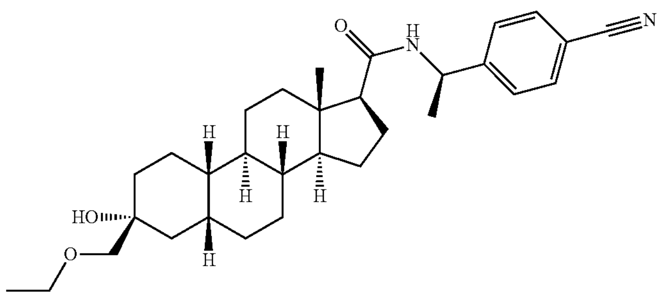 | 48 |
| 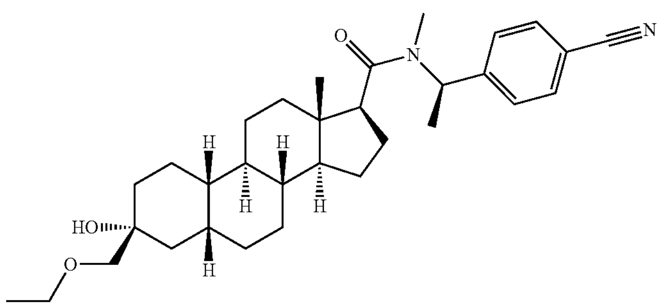 | 49 |
| 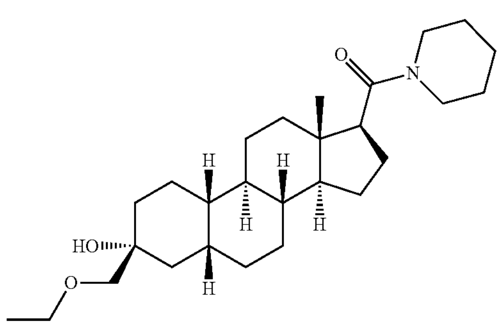 | 50 |

TABLE 1-continued

Exemplary compounds of the invention.

| Structure | Compound Number |
|---|---|
| 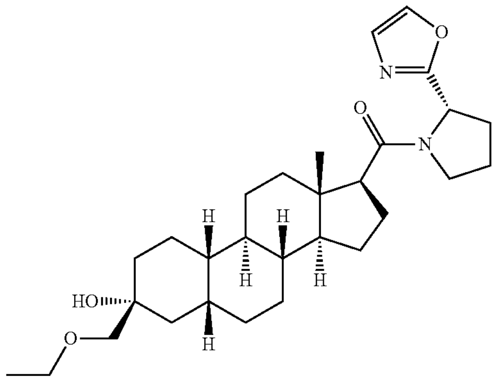 | 55 |
| 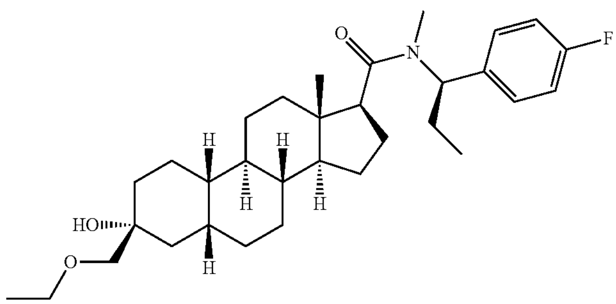 | 56 |
| 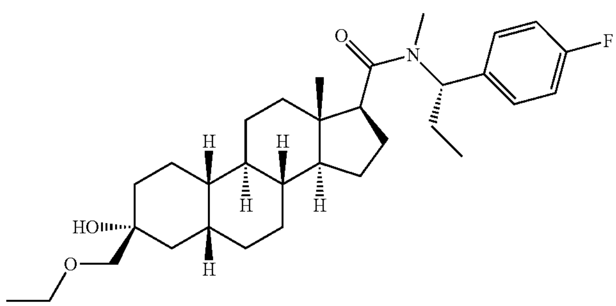 | 57 |
| 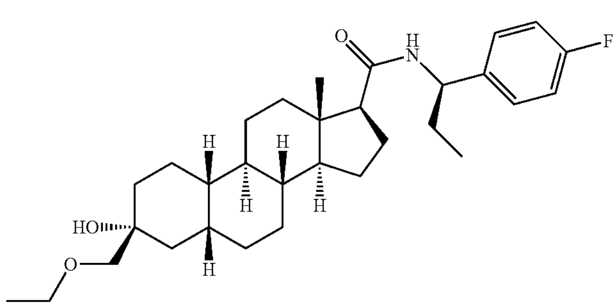 | 58 |

TABLE 1-continued
Exemplary compounds of the invention.
| Structure | Compound Number |
|---|---|
| 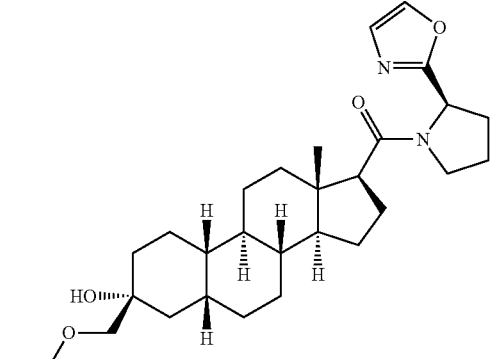 | 60 |
| 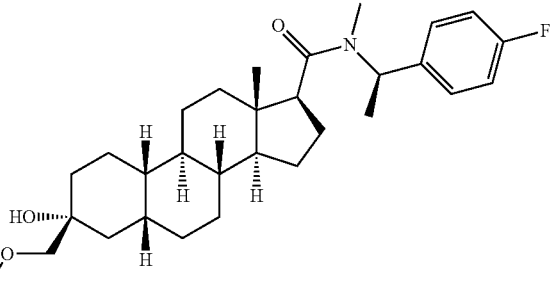 | 61 |
| 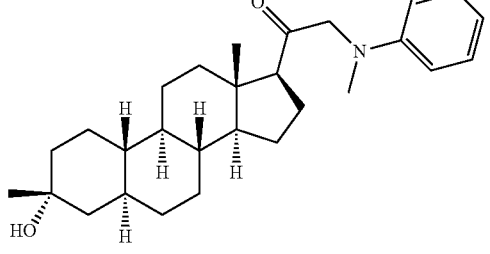 | 63 |
| 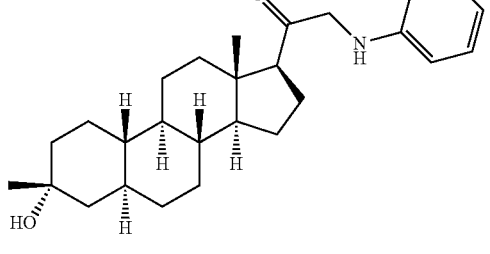 | 64 |
| 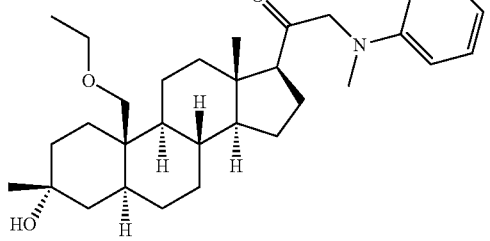 | 65 |

TABLE 1-continued
Exemplary compounds of the invention.
| Structure | Compound Number |
|---|---|
| 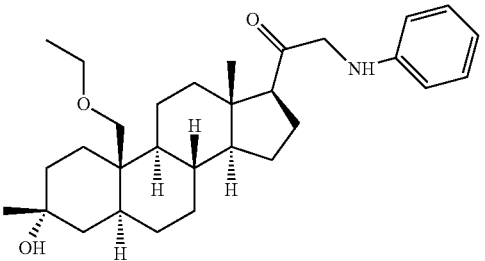 | 66 |
| 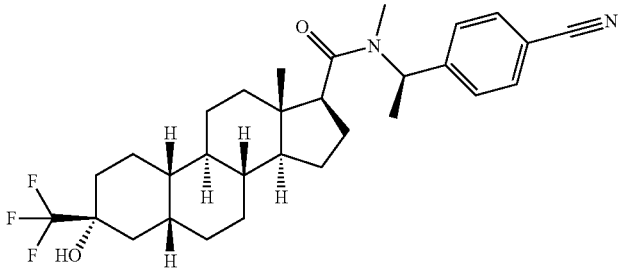 | 69 |
| 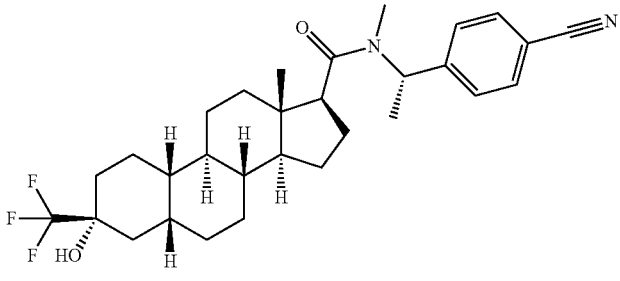 | 70 |
| 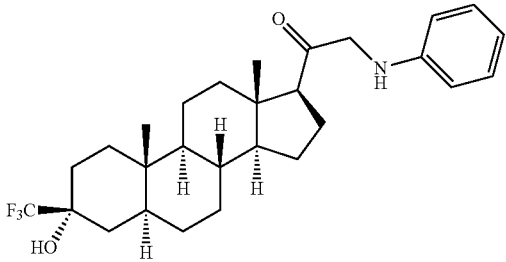 | 73 |
| 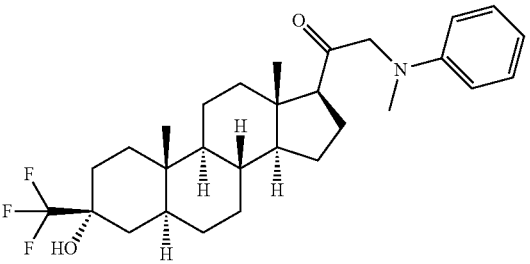 | 74 |

TABLE 1-continued

Exemplary compounds of the invention.

| Structure | Compound Number |
|---|---|
| 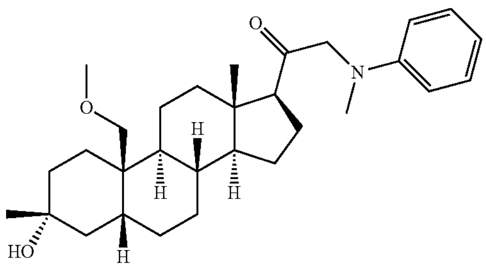 | 75 |
| 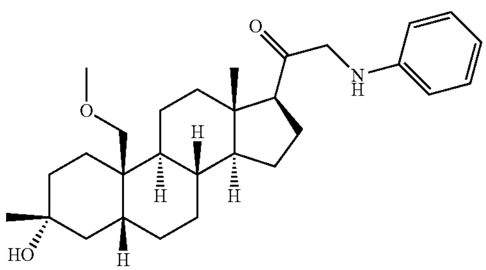 | 76 |
| 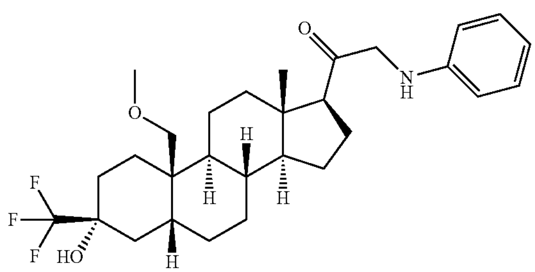 | 77 |
| 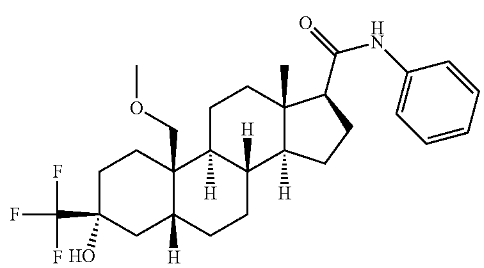 | 78 |
| 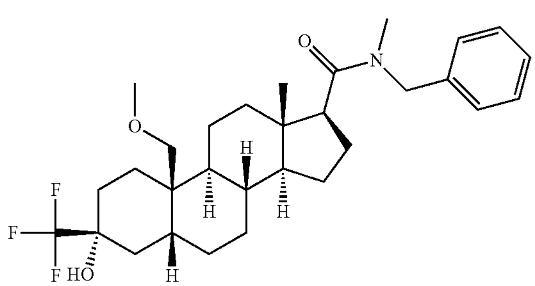 | 79 |

TABLE 1-continued

Exemplary compounds of the invention.

| Structure | Compound Number |
|---|---|
| 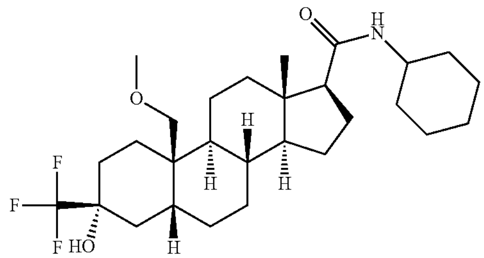 | 80 |
| 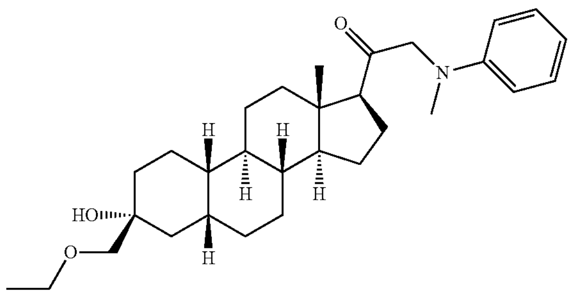 | 83 |
| 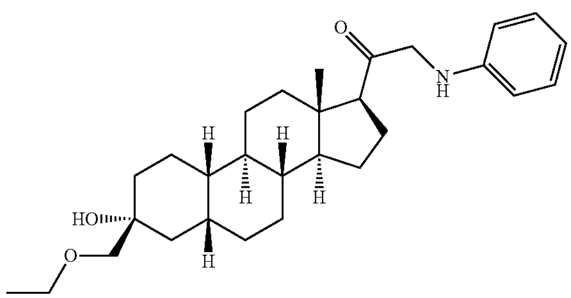 | 84 |
| 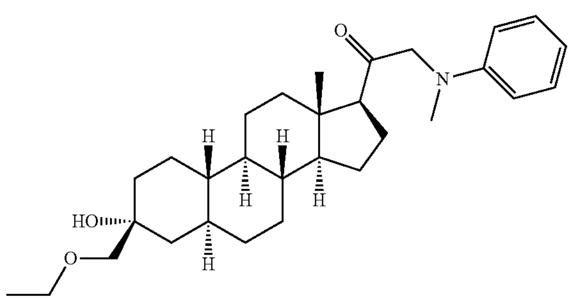 | 85 |
| 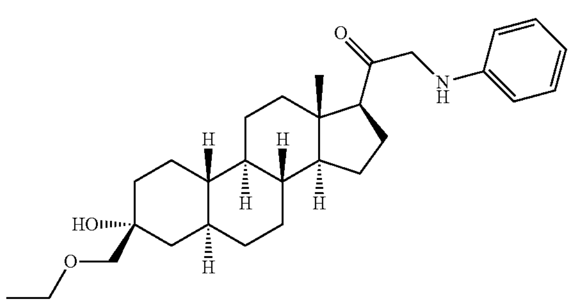 | 86 |

TABLE 1-continued

Exemplary compounds of the invention.

| Structure | Compound Number |
|---|---|
| 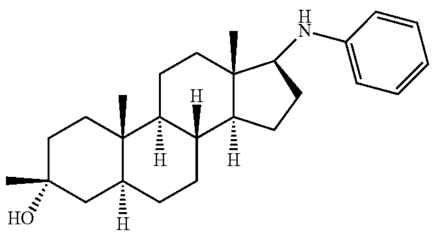 | 87 |
| 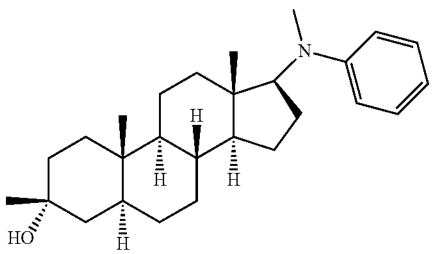 | 88 |
| 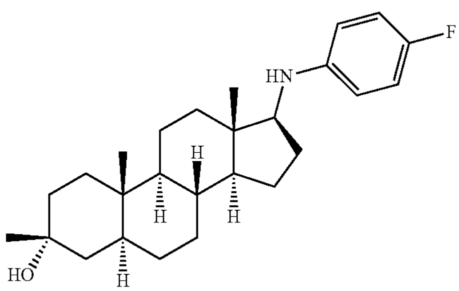 | 89 |
| 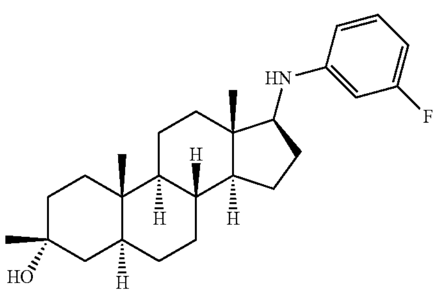 | 90 |
| 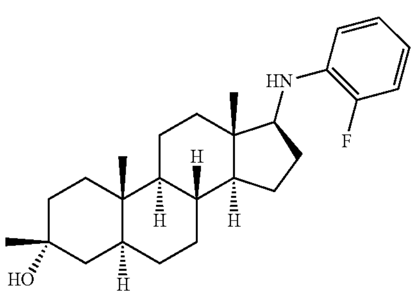 | 91 |

TABLE 1-continued

Exemplary compounds of the invention.

| Structure | Compound Number |
|---|---|
| 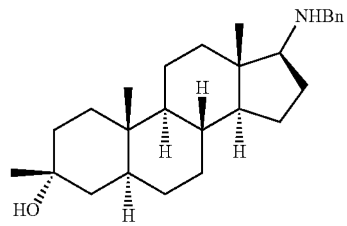 | 92 |
| 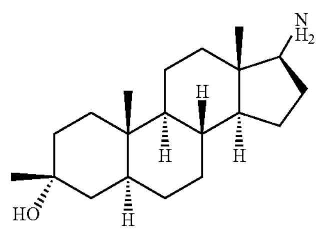 | 93 |
| 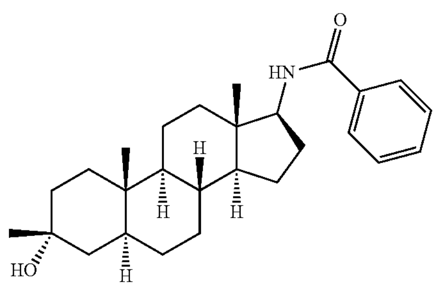 | 94 |
| 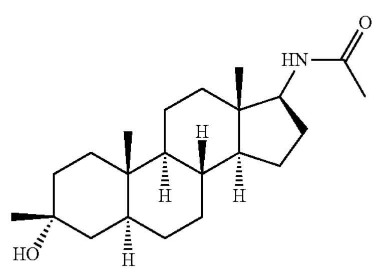 | 95 |
| 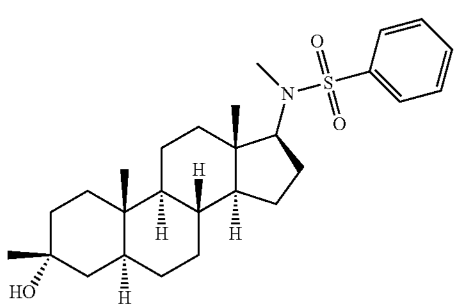 | 96 |

TABLE 1-continued

Exemplary compounds of the invention.

| Structure | Compound Number |
|---|---|
| (steroid structure) | 97 |
| (steroid structure) | 98 |
| (steroid structure) | 99 |
| (steroid structure) | 100 |
| (steroid structure) | 101 |

TABLE 1-continued

Exemplary compounds of the invention.

| Structure | Compound Number |
|---|---|
| 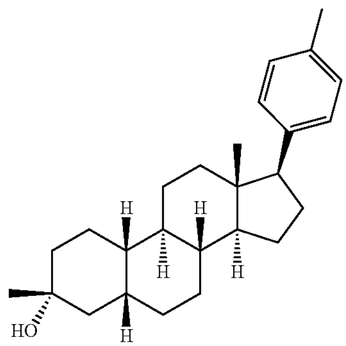 | 102 |
| 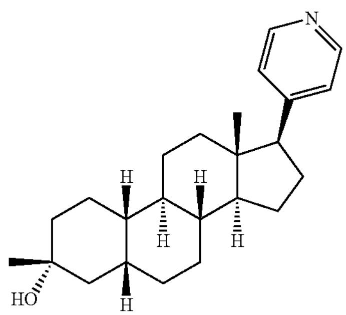 | 103 |
| 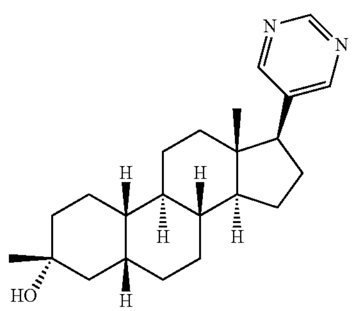 | 104 |
| 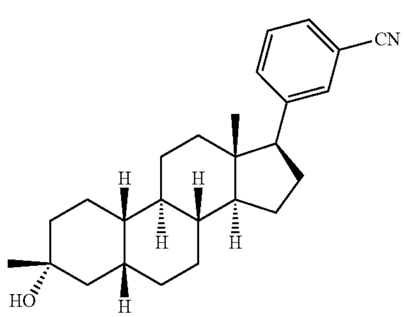 | 105 |

TABLE 1-continued

Exemplary compounds of the invention.

| Structure | Compound Number |
|---|---|
| 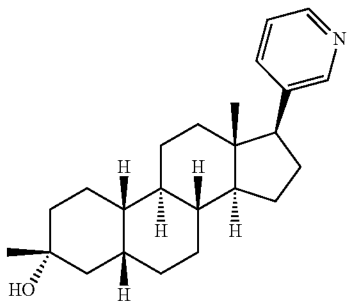 | 106 |
| 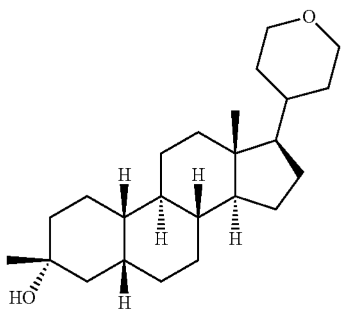 | 107 |
| 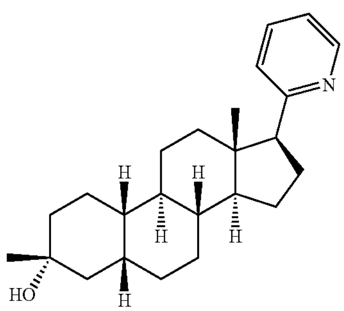 | 108 |
| 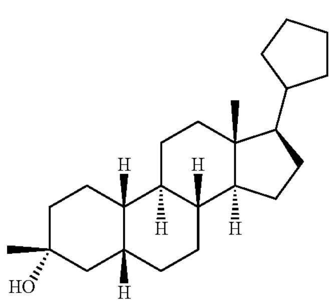 | 109 |

TABLE 1-continued
Exemplary compounds of the invention.
| Structure | Compound Number |
|---|---|
| 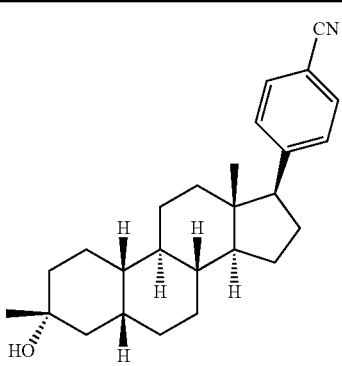 | 110 |
| 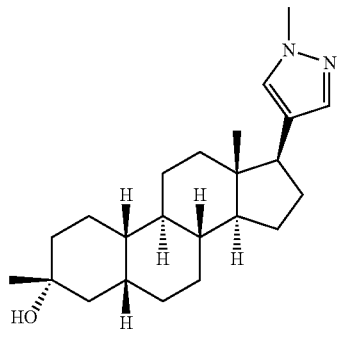 | 111 |
| 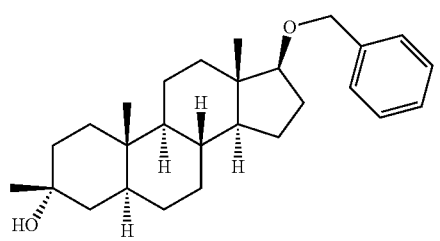 | 112 |
| 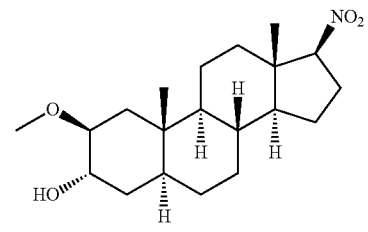 | 118 |
| 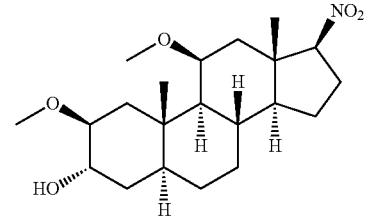 | 119 |

TABLE 1-continued

Exemplary compounds of the invention.

| Structure | Compound Number |
|---|---|
| (steroid structure) | 120 |
| (steroid structure) | 121 |
| (steroid structure) | 122 |
| (steroid structure) | 123 |
| (steroid structure) | 125 |
| (steroid structure) | 125 |

TABLE 1-continued

Exemplary compounds of the invention.

| Structure | Compound Number |
|---|---|
| (steroid structure with OH at top right and HO at bottom left) | 126 |

ALTERNATIVE EMBODIMENTS

In an alternative embodiment, compounds described herein may also comprise one or more isotopic substitutions other than the substitution of $^1H$ with deuterium. For example, hydrogen may also be $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In one aspect, the invention provides a pharmaceutical composition comprising a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present invention can also be administered in sustained release forms or from sustained release drug delivery systems. A description of representative sustained release materials can be found in *Remington's Pharmaceutical Sciences.*

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences,* Sixteenth Edition, E. W. Martin (Mack Publishing Co., Easton, Pa., 1980), and *Remington: The Science and Practice of Pharmacy,* 21$^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 □-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the composition comprises hexapropyl-□-cyclodextrin. In a more particular embodiment, the composition comprises hexapropyl-□-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Methods of Use and Treatment

In an aspect, provided is a method of alleviating or preventing seizure activity in a subject, comprising administering to the subject in need of such treatment an effective amount of a compound of the present invention. In some embodiments, the method alleviates or prevents epileptogenesis.

In some embodiments, such compounds are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression, dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing PMS or PND in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Mood Disorders

Also provided herein are methods for treating a mood disorder, for example clinical depression, postnatal depression or postpartum depression, perinatal depression, atypical depression, melancholic depression, psychotic major depression, cataonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positively, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physiological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method provides therapeutic effect (e.g., as measured by reduction in Hamilton Depression Score (HAM-D)) within 4, 3, 2, 1 days; 96, 84, 72, 60, 48, 24, 20, 16, 12, 10, 8 hours or less. In some embodiments, the therapeutic effect is a decrease from baseline in HAM-D score at the end of a treatment period (e.g., 12, 24, 48 hours after administration; 24, 48, 72, 96 hours or more). In some embodiments, the decrease from baseline in HAM-D score is from severe (e.g., HAM-D score of 24 or greater) to symptom-free (e.g., HAM-D score of 7 or lower). In some embodiments, the baseline score is about 10 to 52 (e.g., more than 10, 15, or 20; 10 to 52, 12 to 52, 15 to 52, 17 to 52, 20 to 52, 22 to 52). In some embodiments, the baseline score is at least 10, 15, or 20. In some embodiments, the HAM-D score at the end of the treatment period is about 0 to 10 (e.g., less than 10; 0 to 10, 0 to 6, 0 to 4, 0 to 3, 0 to 2, 1.8). In some embodiments, the HAM-D score at the end of the treatment period is less than 10, 7, 5, or 3. In some embodiments, the decrease in HAM-D score is from a baseline score of about 20 to 30 (e.g., 22 to 28, 23 to 27, 24 to 27, 25 to 27, 26 to 27) to a HAM-D score at the end of the treatment period is about 0 to 10 (e.g., less than 10; 0 to 10, 0 to 6, 0 to 4, 0 to 3, 0 to 2, 1.8). In some embodiments, the decrease in the baseline HAM-D score to HAM-D score at the end of the treatment period is at least 1, 2, 3, 4, 5, 7, 10, 25, 40, 50, or 100 fold). In some embodiments, the percentage decrease in the baseline HAM-D score to HAM-D score at the end of the treatment period is at least 50% (e.g., 60%, 70%, 80%, 90%). In some embodiments, the therapeutic effect is a decrease from baseline in HAM-D score at the end of a treatment period (e.g., 12, 24, 48 hours after administration; 24, 48, 72, 96 hours or more) at least 10, 15, or 20 points. In some embodiments, the therapeutic effect is a decrease from baseline in HAM-D score at the end of a treatment period (e.g., 12, 24, 48 hours after administration; 24, 48, 72, 96 hours or more) at least 5, 7, or 10 points more relative to the therapeutic effect provided by a placebo treatment.

In some embodiments, the method provides therapeutic effect (e.g., as measured by reduction in Montgomery-Åsberg Depression Rating Scale (MADRS)) within 4, 3, 2, 1 days; 96, 84, 72, 60, 48, 24, 20, 16, 12, 10, 8 hours or less. The Montgomery-Åsberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders. 0-6 indicates normal/symptom absent; 7-19 indicates mild depression; 20-34 indicates moderate depression; and >34 indicates severe depression. In some embodiments, the therapeutic effect is a decrease from baseline in MADRS score at the end of a treatment period (e.g., 12, 24, 48 hours after administration; 24, 48, 60, 72, 96 hours or more). In some embodiments, the decrease from baseline in MADRS score is from severe (e.g., MADRS score of 30 or greater) to symptom-free (e.g., MADRS score of 20 or lower). For example, the mean change from baseline in MADRS total score from treatment with a compound described herein is about −15, −20, −25, −30, while the mean change from baseline in MADRS total score from treatment with placebo is about −15, −10, −5.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is a improvement measured by the EPDS.

In some embodiments, the method provides therapeutic effect (e.g., as measured by reduction in Clinical Global Impression-Improvement Scale (CGI)) within 4, 3, 2, 1 days; 24, 20, 16, 12, 10, 8 hours or less. In some embodiments, the therapeutic effect is a CGI score of 2 or less.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Women's Health Disorders

Provided herein are methods for treating conditions or disorders related to women's health. Conditions or disorders related to women's health include, but are not limited to, Gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breast feeding, and birth defects.

Miscarriage refers to a pregnancy that ends on its own, within the first 20 weeks of gestation.

Abortion referse to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women.

Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer).

It is induced when the ovaries are gravely damaged by, e.g., radiation, chemotherapy, or other medications.

Epilepsy

The compounds described herein, or a pharmaceutically acceptable salt, or a pharmaceutically acceptable composition thereof, can be used in a method described herein, for example in the treatment of a disorder described herein such as epilepsy, status epilepticus, or seizure, for example as described in WO2013/112605 and WO/2014/031792, the contents of which are incorporated herein in their entirety.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, a typical absence non-convulsive status epilepticus, or typical absence non-convulsive status epilepticus.

The compound described herein, or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; a typical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawl, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face.

Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

EXAMPLES

In order that the invention described herein may be more fully understood, the following examples are set forth. The synthetic examples described in this application are offered to illustrate the invention provided herein and are not to be construed in any way as limiting its scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Exemplary general method for preparative HPLC: Column: Durashell. Mobile phase: A: water, B: acetonitrile. % B at 0 min: 41%, % B at 8 min: 71%, flow rate: 35 mL/min, detection wavelength: 220 nm.

Exemplary general method for analytical HPLC: Mobile phase: A: water (10 mM $NH_4HCO_3$), B: acetonitrile Gradient: 5%-95% B in 1.6 or 2 min, flow rate: 1.8 or 2 mL/min; Column: XBridge C18, 4.6*50 mm, 3.5 μm at 45 C.

Exemplary general method for SFC: Column: CHIRALPAK® AD (250 mm*30 mm, 5 μm), A=supercritical $CO_2$, B=MeOH (0.1% $NH_3$—$H_2O$), A:B=70:30, flow rate: 60 mL/min, column temperature: 38° C., nozzle pressure: 100 bar, detection wavelength=220 nm.

Exemplary LCMS conditions include:

30-90AB_2MIN_E

| Column | Xtimate C18 2.1*30 mm, 3 um |
|---|---|
| Mobile Phase | A: water(4 L) + TFA(1.5 mL) |
|  | B: acetonitrile(4 L) + TFA(0.75 mL) |

| TIME(min) | B % |
|---|---|
| 0 | 30 |
| 0.9 | 90 |
| 1.5 | 90 |
| 1.51 | 30 |
| 2 | 30 |

| Flow Rate | 1.2 mL/min |
|---|---|
| wavelength | UV 220 nm |
| Oven Temp | 50° C. |
| MS ionization | ESI |
| Detector | PDA, ELSD |

10-80AB_2MIN_E

| Column | Xtimate C18 2.1*30 mm, 3 um |
|---|---|
| Mobile Phase | A: water(4 L) + TFA(1.5 mL) |
|  | B: acetonitrile(4 L) + TFA(0.75 mL) |

| TIME(min) | B % |
|---|---|
| 0 | 10 |
| 0.9 | 80 |
| 1.5 | 80 |
| 1.51 | 10 |
| 2 | 10 |

| Flow Rate | 1.2 mL/min |
|---|---|
| wavelength | UV 220 nm |
| Oven Temp | 50° C. |
| MS ionization | ESI |
| Detector | PDA, ELSD |

30-90CD_3MIN_E

| Column | Xbrige Shield RP-18, 5 um, 2.1*50 mm |
|---|---|
| Mobile Phase | A: water(1 L) + NH3H2O(0.5 mL) |
|  | B: acetonitrile |

| TIME(min) | B % |
|---|---|
| 0 | 30 |
| 2 | 90 |
| 2.48 | 90 |
| 2.49 | 30 |
| 3 | 30 |

| Flow Rate | 1.0 mL/min |
|---|---|
| wavelength | UV 220 nm |
| Oven Temp | 30° C. |
| MS ionization | ESI |
| Detector | PDA, ELSD |

Steroid Inhibition of TBPS Binding

[$^{35}$S]-t-Butylbicyclophosphorothionate (TBPS) binding assays using rat brain cortical membranes in the presence of 5 mM GABA has been described (Gee et al, *J. Pharmacol. Exp. Ther.* 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [$^{35}$S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition (IC$_{50}$) of specific binding and the maximal extent of inhibition (I$_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [$^{35}$S]-TBPS binding in vitro. These assays are or can be performed in accordance with the above discussed procedures. The results of the TBPS binding assays are shown in Table 2.

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2,6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; PE: petroleum ether; MeCN: acetonitrile; MeOH: methanol; Boc: t-butoxycarbonyl; MTBE: methyl tert-butyl ether; EDCI: N-(3-Dimethylaminopropyl)-N'-ethylcarbodiimide hydrochloride; HATU: 1-[Bis(dimethylamino)methylene]-1H-1,2,3-triazolo[4,5-b] pyridinium 3-oxide hexafluorophosphate.

Example 1. Synthesis of Compound 1

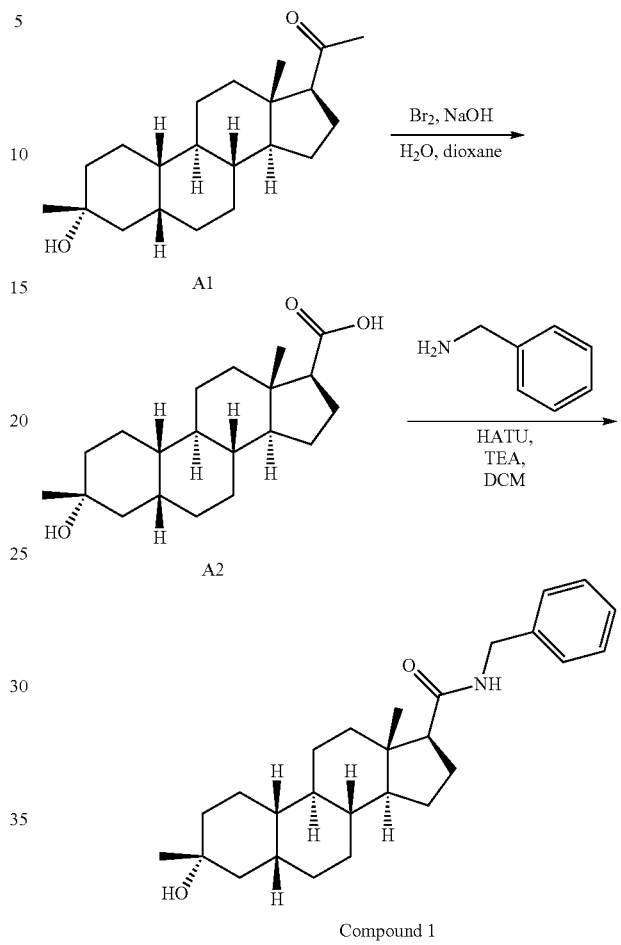

The synthesis of A1 is disclosed in WO2013/56181 A1.

Step 1 (A2).

Liquid bromine (7.46 g, 46.7 mmol) was added slowly to a vigorously stirred sodium hydroxide aqueous solution (62.3 mL, 3 M, 187 mmol) at 0° C. When all the bromine dissolved, the mixture was diluted with cold dioxane (15 mL) and was added slowly to a stirring solution of A1 (5 g, 15.6 mmol) in dioxane (20 mL) and water (15 mL). The homogeneous yellow solution became colorless slowly and a white precipitate formed. The reaction mixture was stirred at 25° C. for 16 hours. The remaining oxidizing reagent was quenched with aqueous Na$_2$S$_2$O$_3$ (30 mL) and the mixture was then heated at 80° C. until the solid material dissolved. Acidification of the solution with hydrochloric acid (3 N) furnished a white precipitate. The solid was collected by filtration and washed with water (3×100 mL) to give a solid, which was dried in vacuo to afford crude product. The crude product was triturated with toluene (40 mL) to give A2 (3.6 g, 72%) as a solid.

$^1$H NMR (CDCl$_3$, 400 MHz) δ 2.43-2.38 (m, 1H), 2.07-2.04 (m, 2H), 1.82-1.79 (m, 4H), 1.57-1.60 (m, 3H), 1.57-1.40 (m, 7H), 1.39-1.30 (m, 8H), 1.29-1.06 (m, 3H), 0.72 (s, 3H).

Step 2 (Compound 1)

To a solution of A2 (100 mg, 0.312 mmol) in DCM (8 mL) was added TEA (156 mg, 1.55 mmol) and HATU (177 mg, 0.468 mmol) at 25° C. After stirring at 25° C. for 30 mins, phenylmethylamine (53.4 mg, 0.499 mmol) was added. The mixture was stirred at 25° C. for 12 h. Water (8 mL) was added. The mixture was extracted with DCM (2×8 mL). The combined organic layers were washed with brine, dried over Na$_2$SO$_4$, concentrated in vacuo to give a crude product, which was purified by prep. HPLC (Column: Xtimate C18 150*25 mm*5 um; Conditions: water (0.05% ammonia hydroxide v/v)-ACN; Gradient 50%-80% B; Gradient Time (min): 10) and lyophilized to give Compound 1 (77 mg, 61%) as a solid $^1$H NMR (CDCl$_3$, 400 MHz) δ 7.40-7.26 (m, 5H), 5.54 (s, 1H), 4.55-4.35 (m, 2H), 2.25-2.10 (m, 2H), 1.96-1.60 (m, 8H), 1.57-1.30 (m, 6H), 1.25-1.15 (m, 8H), 1.15-1.00 (m, 4H), 0.71 (s, 3H).

LCMS Rt=1.797 min in 3 min chromatography, 30-90 CD, purity 100%, MS ESI calcd. For C$_{27}$H$_{40}$NO$_2$$^+$ [M+H]$^+$ 410, found 410.

Example 2. Synthesis of Compound 2

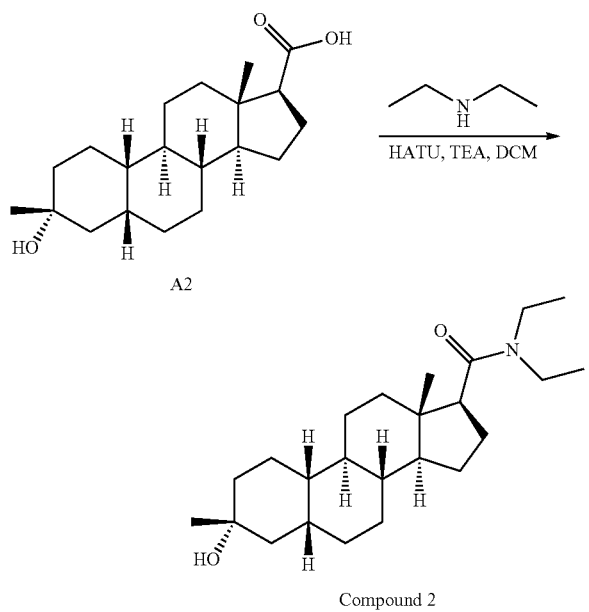

Compound 2

Step 1 (Compound 2).

To a solution of A2 (100 mg, 0.312 mmol) in DCM (8 mL) were added TEA (236 mg, 2.34 mmol) and HATU (266 mg, 0.702 mmol). After stirring for 10 min, diethylamine (54.7 mg, 0.749 mmol) was added. The mixture was stirred at 25° C. for 12 h. The reaction was treated with water (8 mL) and extracted with DCM (2×8 mL). The combined organic layers were washed with brine, dried over Na$_2$SO$_4$, concentrated in vacuo to give a crude product, which was purified by prep. HPLC (Column: Xtimate C18 150*25 mm*5 um; Conditions: water (0.05% ammonia hydroxide v/v)-ACN; Gradient 52%-82% B; Gradient Time (min): 10) and lyophilized to give Compound 2 (100 mg, 57%) as a solid.

$^1$H NMR (CDCl$_3$, 400 MHz) δ 3.77-3.65 (m, 2H), 3.15-2.99 (m, 2H), 2.65-2.55 (m, 1H), 2.30-2.20 (m, 1H), 1.90-1.55 (m, 8H), 1.50-1.30 (m, 7H), 1.30-1.15 (m, 8H), 1.15-1.00 (m, 9H), 0.74 (s, 3H).

LCMS Rt=1.739 min in 3 min chromatography, 30-90 CD, purity 100%, MS ESI calcd. For C$_{24}$H$_{42}$NO$_2$$^+$ [M+H]$^+$ 376, found 376.

Example 3. Synthesis of Compound 3

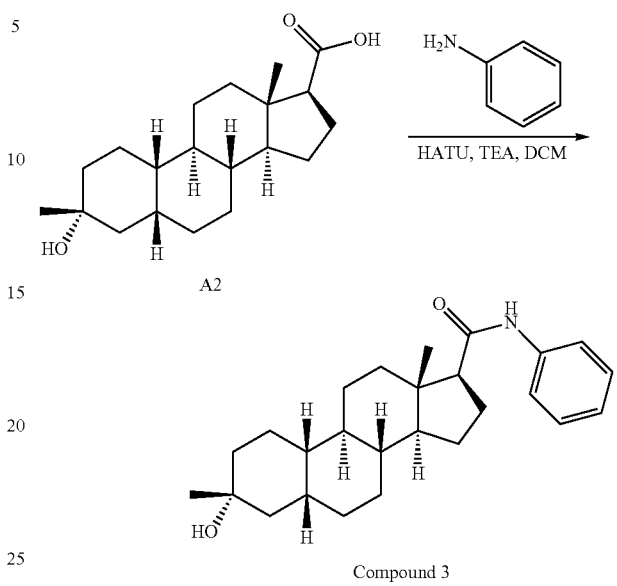

Compound 3

Step 1 (Compound 3).

To a solution of A2 (200 mg, 0.62 mmol) in DCM (8 mL) was added TEA (314 mg, 3.11 mmol) and HATU (355 mg, 0.936 mmol) at 25° C. After stirring at 25° C. for 30 mins, aniline (92.9 mg, 0.998 mmol) was added. The mixture was stirred at 25° C. for 16 h and treated with water (8 mL), extracted with DCM (2×8 mL). The organic layers were washed with brine (2×10 mL), dried over Na$_2$SO$_4$, filtered, concentrated in vacuo to give a crude product, which was triturated with MeOH (12 mL) at 25° C. to give 90 mg of an impure product. The impure product was re-crystallized from MeCN (20 mL) at 65° C. and filtered at 25° C. to give the product, which was dissolved in MeCN (30 mL) at 65° C. and concentrated in vacuo to give Compound 3 (44 mg, 49%) as a solid.

$^1$H NMR (400 MHz, CDCl$_3$) δ 7.51 (d, J=7.8 Hz, 2H), 7.35-7.28 (m, 2H), 7.12-7.05 (m, 1H), 6.95 (brs, 1H), 2.35-2.22 (m, 2H), 2.06-1.98 (m, 1H), 1.89-1.60 (m, 7H), 1.52-1.23 (m, 15H), 1.20-1.04 (m, 3H), 0.75 (s, 3H).

LCMS Rt=0.932 min in 2 min chromatography, 5-95AB_220&254, purity 100%, MS ESI calcd. For C$_{26}$H$_{38}$NO$_2$ [M+H]$^+$ 396, found 396.

Example 4. Synthesis of Compound 4

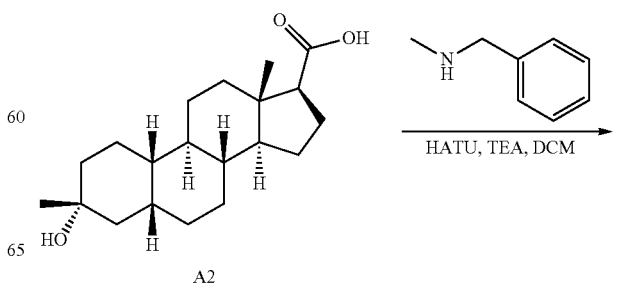

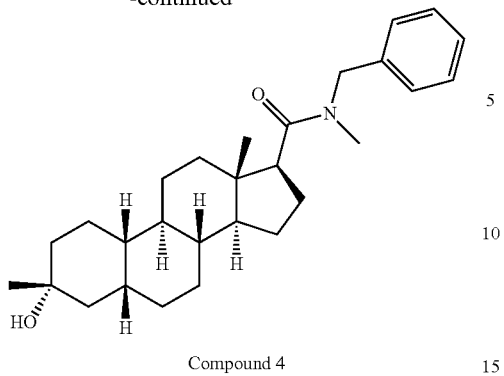

Compound 4

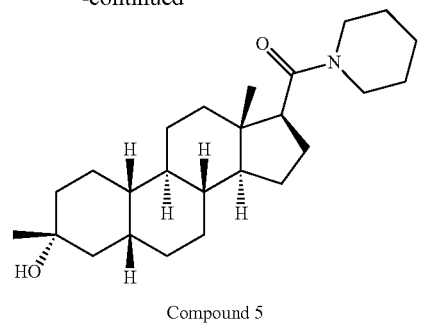

Compound 5

Step 1 (Compound 4).

To a solution of A2 (100 mg, 0.312 mmol) in DCM (5 mL) was added TEA (156 mg, 1.55 mmol) and HATU (177 mg, 0.468 mmol) at 25° C. The mixture was stirred at 25° C. for 30 mins. N-methyl-1-phenylmethanamine (60.4 mg, 0.499 mmol) was added. The mixture was stirred at 25° C. for 1 hour. Water (5 mL) was added. The mixture was extracted with DCM (2×5 mL), washed with brine, dried over $Na_2SO_4$, concentrated in vacuo to give a crude product which was purified by prep. HPLC (Column: Xtimate C18 150*25 mm*5 um; Conditions: water (0.05% ammonia hydroxide v/v)-ACN; Begin B: 57; End B: 87; 100% B Hold Time (min): 2.5; FlowRate (ml/min): 25; Injections: 8) to give a solution of product in water/$CH_3CN$ and concentrated in vacuo to give Compound 4 (109 mg, 83%) as a solid.

$^1$H NMR (400 MHz, $CDCl_3$) δ 7.38-7.28 (m, 2H), 7.26-7.22 (m, 2H), 7.16-7.09 (m, 1H), 5.11-4.83 (m, 1H), 4.40-4.17 (m, 1H), 2.99-2.90 (m, 3H), 2.82-2.67 (m, 1H), 2.38-2.26 (m, 1H), 1.91-1.74 (m, 4H), 1.74-1.59 (m, 4H), 1.54-1.36 (m, 5H), 1.36-1.30 (m, 3H), 1.29-1.20 (m, 6H), 1.20-1.01 (m, 4H), 0.81 (s, 3H).

LCMS Rt=1.325 min in 2 min chromatography, 30-90 AB, purity 100%, MS ESI calcd. For $C_{28}H_{42}NO_2$ [M+H]$^+$ 424, found 424.

Example 5. Synthesis of Compound 5

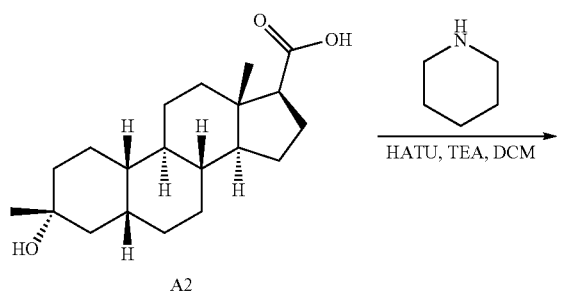

A2

Step 1 (Compound 5).

To a solution of A2 (100 mg, 0.312 mmol) in DCM (5 mL) was added TEA (156 mg, 1.55 mmol) and HATU (177 mg, 0.468 mmol) at 25° C. The mixture was stirred at 25° C. for 1 hour. Piperidine (42.4 mg, 0.449 mmol) was added. The mixture was stirred at 25° C. for 1 hour. Water (8 mL) was added. The mixture was extracted with DCM (2×10 mL), washed with brine, dried over $Na_2SO_4$, concentrated in vacuo. The residue was triturated with acetonitrile (5 mL) at 25° C. to give Compound 5 (34 mg, 28%) as a solid.

$^1$H NMR (400 MHz, $CDCl_3$) δ 3.65-3.40 (m, 4H), 2.75-2.64 (m, 1H), 2.35-2.25 (m, 1H), 1.90-1.75 (m, 4H), 1.75-1.55 (m, 10H), 1.55-1.49 (m, 5H), 1.49-1.18 (m, 10H), 1.18-1.05 (m, 3H), 0.72 (s, 3H).

LCMS Rt=1.896 min in 2.0 min chromatography, 30-90 CD_POS_E.M, purity 100%, MS ESI calcd. for $C_{25}H_{42}NO_2$ [M+H]$^+$ 388, found 388.

Example 6. Synthesis of Compound 6

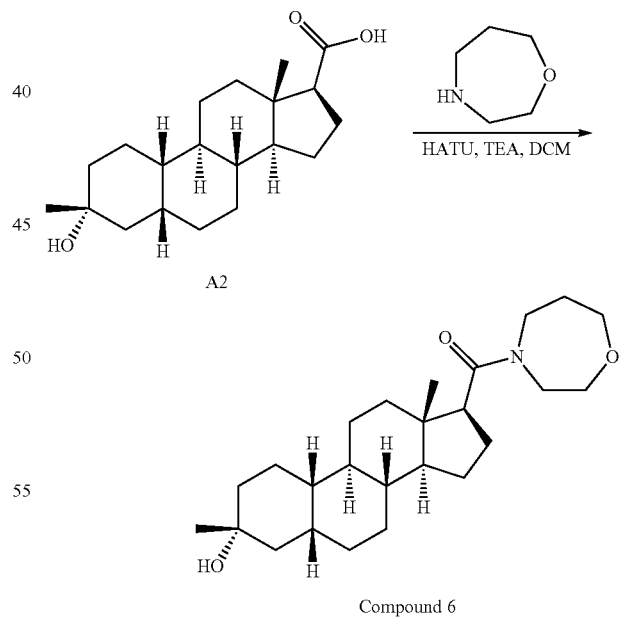

Compound 6

Step 1 (Compound 6).

To a solution of A2 (150 mg, 0.468 mmol) in DCM (6 mL) was added TEA (236 mg, 2.34 mmol) and HATU (266 mg, 0.7 mmol) at 25° C. After stirring at 25° C. for 30 mins, 1,4-oxazepane (75.6 mg, 0.748 mmol) was added. The mixture was stirred at 25° C. for 1 h and quenched with water (8 mL). The mixture was extracted with DCM (2×8 mL). The organic layers were washed with brine (10 mL), dried over $Na_2SO_4$, filtered and concentrated in vacuo to give a crude product, which was purified by prep. HPLC (Column: Waters Xbridge (150 mm*25 mm, 5 um)), gradient: 60-90% B (A=10 mM $NH_4HCO_3/H_2O$, B=MeCN), flow rate: 25 mL/min) to give a solid. The solid was treated water (5 mL), warmed to 80° C. and stirred for 2 h, filtered and concentrated to give Compound 6 (32 mg).

$^1$H NMR (400 MHz, $CDCl_3$) δ 4.02-3.92 (m, 1H), 3.90-3.65 (m, 4H), 3.65-3.62 (m, 1H), 3.52-3.35 (m, 2H), 2.73-2.59 (m, 1H), 2.35-2.18 (m, 1H), 2.05-1.78 (m, 6H), 1.78-1.60 (m, 5H), 1.51-1.38 (m, 5H), 1.36-1.18 (m, 9H), 1.18-1.02 (m, 3H), 0.80-0.70 (s, 3H).

LCMS Rt=0.863 min in 2.0 min chromatography, 30-90AB, purity 100%, MS ESI calcd. for $C_{25}H_{42}NO_3$ $[M+H]^+$ 404, found 404.

Example 7. Synthesis of Compound 7

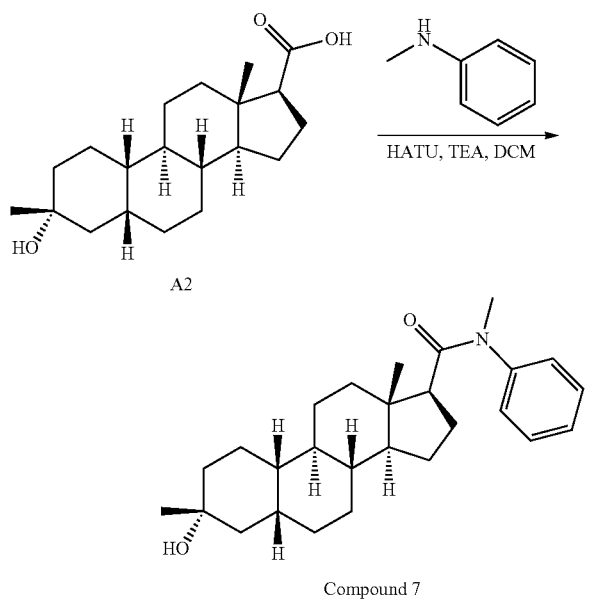

Step 1 (Compound 7).

To a solution of A2 (80 mg, 0.25 mmol) in DCM (3 mL) was added TEA (125 mg, 1.24 mmol) and HATU (142 mg, 0.37 mmol) at 25° C. After stirring at 25° C. for 30 mins, N-methylaniline (42.7 mg, 0.40 mmol) was added. The mixture was stirred at 25° C. for 16 h and quenched with water (5 mL). The mixture was extracted with DCM (2×4 mL). The organic phase was washed with brine (2×8 mL), dried over $Na_2SO_4$, filtered, concentrated in vacuo to give a crude product which was purified by prep. HPLC (Column: Xtimate C18 150*25 mm*5 um; Conditions: water (0.05% ammonia hydroxide v/v)-ACN, 61%-91% B; Gradient Time (min): 10; 100% B Hold Time (min): 2.5; FlowRate (ml/min): 25) to give a solid, which was triturated with MeCN (5 mL) at 25° C. for 4 hours to give Compound 7 (14 mg, 14%) as a solid.

$^1$H NMR (400 MHz, $CDCl_3$) δ 7.50-7.40 (m, 2H), 7.40-7.30 (m, 1H), 7.15-7.05 (m, 2H), 3.26 (s, 3H), 2.50-2.40 (m, 1H), 2.15-2.00 (m, 1H), 1.90-1.60 (m, 6H), 1.50-1.20 (m, 14H), 1.10-0.75 (m, 8H), 0.65-0.50 (m, 1H).

LCMS Rt=1.036 min in 2 min chromatography, 30-90AB, purity 100%, MS ESI calcd. For $C_{27}H_{40}NO_2$ $[M+H]^+$ 410.

Example 8. Synthesis of Compound 8

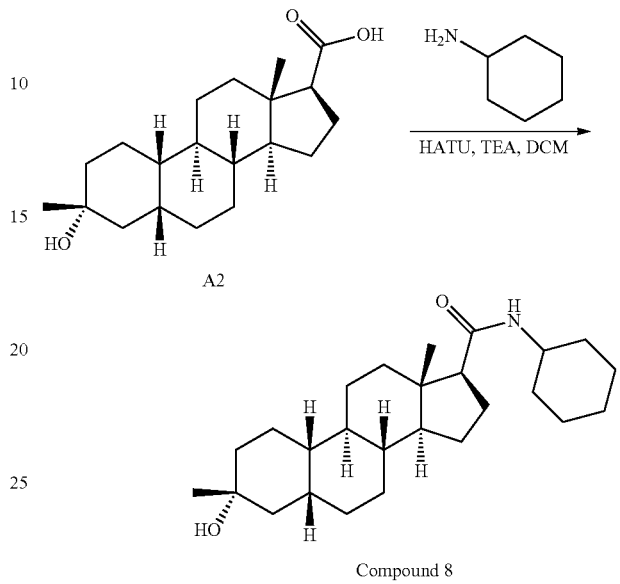

Step 1 (Compound 8).

To a solution of A2 (100 mg, 0.312 mmol) in DCM (4 mL) was added TEA (156 mg, 1.55 mmol) and HATU (112 mg, 0.468 mmol) at 25° C. After stirring at 25° C. for 30 minutes, cyclohexanamine (49.4 mg, 0.499 mmol) was added. The mixture was stirred at 25° C. for 16 hrs, quenched with water (4 mL) and extracted with DCM (2×4 mL). The organic layers were washed with brine (2×5 mL), dried over $Na_2SO_4$, filtered, concentrated in vacuo to give a crude product, which was purified by silica gel chromatography eluted with PE/EtOAc=3/1 to afford a impure product. The impure product was re-crystallized (85° C.) from MeCN (2 mL) and water (20 mL) to give Compound 8 (86 mg, 69%) as a solid.

$^1$H NMR (400 MHz, $CDCl_3$) δ 5.20-5.05 (m, 1H), 3.85-3.70 (m, 1H), 2.25-2.10 (m, 1H), 2.09-2.00 (m, 1H), 1.95-1.55 (m, 12H), 1.54-1.30 (m, 8H), 1.29-1.00 (m, 16H), 0.66 (s, 3H).

LCMS Rt=1.176 min in 2.0 min chromatography, 30-90 AB, purity 100%, MS ESI calcd. for $C_{26}H_{44}NO_2$ $[M+H]^+$ 402, found 402.

Example 9. Synthesis of Compound 9

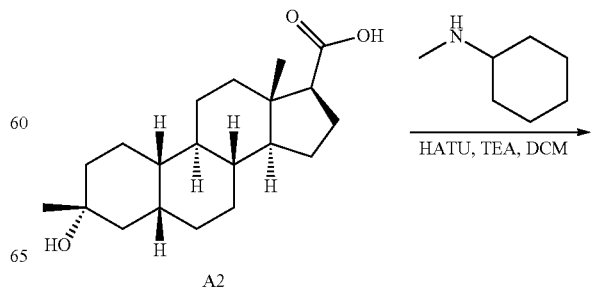

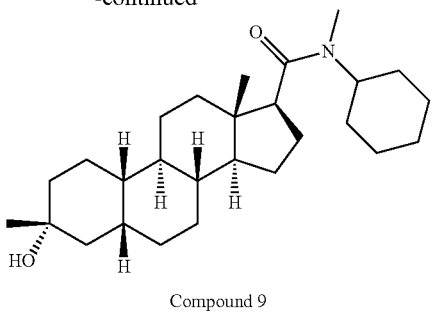

Compound 9

Step 1. (Compound 9).

To a solution of A2 (100 mg, 0.312 mmol) in DCM (4 mL) was added TEA (156 mg, 1.55 mmol) and HATU (112 mg, 0.468 mmol) at 25° C. After stirring at 25° C. for 30 minutes, N-methylcyclohexanamine (56.4 mg, 0.499 mmol) was added. The mixture was stirred at 25° C. for 16 hrs, quenched with water (4 mL) and extracted with DCM (2×4 mL). The organic layers were washed with brine (2×5 mL), dried over Na$_2$SO$_4$, filtered, concentrated in vacuo to give a crude product, which was purified by silica gel chromatography eluted with PE/EtOAc=3/1 to give a solid, which was lyophilized to give Compound 9 (44 mg, 34%) as a solid.

$^1$H NMR (400 MHz, CDCl$_3$) δ 4.55-4.45 (m, 0.5H), 3.80-3.70 (m, 0.5H), 2.90-2.70 (m, 3H), 2.69-2.60 (m, 1H), 2.35-2.20 (m, 1H), 1.90-1.50 (m, 15H), 1.49-1.15 (m, 18H), 1.14-1.00 (m, 3H), 0.73 (s, 3H).

LCMS Rt=1.239 min in 2.0 min chromatography, 30-90 AB, purity 100%, MS ESI calcd. for C$_{27}$H$_{46}$NO$_2$ [M+H]$^+$ 416, found 416.

Example 10. Synthesis of Compound 10

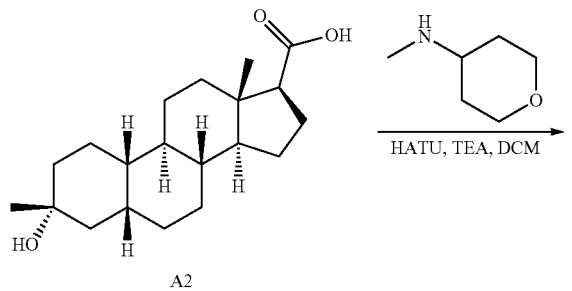

Compound 10

To a solution of A2 (100 mg, 0.312 mmol) in DCM (4 mL) was added TEA (156 mg, 1.55 mmol) and HATU (112 mg, 0.468 mmol) at 25° C. After stirring at 25° C. for 30 minutes, N-methyltetrahydro-2H-pyran-4-amine (57.4 mg, 0.499 mmol) was added. The mixture was stirred at 25° C. for 16 hrs, quenched with water (4 mL) and extracted with DCM (2×4 mL). The organic layers were washed with brine (2×5 mL), dried over Na$_2$SO$_4$, filtered, concentrated in vacuo to give a crude product, which was purified by silica gel chromatography eluted with PE/EtOAc=3/1 to afford the desired compound. The compound was lyophilized to give a solid (80 mg) that was further re-crystallized (85° C.) from MeCN (2 mL) and water (20 mL) to give Compound 10 (66 mg, 51%) as a solid.

$^1$H NMR (400 MHz, CDCl$_3$) δ 4.85-4.70 (m, 0.5H), 4.15-3.95 (m, 2H), 3.55-3.40 (m, 1.5H), 2.90-2.70 (m, 3H), 2.69-2.60 (m, 1H), 2.35-2.20 (m, 1H), 1.90-1.60 (m, 10H), 1.59-1.16 (m, 18H), 1.15-1.00 (m, 3H), 0.72 (s, 3H).

LCMS Rt=1.005 min in 2.0 min chromatography, 30-90 AB, purity 100%, MS ESI calcd. for C$_{26}$H$_{44}$NO$_3$ [M+H]$^+$ 418, found 418.

Example 11. Synthesis of Compound 11

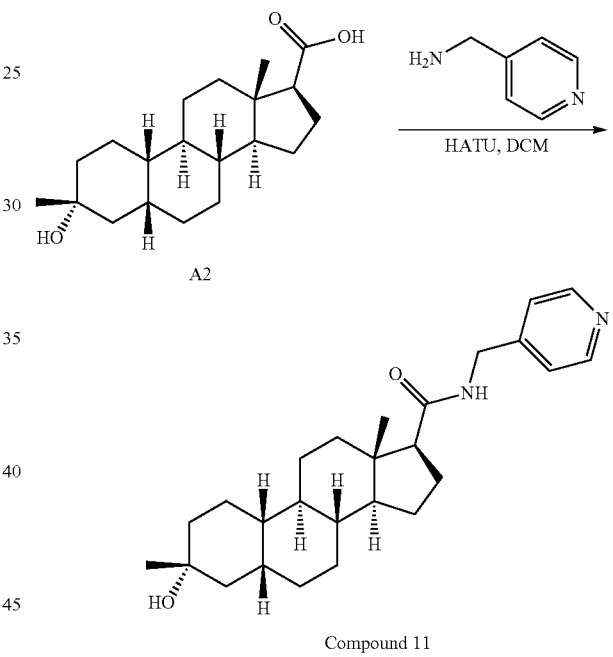

Compound 11

Step 1 (Compound 1).

To a solution of A2 (100 mg, 0.312 mmol) in DCM (5 mL) was added TEA (156 mg, 1.55 mmol) and HATU (177 mg, 0.468 mmol) at 25° C. After stirring at 25° C. for 30 minutes, pyridin-4-ylmethylamine (50.6 mg, 0.468 mmol) was added. The mixture was stirred at 25° C. for 1 h. Water (20 mL) was added. The mixture was extracted with DCM (2×20 mL), washed with brine (20 mL), dried over Na$_2$SO$_4$, concentrated in vacuo to give a crude product, which was purified by flash column (0~30% of EtOAc in PE) to give Compound 11 (68 mg, 53%) as a solid. $^1$H NMR (400 MHz, CDCl$_3$) δ 8.56 (d, J=4.0 Hz, 2H), 7.20 (d, J=4.0 Hz, 2H), 5.68 (br s, 1H), 4.51 (d, J=8 Hz, 1H), 4.44 (d, J=8 Hz, 1H), 2.22-2.15 (m, 2H), 1.91-1.79 (m, 5H), 1.75-1.62 (m, 3H), 1.50-1.37 (m, 6H), 1.35-1.23 (m, 8H), 1.18-1.08 (m, 4H), 0.71 (s, 3H).

LCMS Rt=1.453 min in 3.0 min chromatography, 10-80AB, purity 100%, MS ESI calcd. for C$_{26}$H$_{39}$N$_2$O$_2$ [M+H]$^+$ 411, found 411.

Example 12. Synthesis of Compound 12

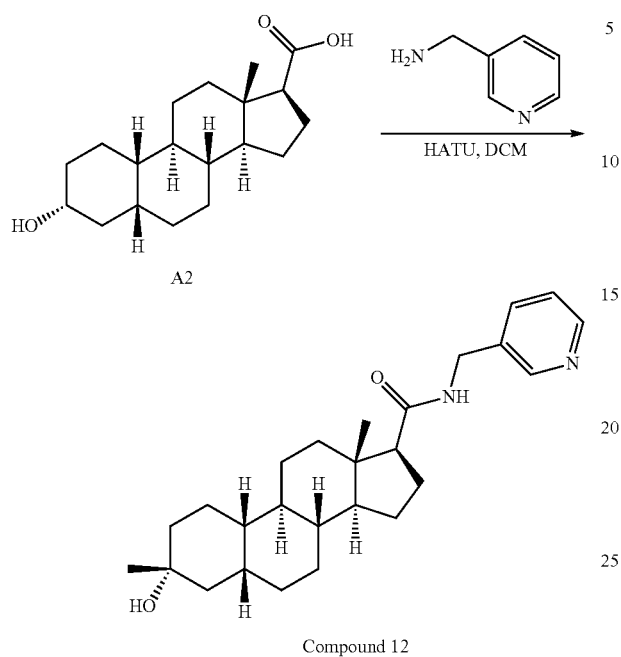

Compound 12

Step 1 (Compound 12)

To a solution of A2 (100 mg, 0.312 mmol) in DCM (5 mL) was added TEA (156 mg, 1.55 mmol) and HATU (177 mg, 0.468 mmol) at 25° C. After stirring at 25° C. for 30 minutes, pyridin-3-ylmethylamine (50.6 mg, 0.468 mmol) was added. The mixture was stirred at 25° C. for 1 h. Water (20 mL) was added. The mixture was extracted with DCM (2×20 mL), washed with brine (20 mL), dried over $Na_2SO_4$, concentrated in vacuo to give a crude product, which was purified by flash column (0~30% of EtOAc in PE) to give Compound 12 (63 mg, 49%) as a solid.

$^1$H NMR (400 MHz, $CDCl_3$) δ 8.55-8.53 (m, 2H), 7.65 (d, J=8.0 Hz, 1H), 7.27 (d, J=8.0 Hz, 1H), 5.63-5.61 (m, 1H), 4.57-4.39 (m, 2H), 2.22-2.11 (m, 2H), 1.89-1.74 (m, 5H), 1.72-1.61 (m, 3H), 1.49-1.36 (m, 6H), 1.31-1.19 (m, 8H), 1.17-1.02 (m, 4H), 0.68 (s, 3H)

LCMS Rt=2.016 min in 4.0 min chromatography, 10-80AB, purity 100%, MS ESI calcd. for $C_{26}H_{39}N_2O_2$ $[M+H]^+$ 411, found 411.

Example 13. Synthesis of Compound 13

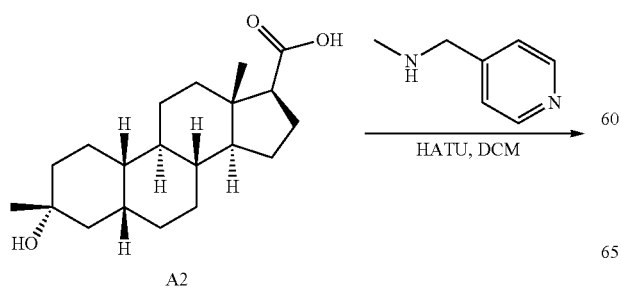

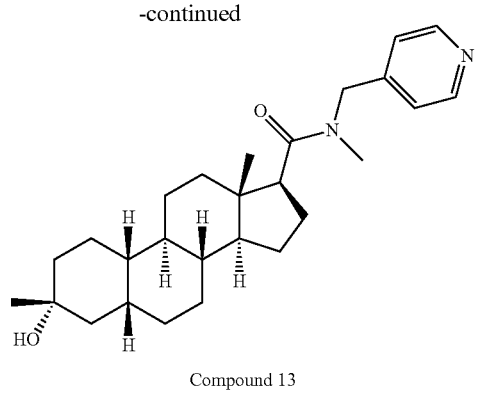

Compound 13

To a solution of A2 (100 mg, 0.312 mmol) in DCM (5 mL) was added TEA (156 mg, 1.55 mmol) and HATU (177 mg, 0.468 mmol) at 25° C. After stirring at 25° C. for 30 mins, N-methyl-1-(pyridin-4-yl)methylamine (57.1 mg, 0.468 mmol) was added. The mixture was stirred at 25° C. for 1 h, quenched with water (20 mL) and extracted with DCM (2×20 mL). The organic layers were washed with brine (20 mL), dried over $Na_2SO_4$, concentrated in vacuo to give a crude product, which was purified by flash silica gel chromatography (0~30% of EtOAc in PE) to give Compound 13 (81 mg, 61%) as a solid.

$^1$H NMR (400 MHz, $CDCl_3$) δ 8.59-8.54 (m, 2H), 7.15 (d, J=4.0 Hz, 1.4H), 7.07 (d, J=4.0 Hz, 0.6H), 5.00 (d, J=20 Hz, 0.3H), 4.89 (d, J=16 Hz, 0.7H), 4.37-4.26 (m, 1H), 3.03 (s, 2.2H), 2.96 (m, 0.8H), 2.81 (t, J=12 Hz 0.8H), 2.56 (t, J=12 Hz 0.2H) 2.34-2.26 (m, 1H), 1.81-1.74 (m, 4H), 1.72-1.61 (m, 3H), 1.52-1.21 (m, 16H), 1.13-1.11 (m, 3H), 0.79 (s, 3H)

LCMS Rt=1.491 min in 3.0 min chromatography, 10-80AB, purity 100%, MS ESI calcd. for $C_{27}H_{41}N_2O_2$ $[M+H]^+$ 425, found 425.

Example 14. Synthesis of Compound 14

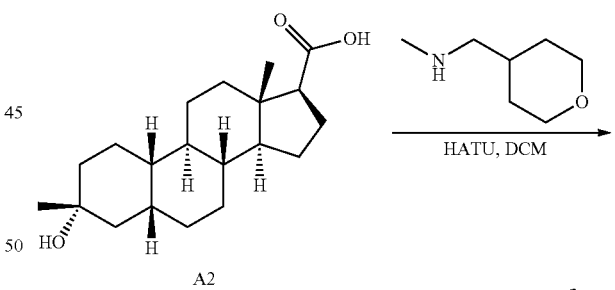

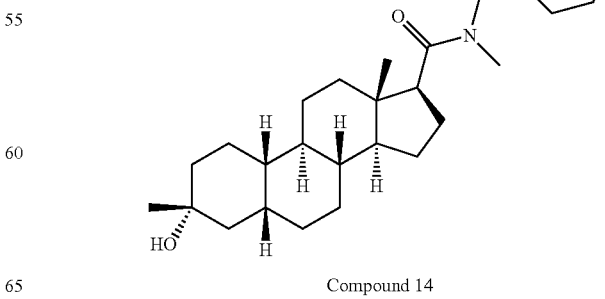

Compound 14

To a solution of A2 (100 mg, 0.312 mmol) in DCM (3 mL) was added TEA (156 mg, 1.55 mmol) and HATU (177 mg, 0.468 mmol) at 25° C. After stirring at 25° C. for 30 minutes, N-methyl-1-(tetrahydro-2H-pyran-4-yl)methylamine (64.4 mg, 0.499 mmol) was added. The mixture was stirred at 25° C. for 16 hrs, quenched with water (15 mL) and extracted with DCM (2×10 mL). The organic layers were washed with brine, dried over Na$_2$SO$_4$, filtered and concentrated in vacuo to give a crude product, which was purified by flash silica gel chromatography (0~40% of EtOAc in PE) to give Compound 14 (31 mg, 23%) as a solid.

$^1$H NMR (400 MHz, CDCl$_3$) δ 4.05-3.91 (m, 2H), 3.69-3.53 (m, 1H), 3.45-3.27 (m, 2H), 3.10-3.03 (m, 2H), 3.02-2.89 (m, 2H), 2.77-2.65 (m, 1H), 2.32-2.16 (m, 1H), 1.99-1.73 (m, 5H), 1.73-1.60 (m, 4H), 1.60-1.56 (m, 1H), 1.55-1.47 (m, 2H), 1.46-1.35 (m, 6H), 1.35-1.18 (m, 10H), 1.17-1.025 (m, 3H), 0.74 (s, 3H).

LCMS Rt=1.013 min in 2 min chromatography, 30-90AB, purity 100%, MS ESI calcd. For C$_{27}$H$_{46}$NO$_3$ [M+H]$^+$ 432, found 432.

Example 15. Synthesis of Compound 15

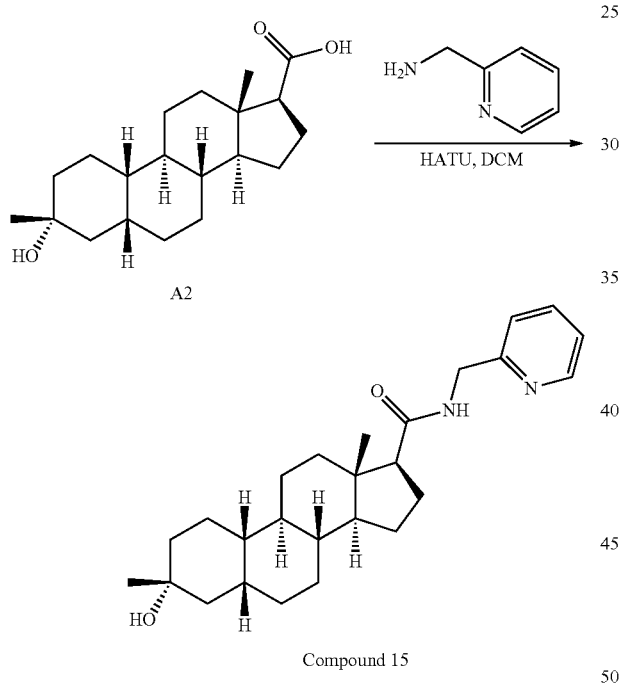

Compound 15

To a solution of A2 (100 mg, 0.312 mmol) in DCM (3 mL) was added TEA (156 mg, 1.55 mmol) and HATU (177 mg, 0.468 mmol) at 25° C. After stirring at 25° C. for minutes, pyridin-2-ylmethylamine (53.9 mg, 0.499 mmol) was added. The mixture was stirred at 25° C. for 16 hrs, quenched with water (15 mL) and extracted with DCM (2×10 mL). The organic layers were washed with brine, dried over Na$_2$SO$_4$, concentrated in vacuo to give 110 mg of crude product, which was purified by prep. HPLC (Column: Kromasil 150*25 mm*10 um; Conditions: water (0.05% ammonia hydroxide v/v)-ACN; Begin B: 40; End B: 70; Gradient Time (min): 8; 100% B Hold Time (min): 2; FlowRate (ml/min): 30; Injections: 6) and concentrated in vacuo to give Compound 15 (26 mg, 24%) as a solid.

$^1$H NMR (400 MHz, CDCl$_3$) δ 8.58-8.50 (m, 1H), 7.70-7.62 (m, 1H), 7.30-7.27 (m, 1H), 7.21-7.16 (m, 1H), 6.64-6.48 (m, 1H), 4.62-4.53 (m, 2H), 2.30-2.16 (m, 1H), 2.03-1.95 (m, 1H), 1.89-1.76 (m, 4H), 1.74-1.59 (m, 4H), 1.50-1.36 (m, 6H), 1.34-1.26 (m, 7H), 1.25-0.99 (m, 5H), 0.67 (s, 3H).

LCMS Rt=0.601 min in 2 min chromatography, 30-90AB, purity 100%, MS ESI calcd. For C$_{26}$H$_{39}$N$_2$O$_2$ [M+H]$^+$ 411, found 411.

Example 16. Synthesis of Compound 16

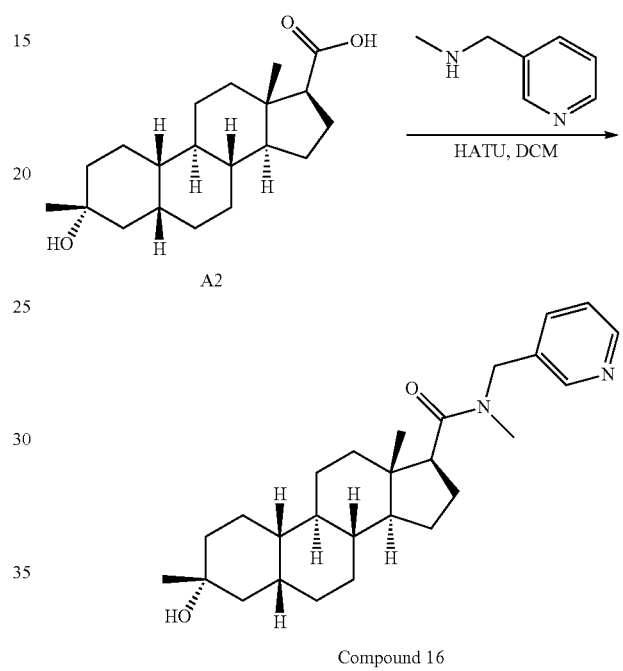

Compound 16

To a solution of A2 (100 mg, 0.312 mmol) in DCM (3 mL) was added TEA (156 mg, 1.55 mmol) and HATU (177 mg, 0.468 mmol) at 25° C. After stirring at 25° C. for 30 minutes, N-methyl-1-(pyridin-3-yl)methylamine (60.9 mg, 0.499 mmol) was added. The mixture was stirred at 25° C. for 16 hrs, quenched with water (15 mL) and extracted with DCM (2×10 mL). The combined organic layers were washed with brine, dried over Na$_2$SO$_4$, concentrated in vacuo to give 120 mg of crude product, which was purified by prep. HPLC (Column: Kromasil 150*25 mm*10 um; Conditions: water (0.05% ammonia hydroxide v/v)-ACN; Begin B: 40; End B: 70; Gradient Time (min): 8; 100% B Hold Time (min): 2; FlowRate (ml/min): 30; Injections: 5) and concentrated to give Compound 16 (6 mg, 5%) as a solid. The NMR of the compound shows rotamers.

$^1$H NMR (400 MHz, CDCl$_3$) δ 8.60-8.44 (m, 2H), 7.66-7.41 (m, 1H), 7.31-7.26 (m, 1H), 5.00-4.90 (m, 0.2H), 4.90-4.76 (m, 0.8H), 4.36-4.28 (m, 0.8H), 4.28-4.20 (m, 0.2H), 2.94 (s, 2.4H), 2.85 (s, 0.6H), 2.75-2.67 (m, 0.8H), 2.67-2.60 (m, 0.2H), 2.35-2.23 (m, 1H), 1.87-1.62 (m, 9H), 1.51-1.38 (m, 6H), 1.36-1.27 (m, 5H), 1.25-1.19 (m, 2H), 1.15-1.05 (m, 3H), 0.83-0.71 (m, 4H).

LCMS Rt=0.647 min in 2 min chromatography, 30-90AB, purity 100%, MS ESI calcd. For C$_{27}$H$_{41}$N$_2$O$_2$ [M+H]$^+$ 425, found 425.

Example 17. Synthesis of Compound

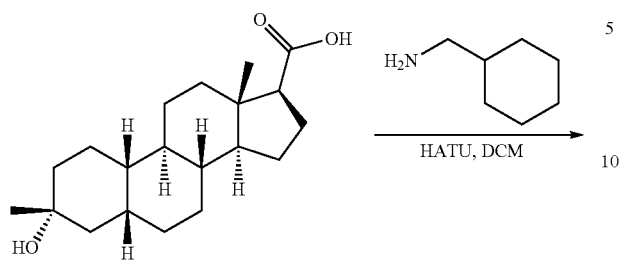

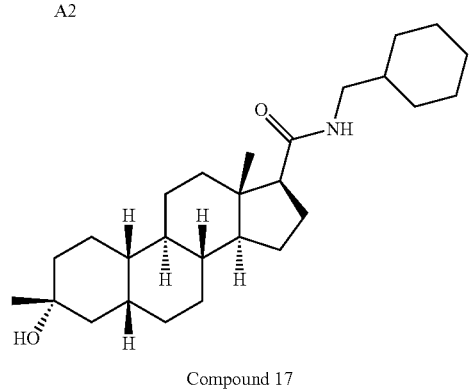

Compound 17

Step 1 (Compound 17).

To a solution of A2 (100 mg, 0.312 mmol) in DCM (3 mL) was added TEA (156 mg, 1.55 mmol) and HATU (177 mg, 0.468 mmol) at 25° C. After stirring at 25° C. for 30 mins, cyclohexylmethanamine (56.4 mg, 0.499 mmol) was added. The mixture was stirred at 25° C. for 16 hrs and treated with water (15 mL). The mixture was extracted with DCM (2×10 mL). The organic layers were washed with brine, dried over $Na_2SO_4$, filtered and concentrated to give a crude product, which was purified by flash silica gel chromatography (0~30% of EtOAc in DCM) to give crude Compound 17 (23 mg, 18%) as a solid. The crude product was re-crystallized from MeOH (15 mL) to give Compound 17 (9 mg, 39%) as a solid.

$^1$H NMR (400 MHz, $CDCl_3$) δ 5.34-5.24 (m, 1H), 3.24-3.13 (m, 1H), 3.09-2.97 (m, 1H), 2.23-2.12 (m, 1H), 2.12-2.06 (m, 1H), 1.94-1.79 (m, 4H), 1.77-1.61 (m, 9H), 1.50-1.34 (m, 8H), 1.32-1.20 (m, 9H), 1.19-1.03 (m, 5H), 0.98-0.87 (m, 2H), 0.68 (s, 3H).

LCMS Rt=1.197 min in 2 min chromatography, 30-90 AB, purity 100%, MS ESI calcd. For $C_{27}H_{46}NO_2$ $[M+H]^+$ 416, found 416.

Example 18. Synthesis of Compound 18

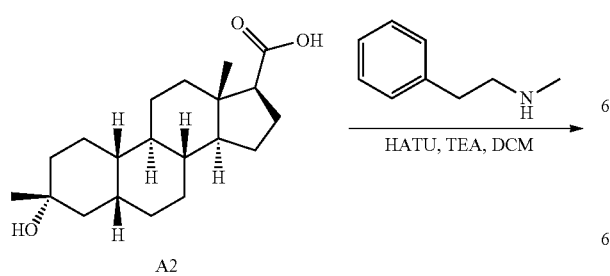

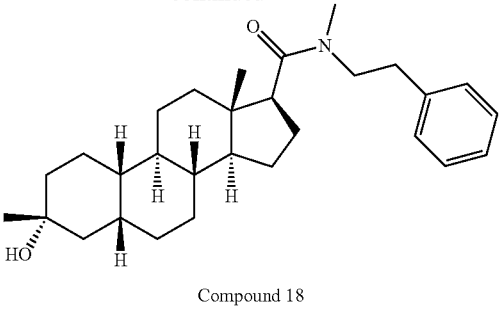

Compound 18

Step 1 (Compound 18).

To a solution of A2 (100 mg, 0.312 mmol) in DCM (5 mL) was added TEA (213 mg, 1.55 mmol) and HATU (177 mg, 0.468 mmol) at 25° C. After stirring at 25° C. for 30 mins, N-methyl-2-phenylethanamine (63.2 mg, 0.468 mmol) was added. The mixture was stirred at 25° C. for 1 h, treated with water (20 mL) and extracted with DCM (2×20 mL). The organic layers were washed with brine (20 mL), dried over $Na_2SO_4$, filtered and concentrated in vacuo to give a crude product, which was purified by flash silica gel chromatography (0~30% of EtOAc in PE) to give Compound 18 (39 mg, 29%) as a solid.

$^1$H NMR (400 MHz, $CDCl_3$) δ 7.37-7.26 (m, 2H), 7.26-7.12 (m, 3H), 4.00-3.83 (m, 1H), 3.42-3.23 (m, 1H), 2.94-2.97 (m, 3H), 2.87-2.76 (m, 2H), 2.67 (t, J=8.0 Hz, 0.6H), 2.43 (t, J=8.0 Hz, 0.4H), 2.31-2.08 (m, 1H), 1.88-1.75 (m, 3H), 1.71-1.58 (m, 4H), 1.50-1.30 (m, 7H), 1.30-0.97 (m, 12H), 0.68-0.70 (m, 3H).

LCMS Rt=3.174 min in 4.0 min chromatography, 10-80AB, purity 100%, MS ESI calcd. for $C_{29}H_{44}NO_2$ $[M+H]^+$ 438, found 438.

Example 19. Synthesis of Compound 19

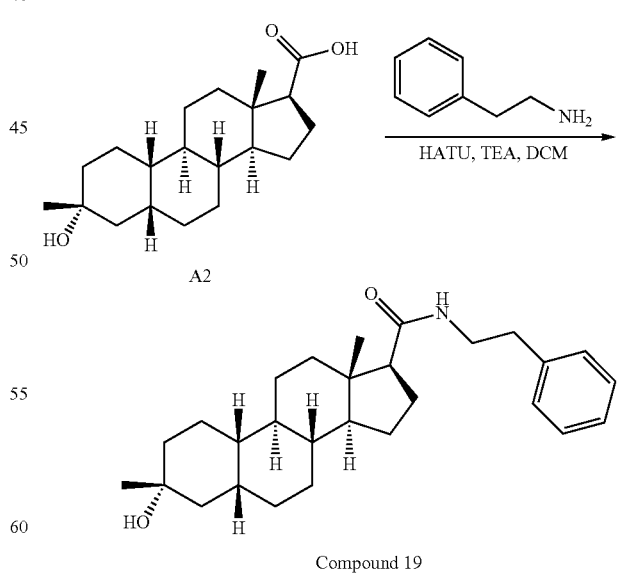

Compound 19

Step 1 (Compound 19).

To a solution of A2 (100 mg, 0.312 mmol) in DCM (5 mL) was added TEA (156 mg, 1.55 mmol) and HATU (177 mg, 0.468 mmol) at 25° C. The mixture was stirred at 25° C. for 30 mins. 2-phenylethanamine (37.8 mg, 0.312 mmol) was added. The mixture was stirred at 25° C. for 12 hrs, treated with water (20 mL) and extracted with DCM (2×20 mL). The organic layers were washed with brine (20 mL), dried over $Na_2SO_4$, concentrated in vacuo to give a crude product, which was purified by flash silica gel chromatography (0~30% of EtOAc in PE) to give Compound 19 (21 mg, 16%) as a solid.

$^1$H NMR (400 MHz, $CDCl_3$) δ 7.33-7.28 (m, 2H), 7.25-7.18 (m, 3H), 5.25-5.20 (m, 1H), 3.66-3.60 (m, 1H), 3.51-3.42 (m, 1H), 2.82 (t, J=8.0 Hz, 2H), 2.19-2.08 (m, 1H), 2.05-2.00 (m, 1H), 1.86-1.76 (m, 3H), 1.74-1.59 (m, 5H), 1.48-1.32 (m, 7H), 1.30-1.22 (m, 6H), 1.15-1.00 (m, 5H), 0.62 (s, 3H).

LCMS Rt=2.344 min in 4.0 min chromatography, 30-90AB, purity 98.4%, MS ESI calcd. for $C_{28}H_{42}NO_2$ $[M+H]^+$ 424, found 424.

Example 20. Synthesis of Compound 20

LCMS Rt=3.095 min in 4.0 min chromatography, 10-80AB, purity 100%, MS ESI calcd. for $C_{28}H_{42}NO_2$ $[M+H]^+$ 424, found 424.

Example 21. Synthesis of Compound 21

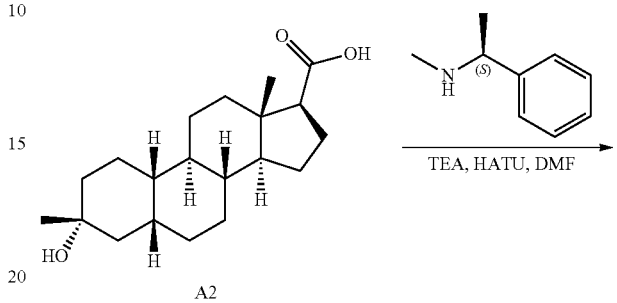

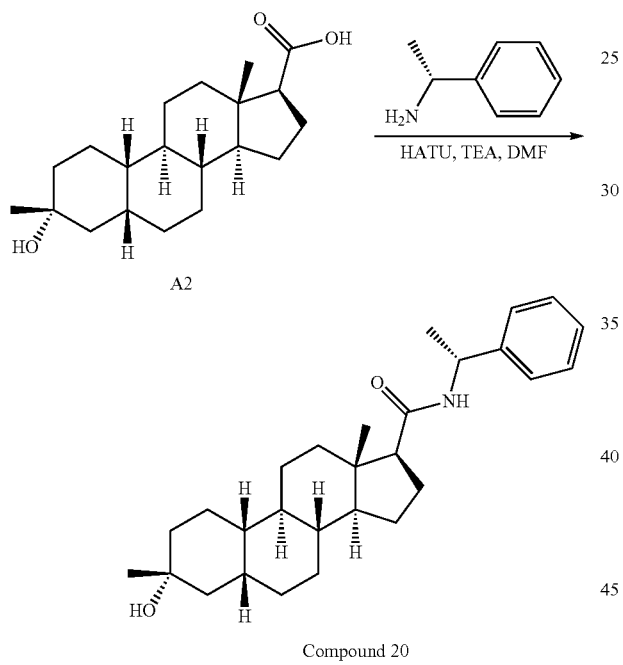

Step 1 (Compound 20).

To a solution of A2 (100 mg, 0.312 mmol) in DMF (5 mL) was added TEA (156 mg, 1.55 mmol) and HATU (177 mg, 0.468 mmol) at 25° C. The mixture was stirred at 25° C. for 30 mins. (R)-1-phenylethanamine (56.7 mg, 0.468 mmol) was added. The mixture was stirred at 25° C. for 12 hrs, treated with water (20 mL) and extracted with DCM (2×20 mL). The organic layers were washed with brine (20 mL), dried over $Na_2SO_4$, filtered and concentrated in vacuo to give a crude product, which was purified by flash silica gel chromatography (0~30% of EtOAc in PE) to give Compound 20 (51 mg, 39%) as a solid.

$^1$H NMR (400 MHz, $CDCl_3$) δ 7.39-7.30 (m, 4H), 7.29-7.27 (m, 1H), 5.45-5.42 (m, 1H), 5.22-5.14 (m, 1H), 2.25-2.14 (m, 1H), 2.08 (t, J=8.0 Hz, 1H), 1.97-1.91 (m, 1H), 1.89-1.79 (m, 3H), 1.77-1.62 (m, 4H), 1.50 (d, J=4.0 Hz, 3H), 1.47-1.34 (m, 6H), 1.32-1.20 (m, 8H), 1.18-1.04 (m, 4H), 0.71 (s, 3H).

Step 1 (Compound 21).

To a solution of A2 (100 mg, 0.312 mmol) in DMF (4 mL) was added TEA (156 mg, 1.55 mmol) and HATU (177 mg, 0.468 mmol) at 25° C. After stirring at 30° C. for 30 mins, (S))—N-methyl-1-phenylethanamine (63.2 mg, 0.468 mmol) was added. The mixture was stirred at 30° C. for 16 h then treated with water (8 mL). The precipitate was collected by filtration and purified by HPLC (Waters Xbridge 150*25 5 u, water (10 mM $NH_4HCO_3$)-ACN, gradient: 55-85% B, flow rate: 25 mL/min) to give Compound 21 (40 mg, 30%) as a solid.

$^1$H NMR (400 MHz, DMSO-$d_6$) δ 7.40-7.32 (m, 2H), 7.21-7.29 (m, 3H), 6.02-5.72 (m, 1H), 3.94-3.81 (m, 1H), 3.15-2.98 (m, 3H), 2.90-2.81 (m, 1H), 2.71-2.62 (m, 3H), 2.38-2.11 (m, 1H), 1.82-1.57 (m, 8H), 1.57-1.20 (m, 10H), 1.19-1.01 (s, 7H), 0.74 (s, 3H).

LCMS Rt=1.174 min in 2 min chromatography, 30-90AB, purity 100%, MS ESI calcd. for $C_{29}H_{44}NO_2$ $[M+H]^+$ 438, found 438.

Example 22. Synthesis of Compound 22

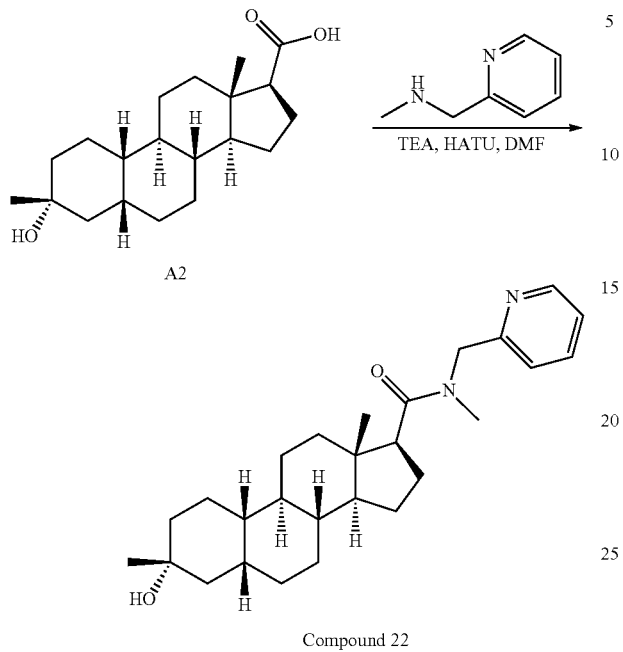

Compound 22

Step 1 (Compound 22).

To a solution of A2 (100 mg, 0.312 mmol) in DMF (4 mL) was added TEA (0.213 mL, 1.55 mmol) and HATU (177 mg, 0.468 mmol) at 30° C. After stirring at 30° C. for 30 mins, N-methyl-1-(pyridin-2-yl) methanamine (60.9 mg, 0.499 mmol) was added. The mixture was stirred at 30° C. for 16 h, treated with water (8 mL), filtered and concentrated. The crude product was purified by HPLC (Waters Xbridge 150*25 5 u, water (10 mM $NH_4HCO_3$)-ACN, gradient: 40-70% B, flow rate: 25 mL/min) to give Compound 22 (13 mg, 10%) as a solid.

$^1$H NMR (400 MHz, DMSO-$d_6$) δ 8.58-8.48 (m, 1H), 7.81-7.70 (m, 1H), 7.30-7.18 (m, 2H), 5.10-4.70 (m, 1H), 4.49-4.45 (m, 1H), 3.95-3.78 (m, 1H), 2.98-2.80 (m, 3H), 2.20-2.05 (m, 3H), 1.85-1.71 (m, 5H), 1.71-1.57 (m, 5H), 1.49-1.19 (m, 5H), 1.19-1.10 (m, 5H), 1.10-0.98 (m, 4H), 0.70 (s, 3H).

LCMS Rt=0.668 min in 2 min chromatography, 30-90AB, purity 100%, MS ESI calcd. for $C_{27}H_{41}N_2O_2$ $[M+H]^+$ 425, found 425.

Example 23. Synthesis of Compound 23

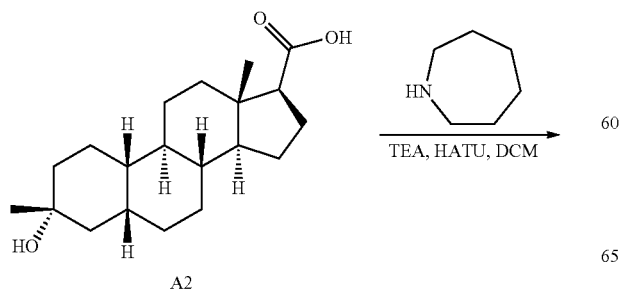

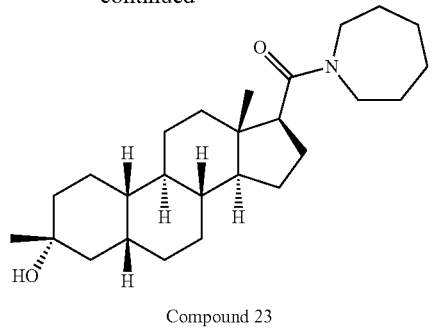

Compound 23

Step 1 (Compound 23).

To a solution of A2 (100 mg, 0.312 mmol) in DCM (2 mL) was added HATU (177 mg, 0.468 mmol), TEA (0.213 mL, 1.55 mmol) and azepane (108 mg, 1.09 mmol) at 25° C. After stirring at 25° C. for 24 hrs, the mixture was poured into water (200 mL) and extracted with DCM (2×200 mL). The combined organic layers were washed with brine (100 mL), dried over anhydrous $Na_2SO_4$, filtered and concentrated. The residue was purified by column chromatography on silica gel (petroleum ether/ethyl acetate=0:1) and lyophilized to afford Compound 23 (78 mg, 62%) as a solid.

$^1$H NMR (400 MHz, $CDCl_3$) δ 3.90-3.70 (m, 2H), 3.30-3.15 (m, 2H), 2.70-2.60 (m, 1H), 2.25-2.15 (m, 1H), 1.85-1.55 (m, 13H), 1.54-1.45 (m, 8H), 1.44-1.05 (m, 13H), 0.76 (s, 3H).

LCMS Rt=1.121 min in 2 min chromatography, 30-90 AB, purity 98%, ESI calcd. for $C_{26}H_{44}NO_2$ $[M+H]^+$ 402, found 402.

Example 24. Synthesis of Compound 24

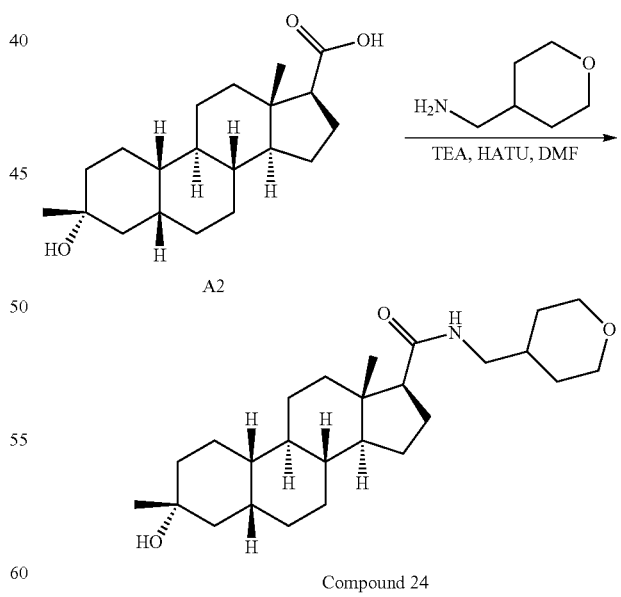

Compound 24

Step 1 (Compound 24).

To a solution of A2 (100 mg, 0.312 mmol) in DCM (2 mL) was added HATU (177 mg, 0.468 mmol), TEA (0.213 mL, 1.55 mmol) and (tetrahydro-2H-pyran-4-yl) methanamine (125 mg, 1.09 mmol) at 25° C. After stirring at 25° C. for 12 hrs, the mixture was poured into water (200 mL) and extracted with DCM (2×200 mL). The combined organic layers were washed with brine (100 mL), dried over anhydrous Na₂SO₄, filtered and concentrated. The residue was purified by column chromatography on silica (petroleum ether/ethyl acetate=0:1) and lyophilized to afford Compound 24 (48 mg, 37%) as a solid.

¹H NMR (400 MHz, CDCl₃) δ 5.40-5.30 (m, 1H), 4.05-3.90 (m, 2H), 3.40-3.30 (m, 2H), 3.25-3.15 (m, 1H) 3.10-3.00 (m, 1H), 2.15-2.05 (m, 2H), 1.90-1.55 (m, 12H), 1.50-1.00 (m, 19H), 0.67 (s, 3H).

LCMS Rt=0.934 min in 2 min chromatography, 30-90 AB, purity 97%, ESI calcd. for $C_{26}H_{44}NO_3$ $[M+H]^+$ 418, found 418.

Example 25. Synthesis of Compound 25

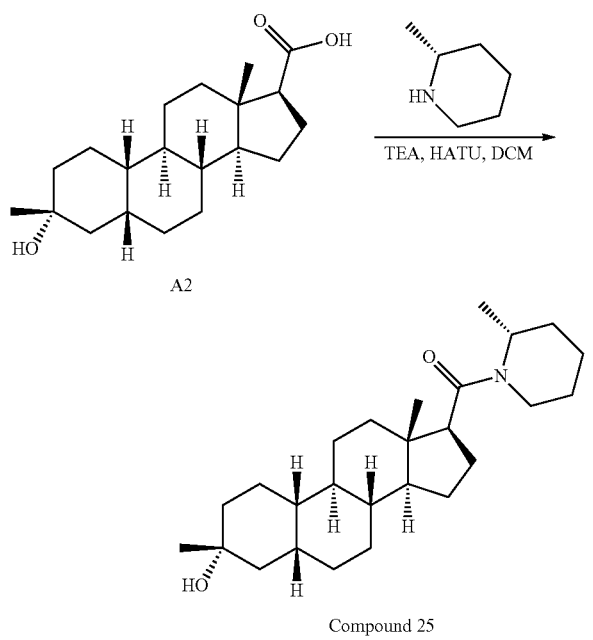

Step 1 (Compound 25) To a solution of A2 (100 mg, 0.312 mmol) in DCM (4 mL) was added TEA (156 mg, 1.55 mmol) and HATU (177 mg, 0.468 mmol) at 25° C. After stirring for 30 mins, (R)-2-methylpiperidine (60.4 mg, 0.499 mmol) was added to the reaction mixture. The reaction mixture was stirred at 25° C. for 2 hours. The reaction mixture was diluted with water (10 mL), extracted with EtOAc (3×10 mL). The combined organic layers were dried over Na₂SO₄, filtered and concentrated under reduced pressure. The residue was triturated with EtOAc (10 mL) and n-hexane (10 mL) to give Compound 25 (23 mg, 18%) as a solid.

¹H NMR (400 MHz, CDCl₃) δ 5.11-3.76 (m, 2H), 3.31-2.99 (m, 1H), 2.77-2.54 (m, 1H), 2.42-2.26 (m, 1H), 1.88-1.74 (m, 3H), 1.73-1.53 (m, 10H), 1.51-1.20 (m, 17H), 1.19-1.10 (m, 5H), 0.70-0.65 (m, 3H)

LCMS, Rt=1.113 min in 2.0 min chromatography, 30-90AB, purity 97.674%, MS ESI calcd. For $C_{26}H_{44}NO_2$ $[M+H]^+$ 402, found 402.

Example 26. Synthesis of Compound 26

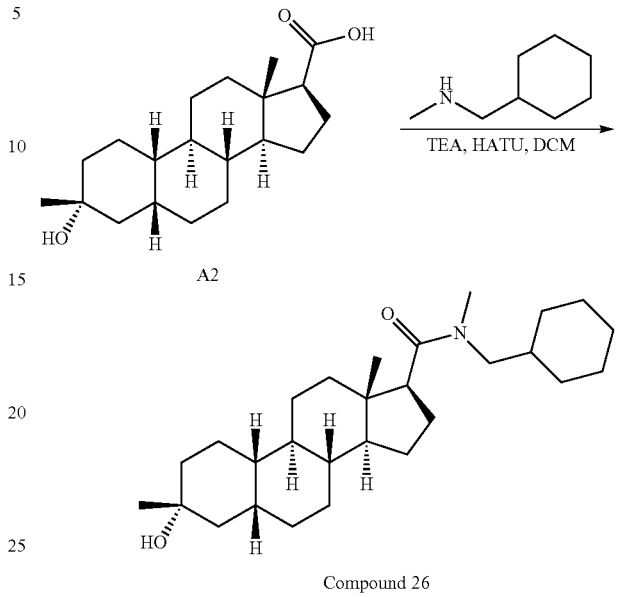

Step 1 (Compound 26).

To a solution of A2 (100 mg, 0.312 mmol) in DCM (4 mL) was added TEA (156 mg, 1.55 mmol) and HATU (177 mg, 0.468 mmol) at 25° C. The mixture was stirred at 25° C. for 30 mins. 1-cyclohexyl-N-methylmethanamine (60.4 mg, 499 mmol) was added to the reaction mixture. The reaction mixture was stirred at 25° C. for 2 hrs. The residue was diluted with water (10 mL), extracted with EtOAc (3×10 mL). The combined organic layers were dried over Na₂SO₄, filtered and concentrated in vacuo. The residue was purified by silica gel chromatography (PE/EtOAc=3/1 to 1/1) to afford Compound 26 (76 mg, 57%) as a solid.

¹H NMR (400 MHz, CDCl₃) δ 3.62-3.49 (m, 1H), 3.02 (s, 1H), 2.93-2.85 (m, 2H), 2.77-2.65 (m, 1H), 2.32-2.19 (m, 1H), 1.88-1.58 (m, 14H), 1.50-1.23 (m, 15H), 1.23-0.81 (m, 9H), 0.73 (m, 3H).

LCMS Rt=1.228 min in 2.0 min chromatography, 30-90AB, purity 100%, MS ESI calcd. for $C_{28}H_{48}NO_2$ $[M+H]^+$ 430, found 430.

Example 27. Synthesis of Compound 27

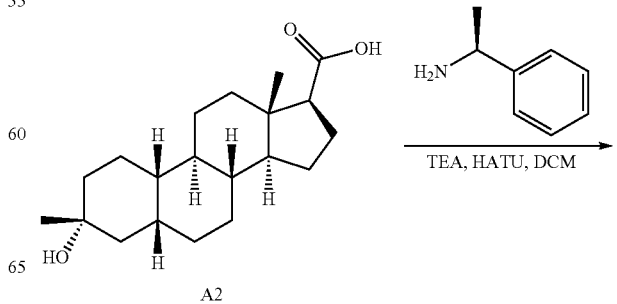

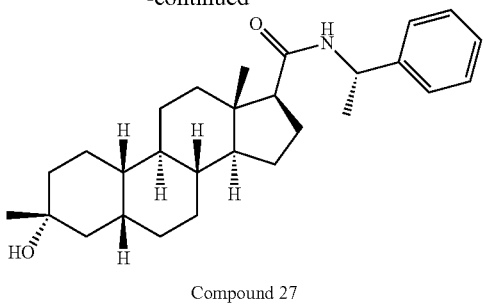

Compound 27

Step 1 (Compound 27).

To a solution of A2 (100 mg, 0.312 mmol) in DCM (4 mL) was added TEA (156 mg, 1.55 mmol) and HATU (177 mg, 0.468 mmol) at 25° C. The mixture was stirred at 25° C. for 30 mins. (S)-1-phenylethanamine (60.4 mg, 0.499 mmol) was added to the reaction mixture. The reaction mixture was stirred at 25° C. for 2 hrs. The residue was diluted with water (10 mL) and extracted with EtOAc (3×10 mL). The combined organic layers were dried over $Na_2SO_4$, filtered and concentrated in vacuo. The residue was triturated with EtOAc (10 mL) and n-hexane (10 mL) to give Compound 27 (28 mg, crude) as a solid, which was further purified by HPLC (Method: Column YMC-Actus Triart C18 100*30 mm*5 um; Conditions: water (0.05% HCl)-ACN; Begin B: 60; End B: 90; Gradient Time (min): 9.5; 100% B Hold Time (min): 2.5; FlowRate (ml/min); 25) to obtain Compound 27 (14 mg, 11%) as a solid.

HNMR (400 MHz, $CDCl_3$) δ 7.36-7.29 (m, 4H), 7.26-7.23 (m, 1H), 5.52-5.46 (m, 1H), 5.19-5.10 (m, 1H), 2.23-2.05 (m, 1H), 1.87-1.59 (t, 8H), 1.51-1.28 (m, 10H), 1.28-1.00 (m, 11H), 0.58 (s, 3H)

LCMS Rt=2.327 in in 4.0 min chromatography, 30-90AB, purity 99%, MS ESI calcd. for $C_{28}H_{42}NO_2$ $[M+H]^+$ 424, found 424.

Example 28. Synthesis of Compound 28

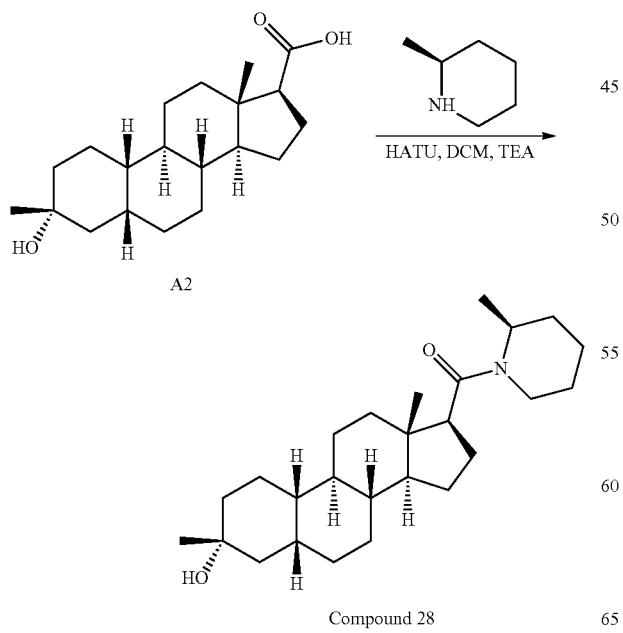

A2

Compound 28

Step 1 (Compound 28).

To a solution of A2 (100 mg, 0.312 mmol) in DCM (3 mL) was added TEA (156 mg, 1.55 mmol) and HATU (177 mg, 0.468 mmol) at 25° C. The mixture was stirred at 25° C. for 30 mins. (S)-2-methylpiperidine (46.4 mg, 0.468 mmol) was added. The mixture was stirred at 25° C. for 16 hrs. The reaction mixture was quenched with water (10 mL and extracted with DCM (2×10 mL). The combined organic layers were washed with brine (20 mL), dried over $Na_2SO_4$, concentrated in vacuo to give a crude product which was purified by flash silica gel chromatography (0~30% of EtOAc in PE) to give Compound 28 (18 mg, 14%) as a solid.

$^1H$ NMR (400 MHz, DMSO-$d_6$, t=80° C.) δ 4.80-4.47 (m, 1H), 4.18-3.83 (m, 2H), 2.99-2.82 (m, 1H), 2.79-2.69 (m, 1H), 2.21-2.02 (m, 2H), 1.82-1.57 (m, 9H), 1.56-1.46 (m, 3H), 1.45-1.18 (m, 11H), 1.17-0.96 (m, 10H), 0.67 (s, 3H).

LCMS Rt=1.123 min in 2 min chromatography, 30-90 AB, purity 100%, MS ESI calcd. For $C_{26}H_{44}NO_2$ $[M+H]^+$ 402, found 402.

Example 29. Synthesis of Compound 29

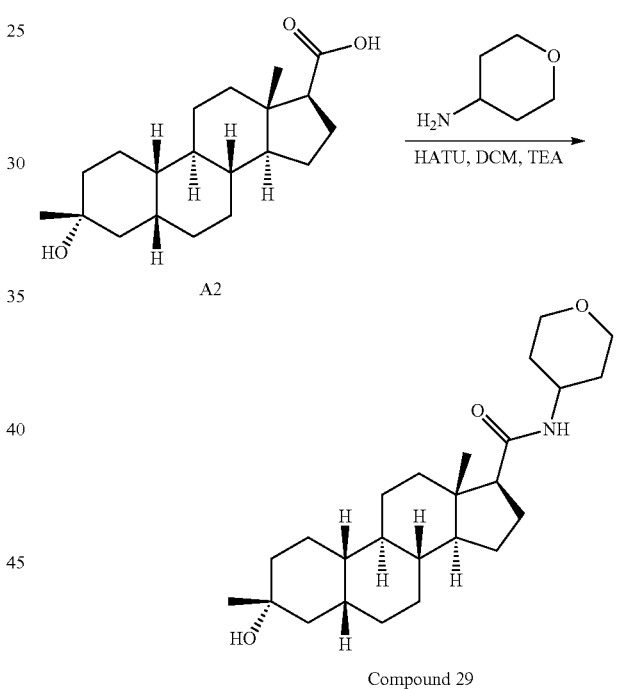

A2

Compound 29

Step 1 (Compound 29).

To a solution of A2 (100 mg, 0.312 mmol) in DCM (3 mL) was added TEA (156 mg, 1.55 mmol) and HATU (177 mg, 0.468 mmol) at 25° C. After stirring at 25° C. for 30 mins, tetrahydro-2H-pyran-4-amine (47.3 mg, 0.468 mmol) was added. The mixture was stirred at 25° C. for 16 hrs and treated with water (10 mL). The mixture was extracted with DCM (2×10 mL). The combined organic layers were washed with brine (20 mL), dried over $Na_2SO_4$, concentrated in vacuo to give a crude product, which was purified by flash silica gel chromatography (0~5% of MeOH in DCM) to give a solid. The crude residue (113 mg) was then triturated with MTBE (8 mL) at 15° C. to give Compound 29 (80 mg, 71%) as a solid. The compound was dissolved in DCM (30 mL) and the solution was washed with citric acid (2×20 mL), dried over anhydrous $Na_2SO_4$, filtered and concentrated in vacuo to give a crude product. The crude product was dissolved in MeCN/H$_2$O=1/2 (30 mL), concentrated in vacuo to remove most of MeCN and lyophilized to give Compound 29 (42 mg, 33%) as a solid.

$^1$H NMR (400 MHz, CDCl$_3$) δ 5.19-5.08 (m, 1H), 4.09-3.99 (m, 1H), 3.98-3.90 (m, 2H), 3.55-3.44 (m, 2H), 2.23-2.11 (m, 1H), 2.10-2.03 (m, 1H), 1.96-1.80 (m, 6H), 1.79-1.62 (m, 4H), 1.52-1.39 (m, 8H), 1.34-1.23 (m, 8H), 1.19-1.04 (m, 4H), 0.67 (s, 3H).

LCMS Rt=0.902 min in 2 min chromatography, 30-90 AB, purity 100%, MS ESI calcd. For C$_{25}$H$_{42}$NO$_3$ [M+H]$^+$ 404, found 404.

Example 30. Synthesis of Compound 30

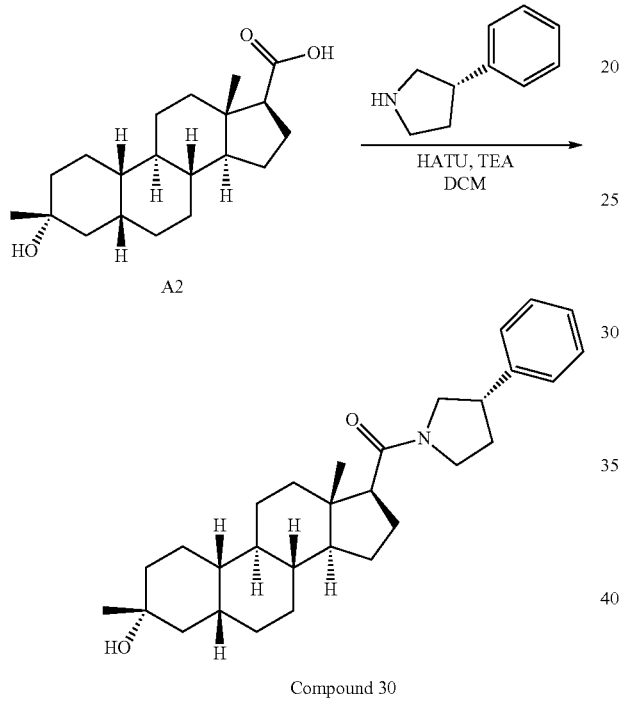

Compound 30

Step 1 (Compound 30).

To a solution of A2 (100 mg, 0.312 mmol) in DCM (3 mL) was added HATU (177 mg, 0.468 mmol) and Et$_3$N (156 mg, 1.55 mmol) at 25° C. After stirring at 25° C. for 0.5 hour, (S)-3-phenylpyrrolidine (73.4 mg, 0.499 mmol) was added. The reaction mixture was stirred at 40° C. for 10 hours, treated by water (10 mL) and extracted with EtOAc (2×10 mL). The combined organic phase was washed with water (2×10 mL) and saturated brine (10 mL), dried over anhydrous Na$_2$SO$_4$, filtered and concentrated. The residue was purified by flash column (0~30% of EtOAc in PE) to give Compound 30 (31 mg, 22%) as a solid.

$^1$H NMR (400 MHz, CDCl$_3$) δ 7.37-7.29 (m, 2H), 7.28-7.21 (m, 3H), 4.14-3.68 (m, 2H), 3.59-3.27 (m, 3H), 2.61-2.49 (m, 1H), 2.39-2.16 (m, 2H), 2.11-1.91 (m, 1H), 1.89-1.64 (m, 9H), 1.49-1.31 (m, 9H), 1.29-1.24 (m, 5H), 1.15-1.02 (m, 3H), 0.85-0.78 (m, 3H).

LCMS Rt=1.095 min in 2 min chromatography, 30-90AB, purity 100%, MS ESI calcd. for C$_{30}$H$_{44}$NO$_2$ [M+H]$^+$ 450, found 450.

SFC Rt=9.574 min in 15 min chromatography, IC_ETOH(DEA)_40_2,5ML_15MIN, 99% de. (Column: Chiralpak IC-3 150×4.6 mm I.D., 3 um; Mobile phase: 40% of ethanol (0.05% DEA) in CO$_2$. Flow rate: 2.5 mL/min Column temperature: 40° C.).

Example 31. Synthesis of Compound 31

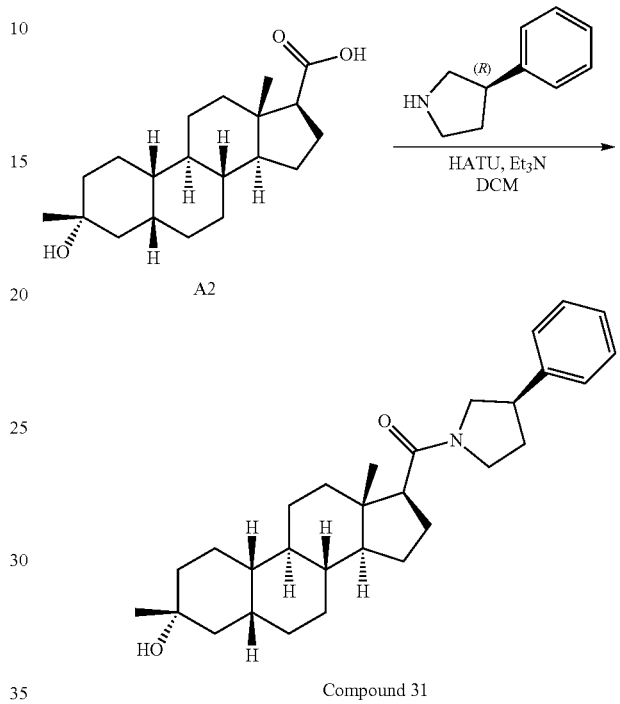

Compound 31

Step 1 (Compound 31)

To a solution of A2 (100 mg, 0.312 mmol) in DCM (3 mL) was added HATU (177 mg, 0.468 mmol) and Et$_3$N (156 mg, 1.55 mmol) at 25° C. After stirring at 25° C. for 0.5 hour, (R)-3-phenylpyrrolidine (73.4 mg, 0.499 mmol) was added at 25° C. The reaction mixture was stirred at 40° C. for 10 hrs and quenched with ice-water (10 mL). The aqueous phase was extracted with EtOAc (3×20 mL). The combined organic phase was washed with brine (2×10 mL), dried over anhydrous Na$_2$SO$_4$, filtered and concentrated. The residue was purified by HPLC (Instrument: BQ; Method: Column YMC-Actus Triart C18 100*30 mm*5 um; Conditions: water (0.05% HCl)-ACN; Gradient 80%-100% B; Gradient Time (min): 9.5) to obtain Compound 31 (8 mg, 6%) as a solid.

HNMR (400 MHz, CDCl$_3$) δ 7.37-7.29 (m, 2H), 7.26-7.21 (m, 2H), 4.04-3.93 (m, 1H), 3.82-3.70 (m, 1H), 3.66-3.28 (m, 3H), 2.64-2.50 (m, 1H), 2.39-2.18 (m, 2H), 2.08-1.95 (m, 1H), 1.90-1.62 (m, 8H), 1.54-1.22 (m, 17H), 1.13-1.05 (m, 2H), 0.79 (s, 3H).

LCMS Rt=1.090 min in 2.0 min chromatography, 30-90AB, purity 100%; ESI calcd. For C$_{30}$H$_{44}$NO$_2$ [M+H]$^+$ 450, found 450.

SFC Rt=11.297 min in 15 min chromatography, IC_ETOH(DEA)_40_2,5ML_15MIN, 100% de. (Column: Chiralpak IC-3 150×4.6 mm I.D., 3 um; Mobile phase: 40% of ethanol (0.05% DEA) in CO$_2$. Flow rate: 2.5 mL/min Column temperature: 40° C.).

Example 32. Synthesis of Compound 32

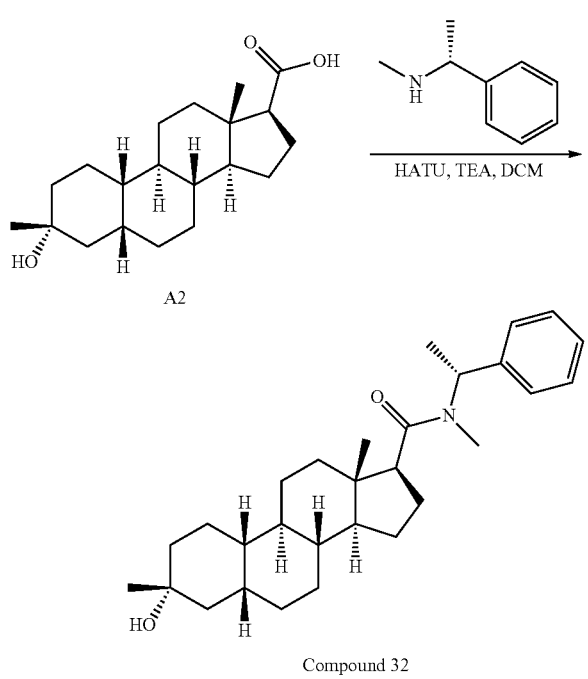

Compound 32

Step 1 (Compound 32).

To a solution of A2 (200 mg, 0.624 mmol) in DCM (2 mL) was added HATU (355 mg, 0.936 mmol) and TEA (125 mg, 1.24 mmol). The mixture was stirred at 25° C. for 20 min. To the mixture was added (R)—N-methyl-1-phenylethanamine (126 mg, 0.936 mmol). The mixture was stirred at 25° C. for another 12 hours. The mixture was poured into water (20 mL) and extracted with EtOAc (2×20 mL). The combined organic layers were washed with brine (2×20 mL), dried over anhydrous $Na_2SO_4$, filtered and concentrated in vacuo. The residue was purified by HPLC (column: Xtimate C18 150*25 mm*5 um, gradient: 64-89% B, conditions: water (0.05% HCl)-ACN, flow rate: 30 mL/min) to give Compound 32 (50 mg) as a solid. The Compound 32 was further purified by SFC (Column: OD (250 mm*30 mm, 5 um), Conditions: 0.1% $NH_3H_2O$ ETOH, Gradient: from 35% to 30%, FlowRate (ml/min): 50 mL/min, 25° C.) to afford Compound 32 (35 mg, 13%) as a solid.

$^1$H NMR (400 MHz, $CDCl_3$) δ 7.37-7.23 (m, 5H), 6.18 (q, J=12.0 Hz, 1H), 2.82-2.54 (m, 4H), 2.39-2.26 (m, 1H), 1.90-1.61 (m, 7H), 1.56 (s, 3H), 1.50-1.20 (m, 16H), 1.16-1.05 (m, 3H), 0.81 (s, 3H).

LCMS Rt=0.952 min in 1.5 min chromatography, 5-95AB, purity 100%, MS ESI calcd. for $C_{29}H_{44}NO_2$ [M+H]$^+$ 438, found 438.

Example 33. Synthesis of Compound 33 and Compound 34

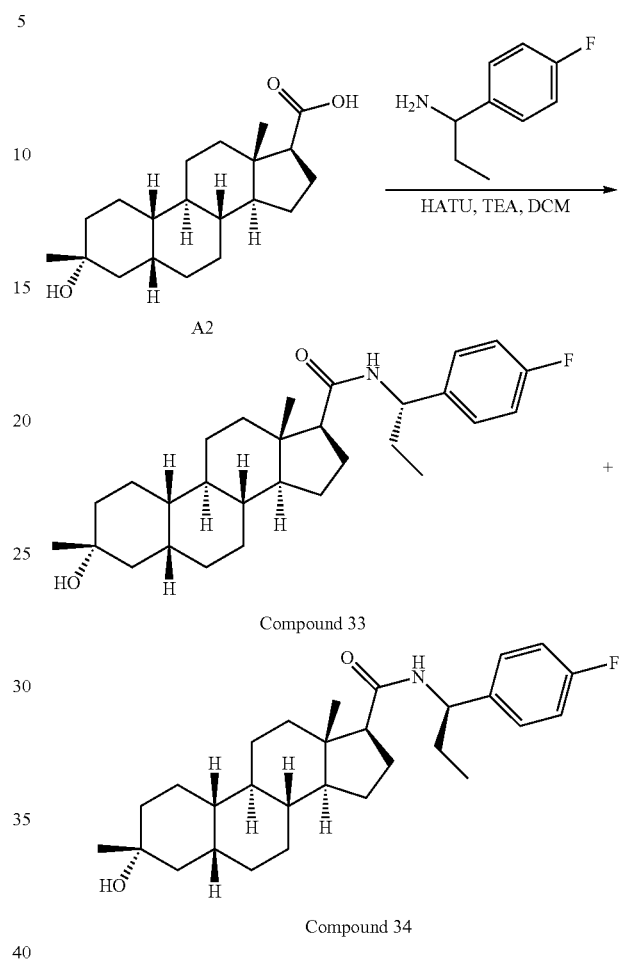

Step 1 (Compound 33 and Compound 34).

To a solution of A2 (1 g, 3.12 mmol) in DCM (10 mL) was added HATU (1.77 g, 4.68 mmol) and TEA (1.57 g, 15.6 mmol) at 25° C. The reaction mixture was stirred at 25° C. for 0.5 hour. 1-(4-fluorophenyl)propan-1-amine (764 mg, 4.99 mmol) was added to the reaction mixture at 25° C. The reaction mixture was stirred at 40° C. for 10 hours. The reaction mixture was treated with water (20 mL). The mixture was extracted with EtOAc (2×20 mL). The combined organic phase was washed with water (2×20 mL) and brine (20 mL), dried over anhydrous $Na_2SO_4$, filtered and concentrated. The residue was purified by flash silica gel chromatography (0~25% of EtOAc in PE) to give Compound 33 (Peak 1, 207 mg, 14%) and Compound 34 (Peak 2, 250 mg, 17%) as a solid.

(250 mg, 0.54 mmol) was further purified by flash column (0~25% of EtOAc in PE) to give Compound 34 (150 mg) as a light solid. Compound 34 The impure was re-purified by SFC (Chiralcel OJ 250*30 5 u), gradient: 25-25% B (A=0.1% $NH_3/H_2O$, B=EtOH), flow rate: 60 mL/min) to give Compound 34 (51 mg, 3%) as a solid.

Compound 33

$^1$H NMR (400 MHz, CDCl3) δ 7.25-7.21 (m, 2H), 7.06-6.96 (m, 2H), 5.46-5.38 (d, J=7.6 Hz, 1H), 4.93-4.82 (q,

J=7.2 Hz, J=15.2 Hz, 1H), 2.22-2.04 (m, 2H), 2.02-1.91 (m, 1H), 1.89-1.62 (m, 10H), 1.49-1.38 (m, 6H), 1.37-1.30 (m, 2H), 1.28-1.26 (m, 4H), 1.22-1.03 (m, 5H), 0.92-0.87 (t, J=7.2 Hz, 3H), 0.70 (s, 3H).

LCMS Rt=1.100 min in 2 min chromatography, 30-90AB, purity 100%, MS ESI calcd. for $C_{29}H_{43}FNO_2$ [M+H]$^+$ 456, found 456.

SFC Rt=3.350 min in 10 min chromatography, OJ-H_EtOH(DEA)_5_40_2.5M, 100% de. (Column: ChiralCel OJ-H 150×4.6 mm I.D., 5 um; Mobile phase: A: $CO_2$ B: Ethanol (0.05% DEA); Gradient: from 5% to 40% of B in 5.5 min and hold 40% for 3 min, then 5% of B for 1.5 min; Flow rate: 2.5 mL/min Column temperature: 40° C.).

SFC of a mixture of Compound 33 and Compound 34; Peak 1: Rt=3.121 min and Peak 2: Rt=3.372 min in 10 min chromatography, conditions: OJ-H_EtOH(DEA)_5_40_2.5M (Column: ChiralCel OJ-H 150×4.6 mm I.D., 5 um Mobile phase: A: $CO_2$ B: Ethanol (0.05% DEA). Gradient: from 5% to 40% of B in 5.5 min and hold 40% for 3 min, then 5% of B for 1.5 min Flow rate: 2.5 mL/min Column temperature: 40° C.).

Compound 34

$^1$H NMR (400 MHz, CDCl$_3$) δ 7.25-7.21 (m, 2H), 7.04-6.96 (m, 2H), 5.49-5.41 (d, J=8 Hz, 1H), 4.89-4.81 (q, J=7.6 Hz, J=15.2 Hz, 1H), 2.22-2.07 (m, 2H), 1.88-1.61 (m, 10H), 1.49-1.29 (m, 7H), 1.28-1.23 (m, 5H), 1.22-0.94 (m, 6H), 0.92-0.84 (t, J=7.2 Hz, 3H), 0.50 (s, 3H).

LCMS Rt=1.085 min in 2 min chromatography, 30-90AB, purity 100%, MS ESI calcd. for $C_{29}H_{43}FNO_2$ [M+H]$^+$ 456, found 456.

SFC Rt=3.116 min in 10 min chromatography, OJ-H_EtOH(DEA)_5_40_2.5M, 100% de. (Column: ChiralCel OJ-H 150×4.6 mm I.D., 5 um; Mobile phase: A: $CO_2$ B: Ethanol (0.05% DEA); Gradient: from 5% to 40% of B in 5.5 min and hold 40% for 3 min, then 5% of B for 1.5 min; Flow rate: 2.5 mL/min Column temperature: 40° C.).

Example 34. Synthesis of Compound 35

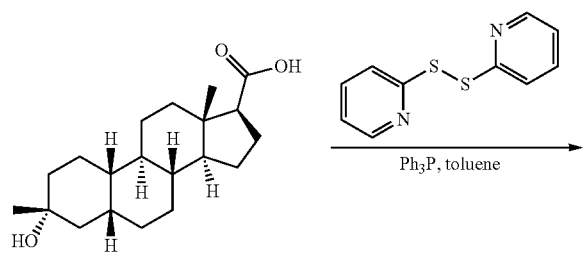

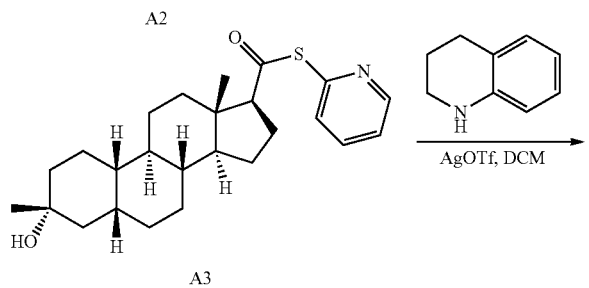

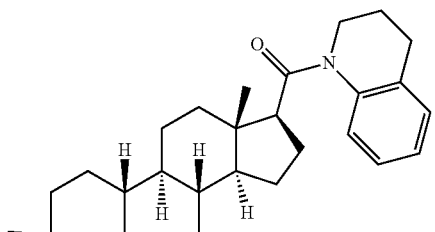

Compound 35

Step 1 (A3).

To a solution of A2 (1 g, 3.12 mmol) in toluene (20 mL) was added 1,2-di(pyridin-2-yl)disulfane (1.37 g, 6.24 mmol) and triphenylphosphine (1.63 g, 6.24 mmol). The mixture was stirred at 25° C. for 16 hrs. The reaction mixture was directly purified by a silica gel chromatography (PE/EtOAc=5/1) to give A3 (750 mg, 58%) as a solid.

$^1$H NMR (400 MHz, CDCl$_3$) δ 8.62-8.61 (m, 1H), 7.74-7.70 (m, 1H), 7.60 (d, J=8 Hz, 1H), 7.28-7.27 (m, 1H), 2.73 (t, J=8 Hz, 1H), 2.26-2.20 (m, 2H), 1.89-1.71 (m, 7H), 1.49-1.27 (m, 10H), 1.26-1.24 (m, 4H), 1.19-1.03 (m, 4H), 0.75 (s, 3H).

Step 2 (Compound 35).

To a solution of A3 (100 mg, 0.242 mmol) in DCM (3 mL) was added AgOTf (62.1 mg, 0.242 mmol), followed by 1,2,3,4-tetrahydroquinoline (48.2 mg, 0.363 mmol) at 25° C. The mixture was stirred at 25° C. for 16 hrs. The reaction mixture was filtered and the residue was washed with DCM (15 mL). The combined organic layers were washed with 1M HCl (10 mL), brine (30 mL), dried over Na$_2$SO$_4$, filtered and concentrated in vacuo to give Compound 35 (125 mg, crude) as an oil. The crude product was purified by HPLC (Column: YMC-Actus Triart C18 100*30 mm*5 um; Conditions: water (0.05% HCl)-CAN; Begin B: 80; End B: 100; Gradient Time (min): 10; 100% B Hold Time (min): 1; FlowRate (ml/min): 25.) to afford Compound 35 (4 mg, 4%) as a solid. LCMS Rt=1.126 min in 2 min chromatography, 30-90AB, purity 100%, MS ESI calcd. for $C_{29}H_{42}NO_2$ [M+H]$^+$ 436, found 436.

$^1$H NMR (400 MHz, CDCl$_3$) δ 7.24-7.04 (m, 4H), 4.44-4.19 (m, 1H), 3.40-3.10 (m, 2H), 2.82-2.58 (m, 2H), 2.37-2.01 (m, 3H), 1.86-1.70 (m, 7H), 1.41-1.23 (m, 13H), 1.08-0.92 (m, 5H), 0.74 (s, 4H).

Example 35. Synthesis of Compound 36

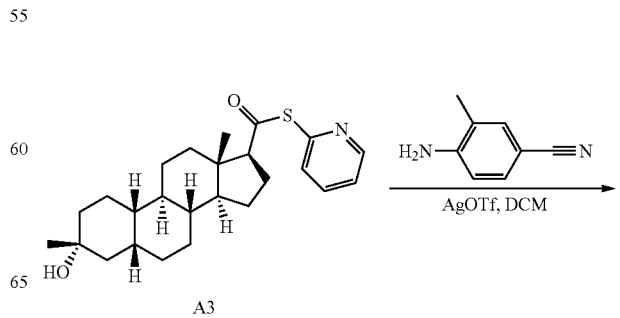

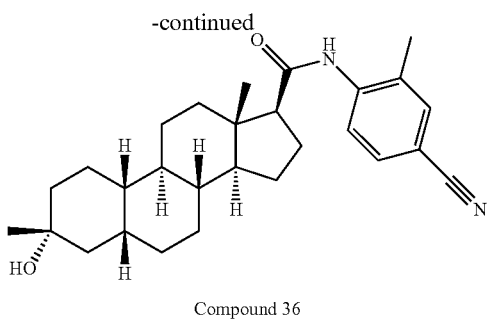

Compound 36

Step 1 (Compound 36).

To a solution of A3 (150 mg, 0.362 mmol) in DCM (3 mL) was added AgOTf (93 mg, 0.362 mmol), followed by 4-amino-3-methylbenzonitrile (71.7 mg, 0.543 mmol) at 25° C. After stirring the reaction at 25° C. for 1 hr, the reaction mixture was filtered and the residue was washed with DCM (15 mL). The combined organic layers were washed with 1M HCl (10 mL), brine (50 mL), dried over $Na_2SO_4$, filtered and concentrated in vacuo to give Compound 36 (130 mg, crude) as an oil. The crude Compound 36 (125 mg, 0.2869 mmol) was purified by HPLC (Method Column: YMC-Actus Triart C18 100*30 mm*5 um; Conditions: water (0.05% HCl)-ACN Begin B: 70; End B: 100; Gradient Time (min): 10; 100% B Hold Time (min): 1; FlowRate (ml/min): 25.) to afford Compound 36 (8 mg, 6%) as a solid.

$^1$H NMR (400 MHz, $CDCl_3$) δ 8.38-8.31 (m, 1H), 7.55-7.48 (m, 1H), 7.46 (s, 1H), 6.96 (s, 1H), 2.40-2.22 (m, 5H), 2.09-1.99 (m, 1H), 1.88-1.75 (m, 6H), 1.50-1.39 (m, 7H), 1.35-1.24 (m, 9H), 1.17-1.06 (m, 3H), 0.75 (s, 3H).

LCMS Rt=1.081 min in 2 min chromatography, 30-90AB, purity 100%, MS ESI calcd. for $C_{28}H_{39}N_2O_2$ $[M+H]^+$ 435, found 435.

Example 36. Synthesis of Compound 37

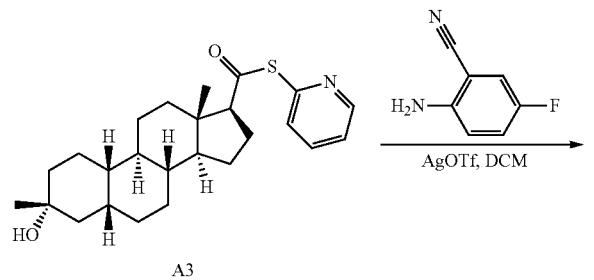

Step 1 (Compound 37).

To a solution of A3 (150 mg, 0.362 mmol) in DCM (3 mL) was added AgOTf (93 mg, 0.362 mmol), followed by adding 2-amino-5-fluorobenzonitrile (73.9 mg, 0.543 mmol) at 25° C. After stirring the reaction at 25° C. for 1 hr, the reaction mixture was filtered and the residue was washed with DCM (15 mL). The combined organic layers were washed with 1M HCl (10 mL), brine (50 mL), dried over $Na_2SO_4$, filtered and concentrated in vacuo to give Compound 37 (136 mg, crude) as an oil. The crude Compound 37 (125 mg, 0.2869 mmol) was purified by HPLC (Method Column: YMC-Actus Triart C18 100*30 mm*5 um; Conditions: water (0.05% HCl)-ACN Begin B: 70; End B: 100; Gradient Time (min): 10; 100% B Hold Time (min): 1; FlowRate (ml/min): 25.) to afford Compound 37 (2 mg, 2%) as a solid.

LCMS Rt=1.044 min in 2 min chromatography, 30-90AB, purity 100%, MS ESI calcd. for $C_{27}H_{34}FN_2O$ $[M+H-H_2O]^+$ 421, found 421.

$^1$H NMR (400 MHz, $CDCl_3$) δ 8.48-8.40 (m, 1H), 7.49-7.42 (s, 1H), 7.33-7.27 (m, 2H), 2.44-2.35 (m, 1H), 2.34-2.21 (m, 1H), 2.19-2.07 (m, 1H), 1.93-1.71 (m, 6H), 1.52-1.37 (m, 7H), 1.36-1.21 (m, 9H), 1.19-1.01 (m, 3H), 0.75 (s, 3H).

Example 37. Synthesis of Compound 38

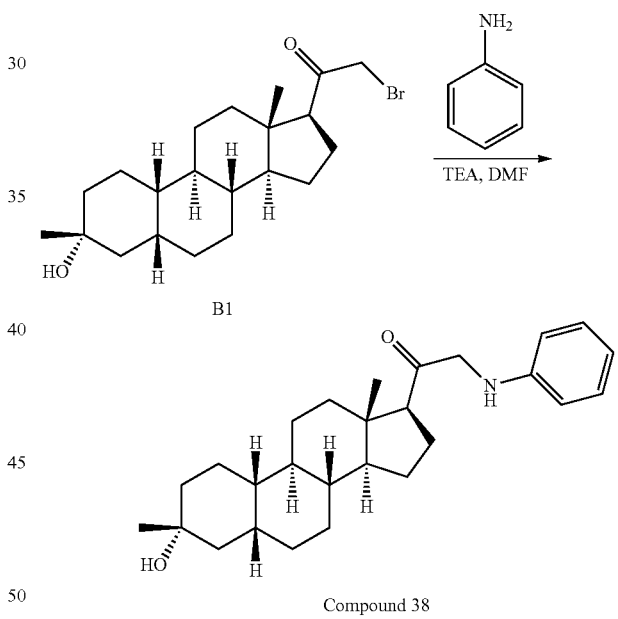

Compound 38

The synthesis of B1 is disclosed in WO2014/169833.

Step 1 (Compound 38).

To a solution of B1 (200 mg, 0.503 mmol) in DMF (5 mL) was added aniline (56.2 mg, 0.604 mmol) and TEA (151 mg, 1.50 mmol) at 25° C. under $N_2$. The mixture was stirred at 25° C. for 18 h to give a yellow solution. The mixture was poured into saturated aqueous LiCl (50 mL) and extracted with EtOAc (3×30 mL). The combined organic phase was washed with saturated brine (2×50 mL), dried over anhydrous $Na_2SO_4$, filtered and concentrated to give a light solid, which was purified by prep-HPLC (Column: YMC-Actus Triart C18 150*30 5 u; Conditions: water (0.05% HCl)-ACN; Gradient 46%-76% B; Gradient Time (min): 8) and lyophilized to give Compound 38 (42.0 mg, 21%) as a light solid.

$^1$H NMR (400 MHz, CDCl$_3$) δ 7.25-7.15 (m, 2H), 6.72-6.68 (m, 1H), 6.62-6.55 (m, 2H), 4.72-4.65 (m, 1H), 4.00-3.85 (m, 2H), 3.52-3.45 (m, 1H), 2.60-2.53 (m, 1H), 2.30-2.15 (m, 1H), 2.00-1.55 (m, 8H), 1.50-1.20 (m, 14H), 1.15-0.90 (m, 3H), 0.65 (s, 3H).

LCMS Rt=1.160 min in 2.0 min chromatography, 30-90 AB, purity 100%, MS ESI calcd. for C$_{27}$H$_{40}$NO$_2$ [M+H]$^+$ 410, found 410.

Example 38. Synthesis of Compound 39

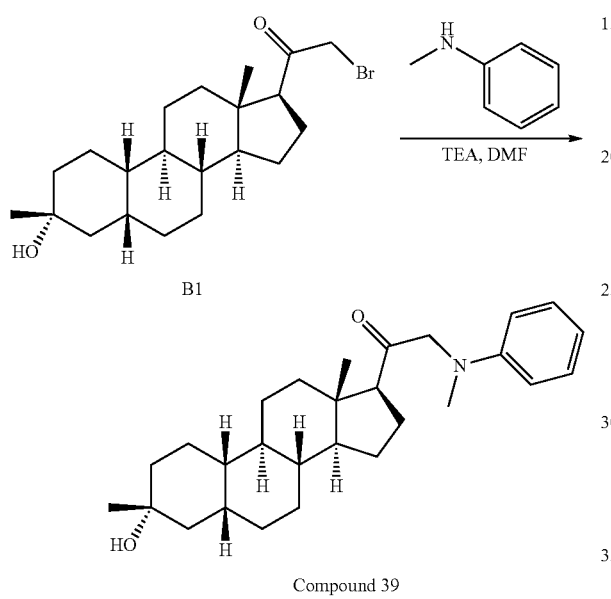

Compound 39

Step 1 (Compound 39).

To a solution of B1 (200 mg, 0.503 mmol) in DMF was added N-methylaniline (64.6 mg, 0.604 mmol) and TEA (151 mg, 1.50 mmol) at 25° C. under N$_2$. The mixture was stirred at 25° C. for 18 h to give a yellow solution. The mixture was poured into aqueous LiCl (50 mL, 1N) and extracted with EtOAc (3×30 mL). The combined organic phase was washed with saturated brine (2×50 mL), dried over anhydrous Na$_2$SO$_4$, filtered and concentrated to give a light solid. The crude product was purified by pre-HPLC (Column: YMC-Actus Triart C18 150*30 5 u; Conditions: water (0.05% HCl)-ACN; Gradient 46%-76% B; Gradient Time (min): 8) to afford an the compound (50 mg, containing residue of ammonium salt) as a light solid. The product was dissolved in DCM (5 mL) and washed with aqueous NaHCO$_3$ (10 mL). The aqueous layer was extracted with DCM (2×10 mL). The combined organic phase was dried over anhydrous Na$_2$SO$_4$, filtered and concentrated to give Compound 39 (21 mg, 10%) as a light solid.

$^1$H NMR (400 MHz, CDCl$_3$) δ 7.25-7.15 (m, 2H), 6.72-6.68 (m, 1H), 6.62-6.55 (m, 2H), 4.10-3.98 (m, 2H), 3.00 (s, 3H), 2.62-2.53 (m, 1H), 2.18-2.07 (m, 1H), 1.98-1.92 (m, 1H), 1.85-1.55 (m, 7H), 1.50-1.35 (m, 7H), 1.35-1.18 (m, 8H), 1.18-1.00 (m, 3H), 0.67 (s, 3H).

LCMS Rt=1.182 min in 2.0 min chromatography, 30-90 AB, purity 100%, MS ESI calcd. for C$_{28}$H$_{42}$NO$_2$ [M+H]$^+$ 424, found 424.

Example 39. Synthesis of Compound 40

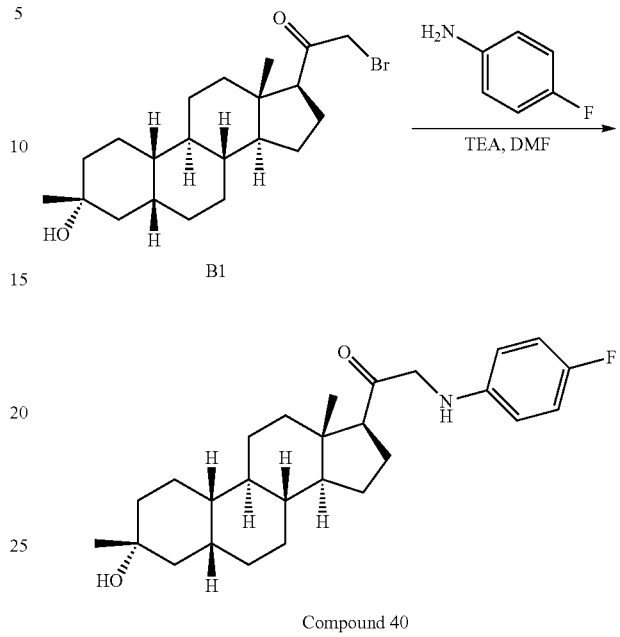

Compound 40

Step 1 (Compound 40).

To a solution of B1 (100 mg, 0.251 mmol) in DMF (5 mL) was added 4-fluoroaniline (33.4 mg, 0.301 mmol) and TEA (76.1 mg, 0.753 mmol) at 25° C. under N$_2$. The mixture was stirred at 25° C. for 16 h to give a yellow solution. The mixture was concentrated to give a light solid. The solid was purified by prep-HPLC (Column: Phenomenex Gemini 150*25 mm*10 um; Conditions: water (0.05% HCl)-ACN; Gradient 60%-100% B; Gradient Time (min): 10) to afford Compound 40 (25 mg, 23%) as a solid.

$^1$H NMR (400 MHz, CDCl$_3$) δ 6.95-6.86 (m, 2H), 6.68-6.60 (m, 2H), 4.00-3.85 (m, 2H), 2.58-2.52 (m, 1H), 2.26-2.12 (m, 1H), 1.95-1.55 (m, 9H), 1.50-1.14 (m, 15H), 1.14-0.96 (m, 3H), 0.63 (s, 3H).

LCMS Rt=0.962 min in 1.5 min chromatography, 5-95 AB, purity 100%, MS ESI calcd. for C$_{27}$H$_{39}$FNO$_2$ [M+H]$^+$ 428, found 428.

Example 40. Synthesis of Compound 41

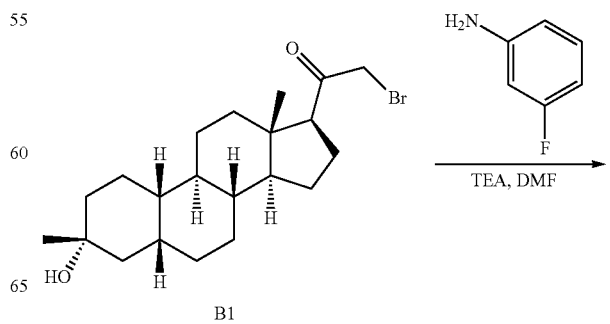

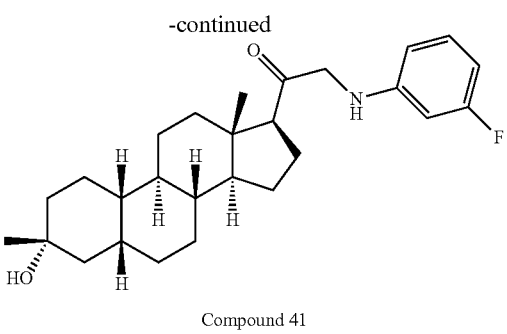

Compound 41

Step 1 (Compound 41).

To a solution of B1 (100 mg, 0.251 mmol) in DMF (5 mL) was added 3-fluoroaniline (33.4 mg, 0.301 mmol) and TEA (76.1 mg, 0.753 mmol) at 25° C. under $N_2$. The mixture was stirred at 25° C. for 16 h to give a yellow solution. The mixture was concentrated to give a light solid. The solid was purified by prep-HPLC (Column: Phenomenex Gemini 150*25 mm*10 um; Conditions: water (0.05% HCl)-ACN; Gradient 60%-100% B; Gradient Time (min): 10) to afford Compound 41 (7 mg, 7%) as a solid.

$^1$H NMR (400 MHz, CDCl$_3$) δ 7.13-7.05 (m, 1H), 6.45-6.33 (m, 2H), 6.30-6.22 (m, 1H), 3.96-3.83 (m, 2H), 2.58-2.52 (m, 1H), 2.26-2.12 (m, 1H), 2.02-1.55 (m, 10H), 1.50-1.14 (m, 14H), 1.14-0.93 (m, 3H), 0.65 (s, 3H).

LCMS Rt=0.988 min in 1.5 min chromatography, 5-95 AB, purity 100%, MS ESI calcd. for $C_{27}H_{39}FNO_2$ [M+H]$^+$ 428, found 428.

Example 41. Synthesis of Compound 42

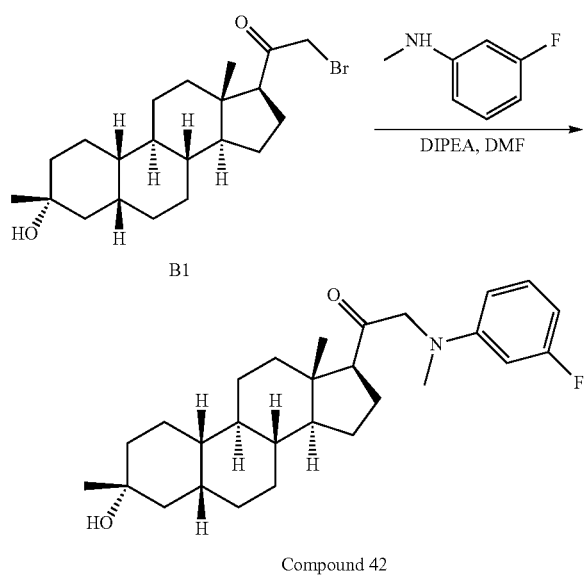

Compound 42

Step 1 (Compound 42). To a suspension of diisopropyl-ethylamine (42.1 mg, 0.326 mmol) in DMF (5 mL) was added 3-fluoro-N-methylaniline (62.7 mg, 0.502 mmol) at 25° C. under $N_2$. After stirring at 25° C. for 30 min, a solution of B1 (100 mg, 0.251 mmol) in DMF (5 mL) was added. The mixture was stirred at 40° C. for 16 h to give a yellow solution. The mixture was concentrated to give a product as a light yellow oil (150 mg, crude), which was purified by HPLC (Column: Phenomenex Gemini C18 250*50 10 u; Conditions: water (0.05% ammonia hydroxide v/v)-ACN; Gradient 80%-90% B; Gradient Time (min): 8) to afford Compound 42 (11 mg, 10%) as a solid.

$^1$H NMR (400 MHz, CDCl$_3$) δ 7.13-7.05 (m, 1H), 6.40-6.20 (m, 3H), 4.08-3.98 (m, 2H), 2.98 (s, 3H), 2.60-2.50 (m, 1H), 2.22-2.08 (m, 1H), 2.05-1.95 (m, 1H), 1.90-1.50 (m, 7H), 1.50-1.35 (m, 7H), 1.35-1.20 (m, 8H), 1.20-1.00 (m, 3H), 0.67 (s, 3H).

LCMS Rt=1.197 min in 2.0 min chromatography, 30-90 AB, purity 100%, MS ESI calcd. for C28H41FNO2 [M+H]$^+$ 442, found 442.

Example 42. Synthesis of Compound 43

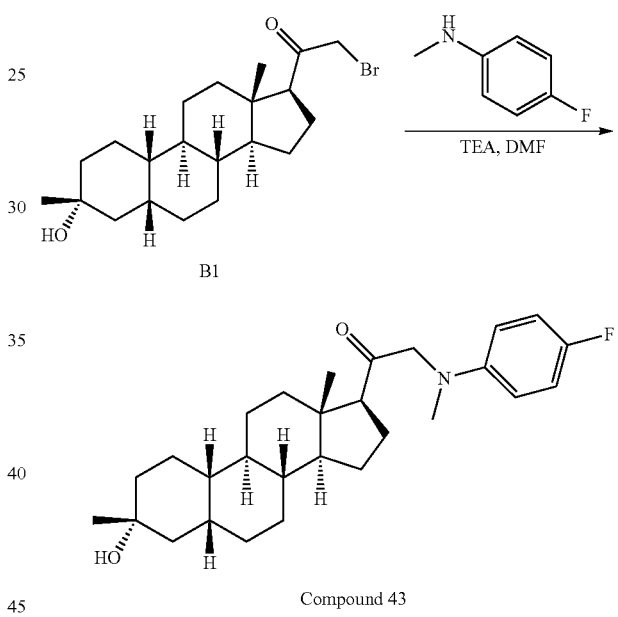

Compound 43

Step 1 (Compound 43).

To a solution of B1 (100 mg, 0.251 mmol) in DMF (5 mL) was added 4-fluoro-N-methylaniline (37.6 mg, 0.301 mmol) and TEA (76.1 mg, 0.753 mmol) at 25° C. under $N_2$. The mixture was stirred at 25° C. for 16 h to give a yellow solution. The reaction was concentrated to give a light solid. The solid was purified by prep-HPLC (Column: Phenomenex Gemini 150*25 mm*10 um; Conditions: water (0.05% HCl)-ACN; Gradient 60%-100% B; Gradient Time (min): 10) to afford Compound 43 (30 mg, 27%) as a solid.

$^1$H NMR (400 MHz, CDCl$_3$) δ 6.95-6.86 (m, 2H), 6.58-6.47 (m, 2H), 4.05-3.95 (m, 2H), 2.97 (s, 3H), 2.60-2.52 (m, 1H), 2.18-2.07 (m, 1H), 1.96-1.51 (m, 9H), 1.51-1.02 (m, 17H), 0.66 (s, 3H).

LCMS Rt=0.971 min in 1.5 min chromatography, 5-95 AB, purity 100%, MS ESI calcd. for $C_{28}H_{41}FNO_2$ [M+H]$^+$ 442, found 442.

Example 43. Synthesis of Compound 44

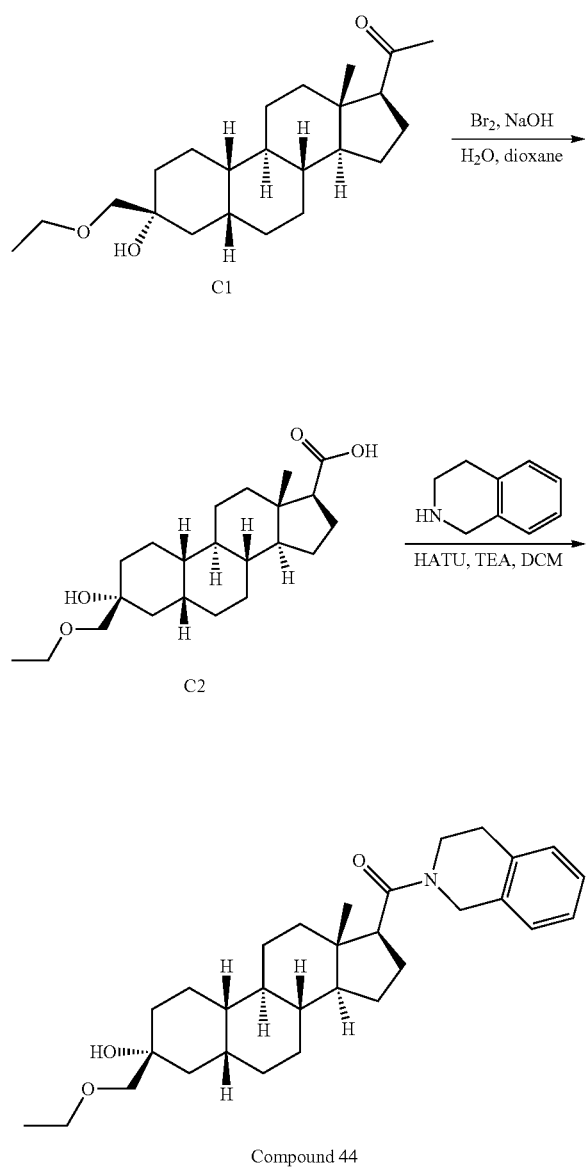

The synthesis of C1 is disclosed in WO2015/180679.

Step 1 (C2).

Liquid bromine (6.55 g, 41.0 mmol) was added slowly to a vigorously stirred sodium hydroxide aqueous solution (54.6 mL, 3 M, 164 mmol) at 0° C. When all the bromine was dissolved, the mixture was diluted with cold dioxane (15 mL) and added slowly to a stirred solution of C1 (5 g, 13.7 mmol) in dioxane (20 mL) and water (15 mL). The homogeneous yellow solution became colorless slowly and a white precipitate formed, and the reaction mixture was stirred at 25° C. for 5 hrs. The remaining oxidizing reagent was quenched by addition of an aqueous $Na_2S_2O_3$ solution (30 mL) and the mixture was then heated to 80° C. until the solid material dissolved. The solution was acidified with HCl (3 M, 40 mL), and a solid precipitated. The solid was filtered and washed with water (3×100 mL) to give a solid, which was dried in vacuo to afford C2 (5 g, crude) as a solid.

$^1$H NMR (400 MHz, $CDCl_3$) δ 11.89 (br s, 1H), 4.13 (br s, 1H), 3.46 (q, J=7.0 Hz, 2H), 3.32-3.26 (m, 2H), 2.29 (t, J=9.2 Hz, 1H), 1.99-1.89 (m, 2H), 1.78-1.46 (m, 7H), 1.41-1.14 (m, 11H), 1.11 (t, J=7.0 Hz, 3H), 1.07-0.91 (m, 3H), 0.62 (s, 3H).

Step 2 (Compound 44).

To a solution of C2 (100 mg, 0.274 mmol) in DCM (3 mL) was added HATU (156 mg, 0.411 mmol) and $Et_3N$ (137 mg, 1.36 mmol) at 25° C. The reaction mixture was stirred at 25° C. for 0.5 hour. 1,2,3,4-Tetrahydroisoquinoline (54.7 mg, 0.411 mmol) was added to the reaction mixture at 25° C. The reaction mixture was stirred at 25° C. for 1 hour. The reaction mixture was quenched with ice-water (10 mL). The aqueous phase was extracted with EtOAc (3×20 mL). The combined organic phase was washed with brine (2×10 mL), dried over anhydrous $Na_2SO_4$, filtered and concentrated. The residue was purified by HPLC (Instrument: BQ; Method: Column YMC-Actus Triart C18 100*30 mm*5 um; Conditions: water (0.05% HCl)-ACN; Begin B: 80 End B: 100; Gradient Time (min): 8; 100% B Hold Time (min): 2; FlowRate (ml/min); 25; Injections: 8) to obtain Compound 44 (65.0 mg, 50%) as a solid.

$^1$H NMR (400 MHz, $CDCl_3$) δ 7.26-7.02 (m, 4H), 4.88-4.65 (m, 2H), 4.00-3.65 (m, 2H), 3.56-3.36 (m, 4H), 2.90-2.66 (m, 3H), 2.35 (m, 1H), 1.80-1.56 (m, 9H), 1.56-0.96 (m, 17H), 0.76-0.72 (m, 3H).

LCMS Rt=0.971 min in 1.5 min chromatography, 5-95 AB, purity 100%, MS ESI calcd. for $C_{31}H_{46}NO_3$ [M+H]$^+$ 480, found 480.

Example 44. Synthesis of Compound 45 and Compound 46

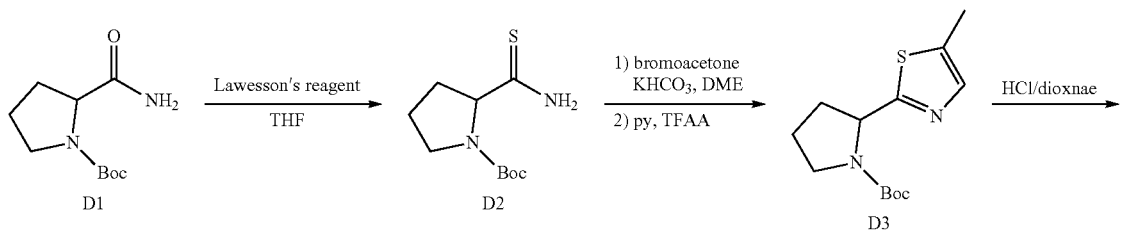

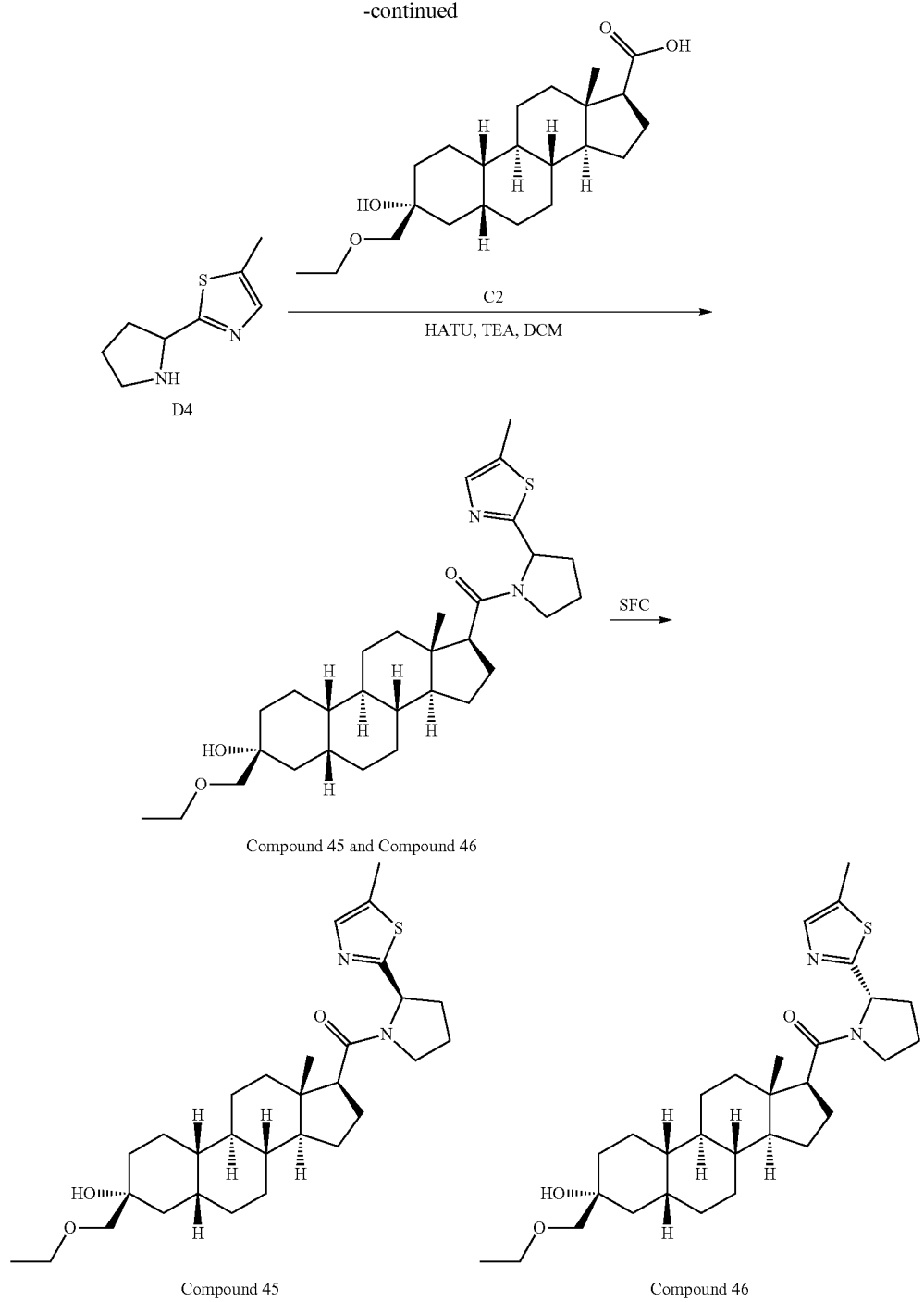

Compound 45 and Compound 46

Compound 45

Compound 46

Step 1 (D2).

To a solution of commercially available D1 (10 g, 46.6 mmol) in THF (60 mL) was added Lawesson's reagent (9.42 g, 23.3 mmol). The mixture was stirred at 20° C. for 1 h. The mixture was concentrated in vacuo. To the residue was added NaHCO$_3$ (120 mL, sat.) and the mixture was stirred at 20° C. for 1 h. The mixture was filtered, the precipitate was washed with water (2×50 mL), dried in vacuo to give D2 (9.5 g, 89%) as a solid.

$^1$H NMR (400 MHz, CDCl$_3$) δ 7.49 (br, 2H), 4.65 (dd, J=3.6, 8.4 Hz, 1H), 3.70-3.30 (m, 2H), 2.70-1.80 (m, 4H), 1.46 (s, 9H).

LCMS Rt=0.814 min in 2.0 min chromatography, 10-80, purity 100%, MS ESI calcd. for C$_5$H$_{11}$N$_2$S [M+H-Me$_2$C=CH$_2$—CO$_2$]$^+$ 131, found 131.

Step 2 (D3).

To a solution of D2 (5 g, 21.7 mmol) in DME (250 mL) was added KHCO$_3$ (17.3 g, 173 mmol) and bromoacetone (8.91 g, 65.1 mmol). The mixture was stirred at 20° C. for 1 h. To the mixture was added pyridine (14.5 g, 184 mmol) and TFAA (18.2 g, 86.8 mmol) at 0° C. The mixture was stirred at 20° C. for 16 h. To the mixture was added NaHCO$_3$ (150 mL, sat.) and the mixture was concentrated in vacuo. The residue was dissolved in EtOAc (200 mL) and washed with water (200 mL), dried over Na$_2$SO$_4$, filtered, concentrated in vacuo and purified by flash column (0~20% EtOAc in PE) to give D3 (3.6 g, 62%) as an oil.

$^1$H NMR (400 MHz, CDCl$_3$) δ 6.73 (s, 1H), 5.38-5.00 (m, 1H), 3.69-3.37 (m, 2H), 2.41 (s, 3H), 2.38-2.11 (m, 2H), 2.00-1.82 (m, 2H), 1.54-1.29 (m, 9H).

LCMS Rt=1.059 min in 2.0 min chromatography, 10-80, purity 97.4% (220 nm), MS ESI calcd. for C$_{13}$H$_{21}$N$_2$O$_2$S [M+H]$^+$ 269, found 269.

Step 3 (D4). To D3 (3.6 g, 13.4 mmol) was added HCl/dioxane (20 mL, 4 M). The mixture was stirred at 20° C. for 15 min. The mixture was concentrated in vacuo. The residue was dissolved in water (25 mL) and washed with MTBE (20 mL). The aqueous phase was basified with Na$_2$CO$_3$ (sat.) till pH=10.

The mixture was extracted with MTBE (2×20 mL). The combined organic layers were dried over Na$_2$SO$_4$, filtered, concentrated in vacuo to give 5-methyl-2-(pyrrolidin-2-yl)thiazole, D4 (1 g, purity 90%, yield 40%) as a light brown oil.

$^1$H NMR (400 MHz, CDCl$_3$) 6.73 (s, 1H), 4.52 (dd, J=6.4 Hz, 8.0 Hz, 1H), 3.18-3.10 (m, 1H), 3.10-3.00 (m, 1H), 2.40 (s, 3H), 2.34-2.22 (m, 1H), 2.21-2.04 (br, 1H), 2.00-1.75 (m, 5H).

LCMS Rt=0.544 min in 2.0 min chromatography, 0-30 AB, purity 100%, MS ESI calcd. for C$_8$H$_{13}$N$_2$S [M+H]$^+$ 169, found 169.

Step 4 (Mixture of Compound 45 and Compound 46).

To a solution of C2 (200 mg, 0.548 mmol) in DCM (5 mL) was added HATU (312 mg, 0.822 mmol) and Et$_3$N (275 mg, 2.73 mmol) at 25° C. The reaction mixture was stirred at 25° C. for 0.5 hour. 5-methyl-2-(pyrrolidin-2-yl)thiazole (D4, 138 mg, 0.822 mmol) was added to the reaction mixture at 25° C. After stirring at 25° C. for 10 hours, the reaction mixture was quenched with ice-water (20 mL) and extracted with DCM (3×5 mL). The combined organic phase was dried over anhydrous Na$_2$SO$_4$, filtered, concentrated to give a racemic mixture of Compound 45 and Compound 46 (200 mg) as an oil that was further purified.

LCMS Rt=0.902 min in 1.5 min chromatography, 5-95AB, purity 65%, MS ESI calcd. for C$_{30}$H$_{47}$N$_2$O$_3$S [M+H]$^+$ 515, found 515.

Step 5 (Compound 45 and Compound 46).

The impure racemic mixture of Compound 45 and Compound 46 (200 mg, 0.388 mmol) was separated by SFC (column: AD (250 mm*30 mm, 5 um), gradient: 45-45% B (A=0.05% NH$_3$/H$_2$O, B=MeOH), flow rate: 60 mL/min) to give Compound 45 (Peak 1, 33 mg, 16%) and Compound 46 (Peak 2, 43 mg, 21%) as a solid.

SFC Peak 1: Rt=5.407 min and Peak 2 Rt=7.126 min in 10 min chromatography, AD_3_IPA_DEA_5_40_25ML. (Column: Chiralpak AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.).

Compound 45

$^1$H NMR (400 MHz, CDCl$_3$) δ 6.83-6.67 (m, 1H), 5.49-5.22 (m, 1H), 3.79-3.59 (m, 2H), 3.56-3.37 (m, 4H), 2.75-2.68 (m, 1H), 2.60-2.53 (m, 1H), 2.50-2.37 (m, 3H), 2.32-1.90 (m, 6H), 1.88-1.65 (m, 7H), 1.49-1.25 (m, 9H), 1.22-1.19 (m, 3H), 1.18-0.99 (m, 4H), 0.98-0.93 (m, 1H), 0.83 (s, 3H).

LCMS Rt=1.261 min in 2.0 min chromatography, 10-80AB, purity 100%, MS ESI calcd. for C$_{30}$H$_{47}$N$_2$O$_3$S [M+H]$^+$ 515, found 515.

SFC Rt=5.390 min in 10 min chromatography, AD_3_EtOH_DEA_5_40_25ML, 100% de. (Column: Chiralpak AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.).

Compound 46

$^1$H NMR (400 MHz, CDCl$_3$) δ 6.80-6.64 (m, 1H), 5.60-5.35 (m, 1H), 3.86-3.73 (m, 1H), 3.64-3.34 (m, 5H), 2.85-2.55 (m, 2H), 2.49-2.36 (m, 3H), 2.33-2.15 (m, 3H), 2.08-1.94 (m, 2H), 1.89-1.58 (m, 8H), 1.51-1.33 (m, 7H), 1.32-1.02 (m, 10H), 0.74 (s, 3H).

LCMS Rt=1.271 min in 2.0 min chromatography, 10-80AB, purity 100%, MS ESI calcd. for C$_{30}$H$_{47}$N$_2$O$_3$S [M+H]$^+$ 515, found 515.

SFC Rt=7.166 min in 10 min chromatography, AD_3_EtOH_DEA_5_40_25ML, 99.8% de. (Column: Chiralpak AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.).

Example 45. Synthesis of Compound 47

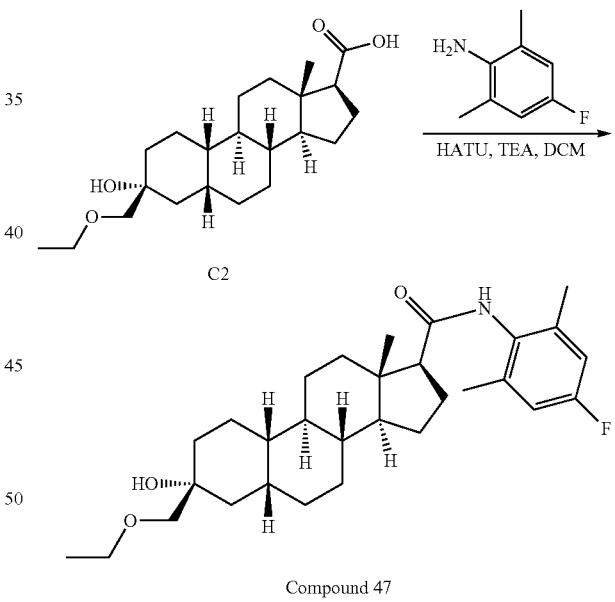

Compound 47

To a solution of C2 (200 mg, 0.548 mmol) in DMF (5 mL) was added HATU (312 mg, 0.822 mmol) and Et$_3$N (275 mg, 2.73 mmol) at 25° C. The reaction mixture was stirred at 25° C. for 0.5 hour. 4-fluoro-2,6-dimethylaniline (114 mg, 0.822 mmol) was added to the reaction mixture at 25° C. After stirring at 50° C. for 10 hours, the reaction mixture was quenched with water (20 mL) and extracted with EtOAc (3×10 mL). The combined organic phase was washed with 3% aqueous LiCl (2×20 mL), dried over anhydrous Na$_2$SO$_4$, filtered, concentrated and purified by flash silica gel chromatography (0-40% of EtOAc in PE) to give 50 mg impure product, which was purified by prep-HPLC (column: YMC- Actus Triart C18 100*30 mm*5 um), gradient: 80-100% B (A=water (0.05% HCl), B=MeCN), flow rate: 25 mL/min) to give Compound 47 (12 mg, 24%) as a solid.

$^1$H NMR (400 MHz, CDCl$_3$) δ 6.82-6.72 (m, 2H), 6.58-6.48 (m, 1H), 3.61-3.33 (m, 4H), 2.88-2.59 (m, 1H), 2.39-2.31 (m, 1H), 2.20 (s, 6H), 2.13-2.05 (m, 1H), 1.94-1.58 (m, 9H), 1.52-1.35 (m, 7H), 1.30-1.06 (m, 9H), 0.81 (s, 3H).

LCMS Rt=1.313 min in 2.0 min chromatography, 10-80AB, purity 100%, MS ESI calcd. for C$_{30}$H$_{45}$FNO$_3$ [M+H]$^+$ 486, found 486.

Example 46. Synthesis of Compound 48 and Compound 49

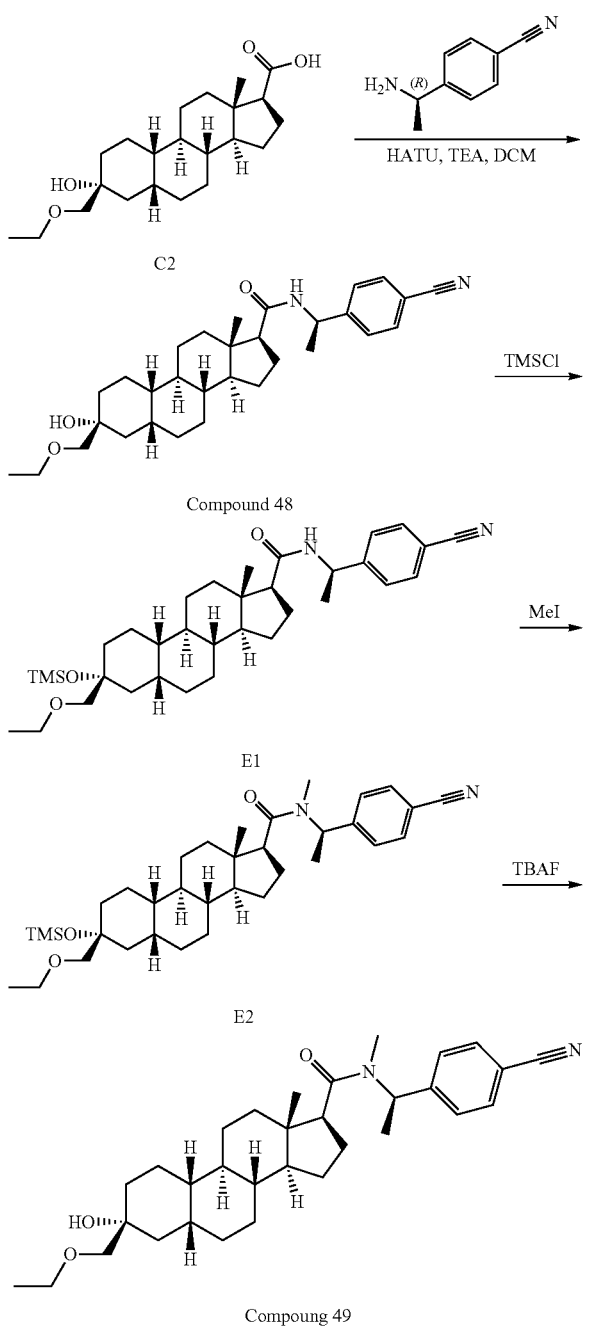

Step 1 (Compound 48).

To a solution of C2 (200 mg, 0.548 mmol) in DCM (5 mL) was added HATU (312 mg, 0.822 mmol) and Et$_3$N (275 mg, 2.73 mmol) at 25° C. The reaction mixture was stirred at 25° C. for 0.5 hour. (R)-4-(1-aminoethyl)benzonitrile (120 mg, 0.822 mmol) was added to the reaction mixture at 25° C. After stirring at 25° C. for 10 hours, the reaction mixture was quenched with water (20 mL) and extracted with EtOAc (3×5 mL). The combined organic phase was washed with saturated brine (2×10 mL), dried over anhydrous Na$_2$SO$_4$, filtered and concentrated to give a residue, which was purified by flash silica gel chromatography (0~60% of EtOAc in PE) and prep-TLC (PE:EtOAc=1:1) to give Compound 48 (150 mg, 55%) as a solid.

$^1$H NMR (400 MHz, CDCl$_3$) 7.65-7.59 (m, 2H), 7.44-7.37 (m, 2H), 5.52-5.44 (m, 1H), 5.22-5.11 (m, 1H), 3.57-3.49 (m, 2H), 3.48-3.38 (m, 2H), 2.74 (s, 1H), 2.21-2.07 (m, 2H), 1.95-1.88 (m, 1H), 1.87-1.62 (m, 7H), 1.51-1.32 (m, 9H), 1.32-1.24 (m, 3H), 1.23-1.18 (m, 4H), 1.17-1.02 (m, 4H), 0.68 (s, 3H).

LCMS Rt=4.765 min in 7.0 min chromatography, 10-80AB, purity 100%, MS ESI calcd. for C$_{31}$H$_{45}$N$_2$O$_3$ [M+H]$^+$ 493, found 493.

Step 2 (E1).

To a solution of Compound 48 (120 mg, 0.275 mmol) in DCM (3 mL) was added imidazole (198 mg, 2.91 mmol) and TMSCl (236 mg, 2.18 mmol) at 20° C. After stirring at 20° C. for 30 minutes, the mixture was quenched with water (10 mL) and extracted with DCM (2×5 mL). The combined organic layers were washed with water (10 mL), dried over Na$_2$SO$_4$, filtered and concentrated in vacuo to give E1 (137 mg, crude) as a solid.

$^1$H NMR (400 MHz, CDCl$_3$) δ 7.65-7.59 (m, 2H), 7.44-7.37 (m, 2H), 5.52-5.44 (m, 1H), 5.22-5.11 (m, 1H), 3.54-3.32 (m, 4H), 2.22-2.09 (m, 2H), 1.97-1.88 (m, 1H), 1.81-1.65 (m, 7H), 1.52-1.41 (m, 6H), 1.38-1.16 (m, 11H), 1.10-0.97 (m, 3H), 0.69 (s, 3H), 0.11 (s, 9H).

Step 3 (E2).

To a solution of E1 (137 mg, 0.242 mmol) in DMF (3 mL) was added NaH (96.6 mg, 2.42 mmol, 60% purity) at 0° C. After stirring at 0° C. under N$_2$ for 10 minutes, MeI (515 mg, 3.63 mmol) was slowly added at 0° C. under N$_2$. After stirring at this temperature for 10 minutes, the reaction mixture was quenched with water (10 mL) and extracted with EtOAc (2×5 mL). The combined organic phase was washed with LiCl (10 mL, 3% i aqueous), dried over Na$_2$SO$_4$, filtered and concentrated to give E2 (140 mg, crude) as a brown oil.

$^1$H NMR (400 MHz, CDCl$_3$) δ 7.71-7.57 (m, 2H), 7.41-7.34 (m, 2H), 6.21-6.12 (m, 0.84H), 5.41-5.28 (m, 0.16H), 3.55-3.31 (m, 4H), 2.78-2.62 (m, 4H), 2.37-2.25 (m, 1H), 1.82-1.65 (m, 9H), 1.53-1.39 (m, 8H), 1.36-1.29 (m, 5H), 1.15-1.04 (m, 6H), 0.91-0.75 (m, 3H), 0.10 (s, 9H).

Step 4 (Compound 49).

A solution of E2 (140 mg, 0.241 mmol) in TBAF (2.4 mL, 2.4 mmol, 1M in THF) was heated at 30° C. for 30 minutes. The mixture was quenched with 50% NH$_4$Cl (10 mL) and extracted with EtOAc (2×5 mL). The combined organic phase was washed with brine (2×10 mL), dried over Na$_2$SO$_4$, filtered, concentrated and purified by flash silica gel chromatography (0~15% of EtOAc in PE) to give Compound 49 (18 mg, 15%) as a solid.

$^1$H NMR (400 MHz, CDCl$_3$) δ 7.71-7.57 (m, 2H), 7.41-7.34 (m, 2H), 6.21-6.12 (m, 0.84H), 5.41-5.28 (m, 0.16H), 3.59-3.33 (m, 4H), 2.79-2.56 (m, 5H), 2.36-2.21 (m, 1H), 1.85-1.61 (m, 8H), 1.52-1.33 (m, 10H), 1.32-1.23 (m, 3H), 1.22-1.17 (m, 4H), 1.16-1.06 (m, 3H), 0.91-0.75 (m, 3H).

LCMS Rt=1.126 min in 2.0 min chromatography, 30-90AB, purity 100%, MS ESI calcd. for $C_{32}H_{47}N_2O_3$ [M+H]$^+$ 507, found 507.

Example 47. Synthesis of Compound 50

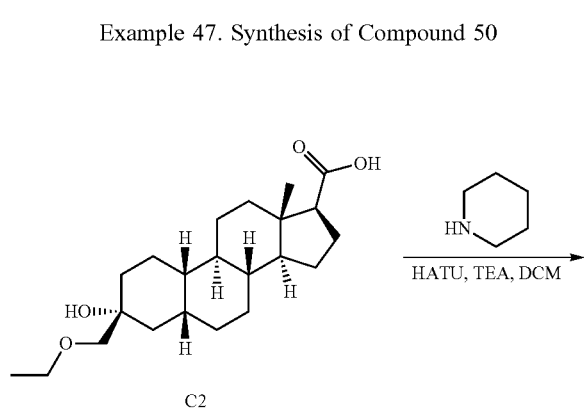

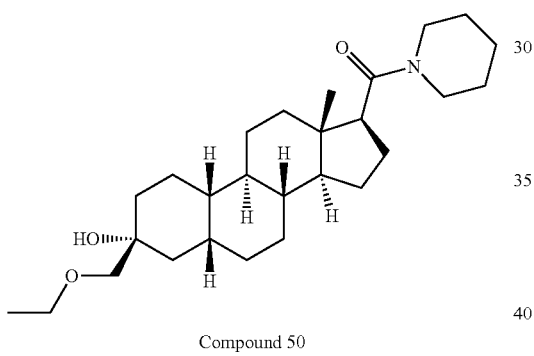

Compound 50

Step 1 (Compound 50).

To a solution of C2 (100 mg, 0.274 mmol) in DCM (3 mL) was added HATU (156 mg, 0.411 mmol) and TEA (137 mg, 1.36 mmol) at 25° C. After stirring at 25° C. for 10 min, piperidine (34.9 mg, 0.411 mmol) was added to the reaction mixture at 25° C. The reaction mixture was stirred at 25° C. for 1 hour and quenched with ice-water (10 mL). The aqueous phase was extracted with EtOAc (3×20 mL). The combined organic phase was washed with brine (2×10 mL), dried over anhydrous Na$_2$SO$_4$, filtered and concentrated. The residue was purified by HPLC (Instrument: BQ; Method: Column YMC-Actus Triart C18 100*30 mm*5 um; Conditions: water (0.05% HCl)-ACN; Begin B: 80; End B: 100; Gradient Time (min): 8; 100% B Hold Time (min): 2; FlowRate (ml/min): 25; Injections: 7) to obtain Compound 50 (78 mg, 66%) as a solid.

$^1$H NMR (400 MHz, CDCl$_3$) δ 3.65-3.38 (m, 8H), 2.75-2.65 (m, 2H), 2.38-2.25 (m, 1H), 1.86-1.56 (m, 12H), 1.50-1.00 (m, 19H), 0.72 (s, 3H).

LCMS Rt=1.104 min in 2 min chromatography, 30-90 AB, purity 100%, MS ESI calcd. for $C_{27}H_{46}NO_3$ [M+H]$^+$ 432, found 432.

Example 48. Synthesis of Compound 51

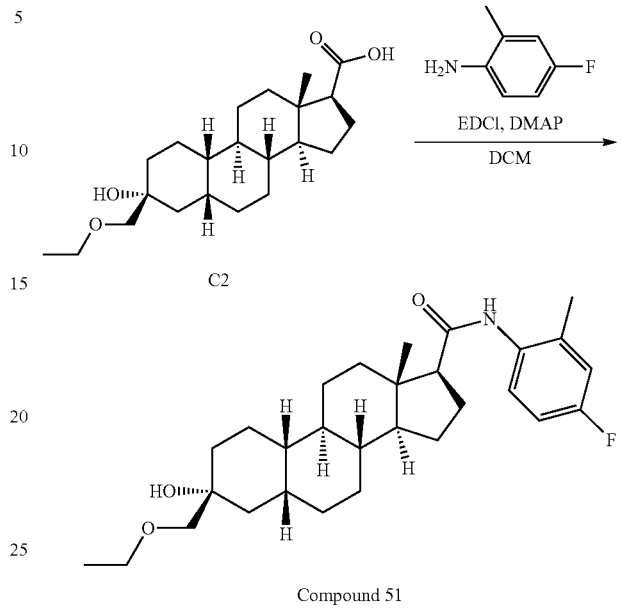

Compound 51

Step 1 (Compound 51).

To a solution of C2 (100 mg, 0.274 mmol) and 4-fluoro-2-methylaniline (41.0 mg, 0.328 mmol) in DCM (3 mL) was added EDCI (78.7 mg, 0.411 mmol) and DMAP (16.7 mg, 0.137 mmol). The mixture was stirred at 30° C. for 3 hrs. The reaction mixture was quenched with water (5 mL) and extracted with DCM (2×5 mL). The combined organic layers were washed with brine (5 mL), dried over anhydrous sodium sulfate, filtered and concentrated. The residue was purified by HPLC (Column: Xtimate C18 150*25 mm*5 um; Condition: water (0.05% HCl)-ACN; Gradient: 60%~90% B; FlowRate: 30 mL/min) to give Compound 51 (23 mg, 18%) as a solid.

$^1$H NMR (400 MHz, CDCl$_3$) δ 7.78-7.72 (m, 1H), 6.92-6.85 (m, 2H), 6.72 (s, 1H), 3.58-3.50 (m, 2H), 3.48-3.38 (m, 2H), 2.35-2.21 (m, 5H), 2.09-2.02 (m, 1H), 1.88-1.71 (m, 6H), 1.69-1.62 (m, 2H), 1.52-1.34 (m, 8H), 1.31-1.09 (m, 9H), 0.77 (s, 3H).

LCMS Rt=1.123 min in 2.0 min chromatography, 30-90AB, purity 100% (HPLC), MS ESI calcd. for $C_{29}H_{43}FNO_3$ [M+H]$^+$ 472, found 472.

Example 49. Synthesis of Compound 52

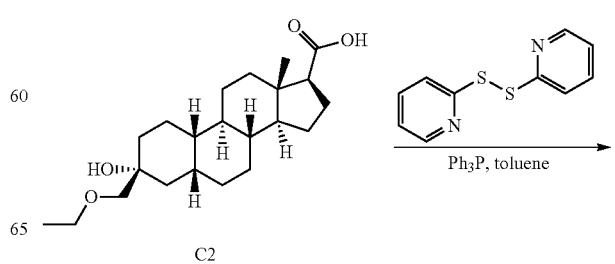

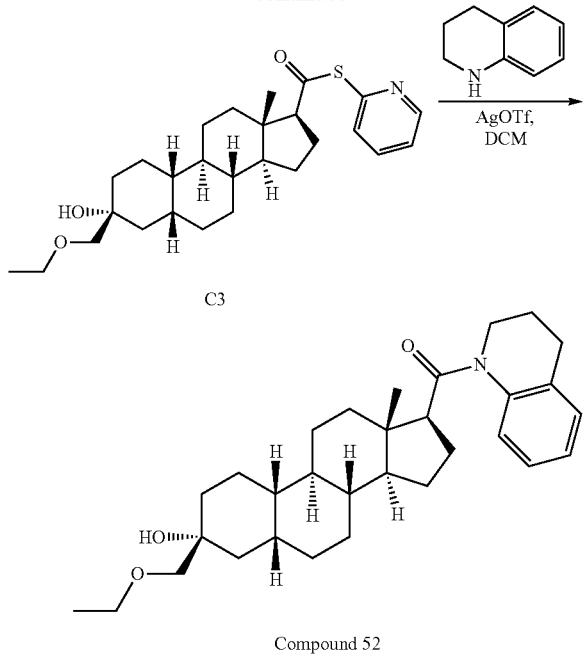

C3

Compound 52

Step 1 (C3).

To a solution of C2 (1 g, 2.74 mmol) in toluene (20 mL) was added 1,2-di(pyridin-2-yl)disulfane (1.2 g, 5.48 mmol) and triphenylphosphine (1.43 g, 5.48 mmol). The mixture was stirred at 25° C. for 16 hrs. The reaction mixture was purified by a silica gel chromatography (PE/EtOAc=5/1) to give C3 (800 mg, 64%) as a solid.

$^1$H NMR (400 MHz, CDCl$_3$) δ 8.62-8.61 (m, 1H), 7.74-7.70 (m, 1H), 7.60 (d, J=8 Hz, 1H), 7.28-7.27 (m, 1H), 3.53 (q, J=7 Hz, 2H), 3.43 (q, J=9.3 Hz, 2H), 2.79-2.68 (m, 2H), 2.28-2.16 (m, 2H), 1.94-1.60 (m, 8H), 1.50-1.33 (m, 7H), 1.30-1.03 (m, 9H), 0.74 (s, 3H).

Step 2 (Compound 52).

To a solution of C2 (100 mg, 0.218 mmol) in DCM (3 mL) was added AgOTf (56 mg, 0.218 mmol), followed by 1,2,3,4-tetrahydroquinoline (43.5 mg, 0.327 mmol) at 25° C. After stirring the reaction at 25° C. for 1 hrs, the reaction mixture was filtered and the filter cake was washed with DCM (15 mL). The combined organic layers were washed with 1M HCl (10 mL), brine (50 mL), dried over Na$_2$SO$_4$, filtered and concentrated in vacuo to give an oil (95 mg) which was purified by HPLC (Column: YMC-Actus Triart C18 100*30 mm*5 um; Conditions: water (0.05% HCl)-ACN; Gradient: 85% B~100% B; FlowRate: 25 mL/min) to give Compound 52 (16 mg, 17%) as a solid.

$^1$H NMR (400 MHz, CDCl$_3$) δ 7.23-7.02 (m, 4H), 4.42-4.22 (m, 1H), 3.54-3.48 (m, 2H), 3.43-3.34 (m, 2H), 3.32-3.12 (m, 2H), 2.79-2.59 (m, 3H), 2.34-2.20 (m, 1H), 2.13-2.03 (m, 1H), 1.82-1.63 (m, 6H), 1.52-1.35 (m, 6H), 1.34-1.24 (m, 4H), 1.22-1.14 (m, 5H), 1.10-0.83 (m, 5H), 0.73 (s, 3H).

LCMS Rt=1.190 min in 2.0 min chromatography, 30-90AB, purity 100%, MS ESI calcd. for C$_{31}$H$_{46}$NO$_3$ [M+H]$^+$ 480, found 480.

Example 50. Synthesis of Compound 53

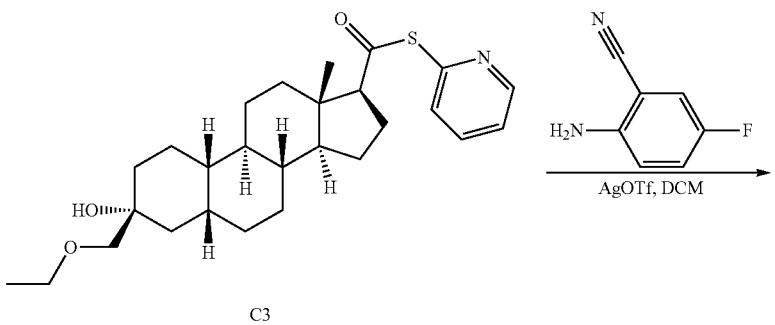

C3

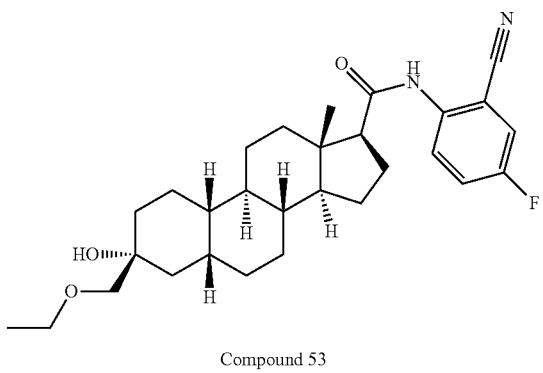

Compound 53

Step 1 (Compound 53).

To a solution of C3 (100 mg, 0.218 mmol) in DCM (3 mL) was added AgOTf (56 mg, 0.218 mmol), followed by 2-amino-5-fluorobenzonitrile (44.5 mg, 0.327 mmol) at 25° C. After stirring the reaction at 25° C. for 1 hrs, the reaction mixture was filtered and the filter cake was washed with DCM (15 mL). The combined organic layers were washed with 1M HCl (10 mL), brine (50 mL), dried over $Na_2SO_4$, filtered and concentrated in vacuo to give an oil (90 mg) which was purified by HPLC (Column: YMC-Actus Triart C18 100*30 mm*5 um; Conditions: water (0.05% HCl)-ACN; Gradient: 75% B~100% B; FlowRate: 25 mL/min) to give Compound 53 (18 mg, 20%) as a solid.

$^1$H NMR (400 MHz, $CDCl_3$) δ 8.46-8.40 (m, 1H), 7.45 (s, 1H), 7.34-7.26 (m, 2H), 3.57-3.50 (m, 2H), 3.48-3.38 (m, 2H), 2.71 (s, 1H), 2.43-2.36 (m, 1H), 2.33-2.21 (m, 1H), 2.16-2.09 (m, 1H), 1.92-1.72 (m, 6H), 1.66-1.59 (m, 2H), 1.52-1.38 (m, 7H), 1.34-1.25 (m, 3H), 1.24-1.17 (m, 4H), 1.16-1.07 (m, 2H), 0.75 (s, 3H).

$^{19}$F NMR (400 MHz, $CDCl_3$) δ −116.43 (s).

LCMS Rt=1.094 min in 2.0 min chromatography, 30-90AB, purity 100%, MS ESI calcd. for $C_{29}H_{40}FN_2O_3$ [M+H]$^+$ 483, found 483.

Example 51. Synthesis of Compound 54

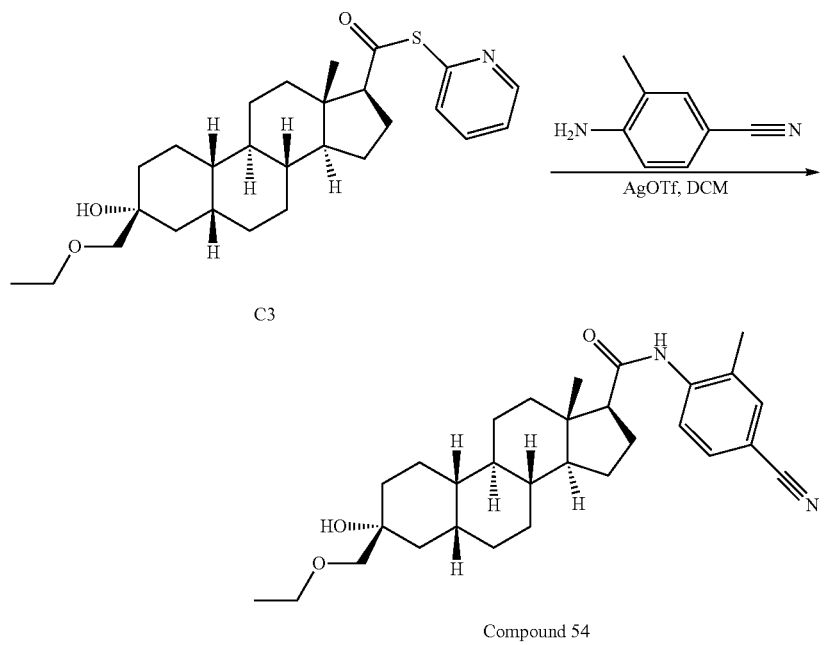

Compound 54

Step 1 (Compound 54).

To a solution of C3 (100 mg, 0.218 mmol) in DCM (3 mL) was added AgOTf (56 mg, 0.218 mmol), followed by 4-amino-3-methylbenzonitrile (43.2 mg, 0.327 mmol) at 25° C. After stirring the reaction at 25° C. for 1 hr, the reaction mixture was filtered and the filter cake was washed with DCM (15 mL). The combined organic layers were washed with 1M HCl (10 mL), brine (50 mL), dried over $Na_2SO_4$, filtered and concentrated in vacuo to give an oil (93 mg) which was purified by HPLC (Column: YMC-Actus Triart C18 100*30 mm*5 um; Conditions: water (0.05% HCl)-ACN; Gradient: 75% B~100% B; FlowRate: 25 mL/min) to give Compound 54 (12 mg, 13%) as a solid.

$^1$H NMR (400 MHz, $CDCl_3$) δ 8.35 (d, J=8.4 Hz, 1H), 7.53-7.48 (m, 1H), 7.46 (s, 1H), 6.96 (s, 1H), 3.57-3.50 (m, 2H), 3.47-3.38 (m, 2H), 2.75 (s, 1H), 2.40-2.24 (m, 5H), 2.06-1.99 (m, 1H), 1.91-1.72 (m, 6H), 1.68-1.60 (m, 2H), 1.50-1.36 (m, 7H), 1.32-1.18 (m, 6H), 1.18-1.04 (m, 3H), 0.75 (s, 2H), 0.77-0.72 (m, 1H).

LCMS Rt=1.129 min in 2.0 min chromatography, 30-90AB, purity 100%, MS ESI calcd. for $C_{30}H_{43}N_2O_3$ [M+H]$^+$ 479, found 479.

Example 52. Synthesis of Compound 55

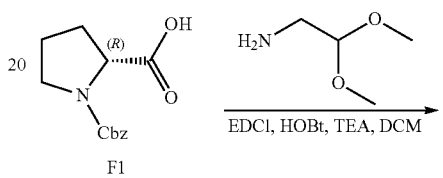

F1

-continued

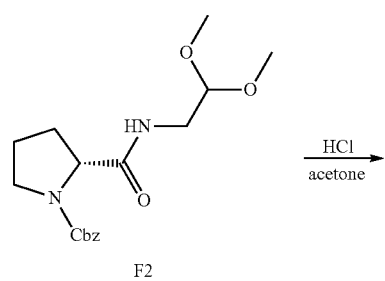

F2

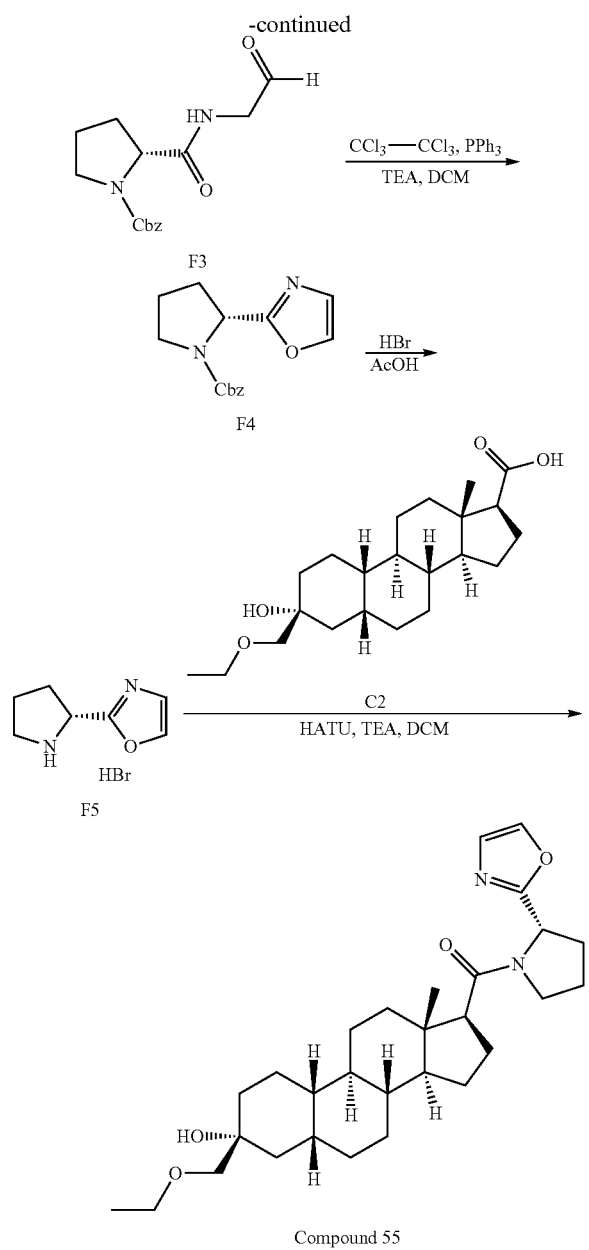

Step 1 (F2).

To a solution of commercially available F1 (20 g, 80.2 mmol) in DCM (200 mL) was added 2,2-dimethoxyethanamine (8.43 g, 80.2 mmol), HOBt (14 g, 104 mmol), EDCI (19.9 g, 104 mmol) and TEA (40.5 g, 401 mmol) at 25° C. The mixture was stirred at 25° C. for 19 hours. The mixture was filtered. The filtrate was washed with water (2×150 mL), brine (2×150 mL), dried over anhydrous Na$_2$SO$_4$, filtered and concentrated in vacuo to give F2 (27 g, crude) as an oil.

Step 2 (F3)

To a solution of F2 (17 g, 50.5 mmol) in acetone (200 mL) was added queues HCl (151 mL, 3M) at 25° C. The mixture was stirred at 25° C. for 16 hours. The mixture was extracted with EtOAc (3×250 mL). The organic phase was washed with water (3×600 mL), sat. NaHCO$_3$ (3×500 mL), brine (3×450 mL), dried over Na$_2$SO$_4$, filtered, concentrated in vacuo to give F3 (5.57 g) as an oil.

Step 3 (F4).

To a stirred solution of F3 (5.57 g, 19.1 mmol) and perchloroethane (9.04 g, 38.2 mmol) in dichloromethane (200 mL) was added PPh$_3$ (10 g, 38.2 mmol). The mixture was stirred at 0° C. for 15 min, Et$_3$N (5.51 mL, 38.2 mmol) was then added and the mixture was stirred at 25° C. for 18 hrs. The mixture was washed with water (2×150 mL), brine (2×150 mL), dried over Na$_2$SO$_4$, filtered, concentrated in vacuo to give a crude product, which was purified by flash silica gel chromatography (0-65% EtOAc in PE) to give F4 (2.7 g, 52%) as a white yellow oil.

$^1$H NMR (400 MHz, CDCl$_3$) δ 7.75-7.45 (s, 1H), 7.10-6.98 (m, 2H), 5.20-4.95 (m, 3H), 3.75-3.45 (m, 2H), 2.40-2.20 (m, 3H), 2.00-1.95 (m, 1H)

Step 4 (F5).

To a solution of F4 (1.3 g, 4.77 mmol) in AcOH (5 mL) was added HBr (10 mL, 35% in AcOH) at 25° C. The mixture was stirred at 25° C. for 4 hours. MTBE (25 mL) was added and solid was produced. The mixture was filtered. The filtered cake was washed with MTBE (15 mL) and dried in vacuo at 50° C. to give F5 (800 mg, 77%) as a solid.

$^1$H NMR (400 MHz, methanol-d$_4$) δ 8.03 (s, 1H), 7.27 (s, 1H), 5.05-4.80 (m, 1H), 3.60-3.45 (m, 2H), 2.60-2.55 (m, 1H), 2.45-2.35 (m, 1H), 2.31-2.20 (m, 2H)

Step 5 (Compound 55).

To a solution of C2 (200 mg, 0.548 mmol) in DCM (5 mL) was added HATU (312 mg, 0.822 mmol) and Et$_3$N (276 mg, 2.73 mmol) at 25° C. The reaction mixture was stirred at 25° C. for 0.5 hour. (S)-2-(pyrrolidin-2-yl)oxazole hydrobromide (180 mg, 0.822 mmmol) was added to the reaction mixture at 25° C. for 18 hours. The reaction mixture was diluted with EtOAc (30 mL) and washed with water (50 mL), brine (50 mL), dried over anhydrous Na$_2$SO$_4$, filtered and concentrated to give the crude. The crude was purified by silica gel chromatography with PE/EtOAc=0/1–1/1 to give Compound 55 (200 mg) as a light solid. Compound 55 was further purified by pre-HPLC (Conditions: water (0.05% ammonia hydroxide v/v)-ACN, Column: Phenomenex Gemini C18 250*50 mm*10 um, Gradient Time: 8 min) to give Compound 55 (100 mg, 50%) as a solid.

$^1$H NMR (400 MHz, CDCl$_3$) δ 7.62-7.50 (m, 1H), 7.14-6.99 (m, 1H), 5.27-5.11 (m, 1H), 3.93-3.29 (m, 7H), 2.77-2.49 (m, 2H), 2.31-1.99 (m, 5H), 1.84-1.60 (m, 8H), 1.49-1.32 (m, 7H), 1.25-1.17 (m, 6H), 1.16-1.03 (m, 3H), 0.85-0.76 (m, 3H)

LCMS Rt=0.977 min in 2.0 min chromatography, 30-90AB, purity 100%; MS ESI calcd. for C$_{29}$H$_{45}$N$_2$O$_4$ [M+H]$^+$ 485, found 485.

SFC Rt=1.488 min in 3.0 min chromatography, AD-H_3UM_4_5_40_4ML_3MIN.M, 100% de. (Column: Chiralpak AD-3 50*4.6 mm I.D., 3 um; Mobile phase: A:CO$_2$ B: iso-propanol (0.05% DEA); Gradient: hold 5% for 0.2 min, then from 5% to 40% of B in 1.4 min and hold 40% for 1.05 min, then 5% of B for 0.35 min; Flow rate: 4 mL/min Column temp: 40° C.).

Example 53. Synthesis of Compound 56 and Compound 57

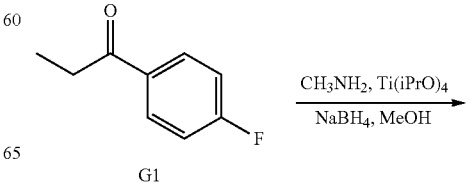

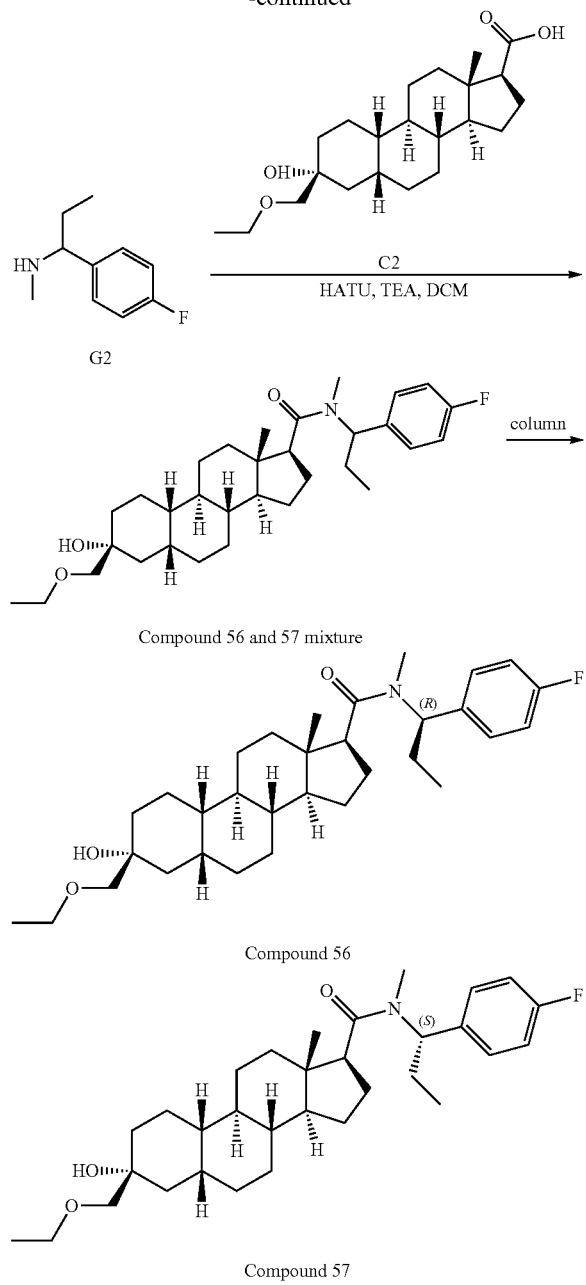

Compound 56 and 57 mixture

Compound 56

Compound 57

Step 1 (G2).

To a solution of titanium(IV) isopropoxide (2.51 g, 8.67 mmol) in methanamine (611 mg, 2M in MeOH) was added commercially available 1-(4-fluorophenyl)propan-1-one (G1, 1 g, 6.57 mmol) at 25° C. The mixture was stirred at 25° C. for 12 hours. To the mixture was added NaBH$_4$ (248 mg, 6.57 mmol). The mixture was stirred at 25° C. for 10 min. The mixture was poured into saturated NH$_4$Cl (10 mL) and water (10 mL). The reaction mixture was filtered and washed with PE (3×10 mL). The filtrate was concentrated to give G2 (400 mg, 36%) as an oil, which was used in next step without further purification.

Step 2 (Mixture of Compound 56 and 57).

To a solution of C2 (200 mg, 0.548 mmol) in DCM (5 mL) was added HATU (312 mg, 0.822 mmol) and Et$_3$N (276 mg, 2.73 mmol) at 25° C. After stirring at 25° C. for 0.5 hour, 1-(4-fluorophenyl)-N-methylpropan-1-amine (G2, 137 mg, 0.822 mmol) was added to the reaction mixture at 25° C. The reaction mixture was stirred at 40° C. for 10 hours. The residue was quenched with ice-water (10 mL). The aqueous phase was extracted with EtOAc (3×20 mL). The combined organic phase was washed with saturated brine (2×10 mL), dried over anhydrous Na$_2$SO$_4$, filtered and concentrated to give a mixture of Compound 56 and 57 (300 mg, crude) as a solid, which was further purified as described in step 3 below.

Step 3 (Compound 56 and Compound 57).

A mixture of Compound 56 and 57 (300 mg, crude) was purified by silica gel chromatography eluted with PE: EtOAc=3/1 to give Compound 56 (35 mg, 12%) as a solid and Compound 57 (46 mg, 15%) as a solid.

Compound 56

$^1$H NMR (400 MHz, CDCl$_3$) δ 7.28-7.21 (m, 2H), 7.08-6.94 (m, 2H), 5.97-5.85 (m, 0.9H), 5.08-4.99 (m, 0.1H), 3.57-3.49 (m, 2H), 3.47-3.36 (m, 2H), 2.74-2.64 (m, 4H), 2.39-2.25 (m, 1H), 2.01-1.90 (m, 1H), 1.88-1.60 (m, 10H), 1.51-1.05 (m, 17H), 0.96 (t, J=7.28, 3H), 0.94 (s, 0.4H), 0.80 (s, 2.6H).

LCMS Rt=5.531 min in 7 min chromatography, 10-80AB, purity 98%, MS ESI calcd. for C$_{32}$H$_{49}$FNO$_3$ [M+H]$^+$ 514, found 514.

SFC Rt=4.251 min in 10 min chromatography, OD_3_EtOH_DEA5_40_25ML, 98% de. (Column: Chiralcel OD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.).

Compound 57

$^1$H NMR (400 MHz, CDCl$_3$) δ 7.29-7.23 (m, 2H), 7.19-7.15 (m, 0.2H), 7.08-6.96 (m, 1.8H), 5.94-5.75 (m, 0.9H), 5.02-4.94 (m, 0.1H), 3.57-3.48 (m, 2H), 3.47-3.36 (m, 2H), 2.79-2.64 (m, 5H), 2.36-2.10 (m, 1H), 2.03-1.96 (m, 1H), 1.86-1.61 (m, 8H), 1.50-0.97 (m, 18H), 0.95-0.88 (m, 3H), 0.87 (s, 0.4H), 0.80 (s, 2.6H).

LCMS Rt=5.485 min in 7 min chromatography, 10-80AB, purity 98%, MS ESI calcd. for C$_{32}$H$_{49}$FNO$_3$ [M+H]$^+$ 514, found 514.

SFC Rt=2.890 min in 10 min chromatography, OD_3_EtOH_DEA_5_40_25ML, 99% de. (Column: Chiralcel OD-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.).

Example 54. Synthesis of Compound 58 and Compound 59

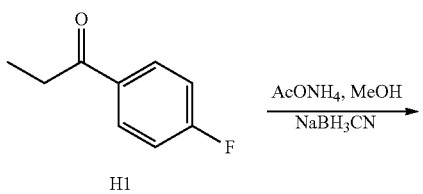

H1

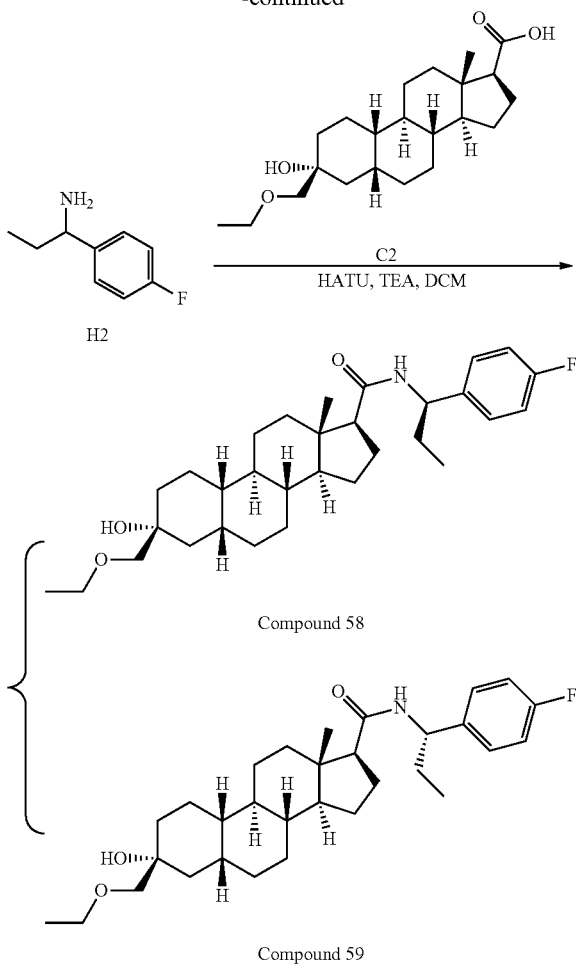

Compound 58

Compound 59

Step 1 (H2).

To a solution of commercially available H1 (3 g, 19.7 mmol) in MeOH (100 mL) was added AcONH$_4$ (15.1 g, 196 mmol) and NaBH$_3$CN (6.18 g, 98.4 mmol) at 20° C. The mixture was stirred at 20° C. for 19 hours. Water (100 mL) was added and a solid was produced. The mixture was filtered. The filtrate was extracted with EtOAc (2×80 mL). The combined organic phase was washed with water (2×100 mL), brine (2×80 mL), dried over Na$_2$SO$_4$, filtered, concentrated in vacuo to give H2 (2.15 g, 71%) as a white yellow oil, which was used in next step without further purification.

Step 2 (Compound 58 and Compound 59).

To a solution of C2 (200 mg, 0.548 mmol) in DCM (5 mL) was added HATU (312 mg, 0.822 mmol) and TEA (276 mg, 2.73 mmol) at 25° C. The reaction mixture was stirred at 25° C. for 0.5 hour. 1-(4-fluorophenyl) propan-1-amine H2 (125 mg, 0.822 mmol) was added to the reaction mixture at 25° C. The reaction mixture was stirred at 40° C. for 10 hours. The residue was quenched with ice-water (10 mL). The aqueous phase was extracted with EtOAc (3×20 mL). The combined organic phase was washed with saturated brine (2×10 mL), dried over anhydrous Na$_2$SO$_4$, filtered and concentrated. The residue was purified by silica gel chromatography eluted with PE: EtOAc=3/1 to give Compound 58 (100 mg, 37%, Rf=0.6 in PE/EtOAc=3/1) as a solid and Compound 59 (100 mg, 37% Rf=0.5 in PE/EtOAc=3/1) as a solid.

Compound 58 (100 mg) was further purified twice by silica gel chromatography and then by SFC (Column: Chiralcel OJ-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to give Compound 58 (23 mg, yield) as a solid.

Compound 59 (100 mg) was purified by SFC twice (Column: Chiralcel OJ-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to afford Compound 59 (17 mg, yield) as a solid.

Compound 58

$^1$H NMR (400 MHz, CDCl$_3$) δ 7.26-7.21 (m, 2H), 7.05-6.98 (m, 2H), 5.46-5.40 (m, 1H), 4.88 (q, J=7.53 Hz, 1H), 3.53 (q, J=7.03 Hz, 2H), 3.43 (q, J=9.54, 2H), 2.73 (s, 1H), 2.22-2.03 (m, 2H), 1.99-1.92 (m, 1H), 1.87-1.61 (m, 9H), 1.51-1.02 (m, 17H), 0.89 (t, J=7.53, 3H), 0.70 (s, 3H).

LCMS Rt=1.334 min in 2.0 min chromatography, 10-80AB, purity 100%, MS ESI calcd. for C$_{31}$H$_{47}$FNO$_3$ [M+H]$^+$ 500, found 500.

SFC Rt=2.890 min in 10 min chromatography, OJ_3_EtOH_DEA5_40_25ML, 98% de. (Column: Chiralcel OJ-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.).

Compound 59

$^1$H NMR (400 MHz, CDCl$_3$) δ 7.25-7.21 (m, 2H), 7.04-6.96 (m, 2H), 5.49-5.40 (m, 1H), 4.85 (q, J=7.36 Hz, 1H), 3.53 (q, J=6.86 Hz, 2H), 3.42 (q, J=9.12 Hz, 2H), 2.72 (s, 1H), 2.22-2.07 (m, 2H), 1.86-1.70 (m, 7H), 1.68-1.62 (m, 2H), 1.49-0.95 (m, 18H), 0.88 (t, J=7.4 Hz, 3H), 0.49 (s, 3H).

LCMS Rt=1.322 min in 2.0 min chromatography, 10-80AB, purity 100%, MS ESI calcd. for C$_{31}$H$_{47}$FNO$_3$ [M+H]$^+$ 500, found 500.

SFC Rt=2.668 min in 10 min chromatography, OJ_3_EtOH_DEA5_40_25ML, 95% de. (Column: Chiralcel OJ-3 150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.).

Example 55. Synthesis of Compound 60

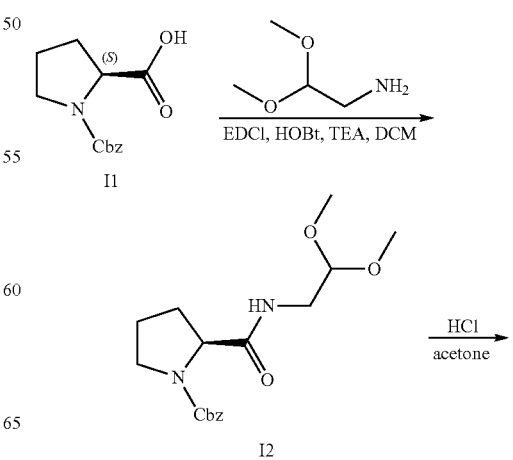

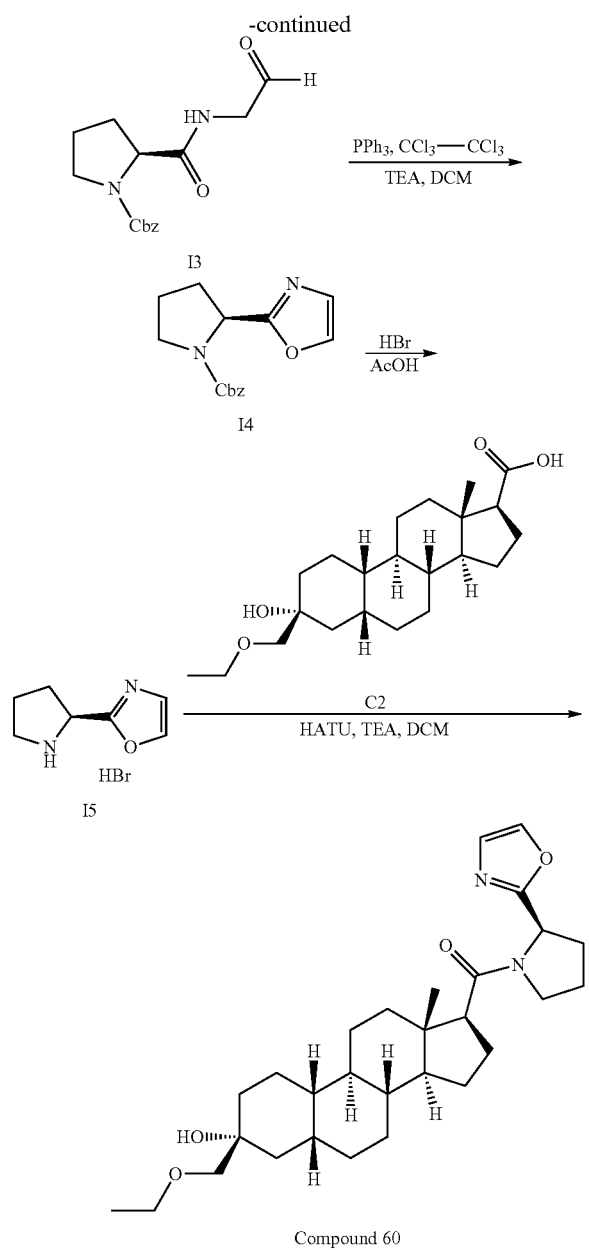

Step 1 (I2).

To a solution of commercially available I1 (20 g, 80.2 mmol) in DCM (200 mL) was added 2, 2-dimethoxyethanamine (8.43 g, 80.2 mmol), HOBt (14 g, 104 mmol), EDCI (19.9 g, 104 mmol) and TEA (40.5 g, 401 mmol) at 25° C. The mixture was stirred at 25° C. for 19 hours. The mixture was filtered, concentrated in vacuo to give a crude product, which was purified by flash silica gel chromatography (0-70% EtOAc in PE) to give I2 (20 g, 74%) as an oil.

$^1$H NMR (400 MHz, CDCl$_3$) δ 7.32 (s, 5H), 5.20-5.00 (m, 2H), 3.55-3.20 (m, 10H), 2.40-1.80 (m, 5H)

Step 2 (I3).

To a solution of I2 (9.9 g, 29.4 mmol) in acetone (200 mL, 29.4 mmol) was added HCl (176 mL, 1 M) at 25° C. The mixture was stirred at 25° C. for 18 hours. The reaction mixture was combined with another batch prepared from 100 mg of I2. The reaction-mixture was extracted with ethyl acetate (3×150 mL). The combined organic phase was washed with water (3×300 mL) and brine (2×200 mL), dried over Na$_2$SO$_4$, filtered and concentrated in vacuo to give I3 (2.4 g, crude) as an oil.

Step 3 (I4).

To a stirred solution of I3 (2.4 g, 8.26 mmol) and perchloroethane (3.9 g, 16.5 mmol) in dichloromethane (100 mL) was added PPh$_3$ (4.32 g, 16.5 mmol). The mixture was stirred at 0° C. for 15 min. TEA (1.66 g, 16.5 mmol) was then added and the mixture was stirred at 25° C. for 18 hours. The mixture was washed with water (2×80 mL), brine (2×80 mL), dried over Na$_2$SO$_4$, filtered, concentrated in vacuo to give a crude product, which was purified by flash silica gel chromatography (0-65% EtOAc in PE) to give I4 (630 mg, 32%) as an oil, which was used directly for the next step.

Step 4 (I5).

To a solution of I4 (530 mg, 1.94 mmol) in AcOH (3 mL) was added HBr (6 mL, 35% in AcOH) at 25° C. The mixture was stirred at 25° C. for 2 hours. MTBE (15 mL) was added and a solid was produced. The mixture was filtered. The filter cake was washed with MTBE (15 mL) and dried in vacuo at 50° C. to give I5 (430 mg, crude) as a solid.

$^1$H NMR (400 MHz, methanol-d$_4$) δ 8.05 (s, 1H), 7.28 (s, 1H), 5.05-4.85 (m, 2H), 3.60-3.45 (m, 2H), 2.60-2.50 (m, 1H), 2.45-2.35 (m, 1H), 2.30-2.21 (m, 2H)

Step 5 (Compound 60)

To a solution of 2 (200 mg, 0.548 mmol) in DCM (5 mL) was added HATU (313 mg, 1.30 mmol) and Et$_3$N (276 mg, 2.73 mmol) at 25° C. The reaction mixture was stirred at 25° C. for 0.5 hour. (R)-2-(pyrrolidin-2-yl)oxazole hydrobromide I5 (180 mg, 0.822 mmmol) was added to the reaction mixture at 25° C. The reaction mixture was stirred at 25° C. for 18 hours. The reaction mixture was diluted with EtOAc (30 mL) and washed with water (50 mL), brine (50 mL), dried over anhydrous Na$_2$SO$_4$, filtered and concentrated to give the crude product, which was purified by silica gel chromatography with PE:EtOAc=0:1-1:1 to give Compound 60 (190 mg) as a solid. The product was further purified by pre-HPLC (Conditions: water (0.05% ammonia hydroxide v/v)-ACN, Column: Phenomenex Gemini C18 250*50 mm*10 um, Gradient Time: 8 min) to give Compound 60 (98 mg) as a solid. The solid was re-purified by SFC (Column: AD (250 mm*30 mm, 10 um), Conditions: 0.1% NH$_3$H$_2$O IPA, Gradient: from 45%, Flow Rate (ml/min): 80 mL/min, 25° C.) to afford Compound 60 (67 mg, 25% as a solid.

$^1$H NMR (400 MHz, CDCl$_3$) δ 7.60-7.50 (m, 1H), 7.10-6.98 (m, 1H), 5.33-5.23 (m, 1H), 3.86-3.70 (m, 1H), 3.66-3.58 (m, 1H), 3.55-3.50 (m, 2H), 3.46-3.38 (m, 2H), 2.74-2.42 (m, 2H), 2.30-2.07 (m, 4H), 2.04-1.94 (m, 2H), 1.86-1.66 (m, 6H), 1.51-1.32 (m, 8H), 1.28-1.04 (m, 10H), 0.77-0.62 (m, 3H).

LCMS Rt=0.977 min in 2.0 min chromatography, 30-90AB, purity 100%; MS ESI calcd. for C$_{29}$H$_{45}$N$_2$O$_4$ [M+H]$^+$ 485, found 485.

SFC Rt=1.961 min in 3 min chromatography, AD-H_3UM_4_5_40_4ML, 100% de. (Column: Chiralpak AD-3 50*4.6 mm I.D., 3 um; Mobile phase: A: CO$_2$ B: iso-propanol (0.05% DEA); Gradient: hold 5% for 0.2 min, then from 5% to 40% of B in 1.4 min and hold 40% for 1.05 min, then 5% of B for 0.35 min; Flow rate: 4 mL/min Column temp: 40° C.).

Example 56. Synthesis of Compound 61 and Compound 62

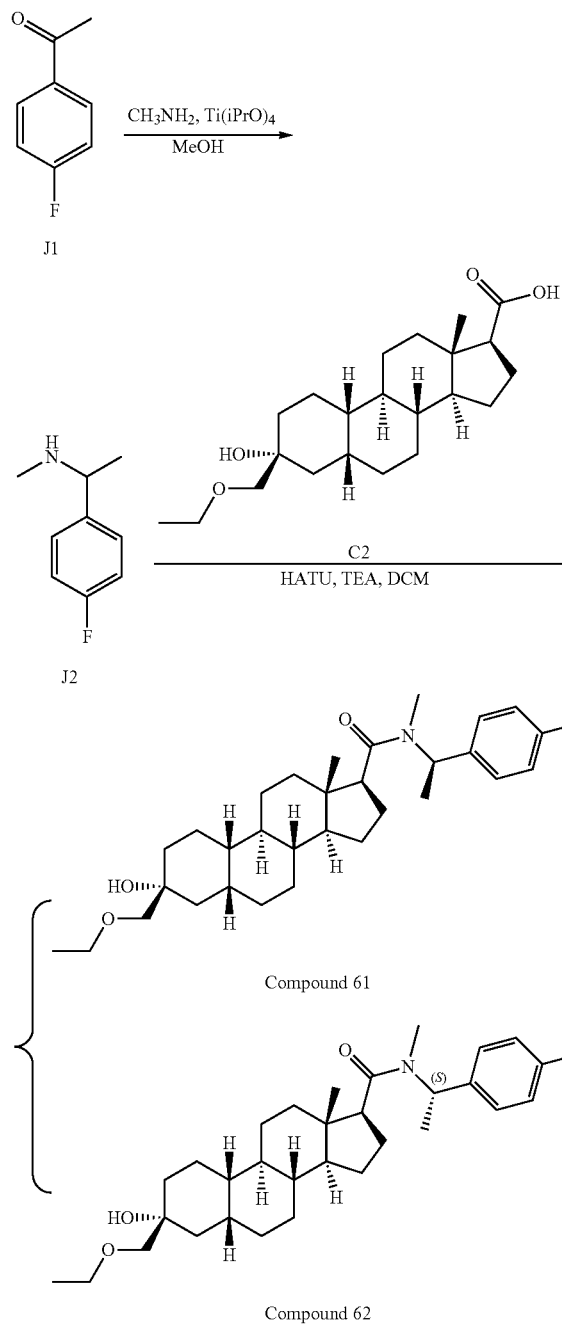

Step 1 (J2). Ti(iPrO)$_4$ (5.31 g, 18.7 mmol) was added to methanamine in MeOH (14.4 mL, 2M, followed by addition of commercially available J1 (2 g, 14.4 mmol). After stirring at 25° C. for 3 hours, NaBH$_4$ (544 mg, 14.4 mmol) was added. The mixture was stirred at 25° C. for 18 hours, quenched with water (15 mL). Solid appeared, which was filtered off. The filtrate was extracted with EtOAc (2×20 mL). The combined organic phase was washed with water (2×40 mL), brine (2×40 mL), dried over Na$_2$SO$_4$, filtered and concentrated in vacuo to give J2 (2.9 g, impure) as an oil, which was used directly.

Step 2. (Compound 61 and Compound 62).

To a solution of C2 (200 mg, 0.548 mmol) in DCM (5 mL) was added HATU (312 mg, 0.822 mmol) and TEA (276 mg, 2.73 mmol) at 25° C. After stirring at 25° C. for 0.5 hours, 1-(4-fluorophenyl)-N-methylethanamine J2 (134 mg, 0.876 mmmol) was added at 25° C. The reaction mixture was stirred at 25° C. for 18 hours, diluted with EtOAc (30 mL), washed with water (50 mL) and brine (50 mL), dried over anhydrous Na$_2$SO$_4$, filtered and concentrated to give the crude. The crude was purified by silica gel chromatography with PE/EtOAc=0/1–10/1 to give Compound 61 (50 mg, Rf=0.50 in PE/EtOAc=2/1) and Compound 62 (50 mg, Rf=0.45 in PE/EtOAc=2/1) as a solid.

The Compound 61 was further purified by SFC (Column: AD (250 mm*30 mm, 5 um), Conditions: 0.1% NH$_3$H$_2$O IPA, Gradient: from 35%, Flow Rate (ml/min): 60 mL/min, 25° C.) to afford Compound 61 (25 mg, 9%) as a solid.

The impure Compound 62 (50 mg, 0.100 mmol) was triturated with hexane (3 mL) to give Compound 62 (40 mg, 14%) as a solid.

Compound 61

$^1$H NMR (400 MHz, CDCl$_3$) δ 7.26-7.22 (m, 2H), 7.09-6.97 (m, 2H), 6.17-6.11 (m, 0.9H), 5.28 (s, 0.1H), 3.56-3.50 (m, 2H), 3.46-3.38 (m, 2H), 2.74-2.67 (m, 5H), 2.57 (s, 0.5H), 2.36-2.27 (m, 1H), 1.84-1.70 (m, 6H), 1.47-1.42 (m, 6H), 1.40-1.32 (m, 4H), 1.30-1.18 (m, 8H), 1.16-1.09 (m, 3H), 0.89 (s, 0.6H), 0.79 (s, 3H).

LCMS Rt=1.173 min in 2.0 min chromatography, 30-90AB, purity 100%; MS ESI calcd. for C$_{31}$H$_{47}$FNO$_3$ [M+H]$^+$ 500, found 500.

SFC Rt=5.128 min in 10 min chromatography, AD_3_IPA_DEA_5_40_25ML, 98.36% de. (Column: Chiralpak AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.) Compound 62

$^1$H NMR (400 MHz, CDCl$_3$) δ 7.26-7.22 (m, 1.6H), 7.17-7.11 (m, 0.4H), 7.06-6.98 (m, 2H), 6.15-6.09 (m, 0.7H), 5.36-5.28 (m, 0.2H), 3.56-3.50 (m, 2H), 3.47-3.37 (m, 2H), 2.82-2.65 (m, 5H), 2.40-2.24 (m, 1H), 1.89-1.68 (m, 5H), 1.67-1.57 (m, 4H), 1.50-1.17 (m, 16H), 1.16-1.04 (m, 3H), 0.82 (s, 3H).

LCMS Rt=1.178 min in 2.0 min chromatography, 30-90AB, purity 100%; MS ESI calcd. for C$_{31}$H$_{47}$FNO$_3$ [M+H]$^+$ 500, found 500.

Example 57. Synthesis of Compound 63

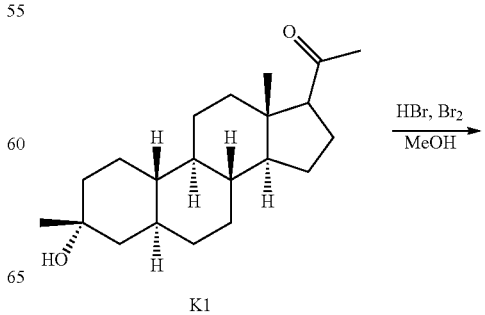

175
-continued

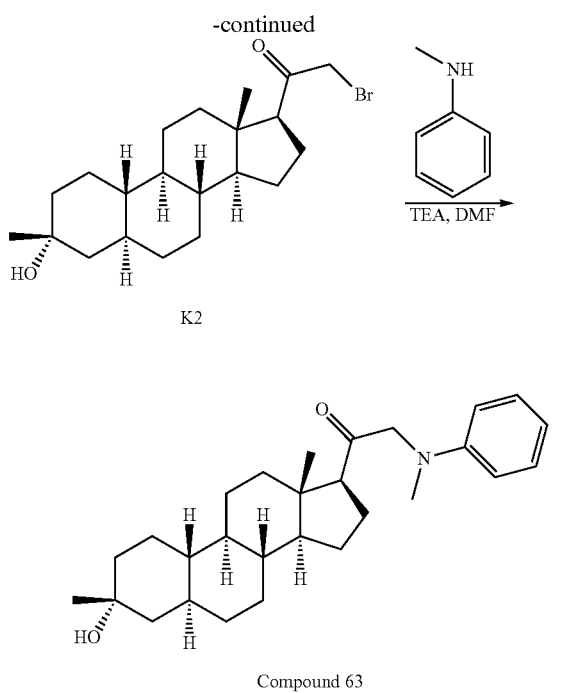

K2

Compound 63

176

Example 58. Synthesis of Compound 64

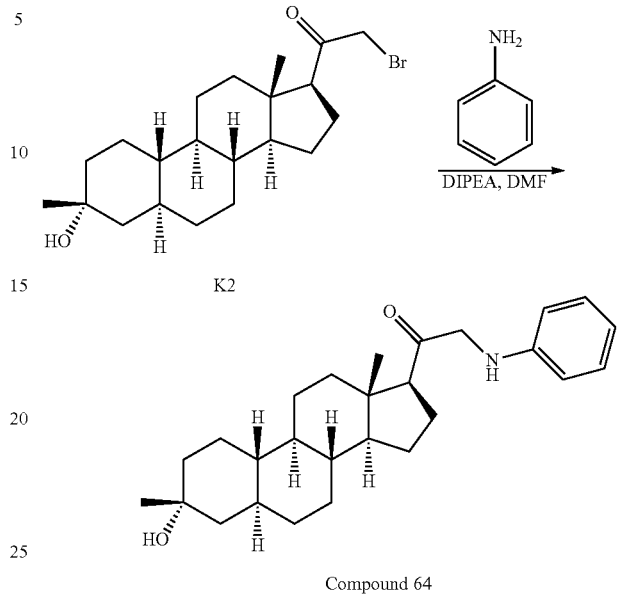

K2

Compound 64

The synthesis of K1 is disclosed in WO2016/123056.

Step 1 (K2).

To a solution of K1 (1 g, 3.13 mmol) in MeOH (10 ml) was added HBr (125 mg, 0.626 mmol, 40% in water) and Br$_2$ (500 mg, 3.19 mmol) at 25° C. The mixture was stirred at 25° C. for 16 hrs. The mixture was quenched with sat. aqueous NaHCO$_3$ (10 mL), treated with water (20 mL), extracted with EtOAc (2×20 mL). The combined organic phase was washed with brine (20 mL), dried over anhydrous Na$_2$SO$_4$, filtered, concentrated in vacuo to afford K2 (1.2 g) as a solid, which was used directly for the next step.

Step 2 (Compound 63).

To a solution of K2 (100 mg, 0.251 mmol) in DMF (5 mL) was added N-methylaniline (32.2 mg, 0.301 mmol) and TEA (76.1 mg, 0.753 mmol) at 25° C. The mixture was stirred at 25° C. for 18 h to give a yellow solution. The mixture was purified by prep-HPLC (Column: Gemini 150*25 5 u; Conditions: water (0.05% HCl)-ACN; Gradient 27%-52% B; FlowRate (ml/min): 30) to afford Compound 63 (4 mg, 4%) as a solid.

$^1$H NMR (400 MHz, CDCl$_3$) δ 7.36-7.29 (m, 2H), 7.17-7.08 (m, 2H), 7.04-6.98 (m, 1H), 4.21-4.11 (m, 2H), 3.18 (s, 3H), 2.56-2.48 (m, 1H), 2.19-2.09 (m, 1H), 1.90-1.74 (m, 3H), 1.69-1.63 (m, 2H), 1.52-1.24 (m, 10H), 1.20 (s, 3H), 1.13-0.92 (m, 6H), 0.73-0.61 (m, 2H), 0.55 (s, 3H)

LCMS Rt=2.147 in in 3.0 min chromatography, 10-80AB, purity 100%, MS ESI calcd. for C$_{28}$H$_{42}$NO$_2$ [M+H]$^+$ 424, found 424.

Step 1 (Compound 64).

To a solution of K2 (60 mg, 0.151 mmol) in DMF (2 mL) was added DIPEA (25.3 mg, 0.196 mmol). The mixture was stirred for 10 min at 20° C. To the mixture was added aniline (18.2 mg, 0.196 mmol). The mixture was stirred another 16 hours at 20° C. The mixture was poured into water (10 mL) and extracted with EtOAc (2×10 mL). The combined organic layers were washed with brine (2×10 mL), dried over anhydrous Na$_2$SO$_4$, filtered and concentrated in vacuo. The residue was purified by prep-HPLC (column: Phenomenex Gemini C18 250*50 mm*10 um, gradient: 70-100% B, Conditions: water (0.05% ammonia hydroxide v/v)-ACN, flow rate: 30 mL/min) to give Compound 64 (10 mg, 16.1%) as a solid.

$^1$H NMR (400 MHz, CDCl$_3$) δ 7.21 (t, J=8 Hz, 2H), 7.76-7.69 (m, 1H), 6.62-6.58 (m, 2H), 4.70 (brs, 1H), 4.41-3.86 (m, 2H), 2.62-2.55 (m, 1H), 2.29-2.19 (m, 1H), 2.01-1.92 (m, 1H), 1.88-1.64 (m, 7H), 1.47-1.16 (m, 10H), 1.13-0.96 (m, 6H), 0.79-0.64 (m, 5H)

LCMS Rt=1.173 min in 2 min chromatography, 30-90AB, purity 95%, MS ESI calcd. for C$_{27}$H$_{40}$NO$_2$ [M+H]$^+$ 410, found 410.

Example 59. Synthesis of Compound 65

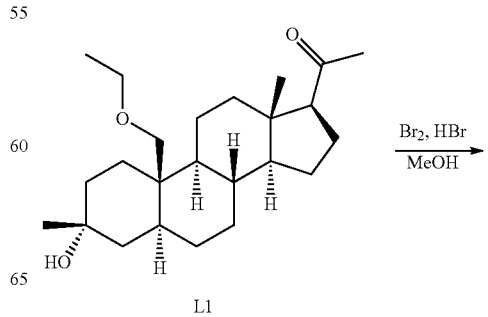

L1

177
-continued

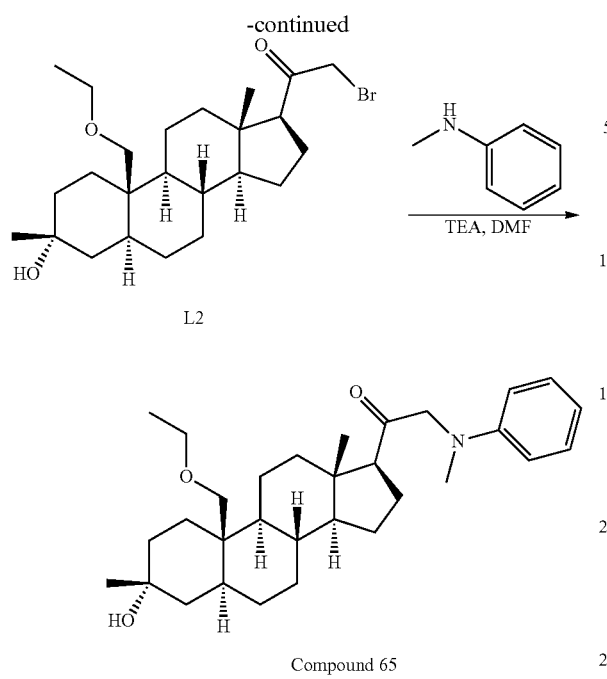

Compound 65

The synthesis of L1 is disclosed in WO2015/27227.

Step 1 (L2).

To a solution of L1 (1.2 g, 2.77 mmol) in MeOH (10 ml) was added HBr (110 mg, 0.554 mmol, 40% in water) and $Br_2$ (442 mg, 2.82 mmol) at 25° C. After stirring at 25° C. for 16 hrs, the mixture was quenched with sat. aq $NaHCO_3$ (10 mL), treated with water (20 mL), extracted with EtOAc (2×20 mL). The combined organic phase was washed with brine (20 mL), dried over anhydrous $Na_2SO_4$, filtered and concentrated in vacuo to afford L2 (1.4 g) as a solid which was used directly for the next step.

Step 2 (Compound 65)

To a solution of L2 (100 mg, 0.219 mmol) in DMF (5 mL) was added N-methylaniline (28 mg, 0.262 mmol) and TEA (66.4 mg, 657 mmol) at 25° C. The mixture was stirred at 25° C. for 18 h to give a yellow solution. The mixture was purified by prep-HPLC (Column: Gemini 150*25 5 u; Conditions: water (0.05% HCl)-ACN; Gradient 62%-87% B; FlowRate (ml/min): 30) to afford (Compound 65) (3 mg, 3%) as a solid.

$^1$H NMR (400 MHz, $CDCl_3$) δ 7.21-7.17 (m, 2H), 6.76-6.70 (m, 1H), 6.66-6.60 (m, 2H), 4.13-3.95 (m, 2H), 3.53-3.50 (s, 1H), 3.43-3.35 (m, 3H), 3.01 (s, 3H), 2.65-2.52 (m, 1H), 2.22-2.13 (m, 1H), 2.05-1.95 (m, 2H), 1.75-1.63 (m, 3H), 1.52-1.45 (m, 5H), 1.26-1.14 (m, 15H), 1.00-0.93 (m, 1H), 0.88-0.77 (m, 2H), 0.67 (s, 3H).

LCMS Rt=1.254 in in 2.0 min chromatography, 30-90AB, purity 95%, MS ESI calcd. for $C_{31}H_{48}NO_3$ $[M+H]^+$ 482, found 482.

178
Example 60. Synthesis of Compound 66

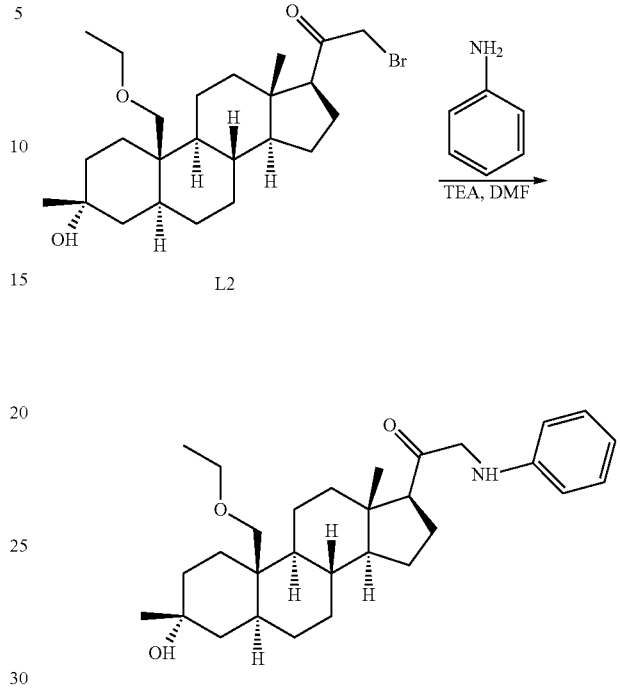

Compound 66

Step 1 (Compound 66).

To a solution of DIPEA (18.2 mg, 0.141 mmol) in DMF (1.5 mL) was added aniline (20.3 mg, 0.218 mmol) at 10° C. under $N_2$. After stirring at 10° C. for 30 min, L2 (50 mg, 0.109 mmol) in DMF (1.5 mL) was added. The reaction mixture was stirred at 40° C. for 16 hours. Another batch of DIPEA (36.5 mg, 0.283 mmol) and aniline (40.6 mg, 0.436 mmol) were added to the reaction mixture. The reaction mixture was heated to 50° C. and stirred at this temperature for another 16 hours. The reaction mixture was treated with water (5 mL) and extracted with EtOAc (2×10 mL). The combined organic layers were washed with brine (10 mL), dried over anhydrous $Na_2SO_4$, filtered and concentrated to give the crude. The crude was purified by prep-HPLC (Conditions: Water (0.05% ammonia hydroxide v/v-ACN), Column: Phenomenex Gemini C18 250*50 mm*10 μm, Gradient Time: 8 min). The solvent was removed to give Compound 66 (19 mg, 37%) as a solid.

$^1$H NMR (400 MHz, $CDCl_3$) δ 7.19 (t, 2H), 6.72 (t, 1H), 6.60 (d, 2H), 4.00-3.86 (m, 2H), 3.52-3.49 (m, 1H), 3.41-3.35 (m, 3H), 2.57 (br t, 1H), 2.29-2.19 (m, 1H), 2.07-1.92 (m, 2H), 1.71 (br d, 4H), 1.65-1.59 (m, 3H), 1.51-1.46 (m, 4H), 1.39-1.24 (m, 5H), 1.23-1.19 (m, 5H), 1.15 (t, 4H), 1.12-1.06 (m, 1H), 1.03-0.94 (m, 1H), 0.65 (s, 3H).

LCMS Rt=2.391 min in 3 min chromatography, 30-90CD, purity 97.8%, MS ESI calcd. for $C_{30}H_{46}NO_3$ $[M+H]^+$ 468, found 468.

Example 61. Synthesis of Compound 67 and Compound 68

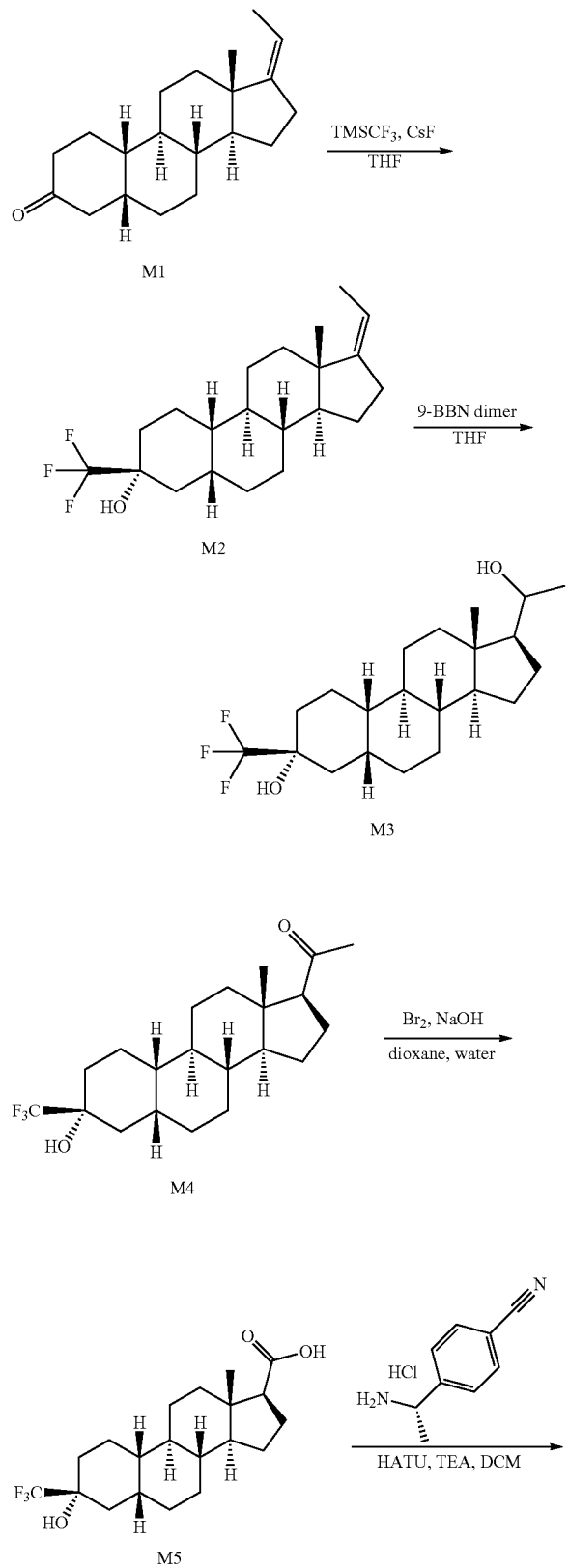

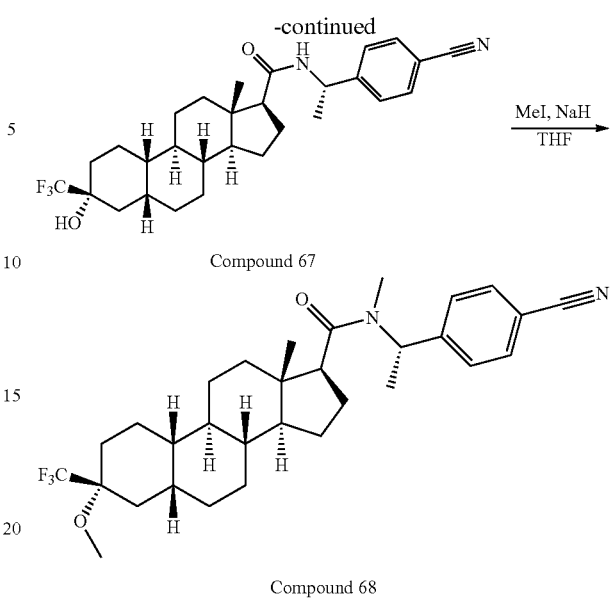

Compound 67

Compound 68

Step 1 (M2).

To a mixture of M2 (5 g, 17.4 mmol) and CsF (1.32 g, 8.70 mmol) in THF (50 mL) was added drop-wise TMSCF$_3$ (6.17 g, 43.4 mmol) at 0° C. The mixture was stirred at 25° C. for 1 h. To the mixture was added TBAF (52 mL, 1 M in THF, 52 mmol). The mixture was stirred at 25° C. for another 2 hrs. The mixture was poured into water (100 mL) and extracted with EtOAc (2×50 mL). The combined organic phase was washed with brine (2×50 mL), dried over anhydrous Na$_2$SO$_4$, filtered and concentrated. The residue was purified by silica gel chromatography (PE/EtOAc=5/1~3/1) to give impure M2 (4.6 g) as a solid. The crude product was re-crystallized from MeCN (3 mL) at 25-50° C. to give M2 (2.64 g, 40%) as a solid.

$^1$H NMR (400 MHz, CDCl$_3$) δ 5.16-5.08 (m, 1H), 2.40-2.13 (m, 3H), 2.05-1.74 (m, 6H), 1.73-1.42 (m, 12H), 1.30-1.04 (m, 6H), 0.88 (s, 3H).

Step 2 (M3).

To a solution of M2 (1 g, 2.80 mmol) in THF (30 mL) was added 9-BBN dimer (2 g, 8.19 mmol) at 0° C. under N$_2$. The solution was stirred at 65° C. for 1 h. After cooling the mixture to 0° C., a solution of NaOH (6 mL, 5 M, 30 mmol) was added very slowly. H$_2$O$_2$ (4 g, 35.2 mmol, 30% in water) was added slowly and the inner temperature was maintained below 10° C. The mixture was stirred at 60° C. under N$_2$ for 1 hour. The mixture was cooled to 30° C. and water (30 mL) was added. The reaction mixture was extracted with EtOAc (30 mL). The organic layer was washed with brine (2×20 mL), dried over anhydrous Na$_2$SO$_4$, filtered and concentrated in vacuum to afford M3 (1.43 g, crude) as an oil.

$^1$H NMR (400 MHz, CDCl$_3$) δ 3.88-3.65 (m, 3H), 1.96-1.76 (m, 6H), 1.73-1.38 (m, 10H), 1.27-1.02 (m, 11H), 0.67 (S, 3H).

Step 3 (M4).

To a solution of M3 (1.43 g, 3.81 mmol) in DCM (15 mL) was added DMP (3.23 g, 7.62 mmol) slowly at 25° C. The mixture was stirred at 25° C. for 1 hour. The mixture was poured into saturated Na$_2$S$_2$O$_3$ (30 mL) and extracted with DCM (2×30 mL). The combined organic layer was washed with brine (2×30 mL), dried over anhydrous Na$_2$SO$_4$, filtered and concentrated in vacuum. The residue was purified by column (PE/EtOAc=5/1~3/1) to give M4 (570 mg, 40%) as a solid.

¹H NMR (400 MHz, CDCl₃) δ 2.57-2.51 (m, 1H), 2.20-1.93 (m, 8H), 1.86-1.44 (m, 13H), 1.81-1.06 (m, 6H), 0.62 (s, 3H).

Step 4 (M5).

Liquid bromine (1.91 g, 12.0 mmol) was added slowly to a vigorously stirred aqueous sodium hydroxides solution (16.0 mL, 3 M, 48.2 mmol) at 0° C. When all the bromine dissolved, the mixture was diluted with cold dioxane (4.5 mL) and added slowly to a stirred solution of M4 (1.5 g, 4.02 mmol) in dioxane (6 mL) and water (4.5 mL). The homogeneous yellow solution became colorless slowly and a white precipitate formed. The reaction mixture was stirred at 25° C. for 5 hrs. The remaining oxidizing reagent was quenched with aqueous Na₂S₂O₃ (30 mL) and the mixture was then heated to 80° C. until the solid material dissolved. The solution was acidified with aqueous HCl (3 M, 30 mL), and a solid was precipitated. The solid was filtered and washed with water (3×50 mL) to give a solid which was dried with toluene (2×40 mL) in vacuo to afford M5 (1.1 g, 73%) as a solid.

¹H NMR (400 MHz, DMSO-d₆) δ 11.89 (br s, 1H), 5.73 (s, 1H), 2.29 (t, J=9.4 Hz, 1H), 1.99-1.87 (m, 4H), 1.85-1.51 (m, 7H), 1.49-1.32 (m, 5H), 1.30-1.15 (m, 4H), 1.12-0.96 (m, 3H), 0.64 (s, 3H).

Step 5 (Compound 67).

To a solution of M5 (200 mg, 0.534 mmol) in DCM (3 mL) was added commercially available (S)-4-(1-aminoethyl)benzonitrile hydrochloride (146 mg, 0.801 mmol), TEA (269 mg, 2.66 mmol) and HATU (304 mg, 0.801 mmol). The mixture was stirred at 25° C. for 1 h. The mixture was washed with water (1 mL) and concentrated in vacuo. The residue was purified by prep-HPLC (Instrument: FB; Column: Phenomenex Gemini C18 250*50 mm*10 um; Conditions: water (0.05% ammonia hydroxide v/v)-ACN; Begin B: 58; End B: 88; Gradient Time (min): 8; 100% B Hold Time (min): 2; FlowRate (ml/min): 30; Injections: 7) to give Compound 67 (170 mg, 63%) as a solid.

¹H NMR (400 MHz, CDCl₃) δ 7.62 (d, J=8.0 Hz, 2H), 7.42 (d, J=8.4 Hz, 2H), 5.53 (d, J=7.2 Hz, 1H), 5.20-5.08 (m, 1H), 2.21-1.89 (m, 5H), 1.86-1.61 (m, 8H), 1.55-1.39 (m, 8H), 1.30-1.04 (m, 7H), 0.55 (s, 3H).

LCMS Rt=1.257 min in 2 min chromatography, 10-80AB, purity 100%, MS ESI calcd. for C₂₉H₃₈F₃N₂O₂[M+H]⁺ 503, found 503.

HPLC Rt=6.04 min in 10 min chromatography, 10-80, 100% d.e.

Step 6 (Compound 68).

To a solution of Compound 67 (120 mg, 0.238 mmol) in DMF (1 mL) was added NaH (9.51 mg, 60%, 0.238 mmol). The mixture was stirred at 20° C. for 15 min. MeI (33.7 mg, 0.238 mmol) was then added and the reaction was stirred at 20° C. for 15 min. The mixture was quenched with water (5 mL) and extracted with EtOAc (2 mL). The organic layer was separated, concentrated in vacuo and purified by flash silica gel chromatography (0~30% EtOAc in PE) to give Compound 68 (10 mg, 8%) as a solid.

¹H NMR (400 MHz, CDCl₃) δ 7.63 (d, J=8.4 Hz, 2H), 7.42 (d, J=8.0 Hz, 2H), 6.16 (d, J=7.6 Hz, 1H), 3.36 (s, 3H), 2.80-2.67 (m, 4H), 2.39-2.24 (m, 1H), 2.10-1.98 (m, 1H), 1.98-1.88 (m, 1H), 1.81-1.62 (m, 8H), 1.52-1.02 (m, 15H), 0.82 (s, 3H).

LCMS Rt=1.254 min in 2 min chromatography, 30-90AB, purity 100%, MS ESI calcd. for C₃₁H₄₂F₃N₂O₂[M+H]⁺ 531, found 531.

Example 62. Synthesis of Compound 69 and Compound 70

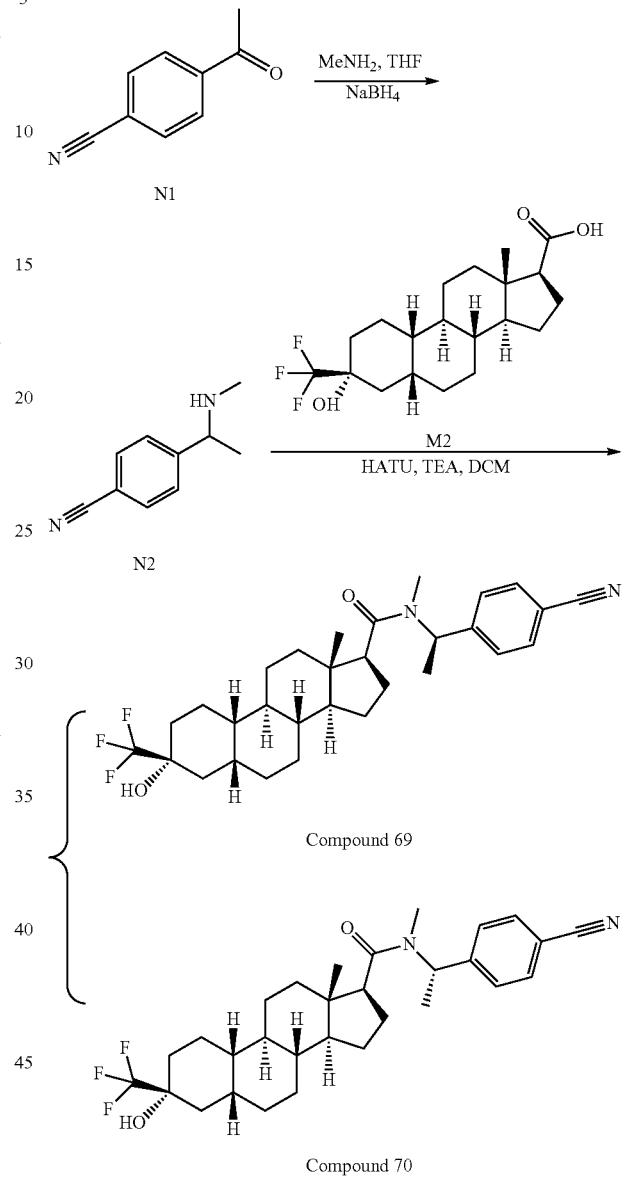

Compound 69

Compound 70

Step 1 (N2).

A solution of commercially available 4-acetylbenzonitrile N1 (1 g, 6.88 mmol) in MeNH₂ (20.6 mL, 41.2 mmol, 2M in EtOH) was stirred at 20° C. for 16 hrs. NaBH₄ (1.30 g, 34.4 mmol) was added and the mixture was stirred at 20° C. for 2 h, quenched with 50% NH₄Cl (50 mL) and extracted with EtOAc (2×20 mL). The combined organic phase was washed with brine (50 mL), dried over Na₂SO₄, filtered, concentrated and purified by silica gel chromatography (0-20% of EtOAc in PE) to give impure compound (900 mg, 82%) as an oil, which was used directly for next step.

¹H NMR (400 MHz, CDCl₃) δ 7.66-7.58 (m, 2H), 7.46-7.40 (m, 2H), 3.75-3.67 (m, 1H), 2.42-2.36 (m, 1H), 2.29 (s, 3H), 1.37-1.31 (m, 3H).

Step 2. (Compound 69 and Compound 70).

To a solution of M2 (160 mg, 0.427 mmol) in DCM (5 mL) was added HATU (249 mg, 0.640 mmol), TEA (215 mg, 2.13 mmol and 4-(1-(methylamino)ethyl)benzonitrile N2 (136 mg, 0.854 mmol). After stirring at 25° C. for 1 h, the reaction mixture was quenched with water (20 mL) and extracted with DCM (3×5 mL). The combined organic phase was washed with HCl (2×20 mL, 2 M), dried over $Na_2SO_4$, filtered, concentrated and purified by preparative TLC (PE/EtOAc=2/1) to give Compound 69 (60 mg) and Compound 70 (35 mg, 16%) as an oil.

60 mg Compound 69 was separated by SFC (column: AD (250 mm*30 mm, 5 um), gradient: 50-50% B (A=0.05% $NH_3/H_2O$, B=MeOH), flow rate: 60 mL/min) to give impure Compound 69 (35 mg), which was further separated by SFC (column: AD (250 mm*30 mm, 5 um), gradient: 50-50% B (A=0.05% $NH_3/H_2O$, B=MeOH), flow rate: 60 mL/min) to give pure Compound 69 (16 mg, 7%) as a solid.

Compound 69

$^1$H NMR (400 MHz, $CDCl_3$) δ 7.72-7.57 (m, 2H), 7.42-7.33 (m, 2H), 6.22-6.12 (m, 0.9H), 5.37-5.28 (m, 0.1H), 2.78-2.57 (m, 4H), 2.37-2.24 (m, 1H), 2.13-1.99 (m, 2H), 1.97-1.88 (m, 1H), 1.87-1.64 (m, 8H), 1.56-1.41 (m, 8H), 1.37-1.06 (m, 7H), 0.92-0.75 (m, 3H).

LCMS Rt=3.583 min in 7.0 min chromatography, 30-90AB, purity 100%, MS ESI calcd. for $C_{30}H_{40}F_3N_2O_2$ [M+H]$^+$ 517, found 517.

Compound 70

$^1$H NMR (400 MHz, $CDCl_3$) δ 7.68-7.60 (m, 2H), 7.41-7.36 (m, 1.5H), 7.31-7.27 (m, 0.5H), 6.20-6.11 (m, 0.8H), 5.41-5.32 (m, 0.2H), 2.77-2.68 (m, 4H), 2.43-2.44 (m, 1H), 2.08-1.89 (m, 3H), 1.85-1.61 (m, 9H), 1.53-1.44 (m, 6H), 1.41-1.24 (m, 4H), 1.24-1.02 (m, 4H), 0.81 (s, 3H).

LCMS Rt=3.489 min in 7.0 min chromatography, 30-90AB, purity 100%, MS ESI calcd. for $C_{30}H_{40}F_3N_2O_2$ [M+H]$^+$ 517, found 517.

Example 63. Synthesis of Compound 71 and 72

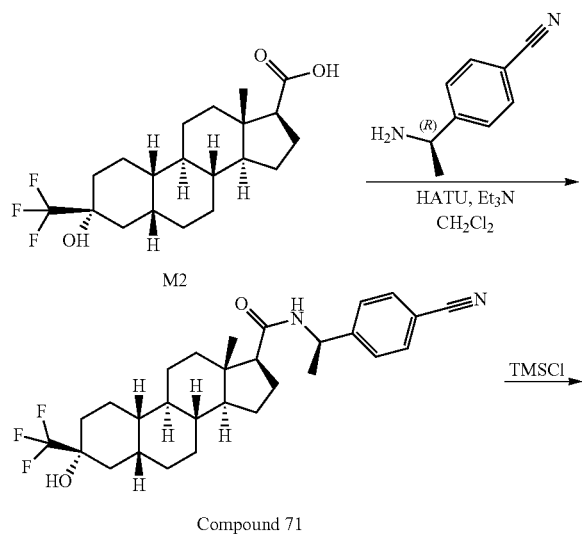

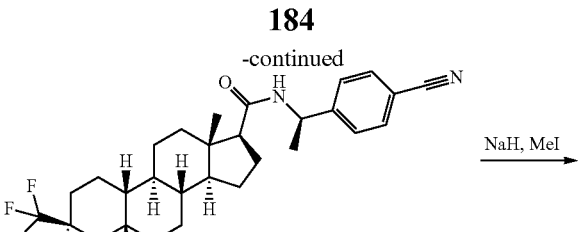

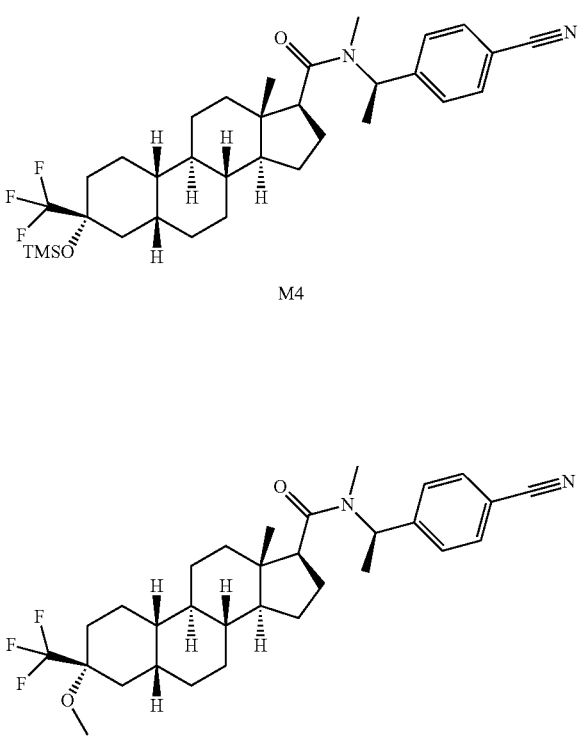

Step 1 (Compound 71).

To a solution of M2 (200 mg, 0.534 mmol) in DCM (5 mL) was added HATU (312 mg, 0.801 mmol), $Et_3N$ (268 mg, 2.66 mmol and (R)-4-(1-aminoethyl)benzonitrile (117 mg, 0.801 mmol). After stirring at 25° C. for 1 h, the reaction mixture was quenched with water (20 mL) and extracted with DCM (3×5 mL). The combined organic phase was dried over $Na_2SO_4$, filtered, concentrated and purified prep-HPLC (column: YMC-Actus Triart C18 100*30 mm*5 um), gradient: 75-100% B (A=water (0.05% HCl), B=MeCN), flow rate: 25 mL/min) to give Compound 71 (200 mg, 75%) as a solid.

$^1$H NMR (400 MHz, $CDCl_3$) δ 7.65-7.59 (m, 2H), 7.44-7.39 (m, 2H), 5.52-5.45 (m, 1H), 5.21-5.12 (m, 1H), 2.20-2.10 (m, 2H), 2.08-1.99 (m, 2H), 1.97-1.89 (m, 2H), 1.87-1.78 (m, 3H), 1.77-1.58 (m, 5H), 1.54-1.45 (m, 6H), 1.35-1.05 (m, 8H), 0.69 (s, 3H).

LCMS Rt=1.287 min in 2.0 min chromatography, 10-80AB, purity 99%, MS ESI calcd. for $C_{29}H_{38}F_3N_2O_2$ [M+H]$^+$ 503, found 503.

Example 64. Synthesis of Compound 73
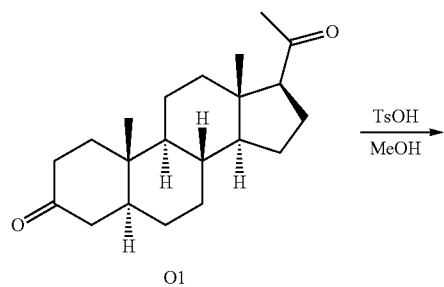
O1
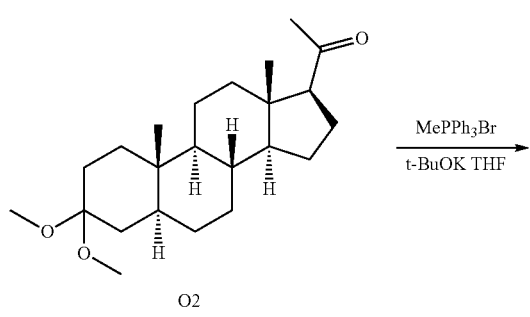
O2
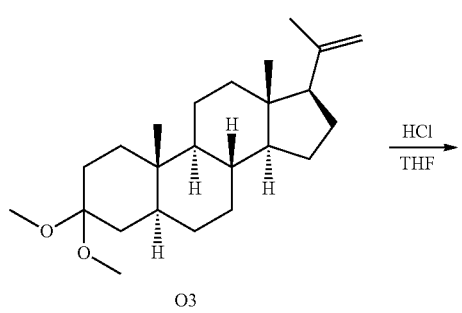
O3
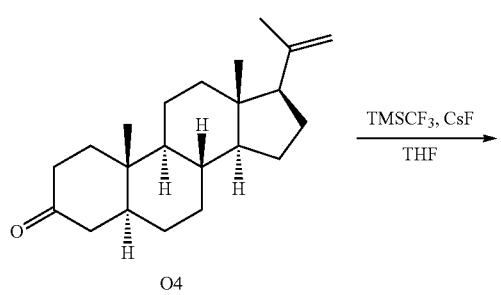
O4
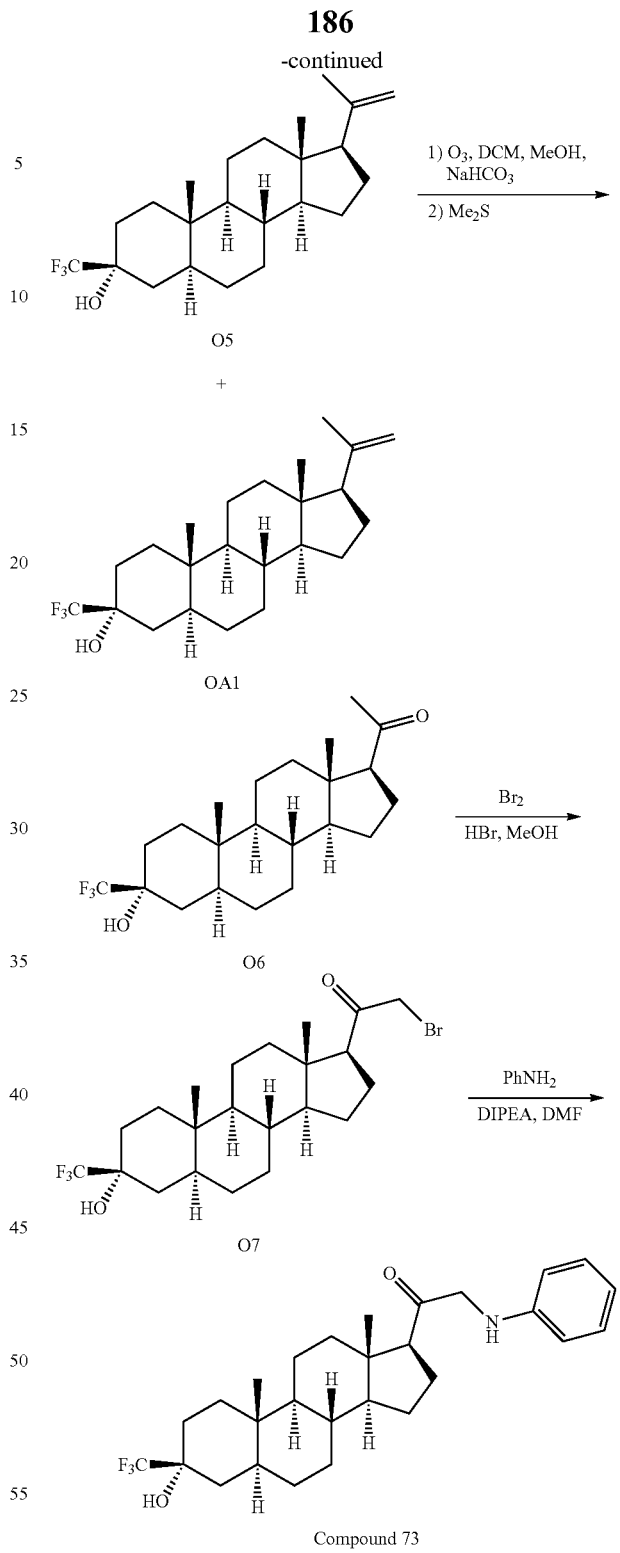
Step 1 (O2): To a solution of O1 (50 g, 157 mmol) in MeOH (500 mL) was added 4-methylbenzenesulfonic acid (2.70 g, 15.7 mmol) at 25° C. The mixture was stirred at 65° C. for 1 h. The reaction mixture was cooled to 25° C. and TEA (2.16 mL, 15.7 mmol) was added. The mixture was stirred for 0.5 h. The precipitate was collected by filtration and washed with methanol (2×100 mL) to give O2 (50 g, crude) as a white solid.

¹H NMR (400 MHz, CDCl₃) δ 3.25-3.05 (m, 6H), 2.60-2.40 (m, 1H), 2.20-2.05 (m, 4H), 2.00-1.95 (m, 1H), 1.90-1.80 (m, 1H), 1.75-1.50 (m, 6H), 1.49-1.05 (m, 12H), 1.04-0.95 (m, 1H), 0.78 (s, 3H), 0.59 (s, 3H).

Step 2 (O3): To a solution of bromo(methyl)triphenylphosphorane (73.2 g, 205 mmol) in THF (500 mL) was added t-BuOK (23.0 g, 205 mmol) at 25° C. The mixture was heated to 45° C. and stirred for 1 h. O2 (50 g, 137 mmol) was added. The mixture was stirred at 45° C. for 2 hrs. The mixture was quenched with NH₄Cl (200 mL) and extracted with THF (3×100 mL). The organic layer was washed brine (200 mL), dried over Na₂SO₄ and filtered to give a mixture of products including O3 (50 g, 500 mL), which was used in next step without further purification.

Step 3 (O4): To a solution of the mixture containing O3 (50 g, 138 mmol) in THF (500 mL) was added aq. HCl (207 mL, 1 M in water). The mixture was stirred at 25° C. for 0.5 h. The mixture was filtered and the filter cake was dissolved in DCM (200 mL) and washed with brine (100 mL), dried over anhydrous Na₂SO₄, filtered and concentrated in vacuum to afford O4 (39 g, 90%) as a solid.

¹H NMR (400 MHz, CDCl₃) δ 4.84 (s, 1H), 4.70 (s, 1H), 2.45-2.20 (m, 3H), 2.15-2.00 (m, 3H), 1.90-1.65 (m, 8H), 1.60-1.50 (m, 2H), 1.45-1.05 (m, 8H), 1.00 (s, 3H) 0.90-0.85 (m, 1H), 0.80-0.75 (m, 1H), 0.58 (s, 3H).

Step 4 (O5): To a solution of O4 (27 g, 85.8 mmol) in THF (200 mL) was added CsF (25.9 g, 171 mmol) and TMSCF₃ (24.3 g, 171 mmol). The mixture was stirred at 10° C. for 1 h. To the mixture was added water (10 mL) and TBAF.3H₂O (30 g). The mixture was stirred at 30° C. for another 2 hrs. The mixture was concentrated in vacuum. The residue was dissolved in EtOAc (500 mL), washed with water (2×500 mL), dried over Na₂SO₄, filtered, concentrated in vacuum and purified by flash column (DCM/EtOAc (1:1) in PE, 0~10%) to give O5 (27 g, 82%) and by-product O5A (3.5 g, 11%) as solids.

O5:
¹H NMR (400 MHz, CDCl₃) δ 4.84 (s, 1H), 4.70 (s, 1H), 2.12-1.94 (m, 3H), 1.89-1.78 (m, 2H), 1.75 (s, 3H), 1.72-1.60 (m, 5H), 1.58-1.48 (m, 2H), 1.45-1.09 (m, 10H), 1.01-0.89 (m, 1H), 0.85 (s, 3H), 0.78-0.68 (m, 1H), 0.56 (s, 3H).

Step 5 (O6).

To a solution of O5 (1 g, 2.6 mmol) in DCM (30 mL) and MeOH (30 mL) was added NaHCO₃ (1 g, 11.9 mmol). To the mixture was bubbled ozone (1 atm) at −78° C. until the mixture turned blue (ca. 2 min). N₂ was bubbled for an additional 5 min until the mixture turned colorless. To the mixture was added Me₂S (1.3 g, 20.9 mmol), and the mixture was stirred at 15° C. for 16 h. The mixture was filtered and concentrated in vacuo, triturated with MeCN (10 mL) to give O6 (0.8 g, 80%) as a solid.

¹H NMR (400 MHz, CDCl₃) δ 2.52 (t, J=8.8 Hz, 1H), 2.21-2.13 (m, 1H), 2.11 (s, 3H), 2.07-1.97 (m, 1H), 1.85-1.52 (m, 10H), 1.47-1.11 (m, 9H), 1.03-0.89 (m, 1H), 0.86-0.76 (m, 4H), 0.61 (s, 3H).

Step 6 (O7).

To a solution of O6 (0.8 g, 2.06 mmol) in MeOH (10 ml) was added HBr (82.2 mg, 0.412 mmol, 40% in water) and Br₂ (329 mg, 2.10 mmol) at 25° C. The mixture was stirred at 25° C. for 16 hrs. The mixture was quenched with sat. aqueous NaHCO₃ (10 mL), treated with water (20 mL), extracted with EtOAc (2×20 mL). The combined organic phase was washed with brine (20 mL), dried over anhydrous Na₂SO₄, filtered, concentrated in vacuo to afford O7 (0.9 g, 94%) as a solid.

¹H NMR (400 MHz, CDCl₃) δ 3.95-3.90 (m, 2H), 2.90-2.75 (m, 1H), 2.25-2.10 (m, 1H), 1.95-1.85 (m, 1H), 1.80-1.50 (m, 10H), 1.45-1.15 (m, 9H), 1.00-0.75 (m, 5H), 0.65 (s, 3H).

Step 7 (Compound 73).

To a solution of DIPEA (21.4 mg, 0.166 mmol) in DMF (3 mL) was added PhNH₂ (23.8 mg, 0.256 mmol) at 25° C. The reaction mixture was stirred at 25° C. for 30 mins. 07 (60 mg, 0.128 mmol) was added. The reaction mixture was stirred at 40° C. for 10 hrs. The reaction mixture was quenched with water (5 mL). The aqueous phase was extracted with EtOAc (3×10 mL). The combined organic phase was washed with brine (2×10 mL), dried over anhydrous Na₂SO₄, filtered and concentrated. The residue was triturated with H₂O (10 mL) at 25° C. to give Compound 73 (20 mg, crude) as a solid, which was purified by HPLC (Instrument: BQ; Method: Column YMC-Actus Triart C18 100*30 mm*5 um; Conditions: water (0.05% HCl)-ACN; Gradient 80%-100% B; Gradient Time (min): 9.5) to obtain Compound 73 (9 mg, 15%) as a solid.

¹H NMR (400 MHz, CDCl₃) δ 7.19 (t, J=8.0 Hz, 2H), 6.72 (t, J=8.0 Hz, 1H), 6.60 (d, J=8.0 Hz, 2H), 4.69 (s, 1H), 4.02-3.85 (m, 2H), 2.61-2.53 (m, 1H), 2.30-2.18 (m, 1H), 2.03-1.92 (m, 1H), 1.83-1.60 (m, 9H), 1.46-1.16 (m, 10H), 1.04-0.92 (m, 1H), 0.84-0.77 (m, 4H), 0.64 (s, 3H).

LCMS Rt=1.228 min in 2.0 min chromatography, 30-90AB, purity 100%, MS ESI calcd. For C₂₈H₃₉F₃NO₂ [M+H]⁺ 478, found 478.

Example 65. Synthesis of Compound 74

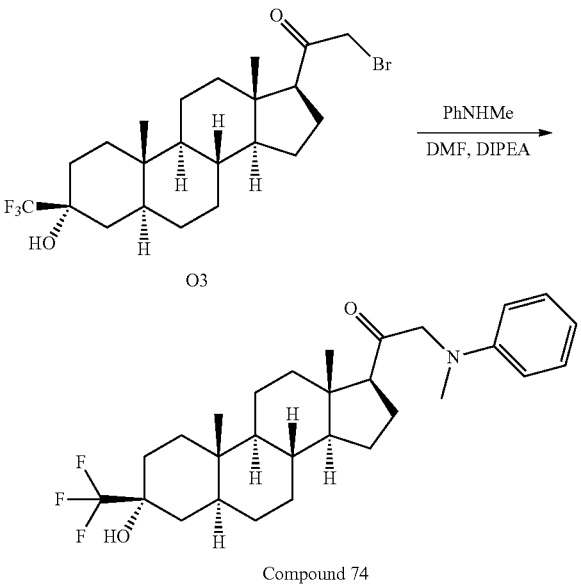

Compound 74

Step 1 (Compound 74).

To a solution of DIPEA (21.4 mg, 0.166 mmol) in DMF (3 mL) was added PhNHMe (27.3 mg, 0.256 mmol) at 25° C. The reaction mixture was stirred at 25° C. for 0.5 hour. 03 (60 mg, 0.128 mmol) was added. The reaction mixture was stirred at 40° C. for 20 h and quenched with water (5 mL). The aqueous phase was extracted with EtOAc (3×10 mL). The combined organic phase was washed with brine (2×10 mL), dried over anhydrous Na₂SO₄, filtered and concentrated. The residue was triturated with H₂O (10 mL)

at 25° C. to give Compound 74 (21 mg, crude) as a solid. The crude product was purified by HPLC (Instrument: BQ; Method: Column YMC-Actus Triart C18 100*30 mm*5 um; Condition: water (0.05% HCl)-ACN; Gradient 80%-100% B; Gradient Time (min): 9.5) to obtain Compound 74 (8 mg, 38%) as a solid.

$^1$H NMR (400 MHz, CDCl$_3$) δ 7.23-7.17 (m, 2H), 6.71 (t, J=8.0 Hz, 1H), 6.60 (d, J=8.0 Hz, 2H), 4.11-3.96 (m, 2H), 2.99 (s, 3H), 2.64-2.57 (m, 1H), 2.22-2.08 (m, 1H), 1.99-1.94 (m, 1H), 1.86-1.57 (m, 9H), 1.46-1.19 (m, 9H), 1.18-0.89 (m, 2H), 0.85-0.76 (m, 4H), 0.67 (s, 3H)

LCMS Rt=1.227 min in 2.0 min chromatography, 30-90AB, purity 100% ESI calcd. For C$_{29}$H$_{41}$F$_3$NO$_2$ [M+H]$^+$ 492 found 492.

Example 66. Synthesis of Compound 75

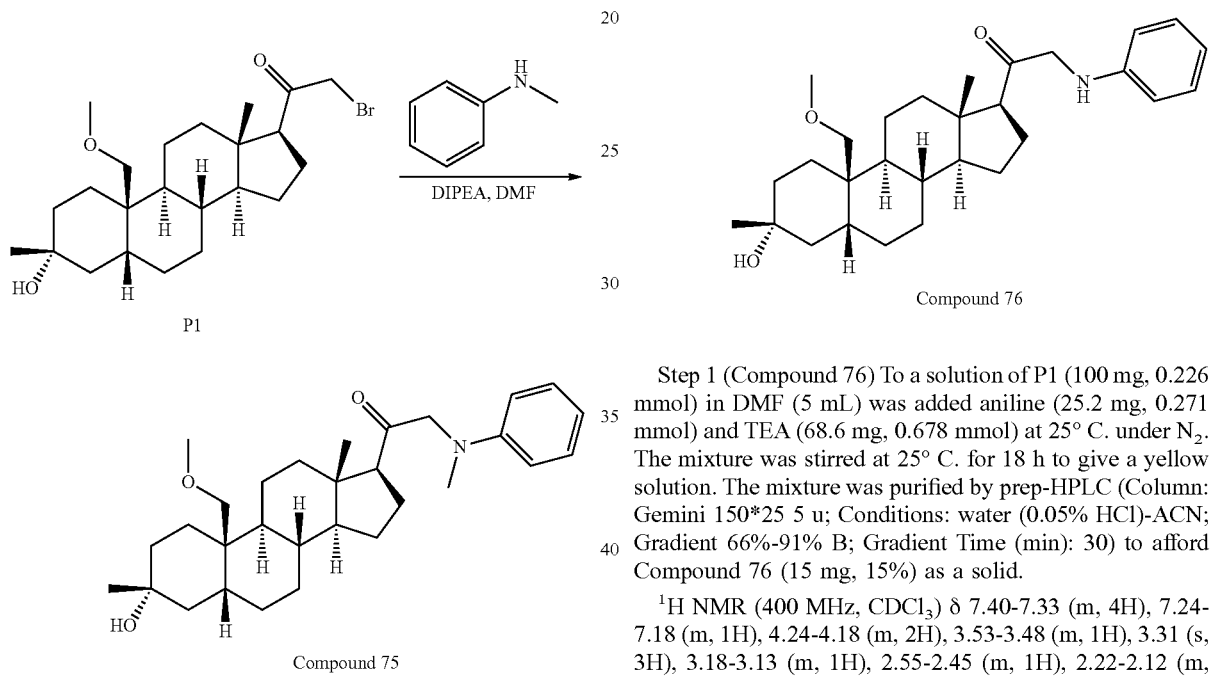

Compound 75

The synthesis of P1 is disclosed in WO02016/123056.

To a solution of DIPEA (18.8 mg, 146 μmol) in DMF (3 mL) was added N-methylaniline (24.2 mg, 226 μmol) at 10° C. under N$_2$ at 10° C. The mixture was stirred at this temperature for 30 mins. Then P1 (50 mg, 0.113 mmol) was added. The mixture was heated at 60° C. for 16 hrs. The mixture was concentrated to give light yellow oil, which was purified by HPLC (Column: Xtimate C18 150*25 mm*5 um; Conditions: water (0.05% HCl)-ACN; Gradient 63%-88% B; Gradient Time (min): 9.5) to afford Compound 75 (7.00 mg, 13%) as a solid.

$^1$H NMR (400 MHz, CDCl$_3$) δ 7.35-7.20 (m, 2H), 7.05-6.86 (m, 3H), 4.08-4.03 (m, 2H), 3.58-3.47 (m, 1H), 3.32 (s, 3H), 3.20-3.12 (m, 1H), 3.11 (s, 3H), 2.54 (brs, 1H), 2.20-2.03 (m, 1H), 1.90 (s, 3H), 1.82-1.33 (m, 12H), 1.33-1.06 (m, 10H), 0.58 (s, 3H).

LCMS Rt=0.943 min in 1.5 min chromatography, 5-95 AB, purity 100%, MS ESI calcd. for C$_{30}$H$_{46}$NO$_3$ [M+H]$^+$ 468, found 468.

Example 67. Synthesis of Compound 76

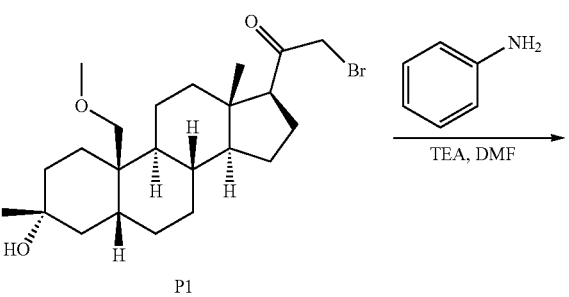

P1

Compound 76

Step 1 (Compound 76) To a solution of P1 (100 mg, 0.226 mmol) in DMF (5 mL) was added aniline (25.2 mg, 0.271 mmol) and TEA (68.6 mg, 0.678 mmol) at 25° C. under N$_2$. The mixture was stirred at 25° C. for 18 h to give a yellow solution. The mixture was purified by prep-HPLC (Column: Gemini 150*25 5 u; Conditions: water (0.05% HCl)-ACN; Gradient 66%-91% B; Gradient Time (min): 30) to afford Compound 76 (15 mg, 15%) as a solid.

$^1$H NMR (400 MHz, CDCl$_3$) δ 7.40-7.33 (m, 4H), 7.24-7.18 (m, 1H), 4.24-4.18 (m, 2H), 3.53-3.48 (m, 1H), 3.31 (s, 3H), 3.18-3.13 (m, 1H), 2.55-2.45 (m, 1H), 2.22-2.12 (m, 1H), 1.92-1.84 (m, 3H), 1.80-1.71 (m, 3H), 1.63-1.40 (m, 10H), 1.28-1.15 (m, 10H), 0.58 (s, 3H).

LCMS Rt=2.014 in in 3.0 min chromatography, 10-80AB, purity 100%, MS ESI calcd. for C$_{29}$H$_{44}$NO$_3$ [M+H]$^+$ 454, found 454.

Example 68. Synthesis of Compound 77

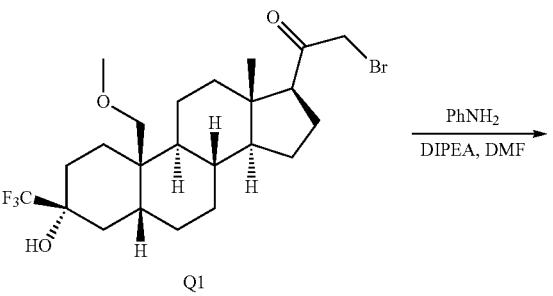

Q1

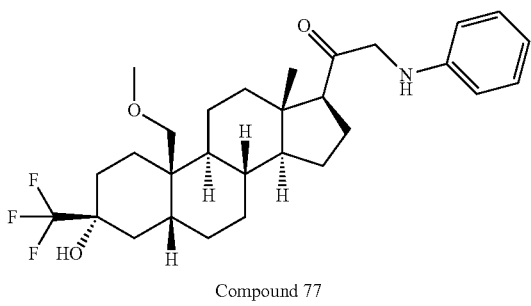

Compound 77

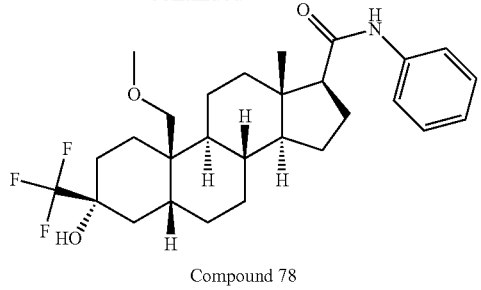

Compound 78

The synthesis of Q1 is disclosed in WO2015/27227 A1.

To a solution of Q1 (80 mg, 0.1614 mmol) in DMF (1 mL) was added DIPEA (52.1 mg, 0.4035 mmol). The mixture was stirred at 20° C. for 10 min. Aniline (37.5 mg, 0.4035 mmol) was added to the reaction mixture. After stirring at 20° C. another 12 hours, the mixture was poured into water (20 mL) and extracted with EtOAc (2×20 mL). The combined organic layers were washed with brine (2×20 mL), dried over anhydrous $Na_2SO_4$, filtered and concentrated in vacuo. The residue was purified by HPLC (column: Phenomenex Gemini C18 250*50 mm*10 um, gradient: 78-88% B, Conditions: water (0.05% ammonia hydroxide v/v)-ACN, flow rate: 30 mL/min) to give Compound 77 (35 mg, 43%) as a solid.

$^1$H NMR (400 MHz, $CDCl_3$) δ 7.22-7.17 (m, 2H), 6.76-6.70 (m, 1H), 6.62-6.59 (m, 2H), 3.28-3.23 (m, 1H), 4.68 (brs, 1H), 4.0-3.87 (m, 2H), 3.50-3.48 (m, 1H), 3.31 (s, 3H), 2.61-2.54 (m, 1H), 2.29-1.68 (m, 11H), 1.65-1.21 (m, 12H), 0.65 (s, 3H).

LCMS Rt=2.273 min in 3 min chromatography, 30-90CD, purity 100%, MS ESI calcd. for $C_{29}H_{41}F_3NO_3$ $[M+H]^+$ 508, found 508.

Example 69. Synthesis of Compound 78

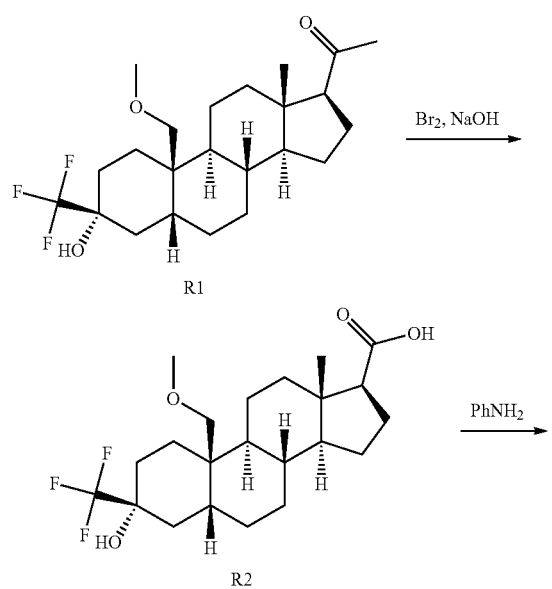

The synthesis of $R^1$ is disclosed in WO2015/27227 A1.

Step 1 ($R^2$).

Liquid bromine (1.9 g, 0.61 mL, 11.9 mmol) was added slowly to a vigorously stirred aqueous solution of sodium hydroxide (9 mL, 4 M, 36 mmol) at 0° C. When all the bromine dissolved, the mixture was diluted with cold dioxane (0.75 mL) and added slowly to a stirred solution of R1 (500 mg, 1.2 mmol) in dioxane (1 mL) and water (0.75 mL). The homogeneous yellow solution became colorless slowly and a white precipitate formed. The reaction mixture was stirred at 25° C. for 16 hours. The remaining oxidizing reagent was quenched with aqueous $Na_2S_2O_3$ (1.5 mL) and the mixture was then heated at 80° C. until the solid material dissolved. Acidification of the solution with hydrochloric acid (3 N) furnished a white precipitate. The solid was filtered and washed with water (3×20 mL) to give a solid, which was dried in vacuo to give $R^2$ (600 mg, crude) as a solid.

$^1$H NMR (400 MHz, $CDCl_3$) δ 5.70 (s, 1H), 3.59-3.44 (m, 1H), 3.26-3.15 (m, 4H), 2.34-2.23 (m, 1H), 2.07-1.32 (m, 17H), 1.27-0.98 (m, 6H), 0.68-0.56 (m, 3H).

LCMS Rt=0.948 min in 2 min chromatography, 30-90AB, purity 97%, MS ESI calcd. for $C_{22}H_{32}F_3O_4$ $[M-H]^-$ 417, found 417.

Step 2 (Compound 78).

To R2 (60 mg, 0.14 mmol) in DCM (3 mL) was added HATU (81.3 mg, 0.21 mmol) and $Et_3N$ (72.3 mg, 0.71 mmol) at 25° C. After stirring at 25° C. for 0.5 hour, aniline (21.2 mg, 0.228 mmol) was added at 25° C. The reaction mixture was stirred at 40° C. for 10 hours and treated with water (10 mL). The mixture was extracted with EtOAc (2×10 mL). The combined organic phase was washed with water (2×10 mL) and saturated brine (10 mL), dried over anhydrous $Na_2SO_4$, filtered and concentrated. The residue was purified by HPLC (column: Xtimate C18 150*25 mm*5 um), Conditions: water (0.225% FA)-ACN, gradient: 75-95% B, Gradient Time: 13 mins, 100% B Hold Time: 2.5 min, flow rate: 25 mL/min) to give Compound 78 (21 mg, 29%) as a solid.

$^1$H NMR (400 MHz, $CDCl_3$) δ 7.54-7.46 (m, 2H), 7.36-7.29 (m, 2H), 7.13-7.06 (m, 1H), 6.93 (s, 1H), 3.54-3.48 (m, 1H), 3.30 (s, 3H), 3.29-3.25 (m, 1H), 2.34-2.23 (m, 2H), 2.17-2.08 (m, 1H), 2.07-1.96 (m, 4H), 1.89-1.61 (m, 7H), 1.51-1.42 (m, 3H), 1.41-1.04 (m, 7H), 0.75 (s, 3H).

LCMS Rt=1.101 min in 2 min chromatography, 30-90AB, purity 100%, MS ESI calcd. for $C_{28}H_{39}F_3NO_3$ $[M+H]^+$ 494, found 494.

Example 70. Synthesis of Compound 79

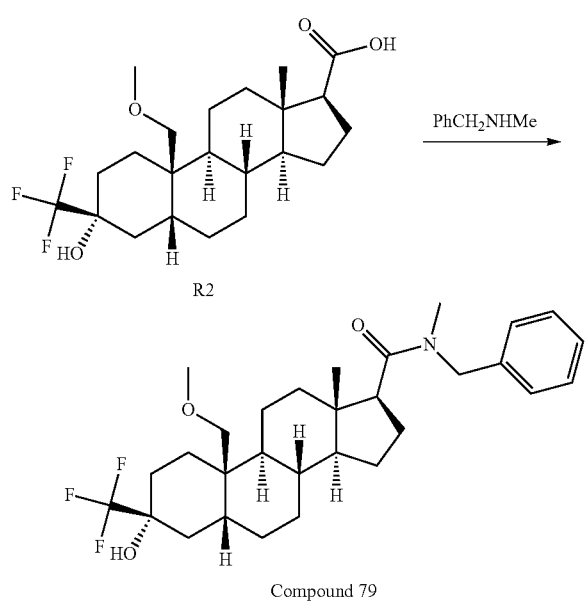

Step 1 (Compound 79). To R2 (100 mg, 0.23 mmol) in DCM (3 mL) was added HATU (135 mg, 0.35 mmol) and Et₃N (120 mg, 1.19 mmol) at 25° C. After stirring at 25° C. for 0.5 hour, N-methyl-1-phenylmethanamine (46 mg, 0.38 mmol) was added at 25° C. The reaction mixture was stirred at 40° C. for 10 hours and treated with water (10 mL). The mixture was extracted with EtOAc (2×10 mL). The combined organic phase was washed with water (2×10 mL) and saturated brine (10 mL), dried over anhydrous Na₂SO₄, filtered and concentrated. The residue was purified by HPLC (column: Xtimate C18 150*25 mm*5 um), Conditions: water (0.225% FA)-ACN, gradient: 70-100% B, Gradient Time: 13 mins, 100% B Hold Time: 2.5 min, flow rate: 25 mL/min) to give Compound 79 (46 mg, 37%) as a solid.

$^1$H NMR (400 MHz, CDCl₃) δ 7.39-7.28 (m, 2H), 7.25-7.17 (m, 2H), 7.16-7.08 (m, 1H), 5.08-4.89 (m, 1H), 4.37-4.21 (m, 1H), 3.56-3.48 (m, 1H), 3.31 (s, 3H), 3.29-3.23 (m, 1H), 3.01-2.91 (m, 3H), 2.83-2.67 (m, 1H), 2.41-2.27 (m, 1H), 2.15-1.86 (m, 4H), 1.84-1.59 (m, 7H), 1.54-1.18 (m, 10H), 1.16-0.98 (m, 1H), 0.80 (s, 3H).

LCMS Rt=1.110 min in 2 min chromatography, 30-90AB, purity 100%, MS ESI calcd. for C₃₀H₄₃F₃NO₃ [M+H]⁺ 522, found 522.

Example 71. Synthesis of Compound 80

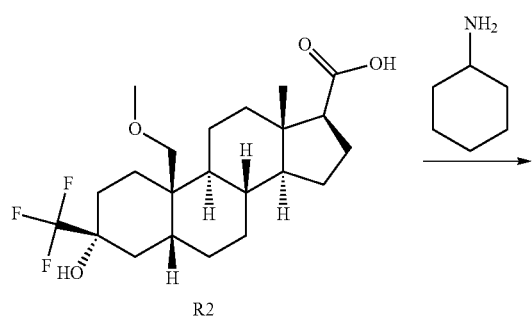

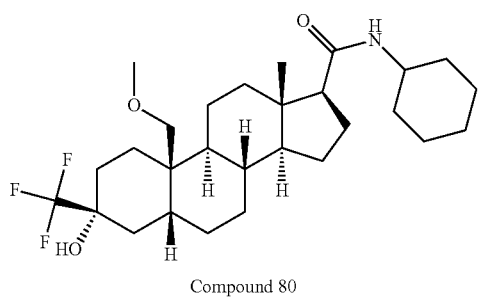

Step 1 (Compound 80). To R2 (100 mg, 0.23 mmol) in DCM (3 mL) was added HATU (135 mg, 0.35 mmol) and Et₃N (120 mg, 1.19 mmol) at 25° C. After stirring at 25° C. for 0.5 hour, cyclohexanamine (37.6 mg, 0.38 mmol) was added at 25° C. The reaction mixture was stirred at 25° C. for 10 hours and treated with water (10 mL). The mixture was extracted with EtOAc (2×10 mL). The combined organic phase was washed with water (2×10 mL) and saturated brine (10 mL), dried over anhydrous Na₂SO₄, filtered and concentrated. The residue was purified by trituration with MeCN (5 mL) to give Compound 80 (49 mg, 40%) as a solid.

$^1$H NMR (400 MHz, CDCl₃) δ 5.16-5.07 (m, 1H), 3.87-3.73 (m, 1H), 3.54-3.47 (m, 1H), 3.30 (s, 3H), 3.29-3.24 (m, 1H), 2.23-1.86 (m, 9H), 1.79-1.62 (m, 8H), 1.55-1.33 (m, 8H), 1.29-1.02 (m, 9H), 0.66 (s, 3H).

LCMS Rt=1.107 min in 2 min chromatography, 30-90AB, purity 97%, MS ESI calcd. for C₂₈H₄₅F₃NO₃ [M+H]⁺ 500, found 500.

Example 72. Synthesis of Compound 81 and Compound 82

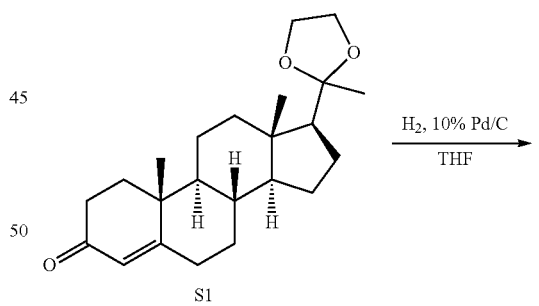

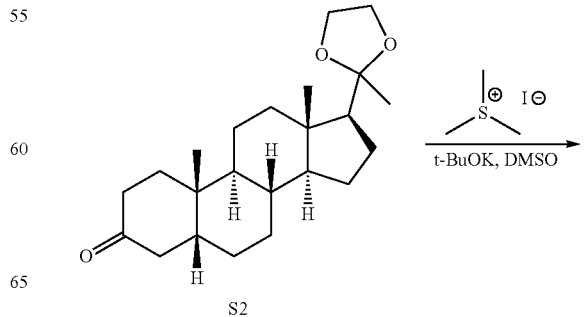

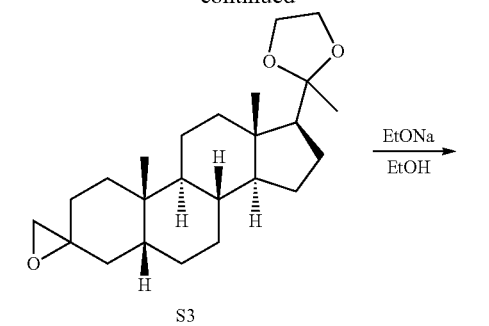

S3

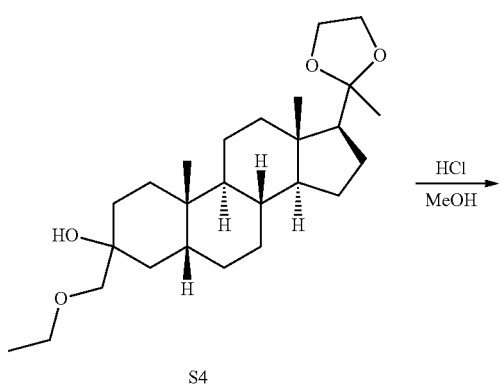

S4

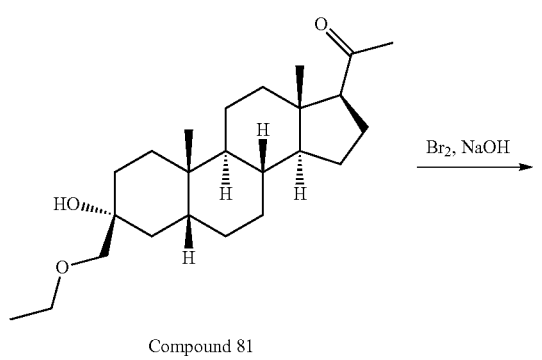

Compound 81

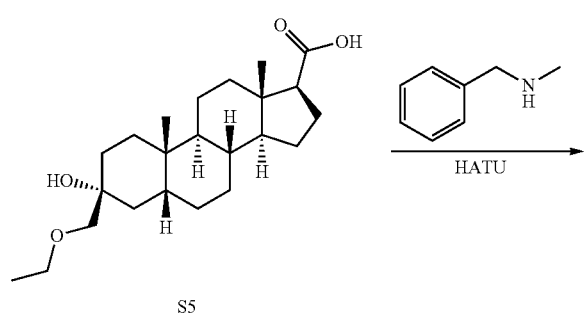

S5

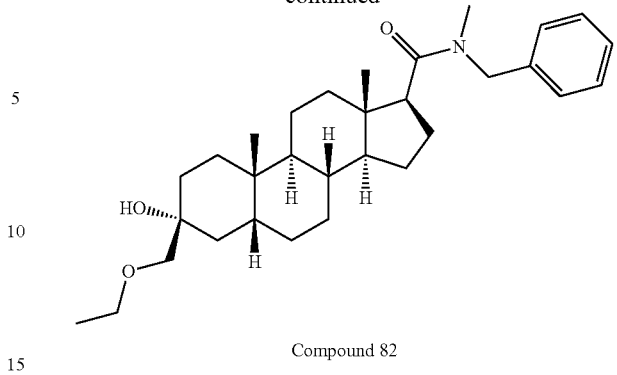

Compound 82

The synthesis of S1 is disclosed in Russian Chemical Bulletin, 2013, vol. 62, 9 p. 2086-2087.

Step 1 (S2).

To a solution of S1 (5.00 g, 13.9 mmol) in THF (100 mL) was added Pd/C (wet, 1.5 g). The mixture was stirred under $H_2$ (15 psi) at 25° C. for 16 hours. The mixture was filtered through a pad of celite and the filtrate was concentrated in vacuo to afford S2 (4.80 g, 96%) as a solid.

$^1$H NMR (400 MHz, $CDCl_3$) δ 4.03-3.80 (m, 4H), 3.74 (s, 2H), 2.74-2.66 (m, 1H), 2.40-1.98 (m, 5H), 1.98-1.56 (m, 6H), 1.56-1.05 (m, 12H), 1.01 (s, 3H), 0.78 (s, 3H).

Step 2 (S3).

A solution of trimethylsulfonium iodide (5.42 g, 26.6 mmol) and NaH (1.06 g, 26.6 mmol, 60% purity) in DMSO (50 mL) was stirred at 25° C. for 1.0 h under $N_2$. To the reaction mixture was added a solution of S2 (4.80 g, 13.3 mmol) in DMSO (20 mL) and the mixture was stirred at 60° C. for 4 hrs. The reaction was treated with water (50 mL) and extracted with EtOAc (2×100 mL). The combined organic phase was washed with brine (100 mL), dried over $Na_2SO_4$, filtered, concentrated to give S3 (4.80 g, 48%) as a solid.

$^1$H NMR (400 MHz, $CDCl_3$) δ 3.89-3.86 (m, 4H), 2.63-2.55 (m, 2H), 2.44-2.33 (m, 1H), 2.07-1.56 (m, 8H), 1.50-1.05 (m, 11H), 1.05-0.93 (m, 7H), 0.93-0.78 (m, 2H), 0.76 (s, 3H).

Step 3 (S4). To anhydrous ethanol (100 mL) was added Na (2.94 g, 128 mmol) in five portions. The mixture was stirred at 25° C. for 2 hours. S3 (4.8 g, 12.8 mmol) in THF (50 mL) was added to the reaction mixture and then was stirred at 60° C. for 5 hrs. After the reaction mixture was cooled to 0° C., the reaction mixture was quenched by addition of $H_2O$ (100 mL). The aqueous phase was extracted with EtOAc (3×100 mL). The combined organic phase was washed with brine (2×100 mL), dried over anhydrous $Na_2SO_4$, filtered and concentrated to give S4 (4.80 g, 89%) as a solid.

$^1$H NMR (400 MHz, $CDCl_3$) δ 4.06-3.85 (m, 3H), 3.76-3.65 (m, 1H), 3.58-3.40 (m, 2H), 3.26-3.18 (m, 1H), 2.08-1.56 (m, 8H), 1.56-1.05 (m, 21H), 1.05-0.78 (m, 5H), 0.73 (s, 3H).

Step 4 (Compound 81).

To a solution of S4 (4.80 g, 11.4 mmol) in methanol (50 mL) was added hydrogen chloride (22.8 mL, 1M in $H_2O$) dropwise at 25° C. The mixture was stirred at 25° C. for 10 min. The mixture was poured into water (50 mL). The aqueous phase was extracted with EtOAc (3×100 mL). The combined organic phase was washed with brine (100 mL), dried over $Na_2SO_4$, filtered and concentrated. The residue was purified by flash silica gel chromatography (0~30% of EtOAc in PE) to give impure product as a solid, which was repurified by silica gel chromatography to give Compound 81 (600 mg) as a light yellow oil, which was triturated with MeCN (10 mL) at 25° C. for 2 hours to give Compound 81 (500 mg, 10%) as a light yellow oil.

The structure of Compound 81 was confirmed by NOE.

$^1$H NMR (400 MHz, CDCl$_3$) δ 3.58-3.49 (q, J=6.8 Hz, J=14 Hz, 2H), 3.47-3.36 (q, J=8.8 Hz, J=20.8 Hz, 2H), 2.72 (s, 1H), 2.57-2.48 (t, J=8.8 Hz, 1H), 2.18-2.13 (m, 1H), 2.10 (s, 3H), 2.04-1.78 (m, 3H), 1.74-1.58 (m, 4H), 1.55-1.32 (m, 8H), 1.31-1.12 (m, 8H), 1.04-0.96 (m, 1H), 0.93 (s, 3H), 0.58 (s, 3H).

LCMS Rt=1.113 min in 2 min chromatography, 30-90AB, purity 100%, MS ESI calcd. for $C_{24}H_{39}O_2$ [M+H—H$_2$O]$^+$ 359, found 359.

Step 5 (S5).

Liquid bromine (848 mg, 0.271 mL, 5.31 mmol) was added slowly to a vigorously stirred aqueous sodium hydroxide solution (5.30 mL, 4 M, 21.2 mmol) at 0° C. When all the bromine dissolved, the mixture was diluted with cold (0° C.) dioxane (2 mL) and was added slowly to a stirred solution of Compound 81 (200 mg, 0.531 mmol) in dioxane (2 mL) and water (1.5 mL). The homogeneous yellow solution became colorless slowly and a white precipitate formed The reaction mixture was stirred at 25° C. for another 16 hours. The remaining oxidizing reagent was quenched with aqueous Na$_2$S$_2$O$_3$ (1.5 mL) and the mixture was then heated at 80° C. until the solid material dissolved. Acidification of the solution with aqueous hydrochloric acid (3 N) furnished a white precipitate. The solid was filtered and washed with water (3×20 mL) to give a solid, which was dried in vacuo to give S5 (380 mg, crude) as an oil.

$^1$H NMR (400 MHz, CDCl$_3$) δ 3.58-3.50 (m, 2H), 3.46-3.38 (m, 2H), 2.42-2.34 (m, 1H), 2.04 (s, 1H), 1.96-1.30 (m, 14H), 1.26-1.10 (m, 11H), 1.03-0.90 (m, 4H), 0.71 (s, 3H).

Step 6 (Compound 82).

To a solution of S5 (200 mg, 0.528 mmol) in DCM (3 mL) was added HATU (301 mg, 0.792 mmol) and Et$_3$N (266 mg, 2.63 mmol) at 25° C. After stirring at 25° C. for 10 min, N-methyl-1-phenylmethanamine (95.9 mg, 0.792 mmol) was added to the reaction mixture at 25° C. The reaction mixture was stirred at 25° C. for 1.5 hours and quenched with ice-water (10 mL). The aqueous phase was extracted with EtOAc (3×20 mL). The combined organic phase was washed with saturated brine (2×10 mL), dried over anhydrous Na$_2$SO$_4$, filtered and concentrated and the resulting residue was purified by flash silica gel chromatography (0~25% of EtOAc in PE) to give Compound 82 (100 mg) as a solid. Compound 82 was redissolved in EtOAc (20 mL) and washed with H$_2$O (3×20 mL), dried over Na$_2$SO$_4$, filtered, concentrated in vacuo to give Compound 82 (78 mg, 31%) as a solid.

$^1$H NMR (400 MHz, CDCl$_3$) δ 7.38-7.29 (m, 2H), 7.25-7.21 (m, 2H), 7.16-7.09 (m, 1H), 5.08-4.88 (m, 1H), 4.37-4.22 (m, 1H), 3.58-3.49 (m, 2H), 3.47-3.33 (m, 2H), 2.99-2.91 (m, 3H), 2.88-2.64 (m, 2H), 2.38-2.26 (m, 1H), 1.98-1.66 (m, 6H), 1.52-0.98 (m, 17H), 1.04-0.96 (m, 1H), 0.94 (s, 3H), 0.78 (s, 3H).

LCMS Rt=1.172 min in 2 min chromatography, 30-90AB, purity 100%, MS ESI calcd. for $C_{31}H_{48}NO_3$ [M+H]$^+$ 482, found 482.

Example 73. Synthesis of Compound 83

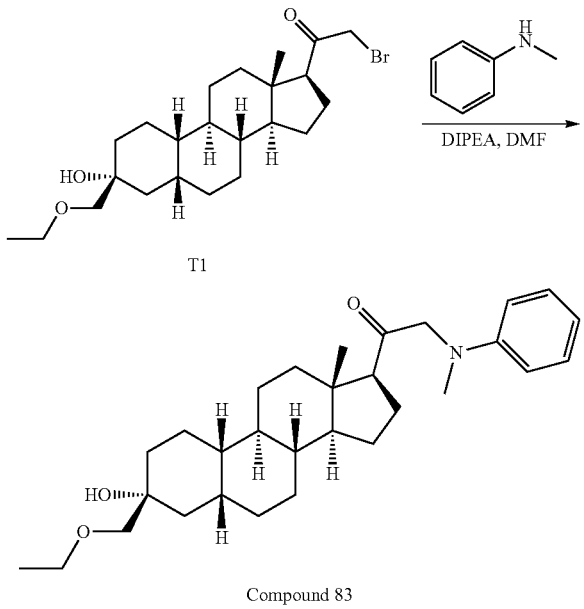

T1

Compound 83

The synthesis of T1 is disclosed in WO2015/180679.

Step 1 (Compound 83).

To a solution of DIPEA (37.8 mg, 0.293 mmol) in DMF (3 mL) was added N-methylaniline (48.4 mg, 0.452 mmol) at 25° C. under N$_2$. After stirring at 25° C. for 30 min, T1 (100 mg, 226 mmol) was added. The mixture was stirred at 50° C. for 16 hours and concentrated to give a light yellow oil, which was purified by HPLC (Column: YMC-Actus Triart C18 100*30 mm*5 um; Conditions: water (0.05% HCl)-ACN; Gradient 80%-100% B; Gradient Time (min): 9.5) to afford Compound 83 (32.0 mg, 30%) as a solid.

$^1$H NMR (400 MHz, CDCl$_3$) δ 7.25-7.18 (m, 2H), 6.75-6.68 (m, 1H), 6.62-6.59 (m, 2H), 4.11-3.98 (m, 2H), 3.58-3.38 (m, 4H), 3.00 (s, 3H), 2.72 (brs, 1H), 2.62-2.56 (m, 1H), 2.22-2.05 (m, 1H), 2.00-1.92 (m, 1H), 1.85-1.53 (m, 7H), 1.53-1.33 (m, 7H), 1.33-1.02 (m, 10H), 0.67 (s, 3H).

LCMS Rt=1.031 min in 1.5 min chromatography, 5-95 AB, purity 100%, MS ESI calcd. for $C_{30}H_{46}NO_3$ [M+H]$^+$ 468, found 468.

Example 74. Synthesis of Compound 84

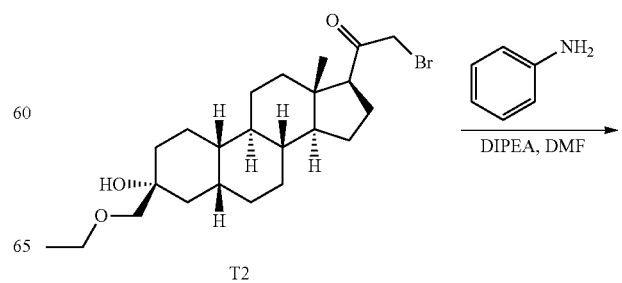

T2

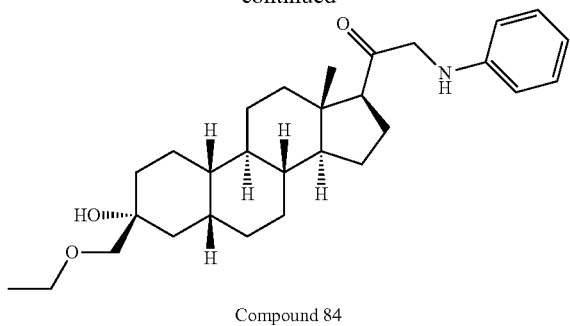

Compound 84

Step 1 (Compound 84).

To a solution of DIPEA (37.8 mg, 293 μmol) in DMF (3 mL) was added aniline (42.0 mg, 452 μmol) at 25° C. under $N_2$. After stirring at 25° C. for 30 min. T1 (100 mg, 0.226 mmol) was added. The mixture was stirred at 50° C. for 16 hours and concentrated to give a light yellow oil, which was purified by HPLC (Column: YMC-Actus Triart C18 100*30 mm*5 um; Conditions: water (0.05% HCl)-ACN; Gradient 75%-100% B; Gradient Time (min): 8) to afford Compound 84 (22.0 mg, 21%) as a solid.

$^1$H NMR (400 MHz, CDCl$_3$) δ 7.25-7.13 (m, 2H), 6.75-6.68 (m, 1H), 6.62-6.53 (m, 2H), 4.69 (brs, 1H), 4.00-3.85 (m, 2H), 3.58-3.35 (m, 4H), 2.73 (s, 1H), 2.62-2.53 (m, 1H), 2.28-2.15 (m, 1H), 1.98-1.90 (m, 1H), 1.85-1.53 (m, 7H), 1.53-1.31 (m, 7H), 1.31-0.98 (m, 10H). 0.84 (s, 3H).

LCMS Rt=0.989 min in 1.5 min chromatography, 5-95 AB, purity 100%, MS ESI calcd. for $C_{29}H_{44}NO_3$ [M+H]$^+$ 454, found 454.

Example 75. Synthesis of Compound 85

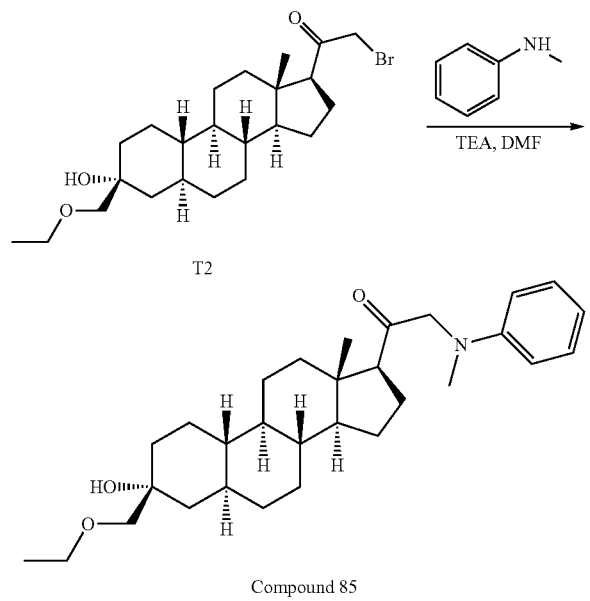

Compound 85

Step 1 (Compound 85).

To a solution of T2 (50 mg, 0.113 mmol) in DMF (5 mL) was added N-methylaniline (14.4 mg, 0.135 mmol) and TEA (34.3 mg, 0.339 mmol) at 25° C. under $N_2$. The mixture was stirred at 25° C. for 18 h to give a yellow solution. The solution was poured into saturated aqueous LiCl (20 mL) and extracted with EtOAc (3×30 mL). The combined organic phase was washed with saturated brine (2×30 mL), dried over anhydrous Na$_2$SO$_4$, filtered and concentrated to give a light solid. The solid was purified by HPLC (Column: Xtimate C18 150*25 mm*5 um; Conditions: water (0.05% HCl)-ACN; Gradient 70%-100% B; Gradient Time (min): 10) to afford Compound 85 (31.0 mg, 59%) as a light solid.

$^1$H NMR (400 MHz, CDCl$_3$) δ 7.25-7.13 (m, 2H), 6.74-6.65 (m, 1H), 6.59-6.54 (m, 2H), 4.10-3.95 (m, 2H), 3.55-3.45 (m, 2H), 3.22 (s, 2H), 3.00 (s, 3H), 2.65-2.54 (m, 1H), 2.30-1.50 (m, 8H), 1.50-1.05 (m, 14H), 1.05-0.70 (m, 3H), 0.70-0.65 (m, 5H).

LCMS Rt=1.029 min in 1.5 min chromatography, 5-95 AB, purity 100%, MS ESI calcd. for $C_{30}H_{46}NO_3$ [M+H]$^+$ 468, found 468.

Example 76. Synthesis of Compound 86

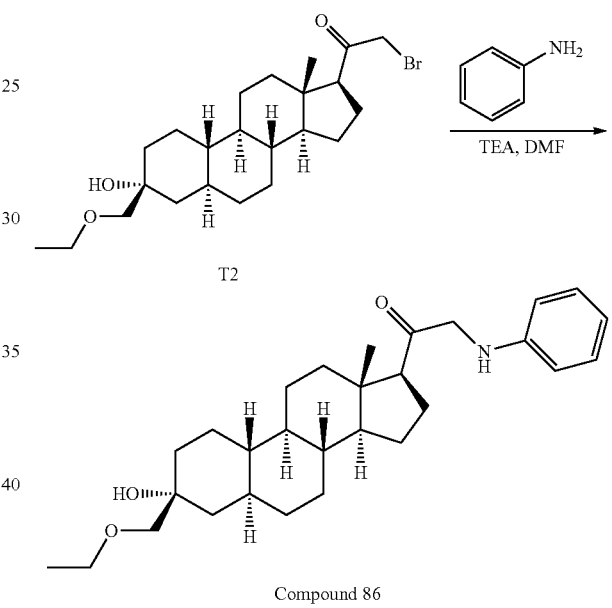

Compound 86

Step 1 (Compound 86).

To a solution of T2 (50 mg, 0.113 mmol) in DMF (5 mL) was added aniline (12.5 mg, 0.135 mmol) and TEA (34.3 mg, 0.339 mmol) at 25° C. under $N_2$. The mixture was stirred at 25° C. for 18 h to give a yellow solution. The mixture was poured into saturated aqueous LiCl (50 mL) and extracted with EtOAc (3×30 mL). The combined organic phase was washed with saturated brine (2×50 mL), dried over anhydrous Na$_2$SO$_4$, filtered and concentrated to give a light solid, which was purified by HPLC (Column: Xtimate C18 150*25 mm*5 um; Conditions: water (0.05% HCl)-ACN; Gradient 70%-100% B; Gradient Time (min): 10) to afford Compound 86 (7.00 mg, 14%) as a light solid.

$^1$H NMR (400 MHz, CDCl$_3$) δ 7.25-7.10 (m, 2H), 6.74-6.65 (m, 1H), 6.59-6.52 (m, 2H), 4.68-4.63 (m, 1H), 4.02-3.82 (m, 2H), 3.55-3.42 (m, 2H), 3.21 (s, 2H), 2.62-2.52 (m, 1H), 2.30-2.15 (m, 1H), 2.10-2.05 (m, 1H), 1.98-1.50 (m, 7H), 1.50-0.92 (m, 15H), 0.90-0.65 (m, 3H), 0.65 (s, 3H).

LCMS Rt=1.019 min in 2.0 min chromatography, 5-95 AB, purity 100%, MS ESI calcd. for $C_{29}H_{44}NO_3$ [M+H]$^+$ 454, found 454.

Example 77. Synthesis of Compound 87 and Compound 88

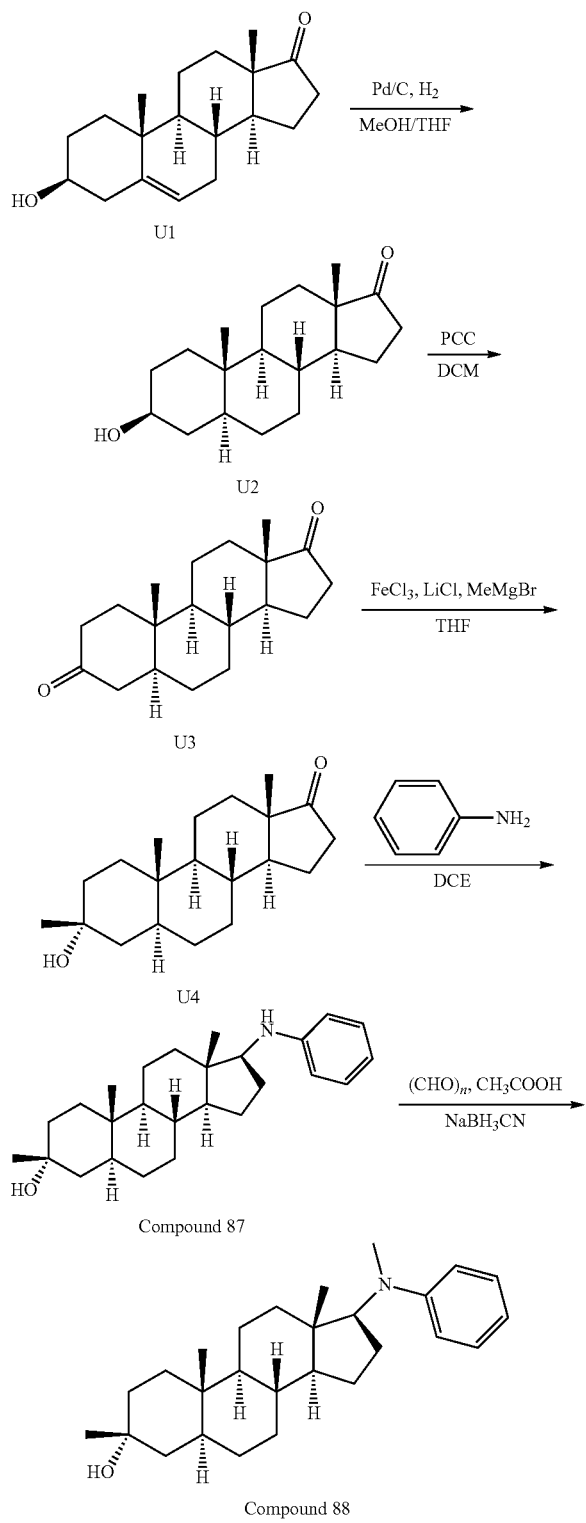

Step 1 (U2).

To a solution of commercially available dehydroisoandrosterone U1 (47 g, 162 mmol) in MeOH (200 mL) and THF (200 mL) was added Pd/C (5 g, <1% water) and the solution was hydrogenated under 30 psi of hydrogen at 25° C. for 48 hrs. The mixture was filtered through a pad of celite and the filtrate was concentrated in vacuo to give U2 (45 g, 91%) as a solid.

$^1$H NMR (400 MHz, CDCl$_3$) δ 3.65-3.54 (m, 1H), 2.49-2.38 (m, 1H), 2.13-1.99 (m, 1H), 1.97-1.88 (m, 1H), 1.87-1.76 (m, 3H), 1.74-1.63 (m, 2H), 1.59-1.07 (m, 12H), 1.03-0.94 (m, 2H), 0.89-0.79 (m, 6H), 0.74-0.63 (m, 1H).

Step 2 (U3).

To a solution of U2 (160 g, 550 mmol) and silica gel (300 g) in DCM (2 L) was added PCC (237 g, 1100 mmol) at 25° C. The mixture was stirred for 1 hr. The solution was filtered and the filter cake was washed with DCM (500 mL). The filtrate was diluted with PE (2 L) and stirred with silica gel (100 g) for 30 min. The silica gel was filtered off and washed with DCM (300 mL). The combined filtrate was concentrated in vacuo to give U3 (150 g, crude) as a solid.

$^1$H NMR (CDCl$_3$, 400 MHz) δ 2.50-2.20 (m, 4H), 2.25-1.90 (m, 4H), 1.85-1.80 (m, 2H), 1.75-1.65 (m, 1H), 1.60-1.45 (m, 3H), 1.45-1.20 (m, 6H), 1.05-0.90 (m, 4H), 0.89-0.75 (m, 4H).

Step 3 (U4).

A suspension of LiCl (6.14 g, 145 mmol, anhydrous) in THF (600 mL, anhydrous) was stirred at 10° C. for 30 mins under N$_2$. FeCl$_3$ (12.3 g, 76.2 mmol, anhydrous) was added at 10° C. The mixture was cooled to −30° C. To the mixture was added MeMgBr (92.3 mL, 3M in diethyl ether) dropwise at −30° C. The mixture was stirred at −30° C. for 10 mins. U3 (20 g, 69.3 mmol) was added at −30° C. The mixture was stirred at −15° C. for 2 hours. To the mixture was added citric acid (400 mL, 10% aq.). The mixture was extracted with EtOAc (3×200 mL). The combined organic phase was washed with saturated brine (300 mL), dried over anhydrous Na$_2$SO$_4$, filtered and concentrated in vacuo to give crude product which was purified by silica gel chromatography (PE/EtOAc=1/10~1/5) to give U4 (18.5 g, 88%) as a solid.

$^1$H NMR (400 MHz, CDCl$_3$) δ 2.45-2.39 (m, 1H), 2.12-2.00 (m, 1H), 1.98-1.88 (m, 1H), 1.84-1.74 (m, 2H), 1.72-1.64 (m, 1H), 1.61-1.42 (m, 7H), 1.33-1.22 (m, 8H), 1.20 (s, 3H), 1.08-0.95 (m, 1H), 0.86 (s, 3H), 0.84-0.79 (m, 1H), 0.77 (s, 3H)

Step 5 (Compound 87).

To a solution of aniline (61 mg, 0.656 mmol) in DCE (2 mL) was added U4 (100 mg, 0.328 mmol) and HOAc (39.3 mg, 0.656 mmol). The mixture was stirred at 15° C. for 10 minutes. Then NaBH(OAc)$_3$ (127 mg, 0.656 mmol) was added. The reaction mixture was stirred at 15° C. for 16 hrs. The mixture was quenched with sat. aqueous NaHCO$_3$ (20 mL) and extracted with DCM (3×10 mL). The combined organic phase was dried over Na$_2$SO$_4$, filtered, concentrated and purified by silica gel chromatography (0-10% of EtOAc in (PE and NH$_3$/H$_2$O, v:v=100:1) to give impure Compound 87 (20 mg) as a solid, which was triturated with hexane (3 mL). The mixture was filtered and the filter cake was washed with hexane (3×1 mL) to give pure Compound 87 (12 mg, 10%) as a solid.

$^1$H NMR (400 MHz, CDCl$_3$) δ 7.17-7.07 (m, 2H), 6.66-6.58 (m, 3H), 3.64-3.52 (m, 1H), 3.46-3.31 (m, 1H), 2.29-2.15 (m, 1H), 1.81-1.58 (m, 4H), 1.53-1.36 (m, 6H), 1.35-1.23 (m, 5H), 1.21-1.07 (m, 8H), 1.00-0.89 (m, 1H), 0.82-0.72 (m, 7H).

LCMS Rt=0.918 min in 2.0 min chromatography, 30-90 AB, purity 100%, MS ESI calcd. for C$_{26}$H$_{40}$NO [M+H]$^+$ 382, found 382.

Step 6 (Compound 88).

To a solution of Compound 87 (500 mg, 1.31 mmol in THF (10 mL) was added acetic acid (157 mg, 2.62 mmol) and paraformaldehyde (486 mg, 5.24 mmol). After stirring at 25° C. for 2.5 hrs, sodium cyanoborohydride (205 mg, 3.27 mmol) was added. The reaction mixture was stirred at 25° C. for 16 hrs and quenched with water (30 mL), extracted with EtOAc (2×30 mL). The organic layers were washed with brine (2×40 mL), dried over $Na_2SO_4$, filtered, concentrated in vacuo to give a residue, which was purified by silica gel chromatography (PE/EtOAc=10/1 to 4/1) to afford Compound 88 (37 mg, 12%) as a solid.

$^1$H NMR (400 MHz, $CDCl_3$) δ 7.23-7.17 (m, 2H), 6.91-6.85 (m, 1H), 6.74-6.67 (m, 2H), 3.76-3.67 (m, 1H), 2.88-2.80 (m, 3H), 2.02-1.62 (m, 5H), 1.62-1.56 (m, 1H), 1.53-1.43 (m, 4H), 1.42-1.31 (m, 2H), 1.31-1.22 (m, 6H), 1.21-1.16 (m, 5H), 1.15-1.04 (m, 1H), 1.03-0.86 (m, 1H), 0.83-0.77 (m, 4H), 0.75 (s, 3H).

LCMS Rt=0.734 min in 2 min chromatography, 30-90AB, purity 100%, MS ESI calcd. For $C_{27}H_{42}NO$ $[M+H]^+$ 396, found 396.

Example 78. Synthesis of Compound 89

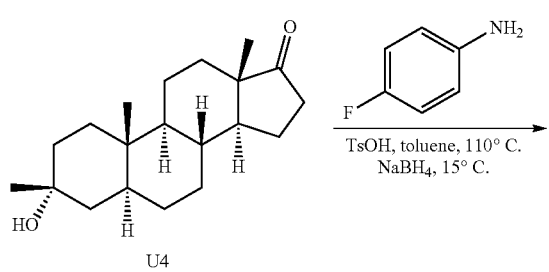

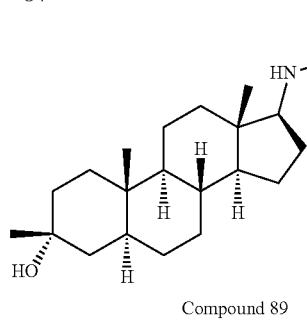

Compound 89

The synthesis of U4 is disclosed in WO2016/61527.

Step 1 (Compound 89).

To a solution of U4 (200 mg, 0.656 mmol) in toluene (3 mL) was added 4-fluoroaniline (145 mg, 1.31 mmol) and 4-methylbenzenesulfonic acid (112 mg, 0.656 mmol) at 15° C. under $N_2$. The mixture was refluxed at 110° C. for 16 hrs. After cooling to 15° C., $NaBH_4$ (49.5 mg, 1.31 mmol) was added. The mixture was poured into water (15 mL) and extracted with DCM (2×20 mL). The combined organic layers were washed with brine (20 mL), dried over $Na_2SO_4$, filtered and concentrated in vacuo. The crude product was purified by flash silica gel chromatography (0~15% of EtOAc in PE) to give Compound 89 (11 mg, 4%) as a solid.

$^1$H NMR (400 MHz, $CDCl_3$) δ 6.87-6.79 (m, 2H), 6.60-6.50 (m, 2H), 3.49-3.37 (m, 1H), 3.36-3.25 (m, 1H), 2.28-2.11 (m, 1H), 1.75-1.62 (m, 3H), 1.60-1.55 (m, 1H), 1.54-1.44 (m, 4H), 1.43-1.32 (m, 2H), 1.31-1.22 (m, 5H), 1.21-1.14 (m, 7H), 1.14-1.06 (m, 1H), 1.03-0.86 (m, 1H), 0.84-0.69 (m, 7H).

LCMS Rt=1.066 min in 2 min chromatography, 30-90AB, purity 100%, MS ESI calcd. For $C_{26}H_{39}FNO$ $[M+H]^+$ 400, found 400.

Example 79. Synthesis of Compound 90

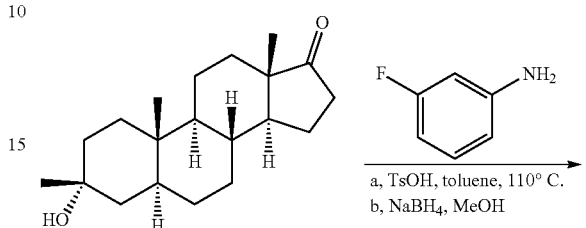

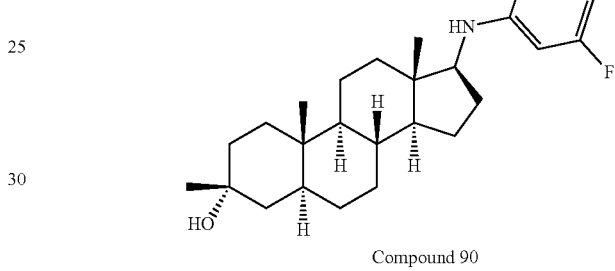

Compound 90

Step 1. (Compound 90).

A solution of U4 (200 mg, 0.656 mmol), 3-fluoroaniline (109 mg, 0.984 mmol), 4-methylbenzenesulfonic acid (56.4 mg, 0.328 mmol) in toluene (5 mL) was stirred at 110° C. for 12 hrs. After cooling to 25° C., $NaBH_4$ (49.5 mg, 1.31 mmol) and 5 mL of MeOH was added. The mixture was stirred at 25° C. for 30 mins, poured into water (20 mL) and extracted with DCM (2×20 mL). The combined organic layers were washed with brine (50 mL), dried over $Na_2SO_4$, filtered and concentrated in vacuo. The residue was purified by HPLC (column: Phenomenex Synergi C18 150*30 mm*4 um, gradient: 95-95% B (A=0.05% HCl-ACN, B=acetonitrile), flow rate: 25 mL/min) to give Compound 90 (16 mg, 6%) as a solid.

The structure was assigned based on a similar reductive amination in the literature (Steroids, 2011, 1098-1102).

$^1$H NMR (400 MHz, $CDCl_3$) δ 7.06-7.00 (m, 1H), 6.38-6.28 (m, 3H), 3.74-3.67 (m, 1H), 3.37-3.30 (m, 1H), 2.26-2.16 (m, 1H), 1.77-1.63 (m, 3H), 1.62-1.57 (m, 2H), 1.54-1.34 (m, 7H), 1.32-1.08 (m, 11H), 1.04-0.85 (m, 2H), 0.83-0.74 (m, 6H).

LCMS Rt=1.309 min in 2.0 min chromatography, 30-90 AB, purity 96.5%, MS ESI calcd. For $C_{26}H_{39}FNO$ $[M+H]^+$ 400, found 400.

Example 80. Synthesis of Compound 91

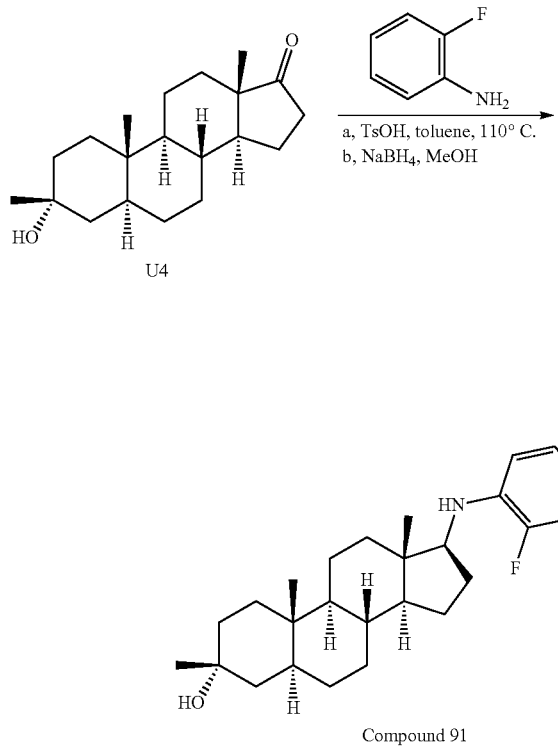

Step 1 (Compound 91).

A solution of U4 (200 mg, 0.656 mmol), 2-fluoroaniline (109 mg, 0.984 mmol), 4-methylbenzenesulfonic acid (56.4 mg, 0.328 mmol) in toluene (5 mL) was stirred at 110° C. for 12 hrs. After cooling to 25° C., NaBH$_4$ (49.5 mg, 1.31 mmol) and 5 mL of MeOH was added. The mixture was stirred at 25° C. for 30 mins, poured into water (30 mL) and extracted with DCM (2×20 mL). The combined organic layers were washed with brine (50 mL), dried over Na$_2$SO$_4$, filtered and concentrated in vacuo. The residue was purified by HPLC (column: Phenomenex Synergi C18 150*30 mm*4 um, gradient: 93-93% B (A=0.05% HCl-ACN, B=acetonitrile), flow rate: 25 mL/min) to give Compound 91 (6 mg, 2%) as a solid.

The structure was assigned based on a similar reductive amination in the literature (Steroids, 2011, 1098-1102).

$^1$H NMR (400 MHz, CDCl$_3$) δ 6.95-6.90 (m, 2H), 6.79-6.74 (m, 1H), 6.56-6.52 (m, 1H), 3.85-3.81 (m, 1H), 3.42-3.35 (m, 1H), 2.27-2.17 (m, 1H), 1.76-1.64 (m, 2H), 1.62-1.32 (m, 10H), 1.30-1.06 (m, 11H), 1.05-0.86 (m, 2H), 0.83-0.66 (m, 6H).

LCMS Rt=1.393 min in 2.0 min chromatography, 30-90 AB, purity 100%, MS ESI calcd. For C$_{26}$H$_{39}$FNO [M+H]$^+$ 400, found 400.

Example 81. Synthesis of Compound 92, Compound 93 and Compound 94

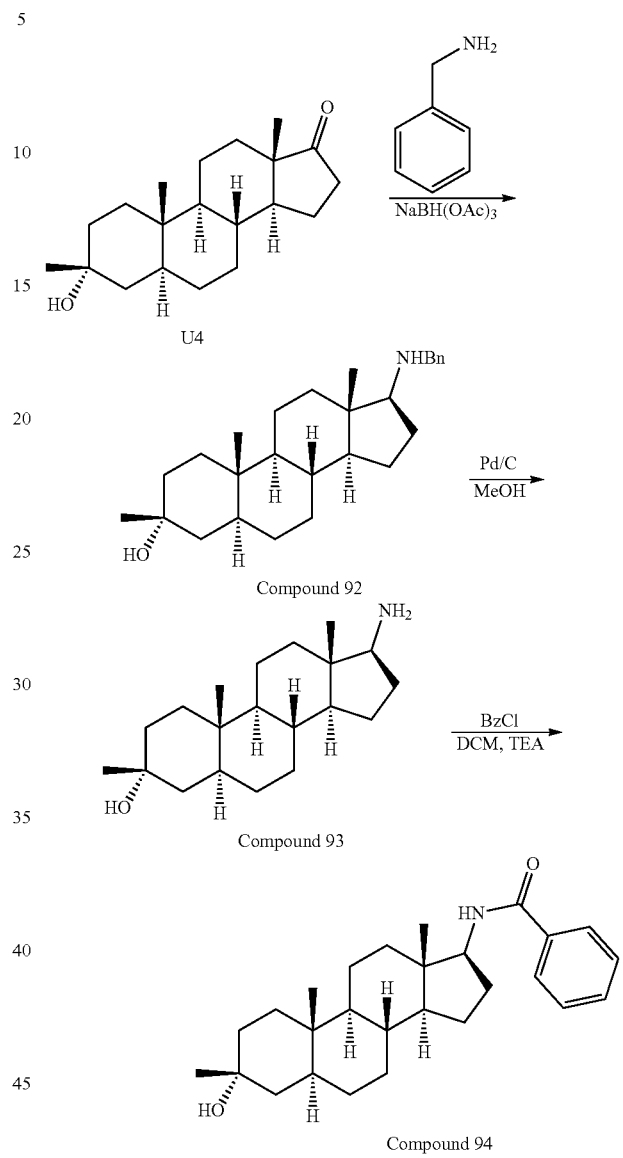

Step 1 (Compound 92)

A solution of U4 (3 g, 9.85 mmol), phenylmethanamine (4.22 g, 39.4 mmol), NaBH(OAc)$_3$ (5.21 g, 24.6 mmol), HOAc (2.36 g, 39.4 mmol) in 1, 2-dichloroethane (30 mL) was stirred at 25° C. for 12 hrs. Saturated Na$_2$CO$_3$ (10 mL) was added to the mixture and stirred for 10 mins. The mixture was poured into water (20 mL) and extracted with DCM (2×100 mL). The combined organic layers were washed with brine (200 mL), dried over Na$_2$SO$_4$, filtered and concentrated in vacuo. The crude product was purified by column chromatography on silica gel (PE/EtOAc=1:1) to give Compound 92 (2.3 g, 59%) as a solid. Compound 92 (100 mg, 0.252 mmol) was repurified by prep-HPLC (column: Gemini 150*25 5 u, gradient: 85-100%, Conditions: water (10 mM NH$_4$HCO$_3$)-ACN, flow rate: 30 mL/min) to give Compound 92 (13 mg, 13%) as a solid.

The structure was assigned based on a similar reductive amination in the literature (Steroids, 2011, 1098-1102).

¹H NMR (400 MHz, CDCl₃) δ 7.41-7.39 (m, 2H), 7.33 (t, J=8 Hz, 2H), 7.28-7.24 (m, 1H), 3.99-3.81 (m, 2H), 2.58 (m, 1H), 2.02-1.91 (m, 2H), 1.66-1.48 (m, 5H), 1.46-1.10 (m, 15H), 1.07-0.82 (m, 7H), 0.77-0.68 (m, 4H).

LCMS Rt=0.783 min in 2.0 min chromatography, 30-90 AB, purity 100%, MS ESI calcd. For $C_{27}H_{42}NO$ [M+H]⁺ 396, found 396.

Step 2 (Compound 93).

To a solution of Compound 92 (2.3 g, 5.81 mmol) in MeOH (30 mL) was added Pd/C (0.5 g, <1% water). Then the solution was hydrogenated under 50 psi of hydrogen at 25° C. for 3 h. The mixture was filtered through a pad of celite and the filtrate was concentrated in vacuo to afford Compound 93 (1.5 g, 85%) as a solid. Compound 93 (100 mg, 0.327 mmol) was purified by silica gel chromatography (DCM/MeOH=10/1) to give Compound 93 (14 mg, 14%) as a solid. as a solid.

¹H NMR (400 MHz, CDCl₃) δ 2.67-2.62 (m, 1H), 2.04-1.95 (m, 1H), 1.72-1.64 (m, 2H), 1.62-1.60 (m, 1H), 1.56-1.46 (m, 4H), 1.40-1.09 (m, 16H), 1.01-0.85 (m, 3H), 0.79-0.71 (m, 4H), 0.62 (s, 3H).

LCMS Rt=4.746 min in 7.0 min chromatography, 30-90 CD, purity 100%, MS ESI calcd. For $C_{20}H_{36}NO$ [M+H]⁺ 306, found 306.

Step 3 (Compound 94).

To a solution of Compound 93 (200 mg, 0.65 mmol) and TEA (164 mg, 1.63 mmol) in DCM (2 mL) was added benzoyl chloride (182 mg, 1.3 mmol) at 25° C. The reaction mixture was stirred at 25° C. for 15 hrs under N₂. The reaction mixture was quenched with a saturated aqueous NH₄Cl (20 mL) solution and extracted with DCM (20 mL×2). The combined organic layers were washed with brine (50 mL), dried over Na₂SO₄, filtered and concentrated in vacuo. The crude product was purified by silica gel column (EtOAc/PE=3/1) to give Compound 94 (120 mg, 45%) as a solid.

¹H NMR (400 MHz, CDCl₃) δ 7.76-7.74 (m, 2H), 7.52-7.47 (m, 1H), 7.45-7.41 (m, 2H), 5.95-5.92 (m, 1H), 4.14-4.07 (m, 1H), 2.26-2.18 (m, 1H), 1.78-1.66 (m, 3H), 1.63-1.58 (m, 1H), 1.53-1.23 (m, 13H), 1.2-1.16 (m, 5H), 1.02-0.92 (m, 2H), 0.87-0.76 (m, 7H).

LCMS Rt=1.355 min in 2.0 min chromatography, 30-90 AB, purity 100%, MS ESI calcd. for $C_{27}H_{40}NO_2$ [M+H]⁺ 410, found 410.

Example 82. Synthesis of Compound 95

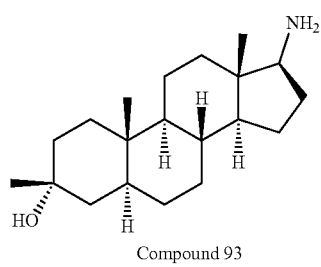

Compound 93

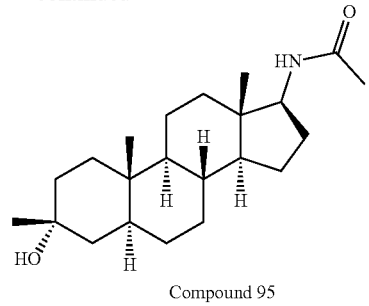

Compound 95

Step 1 (Compound 95).

To a solution of Compound 93 (200 mg, 0.65 mmol) and DMAP (198 mg, 1.63 mmo) in DCM (3 mL) was added acetic anhydride (132 mg, 1.3 mmol) at 25° C. The mixture was stirred at 25° C. for 1 hr. The mixture was poured into water (10 mL) and extracted with DCM (2×10 mL). The combined organic layers were washed with brine (30 mL), dried over Na₂SO₄, filtered and concentrated. The residue was purified by silica gel chromatography (PE/EtOAc=3/1) to give Compound 95 (60 mg, 26% yield) as a solid.

The structure was assigned based on a similar reductive amination in the literature (Steroids, 2011, 1098-1102).

¹H NMR (400 MHz, CDCl₃) δ 5.25-5.23 (m, 1H), 3.91-3.84 (m, 1H), 2.15-2.07 (m, 1H), 1.97 (s, 3H), 1.71-1.62 (m, 3H), 1.54-1.44 (m, 4H), 1.42-1.04 (m, 16H), 0.99-0.88 (m, 1H), 0.81-0.73 (m, 4H), 0.67 (s, 3H).

LCMS Rt=0.869 min in 2 min chromatography, 30-90 AB, purity 100%, MS ESI calcd. For $C_{22}H_{38}NO_2$ [M+H]⁺ 348, found 348.

Example 83. Synthesis of Compound 96

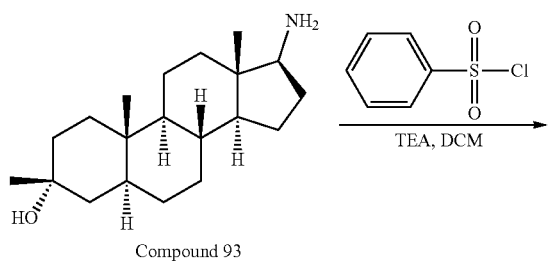

Compound 93

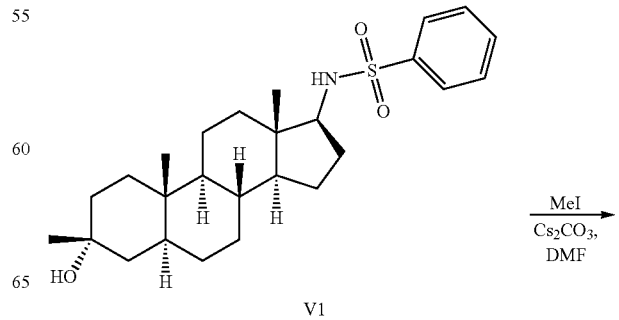

V1

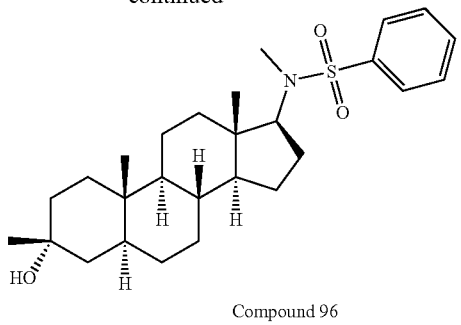

Compound 96

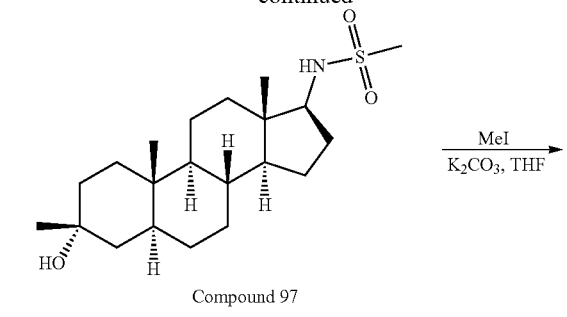

Compound 97

Step 1 (Compound 96).

To a solution of Compound 93 (200 mg, 0.65 mmol) and TEA (164 mg, 1.63 mmol) in DCM (3 mL) was added benzenesulfonyl chloride (229 mg, 1.3 mmol) at 0° C. The mixture was stirred at 25° C. for 1 hr. The mixture was poured into water (10 mL) and extracted with DCM (2×20 mL). The combined organic layer was washed with brine (30 mL), dried over $Na_2SO_4$, filtered and concentrated. The residue was purified by flash column (PE/EtOAc=5/1~3/1) to give V1 (80 mg, 40%) as a solid.

The structure was assigned based on a similar reductive amination in the literature (Steroids, 2011, 1098-1102).

$^1$H NMR (400 MHz, $CDCl_3$) δ 7.88-7.86 (m, 2H), 7.58-7.48 (m, 3H), 4.37-4.34 (m, 1H), 3.09-3.06 (m, 1H), 1.85-1.72 (m, 1H), 1.63-1.39 (m, 11H), 1.38-1.33 (m, 1H), 1.23-1.15 (m, 8H), 0.95-0.75 (m, 6H), 0.72 (s, 3H), 0.65 (s, 3H).

LCMS Rt=1.251 min in 2.0 min chromatography, 30-90 AB, purity 100%, MS ESI calcd. for $C_{26}H_{40}NO_3S[M+H]^+$ 446, found 446.

Step 2 (Compound 96).

To a solution of V1 (40 mg, 0.090 mmol) and $Cs_2CO_3$ (58.3 mg, 0.179 mmol) in DMF (2 mL) was added iodomethane (19 mg, 0.134 mmol) at 25° C. The mixture was stirred at 25° C. for 16 hr. The mixture was poured into water (10 mL) and extracted with EtOAc (2×20 mL). The combined organic layers were washed with brine (30 mL), dried over $Na_2SO_4$, filtered and concentrated. The residue was purified by silica gel chromatography (PE/EtOAc=5/1 to 3/1) to give Compound 96 (32 mg, 78%) as a solid.

$^1$H NMR (400 MHz, $CDCl_3$) δ 7.80-7.78 (m, 2H), 7.57-7.48 (m, 3H), 3.75-3.70 (m, 1H), 2.78 (s, 3H), 1.91-1.89 (m, 1H), 1.66-1.53 (m, 4H), 1.51-1.43 (m, 3H), 1.39-1.09 (m, 15H), 1.02-0.86 (m, 2H), 0.79-0.74 (m, 7H).

LCMS Rt=1.221 min in 2.0 min chromatography, 30-90 AB, purity 98.5%, MS ESI calcd. For $C_{27}H_{40}NO_2S$ $[M-H_2O+H]^+$ 442, found 442.

Example 84. Synthesis of Compound 97 and Compound 98

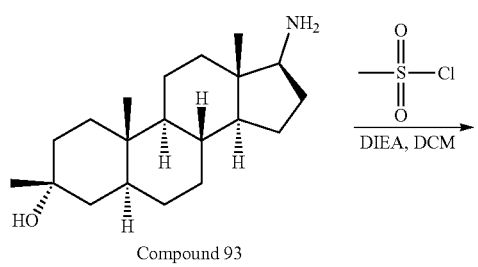

Compound 93

Compound 98

Step 1 (Compound 97).

To a solution of Compound 93 (100 mg, 0.327 mmol) and DIEA (105 mg, 0.817 mmol) in DCM (2 mL) was added methanesulfonyl chloride (74.9 mg, 0.654 mmol) at 0° C. The mixture was stirred at 25° C. for 1 hr. The mixture was poured into water (10 mL) and extracted with DCM (2×10 mL). The combined organic layers were washed with brine (30 mL), dried over $Na_2SO_4$, filtered and concentrated. The residue was purified by flash silica gel chromatography (PE/EtOAc=2/1) to give Compound 97 (50 mg, 40%) as a solid.

The structure was assigned based on a similar reductive amination in the literature (Steroids, 2011, 1098-1102).

$^1$H NMR (400 MHz, $CDCl_3$) δ 4.13-4.11 (m, 1H), 3.28-3.21 (m, 1H), 2.95 (s, 3H), 2.22-2.12 (m, 1H), 1.83-1.78 (m, 1H), 1.70-1.59 (m, 3H), 1.55-1.35 (m, 7H), 1.29-1.09 (m, 11H), 1.05-0.87 (m, 2H), 0.81-0.73 (4H), 0.69 (s, 3H).

LCMS Rt=0.869 min in 2.0 min chromatography, 30-90 AB, purity 98.8%, MS ESI calcd. For $C_{21}H_{36}NO_2S$ $[M-H_2O+H]^+$ 366, found 366.

Step 2 (Compound 98).

To a solution of Compound 97 (40 mg, 0.90 mmol) and $Cs_2CO_3$ (84.7 mg, 260 umol) in DMF (2 mL) was added iodomethane (29.5 mg, 0.208 mmol) at 25° C. After stirring at 25° C. for 16 hr, the mixture was poured into water (10 mL) and filtered. The filter cake was concentrated to give Compound 98 (35 mg, 85%) as a solid.

The structure was assigned based on a similar reductive amination in the literature (Steroids, 2011, 1098-1102).

$^1$H NMR (400 MHz, $CDCl_3$) δ 3.65-3.60 (m, 1H), 2.87 (s, 3H), 2.77 (s, 3H), 1.92-1.81 (m, 2H), 1.75-1.57 (m, 4H), 1.53-1.43 (m, 4H), 1.36-1.12 (m, 13H), 1.06-0.89 (m, 2H), 0.77-0.73 (m, 7H).

MS ESI calcd. For $C_{22}H_{40}NO_3S$ $[M+H]^+$ 398, found 398.

Example 85. Synthesis of Compound 99

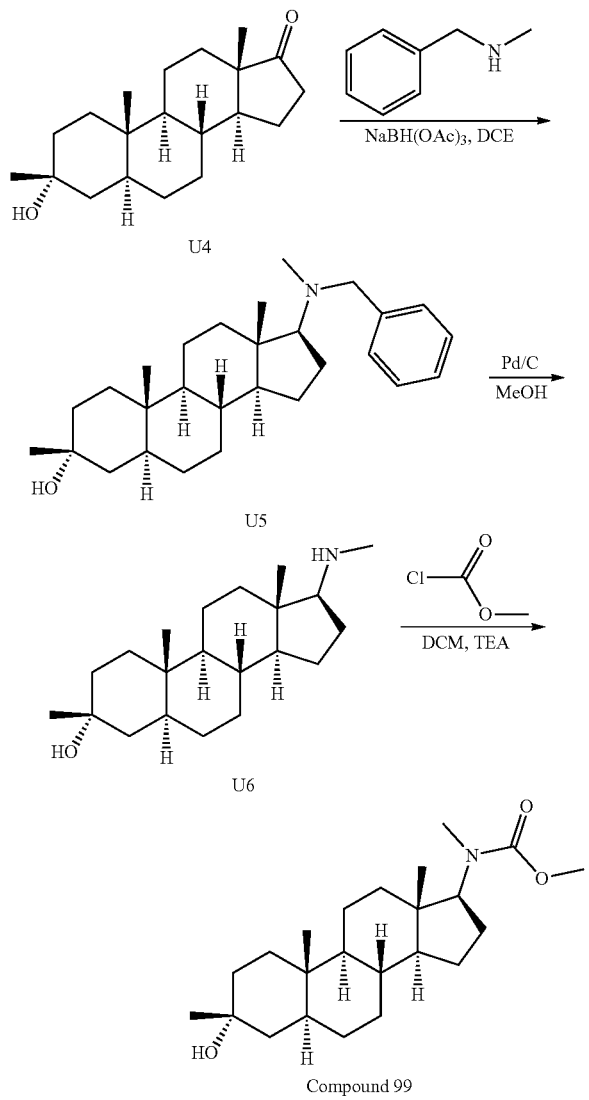

Step 1 (U5).

A solution of U4 (3 g, 9.85 mmol), N-methyl-1-phenylmethanamine (4.77 g, 39.4 mmol), NaBH(OAc)$_3$ (5.21 g, 24.6 mmol) and HOAc (2.36 g, 39.4 mmol) in 1, 2-dichloroethane (30 mL) was stirred at 60° C. for 12 hrs. Then saturated aqueous Na$_2$CO$_3$ (10 mL) was added to the mixture and the mixture was stirred for 10 mins. The mixture was poured into water (20 mL) and extracted with DCM (2×100 mL). The combined organic layers were washed with brine (200 mL), dried over Na$_2$SO$_4$ and filtered concentrated in vacuo. The crude product was purified by column chromatography on silica gel (PE/EtOAc=1/1) to give U5 (0.5 g, 12%) as a solid.

The structure was assigned based on a similar reductive amination in the literature (Steroids, 2011, 1098-1102).

$^1$H NMR (400 MHz, CDCl$_3$) δ 7.34-7.28 (m, 4H), 7.23-7.20 (m, 1H), 3.64-3.36 (m, 2H), 2.18-2.14 (m, 1H), 2.08-2.02 (m, 4H), 1.98-1.89 (m, 1H), 1.69-1.61 (m, 2H), 1.56-1.34 (m, 7H), 1.32-1.04 (m, 12H), 0.98-0.86 (m, 5H), 0.78-0.71 (m, 4H).

Step 2 (U6).

To a solution of U5 (500 mg, 1.22 mmol) in THF/MeOH (10 mL, 1/1) was added Pd/C (0.5 g, water <1%) at 25° C. The solution was hydrogenated under 50 psi of hydrogen at 25° C. for 16 hrs. The mixture was filtered through a pad of celite and the filtrate was concentrated in vacuo to afford U6 (300 mg, 60%) as a solid.

$^1$H NMR (400 MHz, CDCl$_3$) δ 2.45-2.43 (m, 4H), 2.02-1.99 (m, 1H), 1.82-1.80 (m, 1H), 1.68-1.64 (m, 1H), 1.63-1.43 (m, 9H), 1.60-1.36 (m, 6H), 1.35-1.11 (m, 5H), 1.03-0.82 (m, 3H), 0.77-0.74 (m, 4H), 0.69 (s, 3H).

Step 3 (Compound 99).

To a solution of U6 (100 mg, 0.31 mmol) and TEA (69.2 mg, 0.69 mmol) in DCM (3 mL) was added methyl chloroformate (58.9 mg, 0.62 mmol) at 0° C. The mixture was stirred at 25° C. for 1 hr. The mixture was poured into water (10 mL) and extracted with DCM (2×20 mL). The combined organic layers were washed with brine (30 mL), dried over Na$_2$SO$_4$, filtered and concentrated. The residue was purified by silica gel chromatography (PE/EtOAc=5/1~3/1) to give Compound 99 (27 mg, 23%) as a solid.

$^1$H NMR (400 MHz, CDCl$_3$) δ 4.07-3.95 (m, 1H), 3.68 (s, 3H), 2.86 (s, 3H), 1.90-1.31 (m, 1H), 1.77-1.63 (m, 4H), 1.53-1.43 (m, 4H), 1.39-1.15 (m, 13H), 1.10-0.81 (m, 3H), 0.79-0.73 (m, 4H), 0.69 (s, 3H).

LCMS Rt=1.259 min in 2.0 min chromatography, 30-90 AB, purity 99.3%, MS ESI calcd. For C$_{23}$H$_{40}$NO$_3$ [M+H]$^+$ 378, found 378.

Example 86. Synthesis of Compound 100

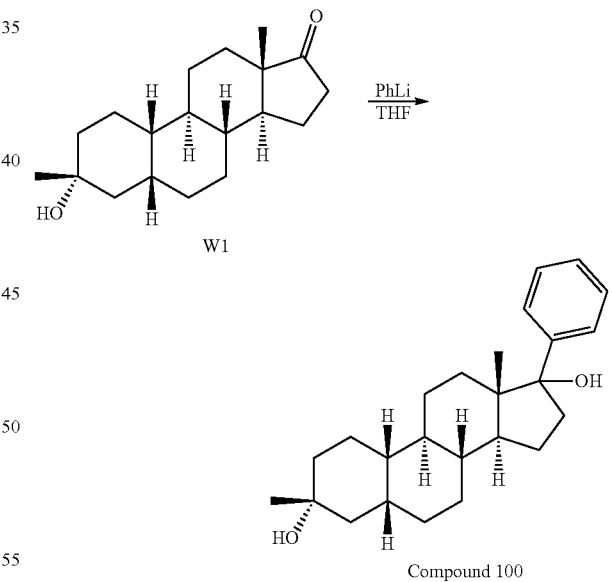

The synthesis of W1 is disclosed in WO2014/169833.

Step 1 (Compound 100).

To a solution of W1 (0.24 g, 0.83 mmol) in THF (10 mL) was added PhLi (11 mL, 1.5 M in ether, 16.5 mmol). The mixture was stirred at 65° C. for 4 h. After cooling, NH$_4$Cl (10 mL, sat.) was added. The mixture was extracted with EtOAc (20 mL). The organic layer was separated, dried over Na$_2$SO$_4$, filtered and concentrated in vacuo, purified by silica gel chromatography (PE/EtOAc=6/1 to 5/1) to give Compound 100 (120 mg) as a light brown oil. The crude was dissolved in MeCN (20 mL) and water (5 mL) was added. The mixture was concentrated in vacuo to yield a brown oil. The residue was dissolved in DCM (3 mL) and concentrated in vacuo to give Compound 100 (83 mg, 27%) as a light solid.

$^1$H NMR (400 MHz, CDCl$_3$) δ 7.40-7.28 (m, 5H), 2.47-2.32 (m, 1H), 2.18-2.05 (m, 1H), 1.86 (brs, 1H), 1.80-1.60 (m, 5H), 1.53-1.41 (m, 5H), 1.34-1.20 (m, 10H), 1.13-0.92 (m, 7H), 0.48-0.37 (m, 1H).

LCMS Rt=0.975 min in 2.0 min chromatography, 30-90AB, purity 98.2%, MS ESI calcd. for C$_{25}$H$_{33}$ [M+H-2H$_2$O]$^+$ 333, found 333.

Example 87. Synthesis of Compound 101

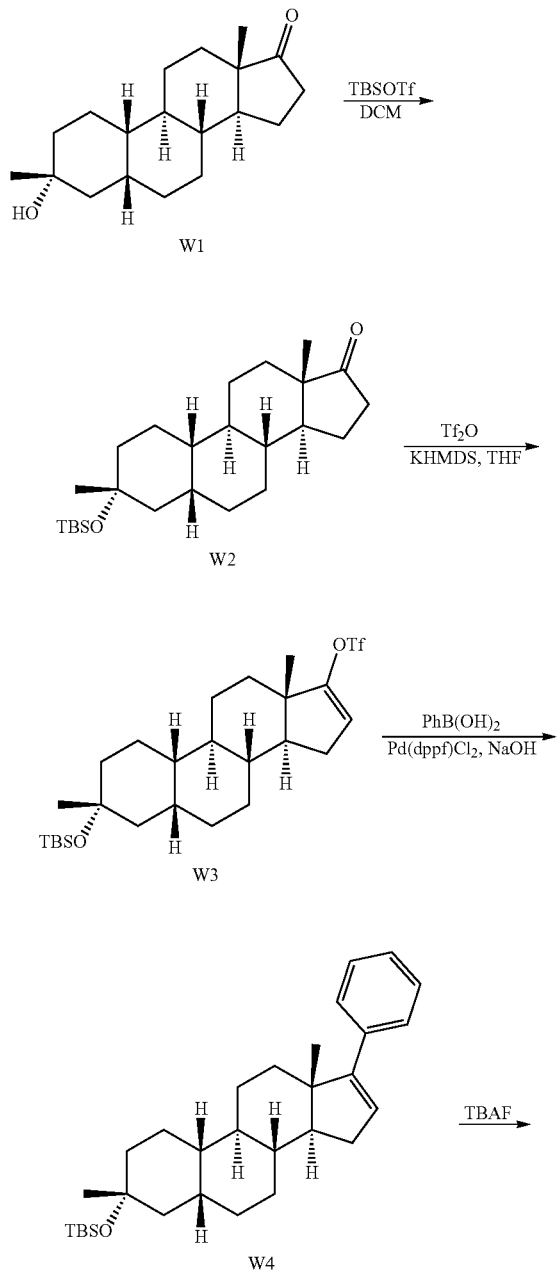

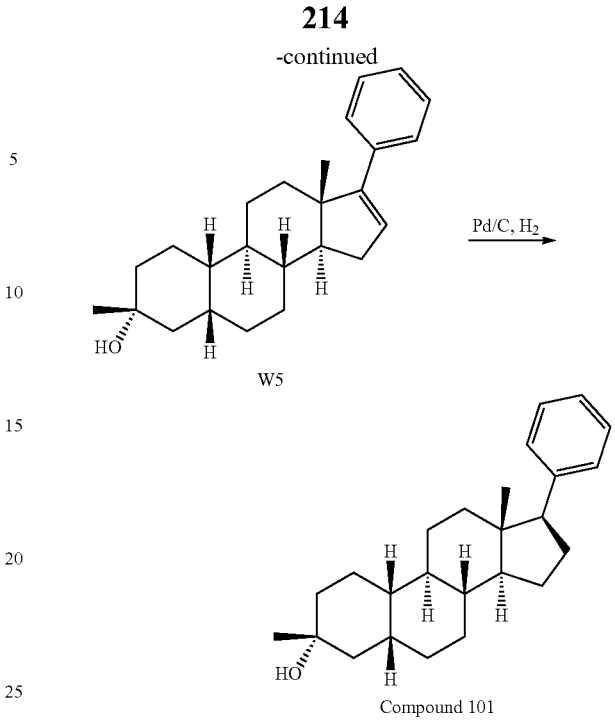

Step 1 (W2).

To a solution of W1 (5 g, 17.2 mmol) and 2, 6-dimethylpyridine (4.59 g, 42.9 mmol) in DCM (100 mL) was added drop-wise tert-butyldimethylsilyl trifluoromethanesulfonate (9.09 g, 34.4 mmol) at 0° C. After stirring at 25° C. for 16 hrs, the reaction mixture was quenched with water (100 mL) and extracted with EtOAc (2×100 mL). The combined organic phase washed with brine (100 mL), dried over Na$_2$SO$_4$, filtered and concentrated in vacuo. The residue was purified by silica gel chromatography (100-200 mesh silica gel, PE/EtOAc=10/1) to afford W2 (6 g, 86%) as an oil.

$^1$H NMR (400 MHz, CDCl$_3$) δ 2.50-2.40 (m, 1H), 2.16-2.05 (m, 1H), 1.96-1.90 (m, 1H), 1.82-1.70 (m, 4H), 1.70-0.95 (m, 18H), 0.95-0.60 (m, 1H), 0.95-0.75 (m, 12H), 0.07 (s, 6H).

Step 2 (W3).

To KHMDS (9.88 mL, 1M in THF) was added a solution of W2 (2 g, 4.94 mmol) in THF (10 mL) at 0° C. After warming to 20° C. and stirring at 20° C. for 30 mins, a solution of 1,1,1-trifluoro-N-phenyl-N-((trifluoromethyl)sulfonyl)methanesulfonamide (2.64 g, 7.41 mmol) in THF (15 mL) was added at 0° C. The mixture was warmed to 20° C. and stirred at 20° C. for 17 hours. Then the mixture was quenched with water (20 mL) and extracted with EtOAc (2×20 mL). The combined organic phase was washed with brine (2×30 mL), dried over Na$_2$SO$_4$, filtered, concentrated in vacuo to give a crude product, which was purified by flash silica gel chromatography (0-10% of EtOAc in PE, 60 mins) to give W3 (1.47 g, 56%) as an oil.

$^1$H NMR (400 MHz, CDCl$_3$) δ 5.56 (s, 1H), 2.25-2.17 (m, 1H), 2.01-1.95 (m, 1H), 1.82-1.60 (m, 7H), 1.55-1.05 (m, 15H), 0.96 (s, 3H), 0.90-0.80 (m, 9H), 0.08 (s, 6H).

Step 3 (W4).

To a mixture of W3 (200 mg, 0.372 mmol), phenylboronic acid (58.8 mg, 0.48 mmol) and Pd(dppf)Cl$_2$ (28.3 mg, 0.0372 mmol) in THF (4 mL), NaOH (0.24 mL, 2 M in water) was added. The mixture was degassed under vacuum and purged with N$_2$. The reaction mixture was stirred at 80° C. for 1 hour. The reaction mixture was quenched with sat.

aqueous NaHCO₃ (3 mL) and extracted with EtOAc (2×10 mL). The combined organic layers were washed with brine (10 mL), dried over Na₂SO₄, filtered, and concentrated. The crude product was purified by flash silica gel chromatography (0% to 5% of EtOAc in PE) to give W4 (232 mg, crude) as an oil.

$^1$H NMR (400 MHz, CDCl₃) δ 7.45-7.38 (m, 2H), 7.35-7.28 (m, 1H), 7.25-7.20 (m, 2H), 5.91-5.87 (m, 1H), 2.28-2.19 (m, 1H), 2.10-1.95 (m, 2H), 1.89-1.62 (m, 7H), 1.59-1.48 (m, 4H), 1.48-1.37 (m, 5H), 1.37-1.18 (m, 6H), 1.02 (s, 3H), 1.02-0.70 (m, 8H), 0.07 (s, 6H).

Step 5 (W5).

To a mixture of W4 (232 mg, 0.499 mmol) in THF (2 mL) was added TBAF (332 mg, 0.998 mmol) at 80° C. After stirring at 80° C. for 18 h, the mixture was cooled to 15° C., treated with water (5 mL) and extracted with EtOAc (3×10 mL). The combined organic phase was washed with brine (2×10 mL), dried over anhydrous Na₂SO₄, filtered and concentrated. The residue was purified by flash silica gel chromatography (0~10% of EtOAc in PE) to give W5 (160 mg, 94% yield for 2 steps) as an oil.

$^1$H NMR (400 MHz, CDCl₃) δ 7.40-7.35 (m, 2H), 7.35-7.25 (m, 1H), 7.25-7.18 (m, 2H), 5.91-5.87 (m, 1H), 2.41-2.38 (m, 1H), 2.25-2.12 (m, 1H), 2.11-1.95 (m, 2H), 1.95-1.81 (m, 3H), 1.80-1.61 (m, 3H), 1.61-1.52 (m, 1H), 1.52-1.48 (s, 3H), 1.48-1.32 (m, 3H), 1.32-1.15 (m, 5H), 1.02 (s, 3H), 0.92-0.82 (m, 3H).

Step 6 (Compound 101).

To a solution of W5 (130 mg, 0.37 mmol) in EtOAc (15 mL) was added Pd/C (wet, 10%, 0.1 g) under N₂. The suspension was degassed under vacuum and purged with H₂ three times. The mixture was stirred under H₂ (15 psi) at 15° C. for 0.5 hours to give a black suspension. The mixture was filtered and concentrated. The residue was purified by flash silica gel chromatography (0~10% of EtOAc in PE) to give Compound 101 (33 mg, 25%) as a solid.

The structure of Compound 101 was confirmed by X-ray crystallography.

$^1$H NMR (400 MHz, CDCl₃) δ 7.31-7.27 (m, 2H), 7.24-7.15 (m, 3H), 2.81-2.75 (m, 1H), 2.12-2.03 (m, 1H), 2.01-1.91 (m, 1H), 1.91-1.78 (m, 4H), 1.71-1.61 (m, 2H), 1.61-1.52 (m, 3H), 1.52-1.41 (m, 4H), 1.41-1.38 (s, 2H), 1.38-1.21 (m, 6H), 1.21-1.09 (m, 2H), 1.05-0.79 (m, 2H), 0.46 (s, 3H).

LCMS Rt=1.398 min in 2 min chromatography, 30-90AB, purity 100%, MS ESI calcd. for C₂₅H₃₅ [M+H—H₂O]⁺ 335, found 335.

Example 88. Synthesis of Compound 102

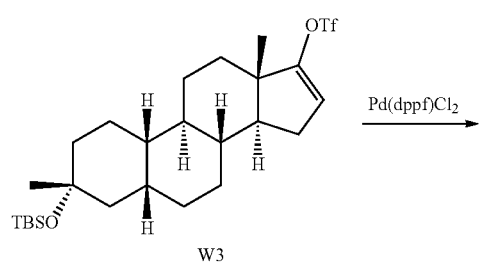

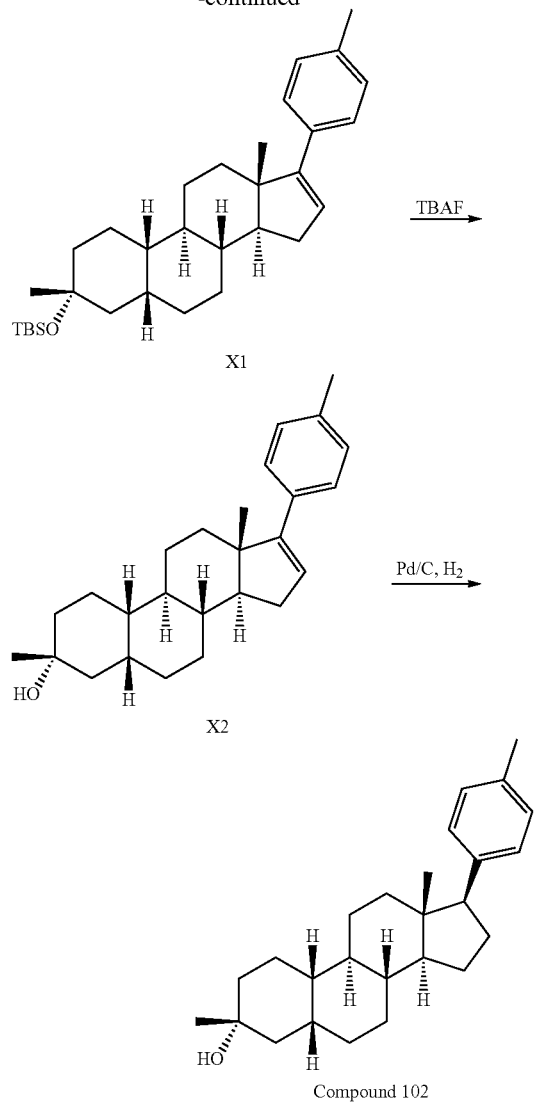

Step 1 (X1).

To a mixture of W3 (200 mg, 0.372 mmol), p-methylphenylboronic acid (65.6 mg, 0.48 mmol) and Pd(dppf)Cl₂ (28.3 mg, 0.0372 mmol) in THF (4 mL), NaOH (0.24 mL, 2 M in water) was added. The mixture was degassed under vacuum and purged with N₂. The reaction mixture was stirred at 80° C. for 1 hour. The reaction mixture was quenched with sat. aqueous NaHCO₃ (3 mL) and extracted with EtOAc (2×5 mL), the combined layers were washed with brine (10 mL), dried over Na₂SO₄, filtered, and concentrated in vacuo. The product was purified by flash chromatography on silica (0% to 5% of EtOAc in PE) to give X1 (240 mg, impure) as an oil.

$^1$H NMR (400 MHz, CDCl₃) δ 7.30-7.25 (m, 2H), 7.12-7.08 (m, 2H), 5.89-5.85 (m, 1H), 2.33 (s, 3H), 2.33-2.15 (m, 1H), 2.11-1.95 (m, 2H), 1.90-1.61 (m, 6H), 1.61-1.58 (m, 1H), 1.53-1.46 (m, 3H), 1.46-1.41 (m, 2H), 1.41-1.35 (m, 2H), 1.35-1.30 (m, 2H), 1.30-1.21 (m, 7H), 1.21-1.08 (m, 1H), 1.01 (s, 3H), 0.90-0.81 (m, 6H), 0.07 (s, 6H).

Step 2 (X2).

To a mixture of X1 (232 mg, 0.484 mmol) in THF (2 mL), TBAF (322 mg, 0.968 mmol) was added at 80° C. After stirring at 80° C. for 18 h, the mixture was cooled to 15° C., treated with water (5 mL) and extracted with EtOAc (3×10 mL). The combined organic phase was washed with saturated brine (10 mL), dried over anhydrous Na₂SO₄, filtered and concentrated. The residue was purified by flash silica gel chromatography (0~10% of EtOAc in PE) to give X2 (100 mg, 56% yield for 2 steps) as an oil.

¹H NMR (400 MHz, CDCl₃) δ 7.32-7.25 (m, 2H), 7.12-7.08 (m, 2H), 5.87-5.84 (m, 1H), 2.33 (s, 3H), 2.22-2.10 (m, 1H), 2.09-1.91 (m, 2H), 1.91-1.81 (m, 3H), 1.79-1.55 (m, 4H), 1.55-1.40 (m, 5H), 1.40-1.12 (m, 9H), 1.00 (s, 3H), 0.90-0.80 (m, 1H).

Step 3 (Compound 102).

To a solution of X2 (100 mg, 0.274 mmol) in EtOAc (5 mL) was added Pd/C (wet, 10%, 0.1 g) under N₂. The suspension was degassed under vacuum and purged with H₂ three times. The mixture was stirred under H₂ (15 psi) at 15° C. for 0.5 hours to give a black suspension. The mixture was filtered and concentrated. The residue was purified by flash silica gel chromatography (0~10% of EtOAc in PE) to give Compound 102 (17 mg, 17%) as a solid.

¹H NMR (400 MHz, CDCl₃) δ 7.12-7.05 (m, 4H), 2.69-2.60 (m, 1H), 2.32 (s, 3H), 2.11-2.01 (m, 1H), 2.00-1.72 (m, 5H), 1.71-1.52 (m, 4H), 1.52-1.42 (m, 3H), 1.42-1.32 (m, 4H), 1.32-1.15 (m, 7H), 1.15-0.90 (m, 3H), 0.46 (s, 3H).

LCMS Rt=1.472 min in 2 min chromatography, 30-90AB, purity 98%, MS ESI calcd. for $C_{26}H_{37}$ [M+H—H₂O]⁺ 349, found 349.

Example 89. Synthesis of Compound 103

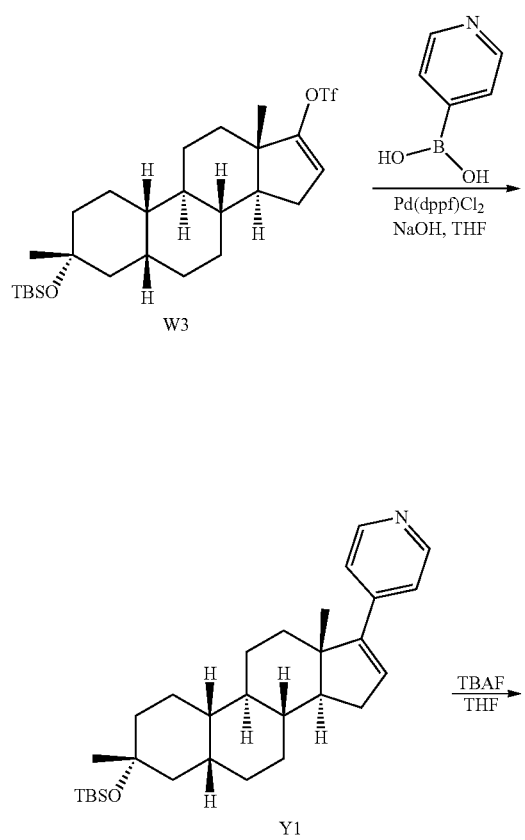

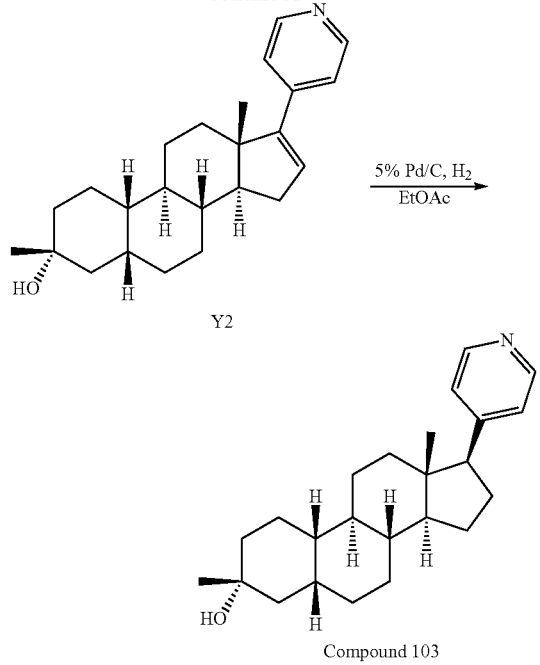

Step 1 (Y1).

To a mixture of W3 (200 mg, 0.372 mmol), pyridin-4-ylboronic acid (59.3 mg, 0.483 mmol) and NaOH (0.241 mL, 2 M in water) in THF (4 mL), Pd(dppf)Cl₂ (5 mg, 0.00656 mmol) was added under N₂. The suspension was stirred at 80° C. for 1 h and then was cooled to ambient temperature. The reaction mixture was quenched with sat. NaHCO₃ (3 mL). The mixture was extracted with EtOAc (2×5 mL). The combined organic layers were washed with brine (10 mL), dried over Na₂SO₄, filtered and concentrated in vacuo. The crude product was purified by flash chromatography on silica gel (0% to 5% of EtOAc in PE) to give Y1 (210 mg, impure) as an oil.

¹H NMR (400 MHz, CDCl₃) δ 8.53-8.45 (d, 2H), 7.31-7.20 (d, 2H), 6.20-6.10 (m, 1H), 2.32-2.20 (s, 1H), 2.12-1.98 (m, 2H), 1.87-1.59 (m, 6H), 1.59-1.42 (m, 4H), 1.42-1.38 (m, 6H), 1.38-1.12 (m, 9H), 1.03 (s, 3H), 0.91-0.81 (m, 5H), 0.06 (s, 6H).

Step 2 (Y2).

To a mixture of Y1 (210 mg, impure) in THF (2 mL) was added TBAF (328 mg, 0.985 mmol). The reaction solution was stirred at 80° C. for 18 hrs. Water (5 mL) was added. The mixture was extracted with EtOAc (2×10 mL). The combined organic layers were washed with brine (5 mL), dried over Na₂SO₄, filtered and concentrated. The residue was purified by flash column (0~30% of EtOAc in PE) to give Y2 (56 mg, 32% yield for 2 steps) as a solid.

¹H NMR (400 MHz, CDCl₃) δ 8.55-8.45 (m 2H), 7.31-7.20 (m, 2H), 6.19-6.15 (m, 1H), 2.30-2.20 (m, 1H), 2.10-1.99 (m, 2H), 1.91-1.80 (m, 3H), 1.80-1.60 (m, 3H), 1.58-1.39 (m, 7H), 1.39-1.12 (m, 9H), 1.03 (s, 3H).

Step 3 (Compound 103).

To a mixture of Y2 (56 mg, 0.159 mmol) in EtOAc (5 mL) Pd/C (100 mg, 5%, wet) was added under N₂. The mixture was stirred under H₂ (15 psi) at 15° C. for 15 hrs to give a black suspension, which was filtered and concentrated to give Compound 103 (10 mg) as a solid.

¹H NMR (400 MHz, CDCl₃) δ 8.52-8.40 (m, 2H), 7.16-7.08 (m, 2H), 2.69-2.60 (m, 1H), 2.11-2.05 (m, 1H), 2.05-

1.90 (m, 1H), 1.90-1.75 (m, 4H), 1.71-1.52 (m, 4H), 1.52-1.45 (m, 3H), 1.38-1.22 (m, 7H), 1.22-0.95 (m, 5H), 0.92-0.81 (m, 2H), 0.45 (s, 3H).

LCMS Rt=0.570 min in 2 min chromatography, 30-90AB, purity 100%, MS ESI calcd. for $C_{24}H_{36}NO$ [M+H]$^+$ 354, found 354.

Example 90. Synthesis of Compound 104

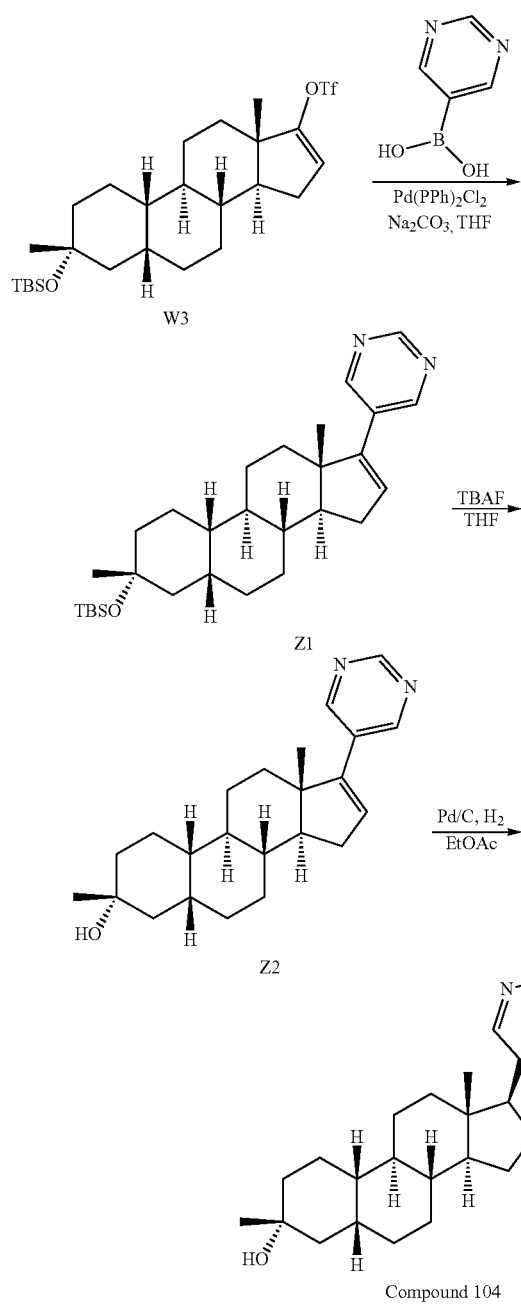

Step 1 (Z1).

To a mixture of W3 (200 mg, 0.372 mmol), pyrimidin-5-ylboronic (69.1 mg, 0.558 mmol) and $Na_2CO_3$ (0.372 mL, 2M in water) in THF (10 mL), was added $Pd(PPh_3)_2Cl_2$ (5 mg, 0.00712 mmol). The mixture was degassed under vacuum and purged with $N_2$. The reaction mixture was stirred at 80° C. for 5 hrs, cooled to ambient temperature, quenched with sat. aqueous $NaHCO_3$ (3 mL) and extracted with EtOAc (2×5 mL). The combined organic layers were washed with brine (10 mL), dried over $Na_2SO_4$, filtered and concentrated. The residue was purified by flash chromatography on silica gel (0% to 15% of EtOAc in PE) to get Z1 (140 mg, 81%) as an oil.

The structure of Compound 104 was confirmed by X-ray crystallography.

$^1$H NMR (400 MHz, CDCl$_3$) δ 9.06 (s, 1H), 8.72 (s, 2H), 6.12-6.08 (m, 1H), 2.35-2.25 (s, 1H), 2.12-1.95 (m, 2H), 1.87-1.51 (m, 7H), 1.62-1.42 (m, 4H), 1.42-1.38 (m, 4H), 1.38-1.12 (m, 7H), 1.00 (s, 3H), 0.91-0.81 (m, 8H), 0.06 (s, 6H).

Step 2 (Z2).

To a mixture of Z1 (140 mg, impure) in THF (2 mL), TBAF (199 mg, 0.598 mmol) was added. The resulting solution was stirred at 80° C. for 18 hrs. Water (5 mL) was added. The mixture was extracted with EtOAc (2×10 mL). The combined organic layers were washed with brine (5 mL), dried over $Na_2SO_4$, filtered and concentrated. The residue was purified by flash silica gel chromatography (0~30% of EtOAc in PE) to give Z2 (70 mg, 67%) as a solid.

$^1$H NMR (400 MHz, CDCl$_3$) δ 9.06 (s, 1H), 8.72 (s, 2H), 6.11-6.05 (m, 1H), 2.32-2.15 (m, 1H), 2.10-1.95 (m, 2H), 1.91-1.72 (m, 4H), 1.72-1.62 (m, 2H), 1.61-1.59 (m, 1H), 1.57-1.42 (m, 5H), 1.42-1.25 (m, 8H), 1.25-1.15 (m, 2H), 1.00 (s, 3H).

Step 3 (Compound 104).

To a mixture of Z2 (100 mg, 0.283 mmol) in EtOAc (5 mL), Pd/C (100 mg, 5%, wet) was added under $N_2$. The mixture was stirred under $H_2$ (15 psi) at 15° C. for 15 hrs to give a black suspension, which was filtered and concentrated to give Compound 104 (31 mg, 31%) as a solid.

$^1$H NMR (400 MHz, CDCl$_3$) 9.06 (s, 1H), 8.58 (s, 2H), 2.70-2.60 (m, 1H), 2.15-1.98 (m, 2H), 1.91-1.78 (m, 4H), 1.75-1.60 (m, 2H), 1.61-1.42 (m, 6H), 1.42-1.31 (m, 7H), 1.31-1.22 (m, 3H), 1.22-1.08 (m, 3H), 0.51 (s, 3H).

LCMS Rt=1.017 min in 2 min chromatography, 30-90AB, purity 100%, MS ESI calcd. for $C_{23}H_{35}N_2O$ [M+H]$^+$ 355, found 355.

Example 91. Synthesis of Compound 105

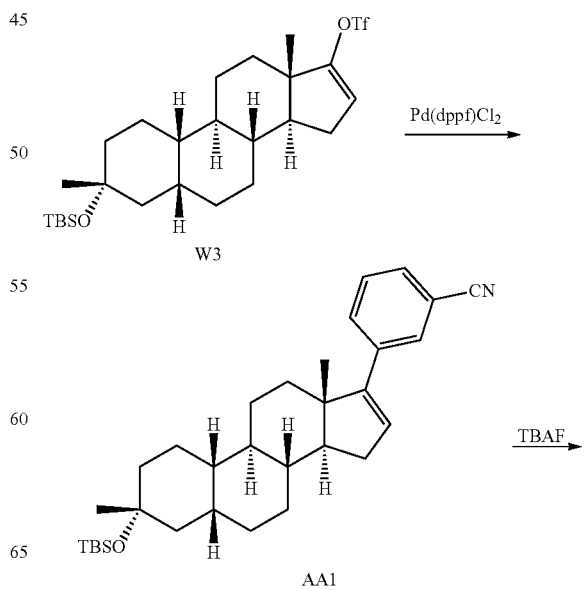

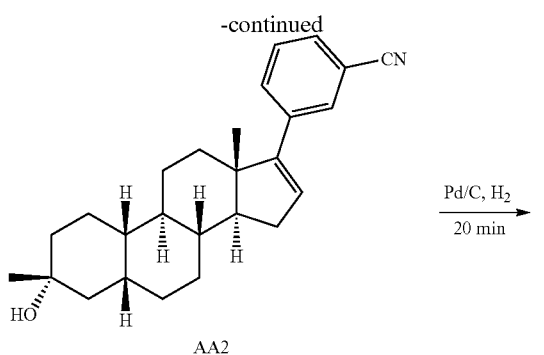

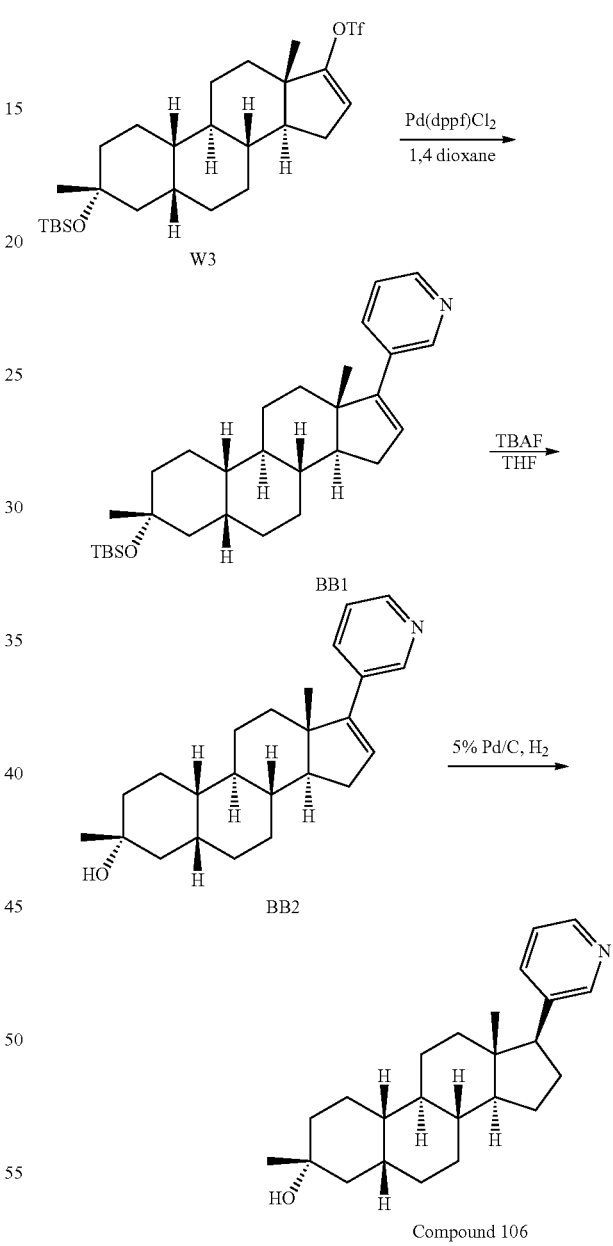

Step 1 (AA1).

To a mixture of W3 (200 mg, 0.372 mmol), (3-cyanophenyl) boronic acid (70.9 mg, 0.483 mmol) and NaOH (0.241 mL, 2M in water) in THF (4 mL) was added Pd(dppf)Cl$_2$ (5 mg). The mixture was degassed under vacuum and purged with N$_2$. After stirring at 80° C. for 1 h, the reaction mixture was quenched with sat. aqueous NaHCO$_3$ (3 mL) and extracted with EtOAc (2×5 mL). The combined organic layers were washed with brine (10 mL), dried over Na$_2$SO$_4$, filtered and concentrated. The residue was purified by flash chromatography on silicagel (0% to 5% of EtOAc in PE) to give AA1 (150 mg, 82%) as an oil.

$^1$H NMR (400 MHz, CDCl$_3$) δ 7.63 (s, 1H), 7.60-7.57 (d, 1H), 7.52-7.47 (d, 1H), 7.41-7.33 (t, 1H), 6.03-5.95 (m, 1H), 2.30-2.20 (m, 1H), 2.08-1.97 (m, 1H), 1.89-1.59 (m, 7H), 1.59-1.38 (m, 6H), 1.38-1.11 (m, 9H), 1.01 (s, 3H), 0.91-0.78 (m, 9H), 0.06 (s, 6H).

Step 2 (AA2).

To a mixture of AA1 (150 mg) in THF (2 mL) was added TBAF (203 mg, 0.612 mmol). The reaction mixture was stirred at 80° C. for 18 hrs to give a black oil. Water (5 mL) was added. The mixture was extracted with EtOAc (2×10 mL), The combined organic layers were washed with brine (5 mL), dried over Na$_2$SO$_4$, filtered and concentrated. The residue was purified by flash silica gel chromatography (0~10% of EtOAc in PE) to give AA2 (80 mg, 70%) as a solid $^1$H NMR (400 MHz, CDCl$_3$) δ 7.63 (s, 1H), 7.60-7.57 (d, 1H), 7.52-7.47 (d, 1H), 7.41-7.33 (m, 1H), 6.03-5.95 (m, 1H), 2.30-2.20 (m, 1H), 2.08-1.93 (m, 2H), 1.91-1.80 (m, 3H), 1.80-1.57 (m, 4H), 1.57-1.32 (m, 5H), 1.32-1.12 (m, 7H), 1.01 (s, 3H), 0.99-0.80 (m, 3H).

Step 3 (Compound 105)

To a mixture of AA2 (80 mg, 0.213 mmol) in EtOAc (5 mL) was added Pd/C (100 mg, 10%, wet) under N$_2$. The mixture was stirred under H$_2$ (15 psi) at 15° C. for 20 min to give a black suspension, which was filtered and concentrated to give Compound 105 (17 mg, 21%) as a solid.

$^1$H NMR (400 MHz, CDCl$_3$) δ 7.51-7.47 (m, 2H), 7.44-7.41 (m, 1H), 7.39-7.32 (m, 1H), 2.79-2.61 (m, 1H), 2.10-1.93 (m, 2H), 1.89-1.74 (m, 4H), 1.71-1.60 (m, 2H), 1.59-1.45 (m, 4H), 1.45-1.37 (m, 4H), 1.37-1.19 (m, 6H), 1.19-0.78 (m, 5H), 0.44 (s, 3H).

LCMS Rt=1.269 min in 2 min chromatography, 30-90AB, purity 100%, MS ESI calcd. for C$_{26}$H$_{34}$N [M+H—H$_2$O]$^+$ 360, found 360.

Example 92. Synthesis of Compound 106

Step 1 (BB1).

To a mixture of W3 (200 mg, 0.372 mmol), pyridin-3-ylboronic acid (68.5 mg, 0.588 mmol) and Na$_2$CO$_3$ (0.74 mL, 2 M in water) in 1,4-dioxane (3 mL) was added Pd(dppf)Cl$_2$ (5 mg, 0.00656 mmol) under N$_2$. After stirring at 80° C. for 1 hr, the reaction mixture was quenched with sat. NaHCO$_3$ (3 mL) and extracted with EtOAc (2×5 mL) The combined organic layers were washed with brine (10 mL), dried over Na₂SO₄, filtered and concentrated. The residue was purified by flash chromatography on silica gel (0% to 5% of EtOAc in PE) to give BB1 (150 mg, 87%) as a solid.

¹H NMR (400 MHz, CDCl₃) δ 8.69-8.60 (m, 1H), 8.49-8.40 (m, 1H), 7.69-7.61 (m, 1H), 7.25-7.15 (m, 1H), 6.05-5.93 (m, 1H), 2.30-2.20 (m, 1H), 2.09-1.95 (m, 2H), 1.87-1.73 (m, 4H), 1.73-1.60 (m, 2H), 1.60-1.45 (m, 3H), 1.45-1.30 (m, 5H), 1.30-1.14 (m, 7H), 1.00 (s, 3H), 0.92-0.82 (m, 9H), 0.06 (s, 6H).

Step 2 (BB2).

To a mixture of BB1 (150 mg) in THF (2 mL), was added TBAF (214 mg, 0.644 mmol). The reaction mixture was stirred at 80° C. for 18 hrs. Water (5 mL) was added to the reaction mixture. The mixture was extracted with EtOAc (2×10 mL). The combined organic layers were washed with brine (5 mL), dried over Na₂SO₄, filtered and concentrated. The residue was purified by flash silica gel chromatography (0~30% of EtOAc in PE) to give BB2 (89 mg, 79%) as a solid.

¹H NMR (400 MHz, CDCl₃) δ 8.69-8.60 (m, 1H), 8.49-8.40 (m, 1H), 7.69-7.61 (m, 1H), 7.26-7.18 (m, 1H), 6.00-5.93 (m, 1H), 2.30-2.20 (m, 1H), 2.09-1.95 (m, 2H), 1.92-1.81 (m, 3H), 1.81-1.61 (m, 3H), 1.61-1.39 (m, 6H), 1.39-1.13 (m, 10H), 1.00 (s, 3H).

Step 3 (Compound 106).

To a mixture of BB2 (79 mg, 0.224 mmol) in EtOAc (5 mL), Pd/C (100 mg, 5%, wet) was added under N₂. The mixture was stirred under H₂ (15 psi) at 15° C. for 15 hrs to give a black suspension, which was filtered and concentrated to give Compound 106 (10 mg, 21%) as a solid.

¹H NMR (400 MHz, CDCl₃) δ 8.50-8.40 (m, 2H), 7.55-7.49 (m, 1H), 7.25-7.18 (m, 1H), 2.73-2.65 (m, 1H), 2.13-1.97 (m, 2H), 1.92-1.77 (m, 4H), 1.61-1.55 (m, 4H), 1.55-1.42 (m, 4H), 1.42-1.31 (m, 5H), 1.31-1.17 (m, 5H), 1.17-0.90 (m, 3H), 0.47 (s, 3H).

LCMS Rt=0.640 min in 2 min chromatography, 30-90AB, purity 100%, MS ESI calcd. for C₂₄H₃₆NO [M+H]⁺ 354, found 354.

Example 93. Synthesis of Compound 107

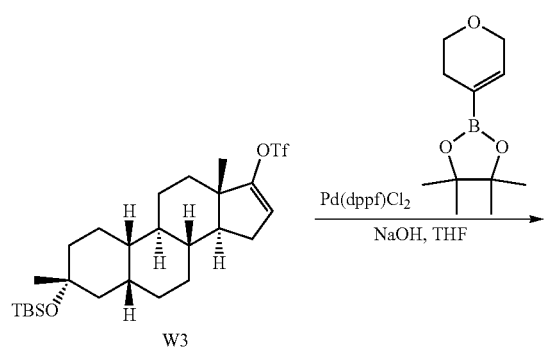

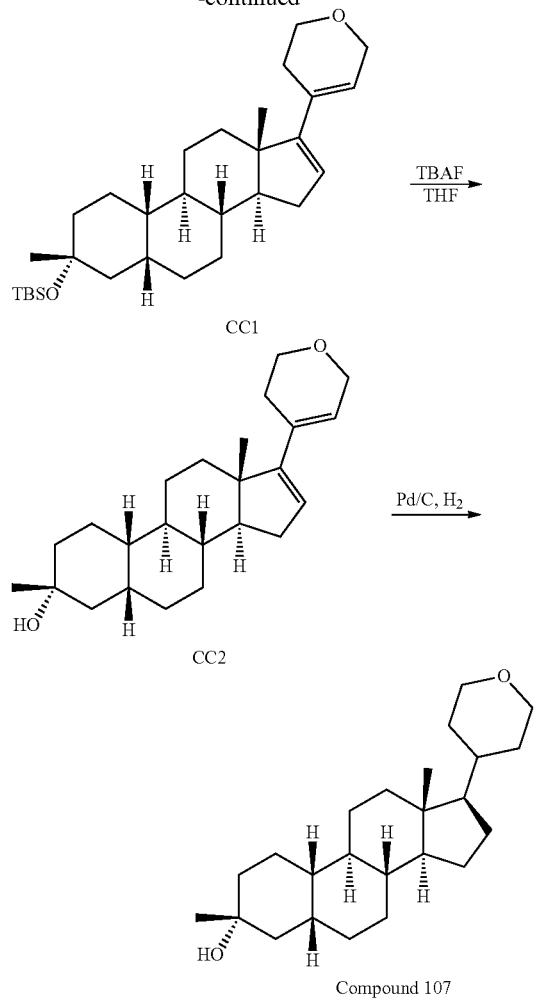

Step 1 (CC1).

To a mixture of W3 (200 mg, 0.372 mmol), 2-(3, 6-di-hydro-2H-pyran-4-yl)-4, 4, 5, 5-tetramethyl-1, 3, 2-dioxa-borolane (101 mg, 0.502 mmol) and NaOH (0.241 mL, 2 M in water) in THF (4 mL) was added Pd(dppf)Cl₂ (5 mg) under N₂. The mixture was stirred at 80° C. for 15 hrs and cooled to ambient temperature. The reaction mixture was quenched with sat. aqueous NaHCO₃ (3 mL) and extracted with EtOAc (2×5 mL). The combined organic layers were washed with brine (10 mL), dried over anhydrous Na₂SO₄, filtered and concentrated. The residue was purified by flash chromatography on silica gel (0% to 5% of EtOAc in PE) to give CC1 (170 mg, 97%) as a solid.

¹H NMR (400 MHz, CDCl₃) δ 5.87-5.80 (m, 1H), 5.68-5.64 (m, 1H), 4.28-4.15 (m, 2H), 3.90-3.70 (m, 2H), 2.39-2.28 (m, 1H), 2.22-2.18 (m, 3H), 1.90-1.79 (m, 5H), 1.69-1.51 (m, 4H), 1.49-1.30 (m, 5H), 1.30-1.09 (m, 8H), 1.04-0.78 (m, 12H), 0.06 (s, 6H).

Step 2 (CC2).

To a mixture of CC1 (170 mg) in THF (2 mL) was added TBAF (240 mg, 0.722 mmol). The reaction mixture was stirred at 80° C. for 18 hrs. Water (5 mL) was added to the reaction mixture, then the mixture was extracted with EtOAc (2×10 mL). The combined organic layers were washed with brine (5 mL), dried over anhydrous Na₂SO₄, filtered and concentrated. The residue was purified by flash silica gel chromatography (0~30% of EtOAc in PE) to give CC2 (70 mg, 55%) as a solid $^1$H NMR (400 MHz, CDCl$_3$) δ 5.87-5.80 (m, 1H), 5.68-5.64 (m, 1H), 4.28-4.15 (m, 2H), 3.90-3.76 (m, 2H), 2.39-2.28 (m, 1H), 2.28-2.07 (m, 3H), 1.90-1.79 (m, 4H), 1.79-1.61 (m, 2H), 1.61-1.39 (m, 9H), 1.39-1.09 (m, 8H), 0.92 (s, 3H).

Step 3 (Compound 107).

To a mixture of CC2 (70 mg, 0.196 mmol) in EtOAc (5 mL), Pd/C (100 mg, 5%, wet) was added under N$_2$. The mixture was stirred under H$_2$ (15 psi) at 15° C. for 15 hrs to give a black suspension, which was filtered and concentrated to give Compound 107 (37 mg, 52%) as a solid.

$^1$H NMR (400 MHz, CDCl$_3$) δ 3.97-3.87 (m, 2H), 3.41-3.28 (m, 2H), 1.94-1.73 (m, 6H), 1.66-1.51 (m, 5H), 1.50-1.33 (m, 8H), 1.33-1.19 (m, 8H), 1.19-0.98 (m, 6H), 0.68 (s, 3H).

LCMS Rt=1.297 min in 2 min chromatography, 30-90AB, purity 100%, MS ESI calcd. for C$_{24}$H$_{39}$O [M+H—H$_2$O]$^+$ 343, found 343.

Example 94. Synthesis of Compound 108

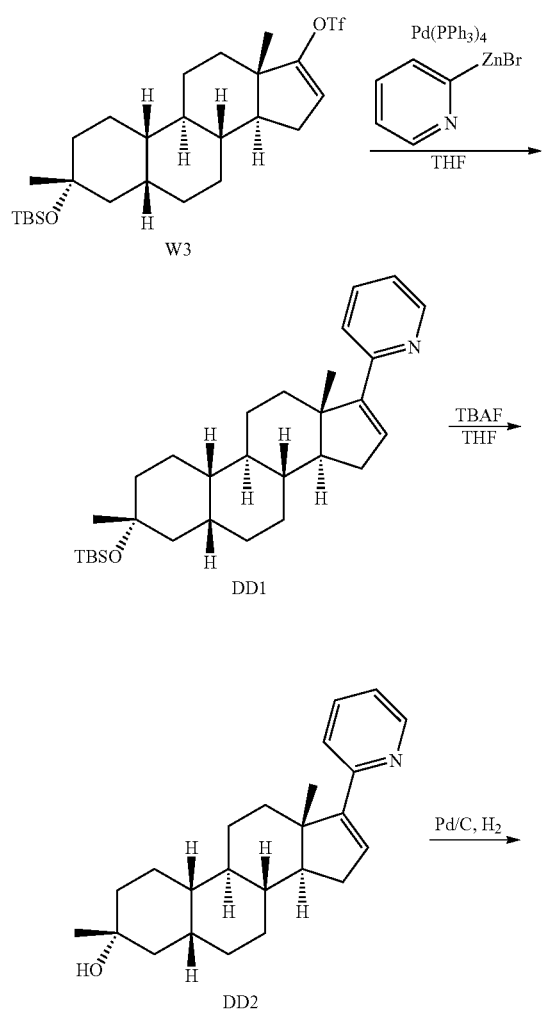

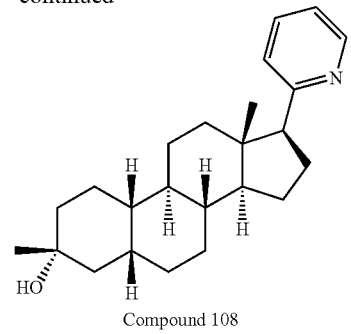

Compound 108

Step 1 (DD1).

To a mixture of W3 (200 mg, 0.372 mmol) in THF (10 mL) was added 2-Pyridylzinc bromide (0.966 mL, 0.5 M) and Pd(PPh$_3$)$_4$ (21.4 mg, 0.0186 mmol) under N$_2$. The reaction mixture was stirred at 80° C. for 15 hrs, then the mixture was quenched with sat. aqueous NaHCO$_3$ (3 mL) and extracted with EtOAc (2×5 mL). The combined organic layers were washed with brine (10 mL), dried over anhydrous Na$_2$SO$_4$, filtered and concentrated. The residue was purified by flash silica gel chromatography (0% to 5% of EtOAc in PE) to get DD1 (170 mg, 99%) as a solid.

$^1$H NMR (400 MHz, CDCl$_3$) δ 8.58-8.52 (m, 1H), 7.60-7.52 (m, 1H), 7.39-7.32 (m, 1H), 7.09-7.03 (m, 1H), 6.37-6.32 (m, 1H), 2.40-2.30 (m, 1H), 2.30-2.19 (m, 1H), 2.10-1.99 (m, 1H), 1.90-1.62 (m, 6H), 1.52-1.29 (m, 9H), 1.29-1.18 (m, 7H), 1.11 (s, 3H), 0.91-0.80 (m, 8H), 0.06 (s, 6H).

Step 2 (DD2).

To a mixture of DD1 (170 mg) in THF (2 mL) was added TBAF (242 mg, 0.728 mmol). The reaction mixture was stirred at 80° C. for 18 hrs to give a black oil. Water (5 mL) was added to the oil. The mixture was extracted with EtOAc (2×10 mL). The combined organic layers were washed with brine (5 mL), dried over Na$_2$SO$_4$, filtered and concentrated. The residue was purified by flash silica gel chromatography (0~10% of EtOAc in PE) to give DD2 (90 mg, 71%) as a solid.

$^1$H NMR (400 MHz, CDCl$_3$) δ 8.58-8.52 (m, 1H), 7.60-7.52 (m, 1H), 7.41-7.34 (m, 1H), 7.12-7.03 (m, 1H), 6.40-6.30 (m, 1H), 2.42-2.32 (m, 1H), 2.28-2.19 (m, 1H), 2.09-1.99 (m, 1H), 1.92-1.79 (m, 3H), 1.79-1.62 (m, 3H), 1.62-1.42 (m, 5H), 1.42-1.32 (m, 5H), 1.32-1.17 (m, 6H), 1.11 (s, 3H).

Step 3 (Compound 108).

To a mixture of DD2 (30 mg, 0.085 mmol) in EtOAc (5 mL) was added Pd/C (50 mg, 5%, wet) under N$_2$. The mixture was stirred under H$_2$ (15 psi) at 15° C. for 15 hrs to give a black suspension, which was filtered and concentrated to give Compound 108 (11 mg, 34%) as a solid.

$^1$H NMR (400 MHz, CDCl$_3$) δ 8.58-8.52 (m, 1H), 7.61-7.51 (m, 1H), 7.18-7.05 (m, 2H), 2.89-2.82 (m, 1H), 2.50-2.39 (m, 1H), 2.01-1.52 (m, 8H), 1.52-1.43 (m, 3H), 1.43-1.29 (m, 6H), 1.29-1.19 (m, 5H), 1.19-0.91 (m, 4H), 0.46 (s, 3H).

LCMS Rt=0.653 min in 2 min chromatography, 30-90AB, purity 100%, MS ESI calcd. for C$_{24}$H$_{36}$NO [M+H]$^+$ 354, found 354.

Example 95. Synthesis of Compound 109

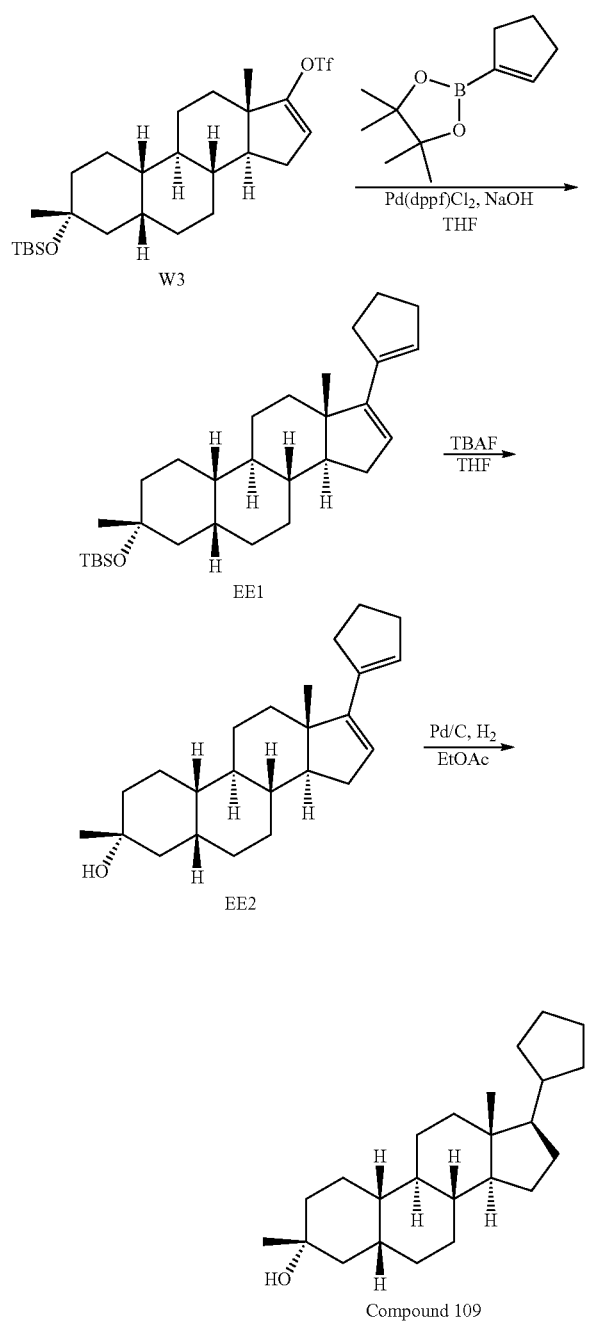

Step 1 (EE1).

To a mixture of W3 (200 mg, 0.372 mmol) in THF (4 mL), 2-(cyclopent-1-en-1-yl)-4, 4, 5, 5-tetramethyl-1, 3, 2-dioxaborolane (93.7 mg, 0.483 mmol) and Pd(dppf)$_2$Cl$_2$ (5 mg) were added under N$_2$. After stirring at 80° C. for 15 hrs, the reaction mixture was quenched with sat. aqueous NaHCO$_3$ (3 mL) and extracted with EtOAc (2×5 mL). The combined organic layers were washed with brine (10 mL), dried over Na$_2$SO$_4$, filtered and concentrated. The residue was purified by flash chromatography on silica (0% to 5% of EtOAc in PE) to give EE1 (160 mg, 95%) as an oil.

$^1$H NMR (400 MHz, CDCl$_3$) δ 5.81-5.75 (m, 1H), 5.54-5.52 (m, 1H), 2.54-2.37 (m, 4H), 2.21-2.10 (m, 1H), 1.91-1.58 (m, 7H), 1.58-1.45 (m, 3H), 1.45-1.31 (m, 6H), 1.31-1.09 (m, 9H), 0.94-0.72 (m, 12H), 0.06 (s, 6H).

Step 2 (EE2).

To a mixture of EE1 (160 mg) in THF (2 mL), TBAF (233 mg, 0.702 mmol) was added. After stirring at 80° C. for 18 hrs, the resulting black oil was treated with water (5 mL) and the mixture was extracted with EtOAc (2×10 mL). The combined organic layers were washed with brine (5 mL), dried over Na$_2$SO$_4$, filtered and concentrated. The residue was purified by flash silica gel chromatography (0~10% of EtOAc in PE) to give EE2 (90 mg, 75%) as an oil.

Step 3 (Compound 109).

To a solution of EE2 (90 mg) in EtOAc (5 mL), Pd/C (100 mg, 5%, wet) was added under N$_2$. The mixture was stirred under H$_2$ (15 psi) at 15° C. for 15 hrs to give a black suspension, which was filtered and concentrated to give Compound 109 (33 mg, 36%) as a solid.

$^1$H NMR (400 MHz, CDCl$_3$) δ 1.91-1.80 (m, 3H), 1.80-1.73 (m, 3H), 1.73-1.62 (m, 3H), 1.62-1.50 (m, 5H), 1.50-1.42 (m, 3H), 1.42-1.34 (m, 5H), 1.34-1.31 (m, 1H), 1.31-1.21 (m, 5H), 1.18-1.08 (m, 4H), 1.08-0.91 (m, 4H), 0.91-0.80 (m, 1H), 0.63 (s, 3H).

LCMS Rt=1.564 min in 2 min chromatography, 30-90AB, purity 100%, MS ESI calcd. for C$_{24}$H$_{39}$ [M+H—H$_2$O]$^+$ 327, found 327.

Example 96. Synthesis of Compound 110

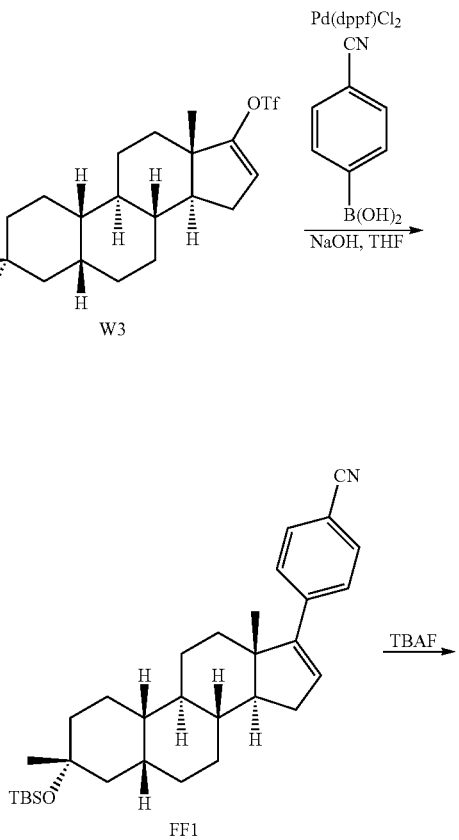

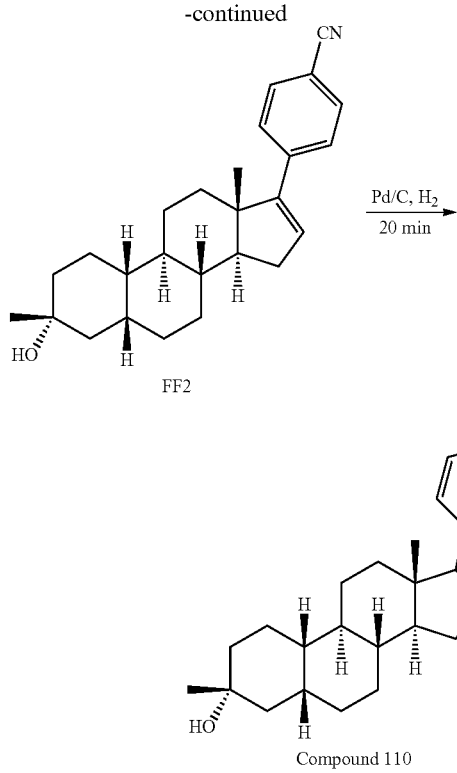

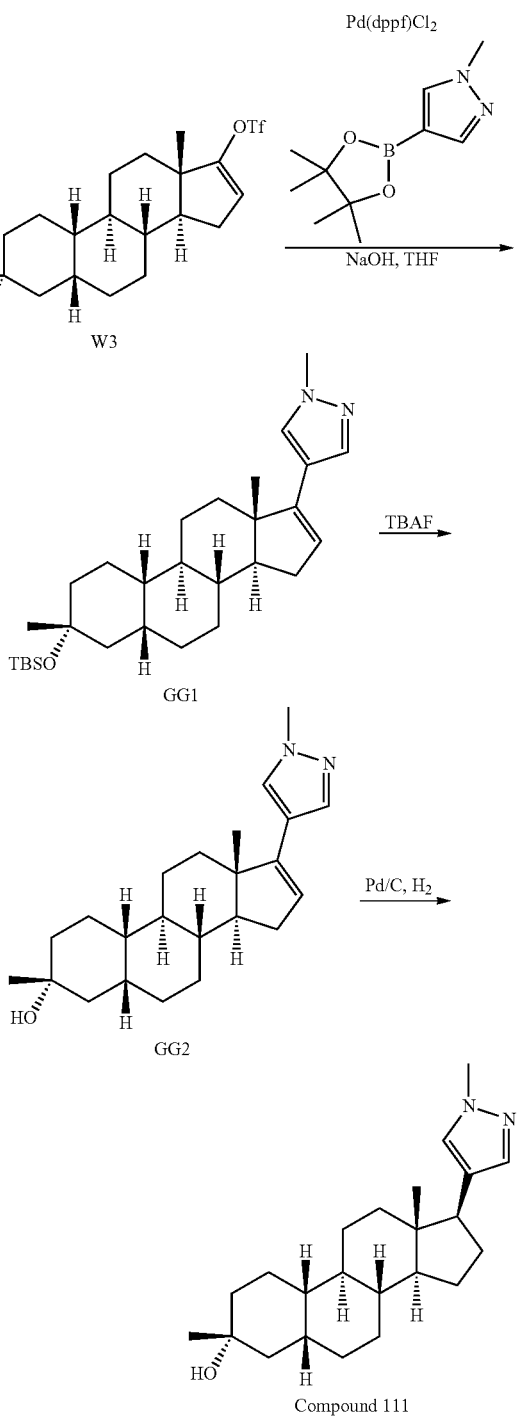

1.78 (m, 4H), 1.71-1.60 (m, 2H), 1.55-1.42 (m, 3H), 1.42-1.38 (m, 4H), 1.37-1.31 (m, 3H), 1.31-1.24 (m, 6H), 1.20-1.11 (m, 1H), 1.11-1.02 (m, 1H), 1.02-0.90 (m, 1H), 0.44 (s, 3H).

LCMS Rt=1.275 min in 2 min chromatography, 30-90AB, purity 99%, MS ESI calcd. for $C_{26}H_{34}N$ $[M+H-H_2O]^+$ 360, found 360.

Example 97. Synthesis of Compound 111

Step 1 (FF1).

To a mixture of W3 (200 mg, 0.372 mmol), (4-cyanophenyl) boronic acid (70.9 mg, 0.483 mmol) and Pd(dppf)Cl$_2$ (5 mg, 0.00656 mmol) in THF (4 mL), NaOH (0.241 mL, 2 M in water) was added. The reaction mixture was stirred at 80° C. under N$_2$ for 1 hour, then cooled to ambient temperature, treated with sat. aqueous NaHCO$_3$ (3 mL) and extracted with EtOAc (2×5 mL). The combined organic layers were washed with brine (10 mL), dried over Na$_2$SO$_4$, filtered, and concentrated. The product was purified by flash chromatography on silica gel (0% to 5% of EtOAc in PE) to give FF1 (230 mg, impure) as an oil.

Step 2 (FF2).

To a mixture of FF1 (230 mg, impure) in THF (2 mL), TBAF (307 mg, 0.921 mmol) was added. The reaction mixture was warmed to 80° C. and stirred for 18 h to give a dark black oil, which was treated with water (5 mL) and extracted with EtOAc (2×10 mL). The combined organic layers were washed with brine (5 mL), dried over Na$_2$SO$_4$, filtered and concentrated. The residue was purified by flash silica gel chromatography (0~30% of EtOAc in PE) to give FF2 (106 mg, 76% yield for 2 steps) as a solid.

$^1$H NMR (400 MHz, CDCl$_3$) δ 7.62-7.53 (m, 2H), 7.49-7.41 (m, 2H), 6.12-6.01 (m, 1H), 2.34-2.19 (m, 1H), 2.21-1.96 (m, 2H), 1.91-1.81 (m, 3H), 1.80-1.60 (m, 3H), 1.60-1.13 (m, 16H), 1.03 (s, 3H).

Step 3 (Compound 110).

To a solution of FF2 (30 mg, 0.0798 mmol) in EtOAc (5 mL) was added Pd/C (wet, 10%, 40 mg) under N$_2$. The suspension was degassed under vacuum and purged with H$_2$ three times. The mixture was stirred under H$_2$ (15 psi) at 15° C. for 0.5 hours to give a black suspension. The reaction mixture was filtered and concentrated to give Compound 110 (12 mg, 40%) as a solid.

$^1$H NMR (400 MHz, CDCl$_3$) δ 7.59-7.53 (m, 2H), 7.32-7.28 (m, 2H), 2.81-2.67 (m, 1H), 2.12-1.95 (m, 2H), 1.89-

Step 1 (GG1).

To a mixture of W3 (200 mg, 0.372 mmol), 1-methyl-4-(4, 4, 5, 5-tetramethyl-1, 3, 2-dioxaborolan-2-yl)-1H-pyrazole (100 mg, 0.483 mmol) and NaOH (0.241 mL, 0.482 mmol, 2M in water) in THF (4 mL) was added Pd(dppf)Cl$_2$ (5 mg). The mixture was degassed under vacuum and purged with N$_2$. After stirring at 80° C. for 1 h, the reaction mixture was quenched with sat. aqueous NaHCO$_3$ (3 mL) and extracted with EtOAc (2×5 mL). The combined organic layers were washed with brine (10 mL), dried over anhydrous Na$_2$SO$_4$, filtered and concentrated. The residue was purified by flash chromatography on silica gel (0% to 30% of EtOAc in PE) to give GG1 (180 mg, impure) as an oil.

$^1$H NMR (400 MHz, CDCl$_3$) δ 7.53 (s, 1H), 7.35 (s, 1H), 5.75-5.71 (m, 1H), 3.85 (s, 3H), 2.20-2.12 (m, 1H), 2.02-1.87 (m, 2H), 1.87-1.72 (m, 4H), 1.72-1.52 (m, 4H), 1.52-1.39 (m, 6H), 1.39-1.12 (m, 12H), 0.97-0.81 (m, 7H), 0.06 (s, 6H).

Step 2 (GG2).

To a mixture of GG1 (180 mg, impure) in THF (2 mL) was added TBAF (255 mg, 0.766 mmol). The reaction mixture was stirred at 80° C. for 18 hrs to give a black oil. Water (5 mL) was added to the oil. The mixture was extracted with EtOAc (2×10 mL). The combined organic layers were washed with brine (5 mL), dried over anhydrous Na$_2$SO$_4$, filtered and concentrated. The residue was purified by flash silica gel chromatography (0~10% of EtOAc in PE) to give GG2 (100 mg, 76% for 2 steps) as a solid 1H NMR (400 MHz, CDCl$_3$) δ 7.53 (s, 1H), 7.35 (s, 1H), 5.81-5.70 (m, 1H), 3.87 (s, 3H), 2.32-2.12 (m, 1H), 2.02-1.91 (m, 2H), 1.91-1.80 (m, 3H), 1.80-1.63 (m, 2H), 1.61-1.38 (m, 7H), 1.38-1.34 (m, 1H), 1.34-1.12 (m, 9H), 0.90 (s, 3H).

Step 3 (Compound 111).

To a mixture of GG2 (80 mg, 0.213 mmol) in EtOAc (5 mL) was added Pd/C (100 mg, 10%, wet) under N$_2$. The mixture was stirred under H$_2$ (15 psi) at 15° C. for 20 min to give a black suspension, which was filtered and concentrated to give Compound 111 (17 mg, 22%) as a solid.

$^1$H NMR (400 MHz, CDCl$_3$) δ 7.30 (s, 1H), 7.11 (s, 1H), 3.85 (s, 3H), 2.58-2.41 (m, 1H), 2.06-1.92 (m, 1H), 1.89-1.60 (m, 6H), 1.55 (s, 3H), 1.51-1.36 (m, 5H), 1.36-1.23 (m, 6H), 1.23-0.95 (m, 5H), 0.91-0.81 (m, 1H), 0.47 (s, 3H).

LCMS Rt=1.075 min in 2 min chromatography, 30-90AB, purity 100%, MS ESI calcd. for C$_{23}$H$_{37}$N$_2$O [M+H]$^+$ 357, found 357.

Example 98. Synthesis of Compound 112

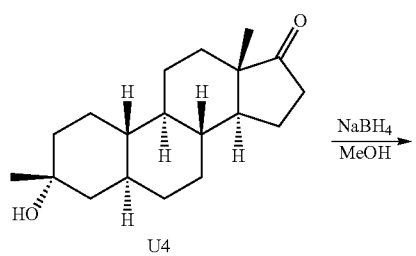

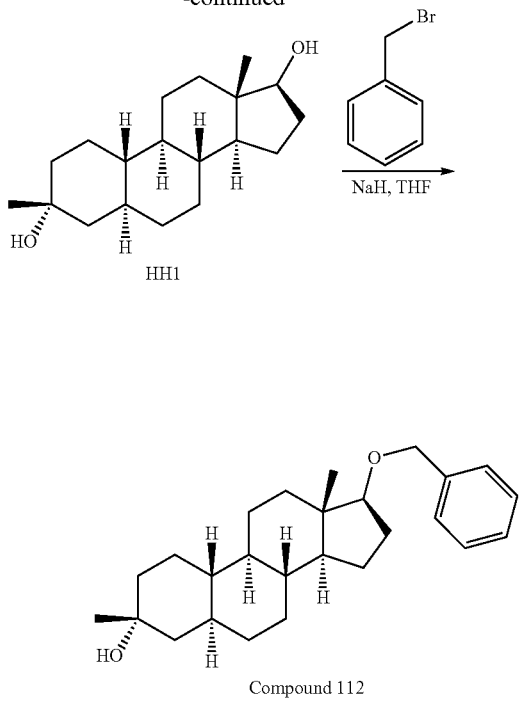

Step 1 (HH1).

To a solution of U4 (2 g, 6.56 mmol) in MeOH (20 mL) was added NaBH$_4$ (495 mg, 13.1 mmol) in portions at 0° C., the reaction mixture was stirred at 0° C. for 1 h, then the mixture was stirred at 15° C. for another 48 hrs. The reaction mixture was quenched with sat. aqueous NH$_4$Cl (20 mL) and extracted with EtOAc (3×20 mL). The combined organic phase was washed with brine (20 mL), dried over anhydrous Na$_2$SO$_4$, filtered and concentrated. The residue was purified by flash silica gel chromatography (0~15% of EtOAc in PE) to give HH1 (1.5 g, 75%) as a solid.

$^1$H NMR (400 MHz, CDCl$_3$) δ 3.65-3.57 (m, 1H), 2.09-2.01 (m, 1H), 1.83-1.74 (m, 1H), 1.73-1.31 (m, 12H), 1.30-1.12 (m, 10H), 1.11-0.84 (m, 3H), 0.77-0.74 (m, 3H), 0.73-0.69 (m, 3H).

Step 2 (Compound 112).

To a solution of HH1 (200 mg, 0.652 mmol) in THF (2 mL) was added NaH (77.8 mg, 1.95 mmol, 60%) in portions at 0° C. The mixture was stirred at 25° C. for 30 min. Then, (bromomethyl)benzene (167 mg, 0.978 mmol) was added drop wise to the solution. The mixture was stirred at 25° C. for 1 hr. The mixture was poured into water (30 mL) and extracted with EtOAc (2×20 mL). The combined organic layers were washed with brine, dried over anhydrous Na$_2$SO$_4$ and concentrated. The residue was purified by column silica gel chromatography (petroleum ether/ethyl acetate=10/1) to afford Compound 112 (30 mg, 12%) as a solid.

$^1$H NMR (400 MHz, CDCl$_3$) δ 7.36-7.30 (m, 4H), 7.24-7.21 (m, 1H), 4.54 (s, 2H), 3.43-3.39 (m, 1H), 2.01-1.90 (m, 2H), 1.69-1.57 (m, 2H), 1.51-1.08 (m, 18H), 0.99-0.85 (m, 3H), 0.82 (s, 3H), 0.76 (s, 3H), 0.74-0.69 (m, 1H).

LCMS Rt=1.344 min in 2.0 min chromatography, 30-90 AB, purity 100%, MS ESI calcd. For C$_{27}$H$_{39}$O [M–H$_2$O+H]$^+$ 379, found 379.

Example 99. Synthesis of Compound 113

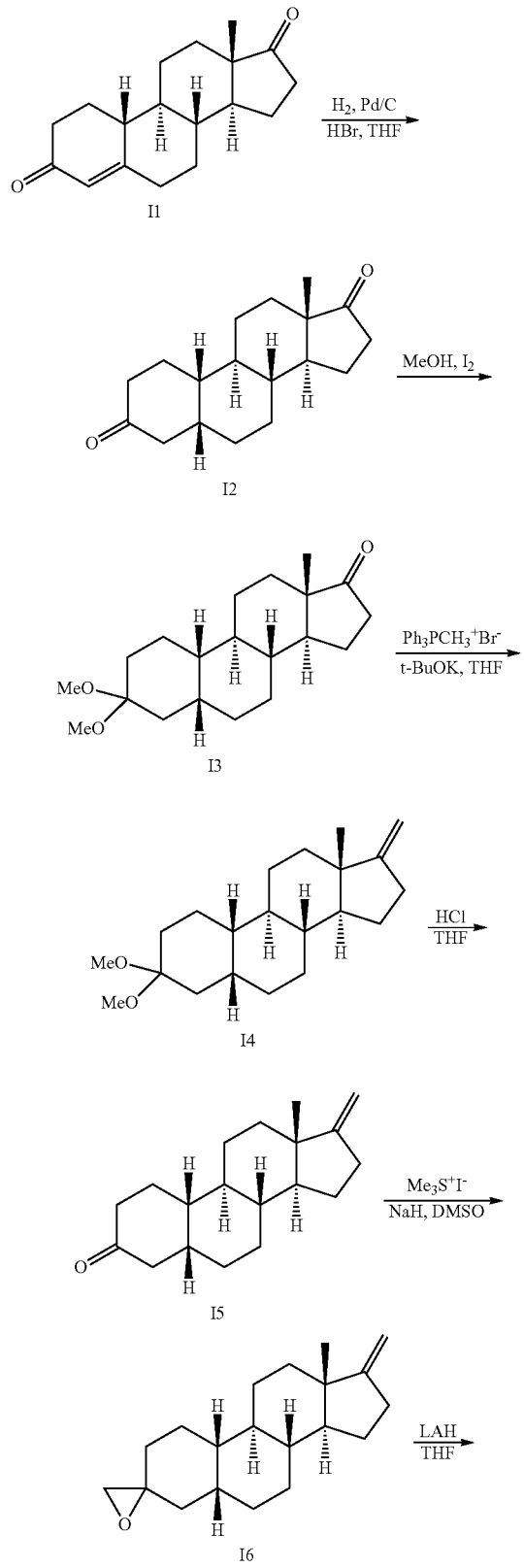
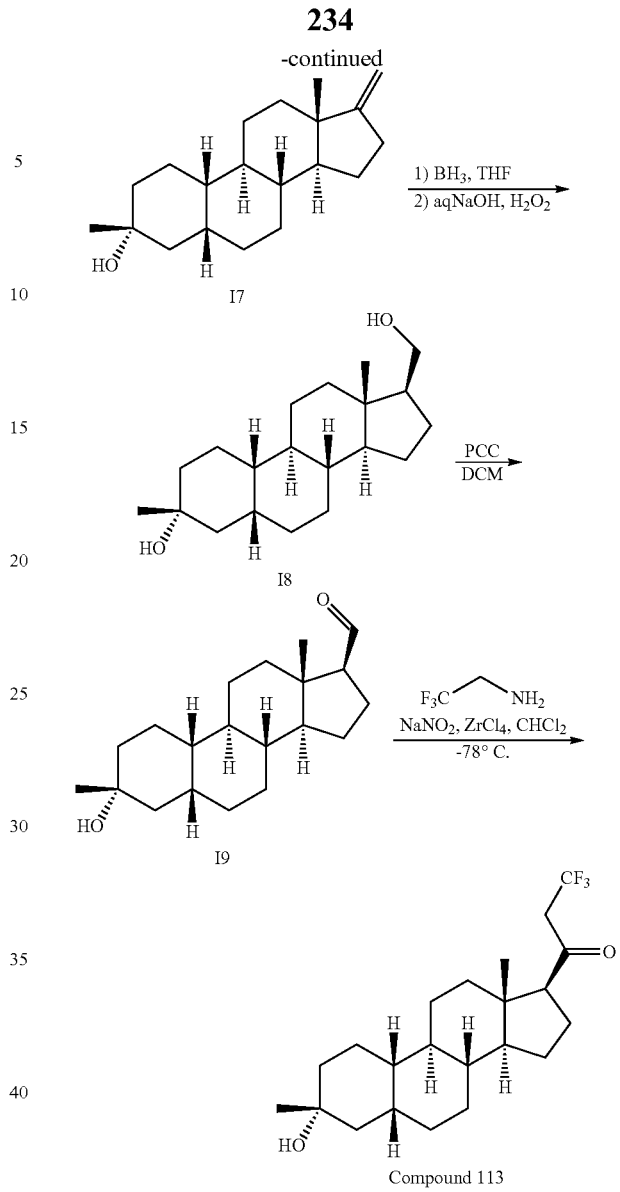

Step 1 (I2).

A mixture of I1 (500 mg, 1.84 mmol) 10% Pd/black (50 mg) and concentrated hydrobromic acid (0.02 mL) in tetrahydrofuran (5 mL) was hydrogenated at 1 atm. for 24 h, then the mixture was filtered through a pad of celite and the filtrate was concentrated in vacuo. Recrystallization from acetone gave I2 (367 mg, 73%).

$^1$H NMR (500 MHz, CDCl$_3$), δ (ppm), 2.58 (t, 1H, J=14 Hz), 2.45 (dd, 1H, J=19 Hz, 9 Hz), 0.98 (s, 3H)

Step 2 (I3).

To a solution of I2 (274 mg, 1.0 mmol) in methanol (4 mL) at room temperature was added iodine (0.1 mmol). After stirring at 60° C. for 12 h, the solvent was removed in vacuo. The crude product was dissolved in dichloromethane (20 mL) and washed with saturated aqueous NaHCO$_3$ (15 mL), brine (20 ml), dried over anhydrous Na$_2$SO$_4$, filtered and concentrated. The residue was purified by chromatography on basic alumina (petroleum ether/ethyl acetate=9:1) to give compound 13 (280 mg, 88%).

$^1$H NMR (500 MHz, CDCl$_3$), δ (ppm), 3.19 (s, 3H), 3.13 (s, 3H), 2.43 (dd, 1H, J=19.2 Hz, 8.8 Hz), 0.83 (s, 3H).

Step 3 (I4).

To a suspension of methyltriphenylphosphonium bromide (10.26 g, 28.84 mmol) in THF (30 mL), was added KOt-Bu (3.23 g, 28.80 mmol). The reaction was heated to 60° C. for 1 h, then I3 (3.23 g, 9.6 mmol) was added to the mixture. The solution was stirred at 60° C. for 15 h. The reaction mixture was diluted with EtOAc (500 mL). The resulting mixture was washed with brine (300 mL) and evaporated in vacuo. The crude residue was then purified by silica gel chromatography (PE:EtOAc=3:1) to afford I4 as a solid (2.1 g, 65%).

Step 4 (I5).

To a solution of I4 (1 g, 3.1 mmol) in THF (20 mL) was added 2 M HCl (2 mL). The solution was stirred at rt for 1 h then the reaction mixture was extracted with EtOAc (100 mL), washed with brine (100 mL) and evaporated in vacuo. The crude residue was purified by silica gel chromatography (PE:EtOAc=10:1) to afford I5 as a solid (710 mg, 2.6 mmol 83%).

$^1$H NMR (500 MHz, CDCl$_3$), δ (ppm), 4.65 (s, 1H), 4.63 (s, 1H), 0.82 (s, 3H).

Step 5 (I6). To a stirred suspension of trimethylsulfonium iodide (6.4 g, 23.5 mmol) in DMSO (10 mL) was added NaH (60%; 800 mg, 31.5 mmol). After stirring at room temperature for 1 h, a suspension of compound I5 (870 mg, 3.2 mmol) in DMSO (5 mL) was added dropwise. After 15 h, the reaction mixture was poured into ice-cold water and extracted with EtOAc (300 mL), washed with brine (100 mL), dried and evaporated in vacuo. The crude residue was then purified by silica gel chromatography (PE:EtOAc=10: 1) to afford a mixture of I6 and its C-3 isomer as a solid (695 mg, 10%).

Step 6 (I7).

To a solution of I6 and its C-3 isomer (129 mg, 0.45 mmol) in THF (10 mL) was added LiAlH$_4$ (50 mg, 1.35 mmol). The mixture was stirred at rt for 1 h, then the reaction mixture was quenched with H$_2$O (5 mL) and extracted with EtOAc (100 mL). The organic layer was washed with brine and evaporated in vacuo and the resulting crude residue was purified by chromatography (PE:EtOAc=3:1) to afford I7 as a solid (62 mg, 48%).

$^1$H NMR (500 MHz, CDCl$_3$), δ (ppm), 4.63 (s, 1H), 4.61 (s, 1H), 1.25 (s, 3H), 0.82 (s, 3H).

Step 7 (I8).

To a solution of I7 (86 mg, 0.3 mmol) in dry THF (5 mL) was added borane-tetrahydrofuran complex (1 mL; 1.0 M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1 mL). After stirring at room temperature for one hour, the mixture was extracted with EtOAc (3×100 mL). The combined organic layers were washed with 10% aqueous Na$_2$S$_2$O$_3$ (100 mL), brine (100 mL), dried over MgSO$_4$, filtered and concentrated to afford crude I8 as a solid (83 mg, 91%). The crude product was used in the next step without further purification.

Step 8 (I9).

To a solution of I8 (150 mg, 0.49 mmol) in DCM (10 mL) was added PCC (320 mg, 1.47 mmol), and the reaction solution was stirred at rt for 2 h. The reaction mixture was then filtered through a pad of celite, evaporated in vacuo and the crude residue was purified by silica gel chromatography (PE:EtOAc=10:1) to afford I9 as a solid (80 mg, 53%).

$^1$H NMR (500 MHz, CDCl$_3$), δ (ppm), 9.77 (s, 1H), 2.31 (t, 1H, J=9 Hz), 1.27 (s, 3H), 0.75 (s, 3H).

Step 9 (Compound 113).

Trifluoroethylamine hydrochloride (90 mg, 0.66 mmol) and NaNO$_2$ (50 mg, 0.79 mmol) were dissolved in a CH$_2$Cl$_2$/water mixture (3 mL/0.1 mL) and stirred for one hour in a sealed Schlenk tube cooled in a water/ice bath. The mixture was then further cooled to −78° C. in a dry-ice/acetone bath and stirred for 10 min, then I9 (0.1 g, 0.33 mmol) and ZrCl$_4$ (100 mg, 0.43 mmol, 1.3 equiv) were added to the mixture. After 45 min, the resulting mixture was quenched by addition of MeOH (3 mL) followed by saturated aqueous NaHCO$_3$ (20 mL), extracted with CH$_2$Cl$_2$ (3×20 mL), dried over MgSO$_4$, and evaporated in vacuo. The crude residue was purified by column chromatography on silica gel (pentane/diethyl ether=10:1) to afford Compound 113 (12 mg, 9%) as a solid.

$^1$H NMR (500 MHz, CDCl$_3$), δ (ppm), 3.20 (m, 2H), 2.57 (1H, t, J=9 Hz), 2.22-2.15 (m, 1H), 1.27 (s, 3H), 0.65 (s, 3H).
$^{19}$FNMR (376.5 MHz, CDCl$_3$), δ (ppm), −62.28

Example 100. Synthesis of Compound 114 and Compound 115

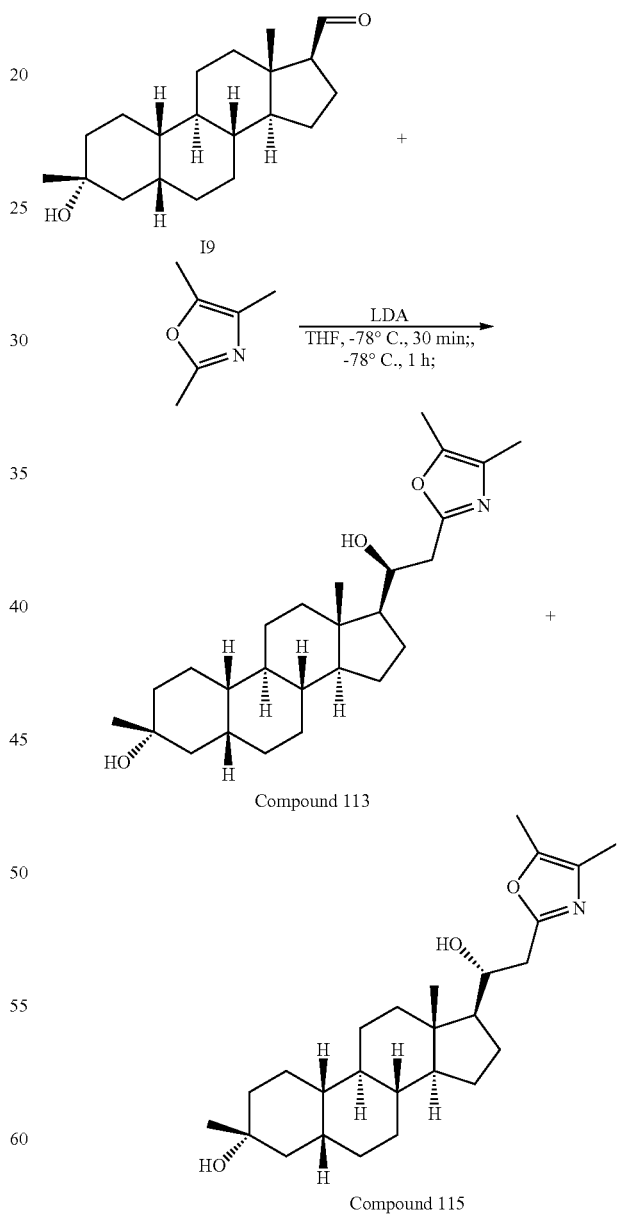

Step 1 (Compound 114 and Compound 115).

To a stirred solution of 2,4,5-trimethyloxazole (0.37 g, 3.3 mmol) in 10 mL of THF was added LDA (2.0 M; 0.82 mL, 1.64 mmol) at −78° C. After stirring at −78° C. for 30 min, a solution of I9 (0.1 g, 0.33 mmol) in 2 mL of THF was added dropwise at −78° C. After stirring at −78° C. for 1 h, the reaction mixture was poured into ice-cold water. The mixture was extracted with EtOAc (3×100 mL), washed with brine (3×100 mL), dried (MgSO₄), filtered, and evaporated in vacuo. The resulting crude residue was purified by prep-HPLC to afford Compound 114 (54 mg, 35% yield) as a solid, and Compound 115 (22 mg, 16.1% yield) as a solid.

Compound 114

¹H NMR (500 MHz, CDCl₃), δ (ppm), 4.0 (1H, t, J=7 Hz), 3.68 (s, 1H), 2.94 (1H, d, J=13 Hz), 2.70 (dd, 1H, J=16 Hz, 10 Hz), 2.20 (s, 3H), 2.03 (s, 3H), 1.26 (s, 3H), 0.72 (s, 3H).

Compound 115

¹H NMR (500 MHz, CDCl₃), δ (ppm), 3.96 (1H, t, J=7 Hz), 3.40-3.60 (1H, br), 2.82 (1H, d, J=13 Hz), 2.62 (dd, 1H, J=16 Hz, 9 Hz), 2.20 (s, 3H), 2.03 (s, 3H), 1.26 (s, 3H), 0.78 (s, 3H).

Example 101. Synthesis of Compound 116 and Compound 117

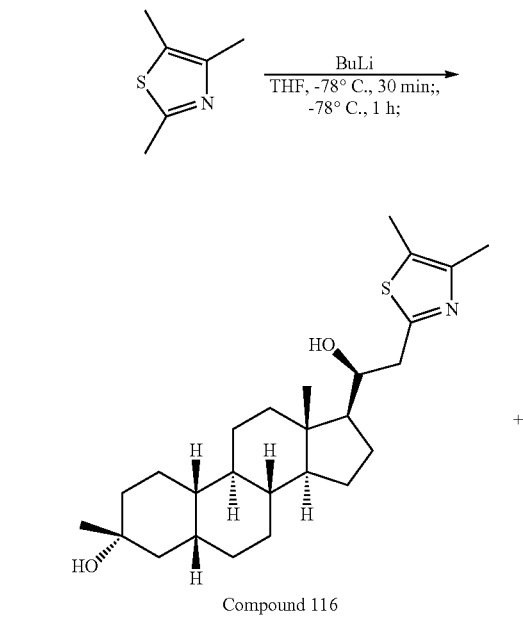

Compound 116

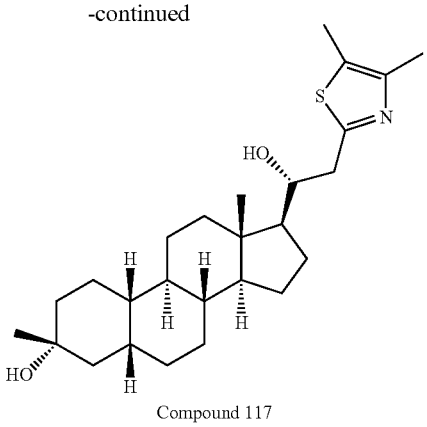

Compound 117

Step 1 (Compound 116 and Compound 117).

To a stirred solution of 2,4,5-trimethylthiazole (0.21 g, 1.64 mmol) in 10 mL of THF was added nBuLi (2.5 M; 0.66 mL, 1.64 mmol) at −78° C. After stirring at −78° C. for 30 min, a solution of I9 (0.1 g, 0.33 mmol) in 2 mL of THF was added dropwise at −78° C. After stirring at −78° C. for 1 h, the reaction mixture was poured into ice-cold water and extracted with EtOAc (3×100 mL), washed with brine (3×100 mL), dried (MgSO₄), filtered, and evaporated in vacuo, then purified by prep-HPLC to afford Compound 116 (44 mg, 31% yield) as a solid and Compound 117 (27 mg, 19% yield) as a solid.

Compound 116

¹H NMR (500 MHz, CDCl₃), δ (ppm), 4.10 (bs, 1H), 3.97 (t, 1H, J=8.6 Hz), 3.14 (dd, 1H, J=15.3 Hz, J=2.8 Hz), 2.88 (dd, 1H, J=14.8 Hz, J=9.6 Hz), 2.30 (s, 3H), 2.27 (s, 3H), 1.25 (s, 3H), 0.72 (s, 3H).

Compound 117

¹H NMR (500 MHz, CDCl₃), δ (ppm), 3.91 (t, 1H, J=8.4 Hz), 3.03 (dd, 1H, J=14.4 Hz, J=1.9 Hz), 2.78 (dd, 1H, J=14.4 Hz, J=7.8 Hz), 2.30 (s, 3H), 2.27 (s, 3H), 1.25 (s, 3H), 0.77 (s, 3H).

Example 102. Synthesis of Compound 118

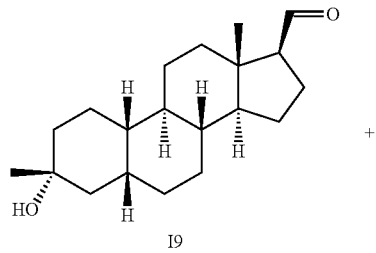

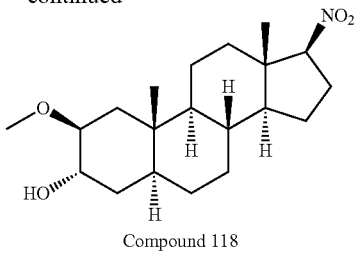

Compound 118

The synthesis of 1A is described in WO 2015/010054.

Step 1:

Hydroxylamine hydrochloride (154 mg, 2.2 mmol) was added to a solution of compound 1A (350 mg, 1.09 mmol) in anhydrous pyridine (10 mL). The solution was allowed to stir at 20° C. for 12 h. The reaction mixture was poured into water (20 mL). The solid was collected and dried to give compound 1B (280 mg, 76%) as an off-solid.

$^1$H NMR: (400 MHz, CDCl$_3$) δ 6.82 (br, 1H), 3.92-3.85 (m, 1H), 3.31-3.22 (m, 4H), 2.47-2.37 (m, 2H), 1.90-1.52 (m, 6H), 1.45-0.94 (m, 12H), 0.87 (s, 3H), 0.82 (s, 3H), 0.78-0.67 (m, 1H).

Step 2:

A solution of KHCO$_3$ (500 mg, 5 mmol) in H$_2$O (5 mL) was added to a solution of NBS (440 mg, 2.5 mmol) in dioxane (5 mL). The suspension was allowed to stir at room temperature for 0.25 h and a solution of compound 1B (280 mg, 0.835 mmol) in dioxane (10 mL) was added in dropwise manner. A pale green color rapidly developed, and the reaction was allowed to stir at room temperature for 10 h. The solution was cooled to 0° C. and NaBH$_4$ (220 mg, 5.85 mmol) was added in portions. A large amount of gas evolution was observed and the reaction was allowed to stir overnight, gradually warming to room temperature. The reaction was quenched with saturated aqueous NH$_4$Cl (20 mL). The resulting suspension was partitioned between water (20 mL) and EtOAc (50 mL), and the organic layer was separated. The aqueous layer was then extracted with EtOAc (3×20 mL) and organic extracts combined, washed with brine (20 mL), dried (Na$_2$SO$_4$), and concentrated under reduced pressure. The resulting oil was purified by column chromatography on silica gel (petrol ether:ethyl acetate=5:1) to give Compound 118 (70 mg, 24%) as an off-white powder.

$^1$H NMR: (400 MHz, CDCl$_3$) δ 4.36 (t, J=8.8 Hz, 1H), 3.99-3.92 (m, 1H), 3.37-3.30 (m, 4H), 2.60-2.48 (m, 1H), 2.12-2.02 (m, 2H), 1.95-1.62 (m, 5H), 1.50-1.38 (m, 3H), 1.37-1.23 (m, 8H), 1.03-0.94 (m, 1H), 0.93 (s, 3H), 0.80-0.75 (m, 1H), 0.71 (s, 3H).

Example 103. Synthesis of Compound 119

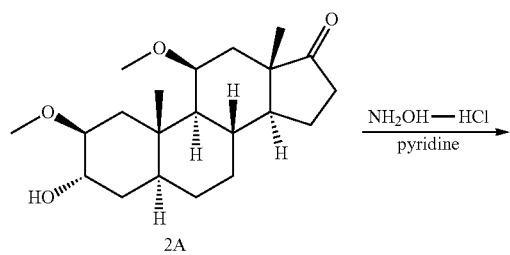

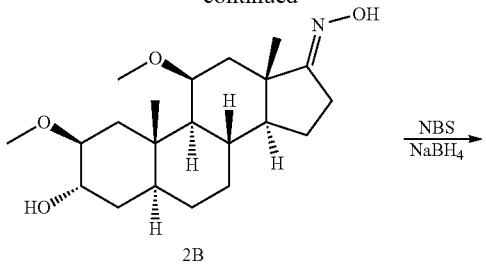

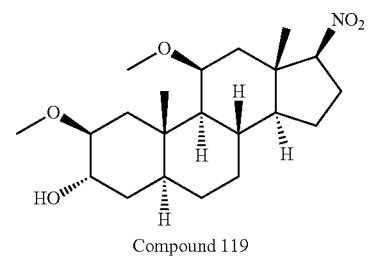

Compound 119

The synthesis of 2A is described in WO 2015/010054.

Step 1:

Hydroxylamine hydrochloride (178 mg, 2.58 mmol) was added to 2A (300 mg, 0.86 mmol) in anhydrous pyridine (3 mL). The solution was allowed to room temperature for 12 hours. Water was added slowly, then the off-solid was precipitated. The solid was filtered and evaporated to dryness. 2B (200 mg, 64%) was collected. It was used to next step without purification.

$^1$H NMR: (400 MHz, methanol-d4) δ 3.83-3.80 (m, 1H), 3.81-3.70 (m, 1H), 2.44-2.43 (m, 3H), 1.95-1.11 (m, 12H), 1.09 (s, 3H), 1.03 (s, 3H), 1.02-0.98 (m, 1H), 0.88-0.81 (m, 1H).

Step 2:

A solution of K$_2$CO$_3$ (330 mg, 3.3 mmol) in H$_2$O (3 mL) was added to a solution of NBS (290 mg, 1.65 mmol) in dioxane (2 mL). The suspension was allowed to stir at room temperature for 15 minutes and 2B (200 mg, 0.55 mmol) in dioxane (3 mL) was added in a dropwise manner. A pale green color rapidly developed, and the reaction was allowed to stir at room temperature for 10 hours. The solution was cooled to 0° C. and NaBH$_4$ (146.3 mg, 3.85 mmol) was added in portions. A large amount of gas evolution was observed and the reaction was allowed to stir overnight, gradually warming to room temperature. The reaction was quenched with saturated aqueous NH$_4$Cl (30 mL) and extracted with EtOAc (3×50 mL). The organic extracts combined, washed with brine (100 mL), dried over anhydrous Na$_2$SO$_4$ and concentrated under reduced pressure. The residue was purified by column chromatography (petroleum ether:ethyl acetate=10:1) to afford Compound 119 (73 mg, 35%) as an off-solid.

$^1$H NMR: (400 MHz, CDCl$_3$) δ 4.33-4.30 (m, 1H), 3.96-3.95 (m, 1H), 3.71-3.31 (m, 1H), 3.34-3.30 (m, 4H), 3.23 (s, 3H), 2.55-2.51 (m, 2H), 2.10-1.92 (m, 1H), 1.89-1.74 (m, 5H), 1.54-1.10 (m, 9H), 1.08 (s, 3H), 0.98-0.91 (m, 1H), 0.89 (s, 3H), 0.79-0.76 (m, 1H).

Example 104. Syntheses of Compounds 120 and 121

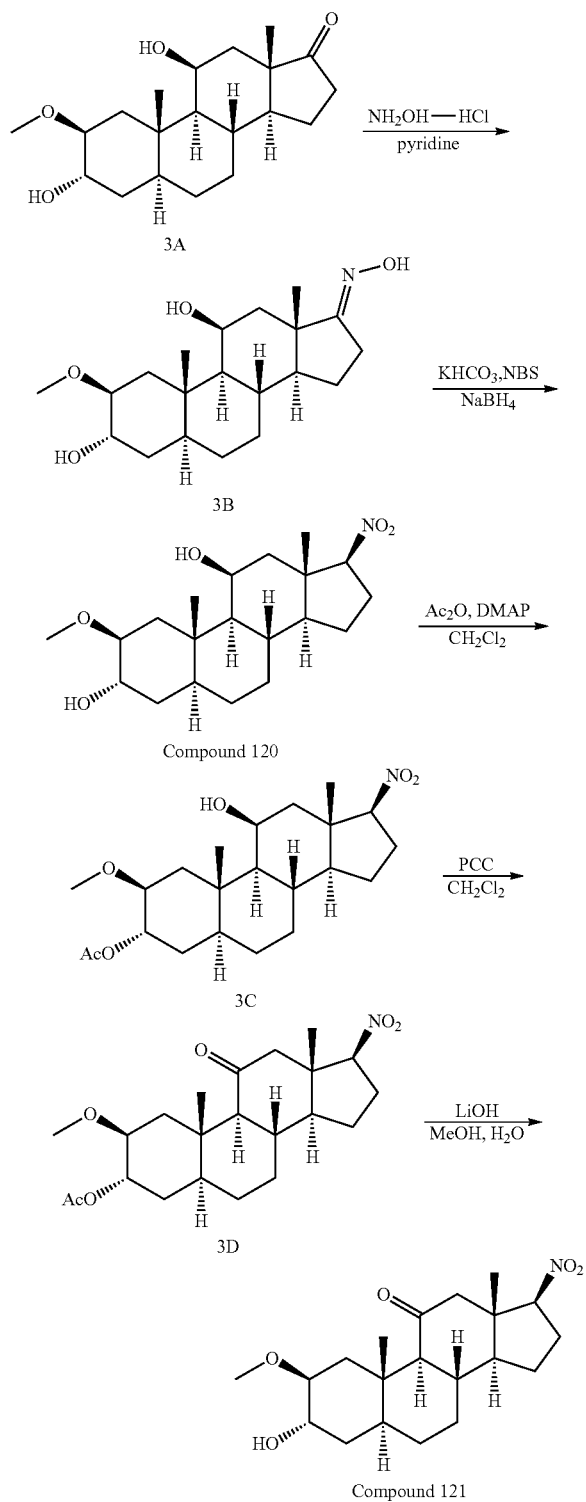

The synthesis of 3A is described in WO 2015/010054.

Step 1:

Hydroxylamine hydrochloride (509 mg, 7.32 mmol) was added to 3A (800 mg, 2.38 mmol) in anhydrous pyridine (5 mL). The solution was allowed to stir at room temperature for 12 hours. The mixture was extracted with EtOAc (50 mL) and H$_2$O (40 mL). The organic phase was washed with HCl (80 mL, 0.5 M), dried over Na$_2$SO$_4$ and evaporated to give the crude product 3B (700 mg, 84%) as an off-solid.

Step 2:

A solution of K$_2$CO$_3$ (1.20 g, 11.96 mmol) in H$_2$O (8 mL) was added to a solution of NBS (1.05 g, 5.97 mmol) in dioxane (3 mL). The suspension was allowed to stir at room temperature for 15 minutes and 3B (700 mg, 1.99 mmol) in dioxane (3 mL) was added in a dropwise manner. The reaction was allowed to stir at room temperature for 10 hours. The solution was cooled to 0° C. and NaBH$_4$ (529.34 mg, 13.93 mmol) was added in portions. A large amount of gas evolution was observed and the reaction was allowed to stir overnight, gradually warming to room temperature. The reaction was quenched with saturated aqueous NH$_4$Cl (30 mL) and extracted with EtOAc (3×50 mL). The organic extracts combined, washed with brine (100 mL), dried over anhydrous Na$_2$SO$_4$ and concentrated under reduced pressure. The residue was purified by column chromatography on silica gel (petroleum ether: ethyl acetate=10:1) to afford Compound 120 (400 mg, 55%) as an off-solid.

$^1$H NMR: (400 MHz, CDCl$_3$) δ 4.41-4.33 (m, 1H), 4.30-4.28 (m, 1H), 3.97-3.90 (m, 1H), 3.36-3.35 (m, 4H), 2.56-2.52 (m, 1H), 2.25-2.21 (m, 1H), 2.08-2.00 (m, 2H), 1.89-1.53 (m, 4H), 1.51-1.20 (m, 8H), 1.17-1.10 (m, 4H), 1.09-1.07 (m, 1H), 1.10-0.94 (m, 4H), 0.83-0.79 (m, 1H).

Step 3:

To a stirred solution of Compound 120 (250 mg, 0.68 mmol) in CH$_2$Cl$_2$ (3 mL) was added Ac$_2$O (69.54 mg, 0.68 mmol) and DMAP (17 mg, 0.14 mmol). Then Et$_3$N (137.5 mg, 1.36 mmol) was added. The mixture was stirred at room temperature for 3 hours. The mixture was treated with water and extracted with CH$_2$Cl$_2$ (2×50 mL), and the organic layer was washed with brine (100 mL), dried over anhydrous Na$_2$SO$_4$, then concentrated to obtain crude product 3C (200 mg, 80%), which was used to the next step without purification.

Step 4:

To a stirred solution of 3C (200 mg, 0.49 mmol) in CH$_2$Cl$_2$ (3 mL) was added PCC (211 mg, 0.98 mmol). The mixture was stirred at room temperature for 12 hours. The mixture was filtered, and the filtrate was concentrated to give the crude product, which was purified by flash column chromatography on silica gel (petroleum ether:ethyl acetate=5:1) to afford 3D (130 mg, 65%) as an off-solid.

Step 5:

To a stirred solution of 3D (130 mg, 0.32 mmol) in MeOH (3 mL) and H$_2$O (1 mL) was added LiOH (60.8 mg, 1.60 mmol). The mixture was stirred at 50° C. for 4 hours. The solvent was removed, and the residue was treated with water, then extracted with EtOAc (2×50 mL). The organic phase was washed with brine (100 mL), dried over anhydrous Na$_2$SO$_4$, then evaporated to give the crude product, which was purified by preparative HPLC to afford Compound 121 (41 mg, 18%) as an off-solid.

$^1$H NMR: (400 MHz, CDCl$_3$) δ 4.57-4.52 (m, 1H), 4.30-4.28 (m, 1H), 3.93-3.92 (m, 1H), 3.37 (s, 3H), 3.28-3.27 (m, 1H), 2.78-2.74 (m, 1H), 2.64-2.57 (m, 2H), 2.46-2.43 (m, 1H), 2.25-2.19 (m, 1H), 1.90-1.73 (m, 6H), 1.53-1.48 (m, 2H), 1.33-1.20 (m, 3H), 1.18-1.10 (m, 5H), 0.68 (s, 3H).

Example 105. Syntheses of Compounds 5 and 6

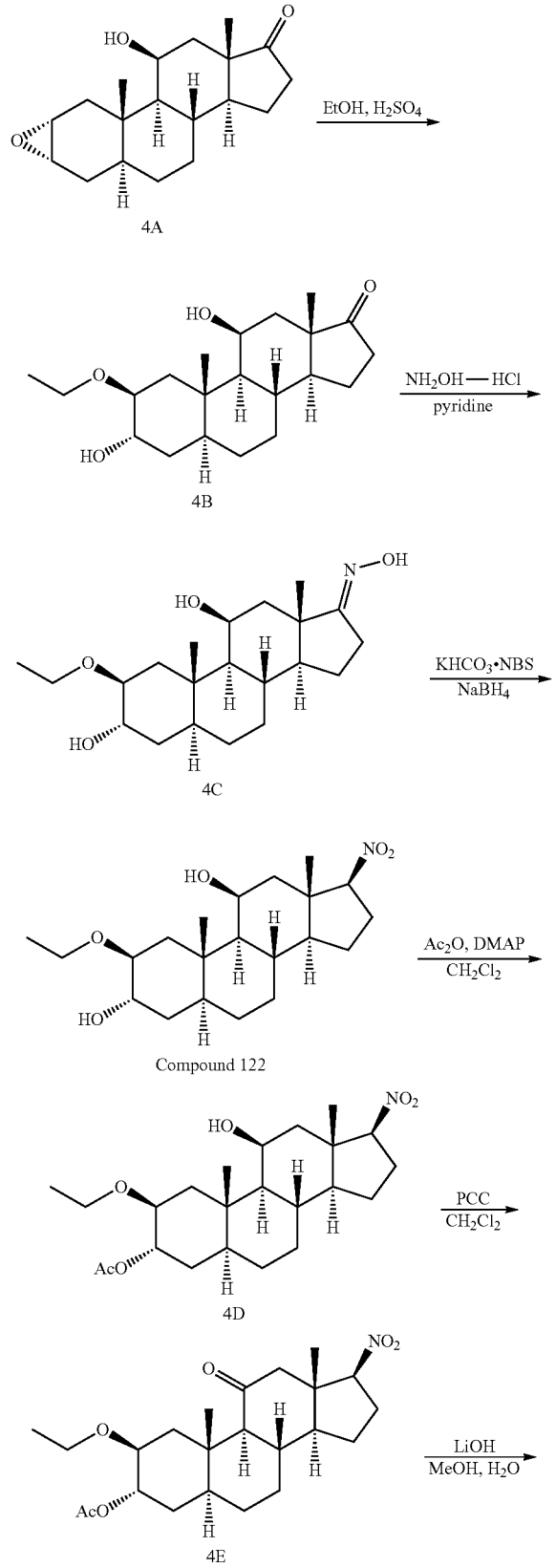

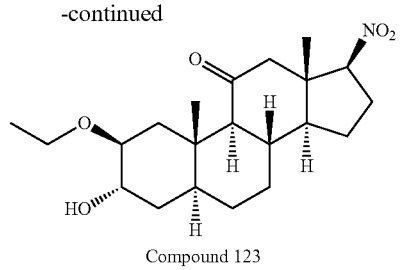

Compound 123

The synthesis of 4A is described in WO 2015/010054.

Step 1:

A solution of 4A (2.0 g, 6.57 mmol) in EtOH (20 mL) was treated with 5 drops of fuming $H_2SO_4$ at room temperature. After 1 hour, the reaction mixture was quenched with aqueous $NaHCO_3$ (10 mL). The resulting solution was extracted with 2×100 mL of ethyl acetate and the organic layers combined and dried over anhydrous sodium sulfate. The organic phase was concentrated under vacuum. The crude product was purified by column chromatography on silica gel (petroleum ether:ethyl acetate=6:1) to give 4B (800 mg, 35%) as an off-solid.

$^1$H NMR: (400 MHz, $CDCl_3$) δ 4.44-4.41 (m, 1H), 3.94-3.93 (m, 1H), 3.61-3.57 (m, 1H), 3.45-3.454 (m, 1H), 3.42-3.41 (m, 1H), 2.50-2.44 (m, 1H), 2.09-1.83 (m, 7H), 1.61-1.58 (m, 3H), 1.45-1.20 (m, 14H), 1.18-1.12 (m, 4H), 1.10 (s, 3H), 1.06-1.02 (m, 1H), 0.83-0.80 (m, 1H).

Step 2:

Hydroxylamine hydrochloride (458 mg, 6.60 mmol) was added to 4B (770 mg, 2.20 mmol) in anhydrous pyridine (5 mL). The solution was allowed to stir at room temperature for 12 hours. The mixture was extracted with EtOAc (100 mL) and $H_2O$ (80 mL). The organic phase was washed with HCl (80 mL, 0.5 M), dried over $Na_2SO_4$ and evaporated to give the crude product 4C (720 mg, 90%) as an off-solid.

Step 3:

A solution of $K_2CO_3$ (1.15 g, 11.5 mmol) in $H_2O$ (5 mL) was added to a solution of NBS (1.0 g, 5.73 mmol) in dioxane (3 mL). The suspension was allowed to stir at room temperature for 15 minutes and 4C (700 mg, 1.91 mmol) in dioxane (3 mL) was added in a dropwise manner. The reaction was allowed to stir at room temperature for 10 hours. The solution was cooled to 0° C. and $NaBH_4$ (508.46 mg, 13.37 mmol) was added in portions. A large amount of gas evolution was observed and the reaction was allowed to stir overnight, gradually warming to room temperature. The reaction was quenched with saturated aqueous $NH_4Cl$ (30 mL) and extracted with EtOAc (3×50 mL). The organic extracts combined, washed with brine (100 mL), dried over anhydrous $Na_2SO_4$ and concentrated under reduced pressure. The residue was purified by column chromatography on silica gel (petroleum ether: ethyl acetate=5:1) to afford the Compound 5 (350 mg, 48%) as an off-solid.

$^1$H NMR: (400 MHz, $CDCl_3$) δ 4.41-4.40 (m, 1H), 4.33-4.28 (m, 1H), 4.00-3.90 (m, 1H), 3.62-3.60 (m, 1H), 3.45-3.42 (m, 1H), 3.40-3.38 (m, 1H), 2.56-2.53 (m, 1H), 2.25-2.21 (m, 1H), 2.10-2.00 (m, 2H), 1.89-1.70 (m, 4H), 1.54-1.19 (m, 8H), 1.18-1.15 (m, 7H), 1.12-1.10 (m, 1H), 1.05-0.98 (m, 4H), 0.83-0.79 (m, 1H).

Step 4:

To a stirred solution of Compound 122 (350 mg, 0.92 mmol) in $CH_2Cl_2$ (3 mL) was added $Ac_2O$ (93.6 mg, 0.92 mmol) and DMAP (22.5 mg, 0.18 mmol). Then $Et_3N$ (196.2 mg, 1.94 mmol) was added. The mixture was stirred at room temperature for 3 hours. The mixture was treated with water and extracted with CH$_2$Cl$_2$ (2×50 mL), and the organic layer was washed with brine (100 mL), dried over anhydrous Na$_2$SO$_4$, then concentrated to obtain crude 4D (147 mg, 38%), which was used in the next step without purification.

Step 5:

To a stirred solution of 4D (110 mg, 0.26 mmol) in CH$_2$Cl$_2$ (3 mL) was added PCC (112 mg, 0.52 mmol). The mixture was stirred at room temperature for 12 hours. The mixture was filtered, and the filtrate was concentrated to give the crude product, which was purified by flash column chromatography (petroleum ether:ethyl acetate=5:1) to afford 4E (88 mg, 81%) as an off-solid.

$^1$H NMR: (400 MHz, CDCl$_3$) δ 4.92-4.90 (m, 1H), 4.56-4.52 (m, 1H), 3.67-3.63 (m, 1H), 3.45-3.40 (m, 2H), 2.78-2.75 (m, 1H), 2.64-2.61 (m, 2H), 2.46-2.42 (m, 1H), 2.26-2.19 (m, 1H), 2.05 (s, 3H), 1.91-1.70 (m, 5H), 1.51-1.20 (m, 6H), 1.18-1.15 (m, 6H), 1.104-1.00 (m, 1H), 0.90-0.80 (m, 2H), 0.68 (s, 3H).

Step 6:

To a stirred solution of 4E (88 mg, 0.21 mmol) in MeOH (2 mL) and H$_2$O (1 mL) was added LiOH (40 mg, 1.68 mmol). The mixture was stirred at 50° C. for 4 hours. The solvent was removed, and the residue was treated with water, then extracted with EtOAc (2×30 mL). The organic phase was washed with brine (50 mL), dried over anhydrous Na$_2$SO$_4$, then evaporated to give the crude product, which was purified by flash column chromatography on silica gel (petroleum ether:ethyl acetate=3:1) to afford the Compound 123 (28 mg, 34%) as an off-solid.

$^1$H NMR: (400 MHz, CDCl$_3$) δ 4.57-4.52 (m, 1H), 3.91-3.90 (m, 1H), 3.75-3.70 (m, 1H), 3.39-3.34 (m, 2H), 2.74-2.69 (m, 1H), 2.66-2.61 (m, 2H), 2.45-2.42 (m, 1H), 1.90-1.77 (m, 5H), 1.41-1.36 (m, 1H), 1.33-1.20 (m, 6H), 1.18-1.15 (m, 8H), 1.33-1.20 (m, 3H), 0.90-0.81 (m, 1H), 0.68 (s, 3H).

Example 106. Syntheses of Compounds 124 and 125

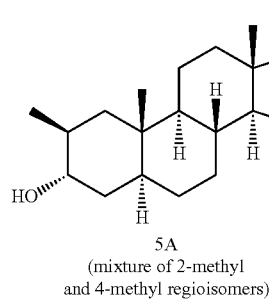

5A
(mixture of 2-methyl and 4-methyl regioisomers)

BzCl
pyridine, 20° C.

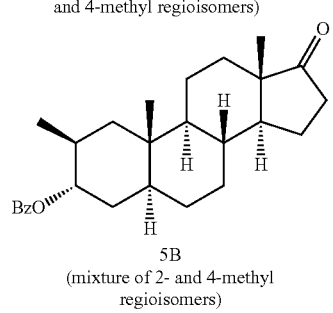

5B
(mixture of 2- and 4-methyl regioisomers)

NaBH$_4$, CeCl$_3$—7H$_2$O
MeOH, THF, 0° C.
Yield: 73% of 2 steps

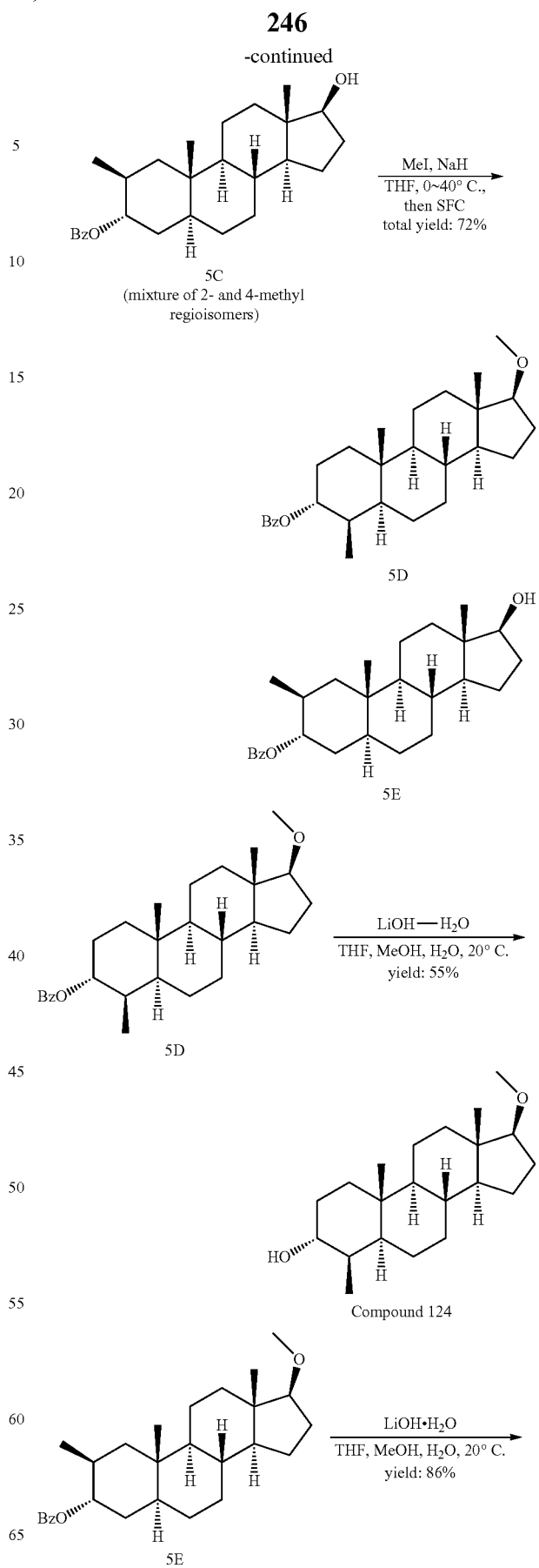

-continued

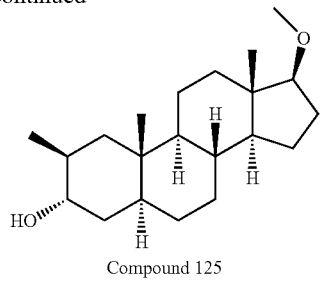

Compound 125

The synthesis of 5A is described in WO 2015/010054.

Step 1:

To a solution of mixture 5A (0.6 g, 2 mmol) in pyridine (5 mL) was added benzoyl chloride (0.8 g, 5.7 mmol). The mixture was then stirred at 20° C. for 2 hours. To the mixture was then added aq. $NaHCO_3$, extracted with ethyl acetate. The organic layer was separated, dried over $Na_2SO_4$, concentrated under vacuum to give mixture 5B (0.9 g, crude) as a light yellow oil.

$^1$H NMR: (400 MHz, $CDCl_3$) δ 8.10-8.00 (m, 2H), 7.58-7.52 (m, 1H), 7.49-7.40 (m, 2H), 5.09-5.00 (m, 1H), 2.49-2.39 (m, 1H), 2.20-1.45 (m, 14H), 1.40-0.75 (m, 15H).

To a solution of mixture 5B (0.9 g, crude) in THF (4 mL) and MeOH (6 mL) was added $CeCl_3 \cdot 7H_2O$ (0.87 g, 2.2 mmol). The mixture was stirred at 0° C. for 15 minutes. $NaBH_4$ (90 mg, 2.4 mmol) was then added in portions at 0° C. as monitored by TLC. To the mixture was then added aq. $NH_4Cl$ and then extracted with ethyl acetate. The organic layer was separated, dried over $Na_2SO_4$, concentrated under vacuum, purified by column chromatography on silica gel (petrol ether:ethyl acetate=8:1 to 5:1) to give mixture 5C (0.6 g, 73% of 2 steps) as an off-solid.

$^1$H NMR: (400 MHz, $CDCl_3$) δ 8.08-8.00 (m, 2H), 7.58-7.52 (m, 1H), 7.49-7.41 (m, 2H), 5.08-4.98 (m, 1H), 3.64 (t, J=8.6 Hz, 1H), 2.20-0.65 (m, 31H).

Step 2:

To a suspension of NaH (120 mg, 60%, 3 mmol) in THF (3 mL) was added a solution of mixture 5D (0.6 g, 1.5 mmol) in THF (2 mL). The mixture was stirred at 0° C. for 30 minutes. MeI (850 mg, 6 mmol) was then added and the mixture was then stirred at 40° C. for 5 hours. The mixture was then poured into aq. $NH_4Cl$, extracted with ethyl acetate. The organic layer was separated, dried over $Na_2SO_4$, concentrated under vacuum, purified by column chromatography on silica gel (petrol ether: ethyl acetate=40:1). The mixture was then subjected to SFC to obtain 5D (350 mg) and 5E (100 mg, total yield: 72%) as off-solids.

$^1$H NMR (5D): (400 MHz, $CDCl_3$) δ 8.20-8.08 (m, 2H), 7.63-7.55 (m, 1H), 7.52-7.44 (m, 2H), 5.08-5.00 (m, 1H), 3.37 (s, 3H), 3.24 (t, J=8.4 Hz, 1H), 2.20-1.40 (m, 13H), 1.37-0.70 (m, 17H).

$^1$H NMR (5E): (400 MHz, $CDCl_3$) δ 8.20-8.08 (m, 2H), 7.61-7.53 (m, 1H), 7.51-7.42 (m, 2H), 5.10-5.04 (m, 1H), 3.36 (s, 3H), 3.24 (t, J=8.4 Hz, 1H), 2.08-1.15 (m, 16H), 1.07-0.70 (m, 14H).

Step 3a:

To a solution of 5D (150 mg, 0.35 mmol) in THF (4 mL) was added MeOH (2 mL) and a solution of $LiOH \cdot H_2O$ (0.3 g, 7 mmol) in water (1 mL). The mixture was stirred at 30° C. for 2 days. The mixture was extracted with ethyl acetate. The organic layer was dried over $Na_2SO_4$, purified by column chromatography (petrol ether:ethyl acetate=10:1) to give Compound 124 (61 mg, 55%) as an off-solid.

$^1$H NMR: (400 MHz, $CDCl_3$) δ 3.80-3.75 (m, 1H), 3.34 (s, 3H), 3.21 (t, J=8.4 Hz, 1H), 2.05-1.09 (m, 19H), 0.95-0.83 (m, 8H), 0.77-0.67 (m, 4H).

Step 3b:

To a solution of 5E (300 mg, 0.7 mmol) in THF (4 mL) was added MeOH (2 mL) and a solution of $LiOH \cdot H_2O$ (0.3 g, 7 mmol) in water (1 mL). The mixture was stirred at 30° C. for 2 days. The mixture was extracted with ethyl acetate. The organic layer was dried over $Na_2SO_4$, purified by column chromatography on silica gel (petrol ether:ethyl acetate=10:1) to give Compound 125 (189 mg, 86%) as a solid.

$^1$H NMR (ST-400-135): (400 MHz, $CDCl_3$) δ 3.75-3.65 (m, 1H), 3.34 (s, 3H), 3.21 (t, J=8.4 Hz, 1H), 2.05-1.84 (m, 3H), 1.75-1.08 (m, 16H), 1.05-0.82 (m, 8H), 0.76-0.64 (m, 4H).

Example 107. Synthesis of Compound 126

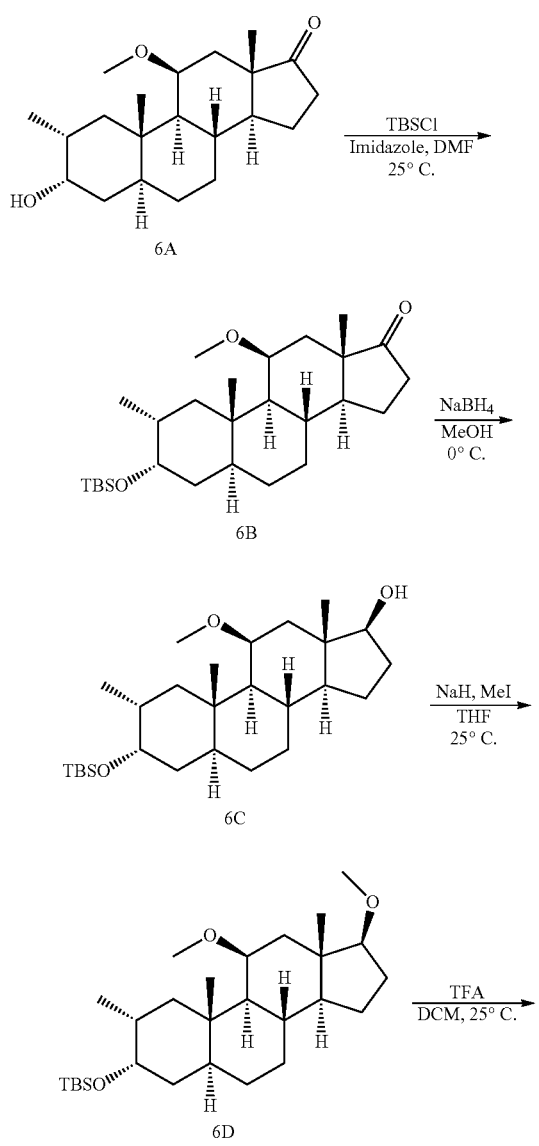

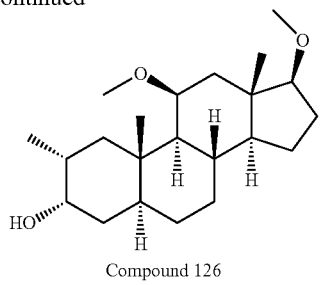

Compound 126

The synthesis of 6A is described in WO 2015/010054.

Step 1:

To a solution of 6A (0.3 g, 0.9 mmol) in DMF (5 mL) was added imidazole (0.18 g, 2.7 mmol) and TBSCl (0.27 g, 1.8 mmol). The mixture was stirred at 25° C. for 16 hours. To the mixture was added water, extracted with petrol ether/ethyl acetate (8:1). The organic layer was separated, dried over $Na_2SO_4$, concentrated under vacuum to give 6B (0.4 g, quantitative) as an oil.

$^1$H NMR: (400 MHz, $CDCl_3$) δ 3.78-3.68 (m, 2H), 3.23 (s, 3H), 2.52-2.43 (m, 1H), 2.30-2.20 (m, 1H), 2.06-1.88 (m, 4H), 1.70-0.70 (m, 32H), 0.13 (s, 6H).

Step 2:

To a solution of 6B (0.4 g, 0.9 mmol) in tetrahydrofuran (2 mL) and MeOH (4 mL) was added $NaBH_4$ (0.08 g, 2 mmol) at 0° C. The mixture was stirred at 0° C. for 5 minutes. $NH_4Cl$ (aq.) was then added. The mixture was extracted with ethyl acetate. The combined organic layer was separated, dried over $Na_2SO_4$, concentrated under vacuum to give 6C (0.5 g, crude product) as an off-solid.

$^1$H NMR: (400 MHz, $CDCl_3$) δ 3.75-3.55 (m, 2H), 3.22 (s, 3H), 2.30-2.25 (m, 1H), 2.08-2.00 (m, 1H), 1.70-1.55 (m, 6H), 1.50-1.08 (m, 9H), 0.98-0.85 (m, 22H), 0.11 (s, 6H).

Step 3:

To a solution of 6C (0.5 g, 1.1 mmol) in tetrahydrofuran (5 mL) was added NaH (0.2 g, 60%, 5 mmol) at 15° C. The mixture was stirred at 25° C. for 30 minutes. To the mixture was then added MeI (1.4 g, 10 mmol). The mixture was stirred at 25° C. for 16 hours. To the mixture was then added $NH_4Cl$ (aq.), extracted with ethyl acetate. The organic layer was then separated, dried over anhydrous sodium sulfate, concentrated under vacuum to give 6D (0.5 g, crude) as an off-solid.

$^1$H NMR: (400 MHz, $CDCl_3$) δ 3.75-3.62 (m, 2H), 3.35 (s, 3H), 3.25-3.15 (m, 4H), 2.40-2.30 (m, 1H), 2.03-1.92 (m, 1H), 1.70-1.60 (m, 3H), 1.50-0.75 (m, 32H), 0.14 (s, 6H).

Step 4:

To a solution of 6D (0.5 g, 1.1 mmol) in $CH_2Cl_2$ (5 mL) was added $CF_3COOH$ (0.5 mL). The mixture was stirred at 25° C. for 3 hours. To the mixture was then added $NaHCO_3$ (aq.). The organic layer was separated, dried over anhydrous sodium sulfate, concentrated under vacuum, purified by column chromatography (petrol ether:ethyl acetate=8:1) to give compound 125 (119 mg, 37% over 3 steps) as an off-solid.

$^1$H NMR: (400 MHz, $CDCl_3$) δ 3.83-3.75 (m, 1H), 3.70-3.63 (m, 1H), 3.36 (s, 3H), 3.25 (s, 3H), 3.20 (t, J=8 Hz, 1H), 2.42-2.30 (m, 1H), 2.05-1.95 (m, 1H), 1.85-1.72 (m, 3H), 1.65-1.10 (m, 12H), 1.05-0.90 (m, 11H), 0.83-0.75 (m, 1H).

Example 108. Synthesis of Compound 127

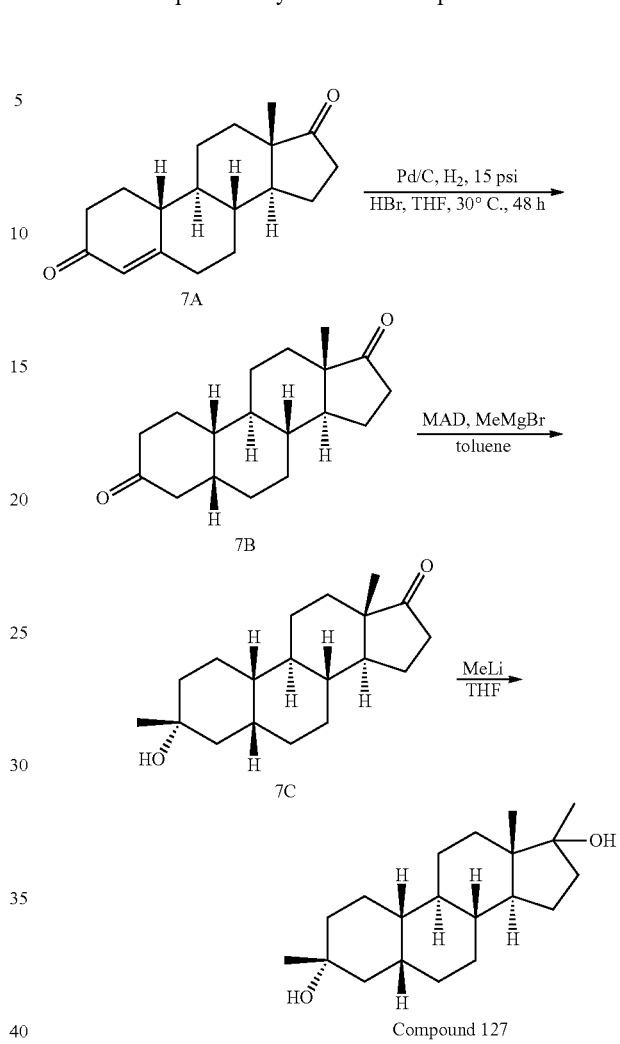

Compound 127

Step 1:

To a solution of 7A (50 g, 146 mmol) and Pd/C (2.5 g, 10% Palladium on carbon, 50% water wet) in THF (500 mL) was added concentrated hydrobromic acid (1.0 mL, 48% in water). The reaction was hydrogenated under 15 psi of hydrogen at 25° C. for 16 h. The reaction was conducted in parallel for 4 times. The reaction mixture was filtered through a pad of celite and washed with THF (1 L×3) and DCM (1 L×3). The filtrate was concentrated in vacuum to give 7B (196 g, crude).

$^1$H NMR (400 MHz, $CDCl_3$) δ 2.64-2.53 (m, 1H), 2.52-2.41 (m, 1H), 2.30-2.03 (m, 6H), 2.01-1.91 (m, 1H), 1.90-1.69 (m, 3H), 1.68-1.48 (m, 5H), 1.47-1.29 (m, 4H), 1.28-1.13 (m, 2H), 0.68 (s, 3H).

Step 2:

To a solution of 2,6-di-tert-butyl-4-methylphenol (240 g, 1.08 mol) in toluene (150 mL) was added drop-wise $AlMe_3$ (270 mL, 540 mmol, 2 M in toluene) at 0° C. The mixture was stirred at 25° C. for 1 h. 7B (50 g, 182 mmol) in toluene (200 mL) was added drop wise to the solution at −70° C. After stirring at −70° C. for 1 h, MeMgBr (63.6 ml, 190 mmol, 3M in ethyl ether) was added drop wise at −70° C. The resulting solution was stirred at −70° C. for 1 hrs. The reaction was quenched by saturated aqueous $NH_4Cl$ (200 mL) at −70° C. After stirring at 25° C. for 0.5 h, the resulting mixture was filtered through a celite pad and the pad was washed with EtOAc (500 mL). The combined organic layer was separated, washed with brine (500 mL×2) and concentrated in vacuum. The crude product was purified by silica gel column eluted with PE/EtOAc=50/1 to 3/1 to give 7C (25 g, 47%) as an off-solid.

$^1$H NMR (400 MHz, CDCl$_3$) δ 2.47-2.40 (m, 1H), 2.12-2.03 (m, 1H), 1.96-1.75 (m, 6H), 1.71-1.61 (m, 1H), 1.54-1.32 (m, 7H), 1.30-1.02 (m, 11H), 0.86 (s, 3H).

Step 3:

To a solution of 7C (0.1 g, 0.34 mmol) in THF (5 mL) was added MeLi (4.29 mL, 1.6 M) at 15° C. The mixture was stirred at 15° C. for 16 h and 50° C. for 1 h and quenched with NH$_4$Cl (5 mL, sat.). The mixture was extracted with EtOAc (20 mL). The organic layer was separated, dried over Na$_2$SO$_4$, filtered and concentrated in vacuum to give a crude material, which was purified by silica gel column (PE/EtOAc=4/1 to 3/1) to give crude Compound 126 (80 mg) as an off-solid. The crude product was dissolved in MeCN (10 mL) at 50° C. Water (3 mL) was added. The mixture was concentrated in vacuum at 15° C. to 5 mL and an off-solid was formed. The mixture was filtered. The solid was washed with MeCN/water (5 mL, 1:1), dried in vacuum to give Compound 126 (49 mg, yield: 47%) as an off-solid.

$^1$H NMR (400 MHz, CDCl$_3$) δ 1.90-1.60 (m, 7H), 1.57-1.38 (m, 8H), 1.37-1.18 (m, 13H), 1.17-0.99 (m, 3H), 0.85 (s, 3H).

LCMS Rt=0.818 min in 2.0 min chromatography, 30-90 AB, purity 100%, MS ESI calcd. for C$_{20}$H$_{31}$ [M+H-2H$_2$O]$^+$ 271, found 271.

TABLE 2

| TBPS Data | | |
|---|---|---|
| Compound structure | Compound number | TBPS IC$_{50}$ (nM) |
| [structure] | 1 | C |
| [structure] | 2 | D |
| [structure] | 3 | A |

TABLE 2-continued

TBPS Data

| Compound structure | Compound number | TBPS IC$_{50}$ (nM) |
|---|---|---|
| [Steroid with N-benzyl-N-methyl carboxamide at C17, 3α-OH, 3β-methyl] | 4 | B |
| [Steroid with piperidinyl carbonyl at C17, 3α-OH, 3β-methyl] | 5 | C |
| [Steroid with 1,4-oxazepanyl carbonyl at C17, 3α-OH, 3β-methyl] | 6 | E |
| [Steroid with N-methyl-N-phenyl carboxamide at C17, 3α-OH, 3β-methyl] | 7 | E |
| [Steroid with N-cyclohexyl carboxamide at C17, 3α-OH, 3β-methyl] | 8 | C |

TABLE 2-continued
TBPS Data
| Compound structure | Compound number | TBPS IC$_{50}$ (nM) |
|---|---|---|
| 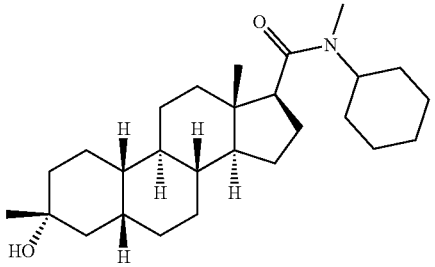 | 9 | D |
| 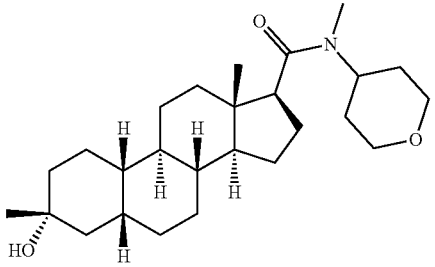 | 10 | D |
| 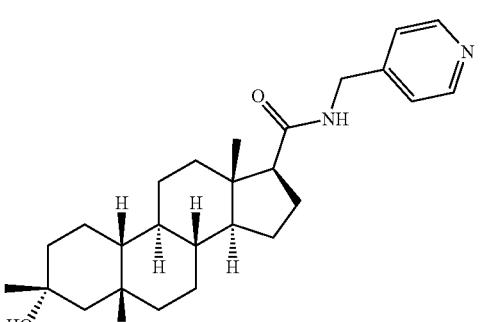 | 11 | E |
| 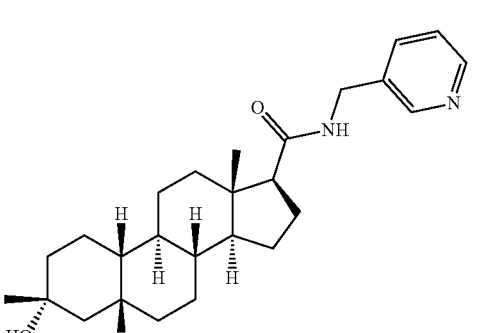 | 12 | E |
| 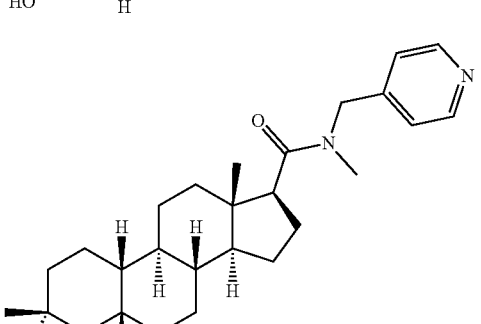 | 13 | D |

TABLE 2-continued

TBPS Data

| Compound structure | Compound number | TBPS IC$_{50}$ (nM) |
|---|---|---|
| 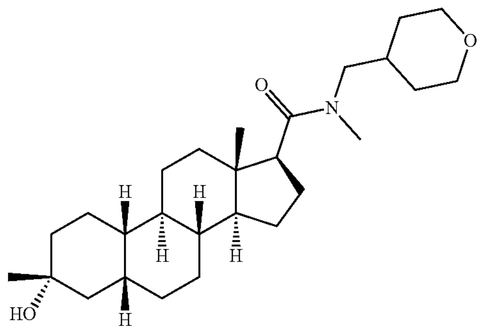 | 14 | E |
| 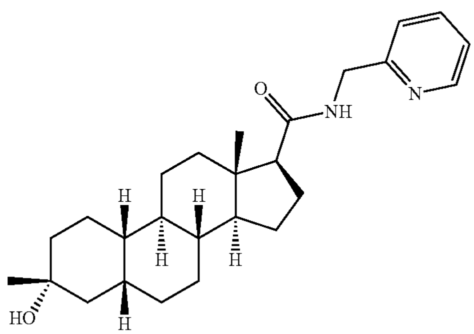 | 15 | D |
| 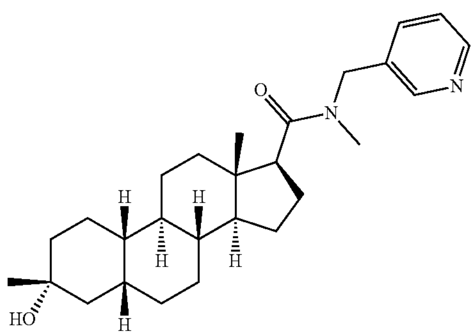 | 16 | D |
| 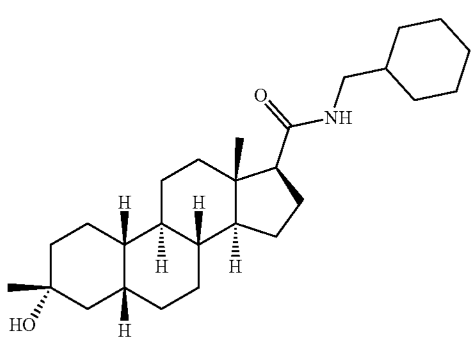 | 17 | D |

TABLE 2-continued
TBPS Data
| Compound structure | Compound number | TBPS IC$_{50}$ (nM) |
|---|---|---|
| 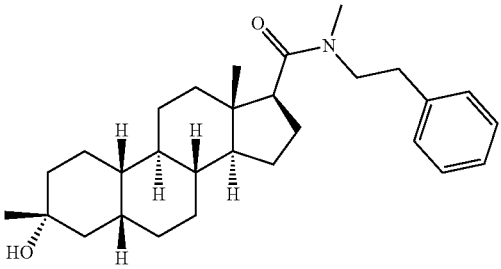 | 18 | C |
| 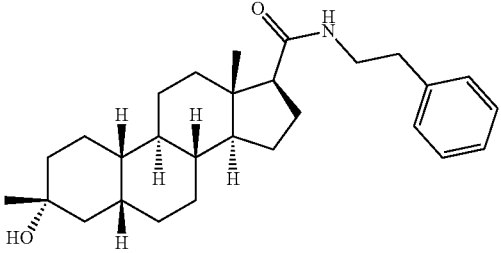 | 19 | D |
| 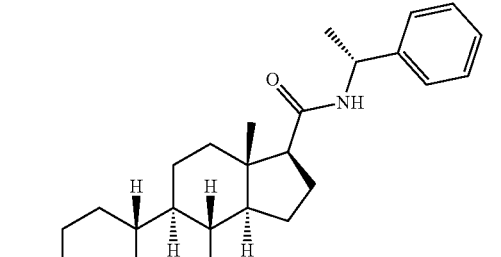 | 20 | D |
| 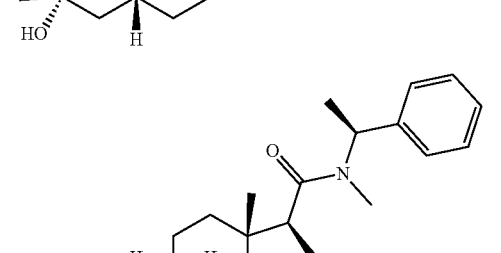 | 21 | B |
| 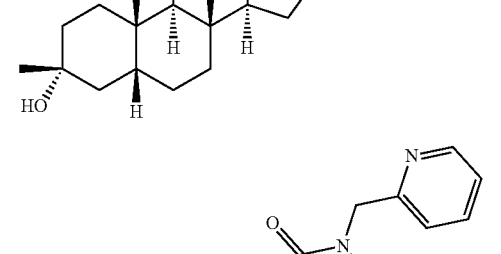 | 22 | E |

TABLE 2-continued

TBPS Data

| Compound structure | Compound number | TBPS IC$_{50}$ (nM) |
|---|---|---|
| 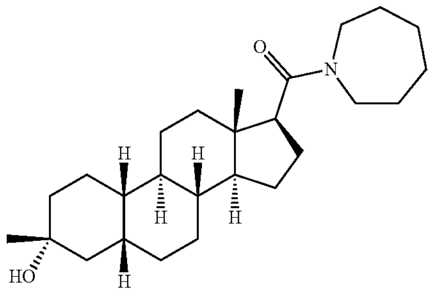 | 23 | D |
| 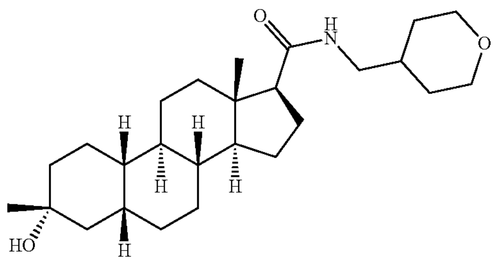 | 24 | E |
| 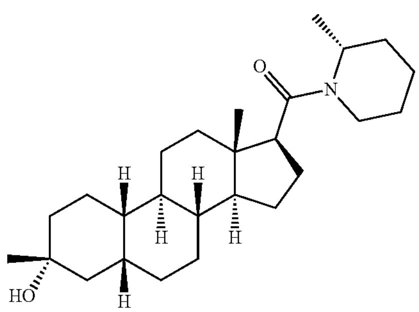 | 25 | D |
| 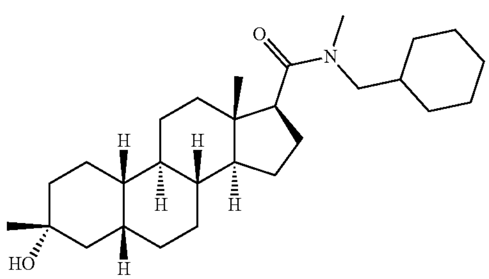 | 26 | D |
| 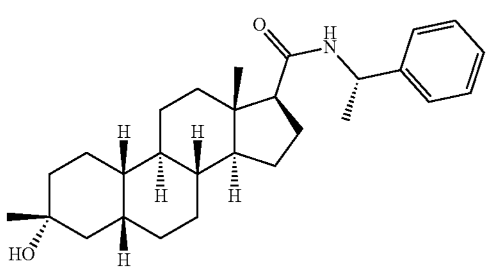 | 27 | D |

TABLE 2-continued

TBPS Data

| Compound structure | Compound number | TBPS IC$_{50}$ (nM) |
|---|---|---|
| (steroid with 3α-OH, 3β-methyl, 5β-H, 17β-(2-methylpiperidin-1-yl)carbonyl) | 28 | D |
| (steroid with 3α-OH, 3β-methyl, 5β-H, 17β-(tetrahydropyran-4-yl)aminocarbonyl) | 29 | E |
| (steroid with 3α-OH, 3β-methyl, 5β-H, 17β-((3-phenylpyrrolidin-1-yl)carbonyl)) | 30 | D |
| (steroid with 3α-OH, 3β-methyl, 5β-H, 17β-((3-phenylpyrrolidin-1-yl)carbonyl), other stereoisomer) | 31 | C |

TABLE 2-continued

| TBPS Data | | |
|---|---|---|
| Compound structure | Compound number | TBPS IC$_{50}$ (nM) |
| [structure] | 32 | B |
| [structure] | 33 | D |
| [structure] | 34 | D |
| [structure] | 35 | D |
| [structure] | 36 | — |

TABLE 2-continued

TBPS Data

| Compound structure | Compound number | TBPS IC$_{50}$ (nM) |
|---|---|---|
| 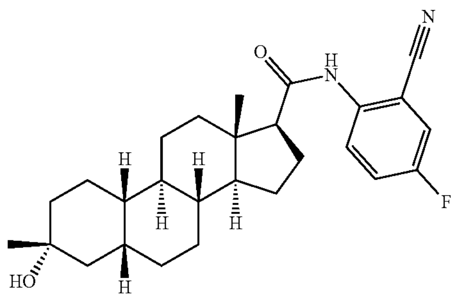 | 37 | B |
| 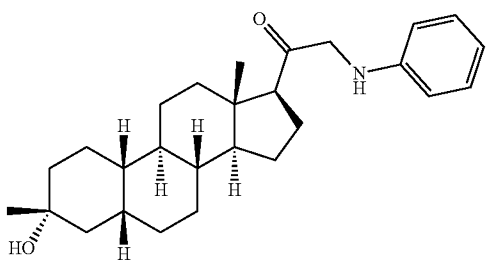 | 38 | A |
| 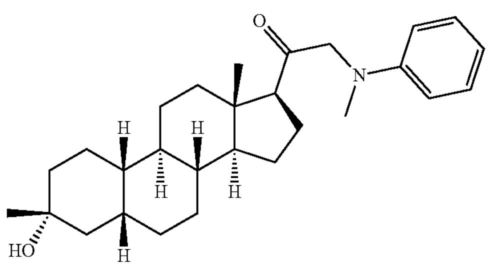 | 39 | C |
| 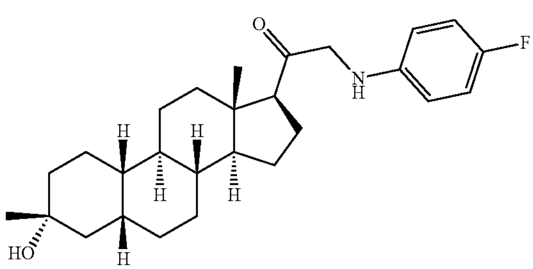 | 40 | A |
| 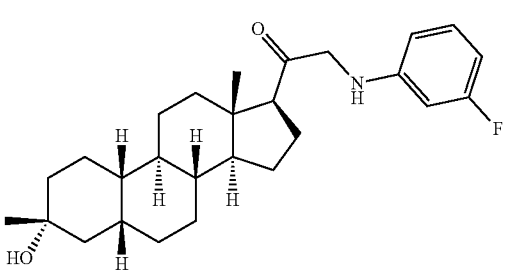 | 41 | A |

TABLE 2-continued

| TBPS Data | | |
|---|---|---|
| Compound structure | Compound number | TBPS IC$_{50}$ (nM) |
| (steroid with 3-OH, 3-methyl, 5β-H, 17-C(O)CH$_2$-N(CH$_3$)-(3-fluorophenyl)) | 42 | B |
| (steroid with 3-OH, 3-methyl, 5β-H, 17-C(O)CH$_2$-N(CH$_3$)-(4-fluorophenyl)) | 43 | B |
| (steroid with 3-OH, 3-CH$_2$OEt, 5β-H, 17-C(O)-tetrahydroisoquinoline) | 44 | C |
| (steroid with 3-OH, 3-CH$_2$OEt, 5β-H, 17-C(O)NH-CH(CH$_3$)-(4-cyanophenyl)) | 48 | D |
| (steroid with 3-OH, 3-CH$_2$OEt, 5β-H, 17-C(O)N(CH$_3$)-CH(CH$_3$)-(4-cyanophenyl)) | 49 | C |

TABLE 2-continued

TBPS Data

| Compound structure | Compound number | TBPS IC$_{50}$ (nM) |
|---|---|---|
| 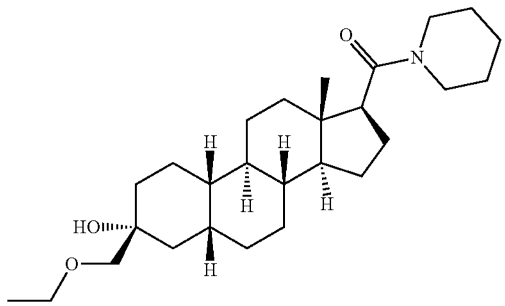 | 50 | D |
| 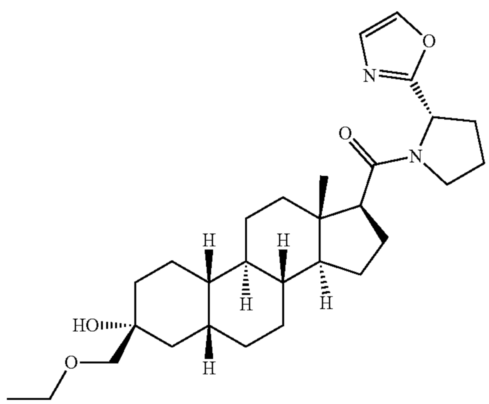 | 55 | E |
| 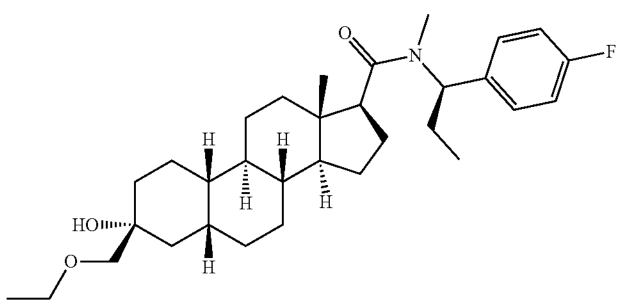 | 56 | D |
| 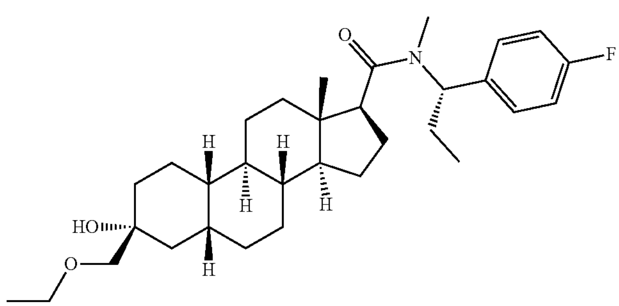 | 57 | D |

TABLE 2-continued

TBPS Data

| Compound structure | Compound number | TBPS IC$_{50}$ (nM) |
|---|---|---|
| 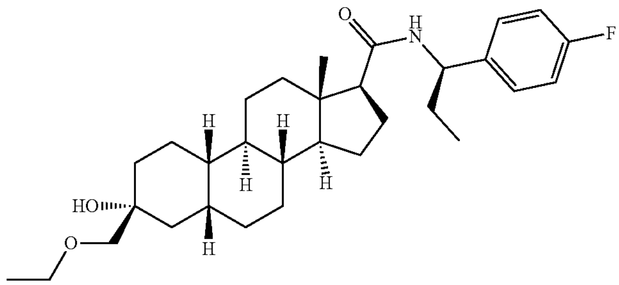 | 58 | E |
| 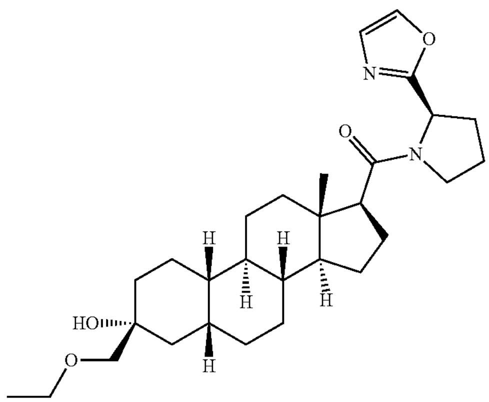 | 60 | E |
| 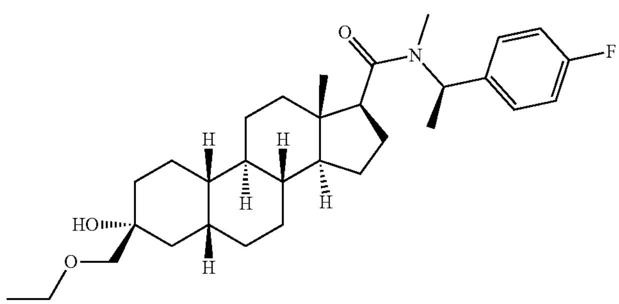 | 61 | D |
| 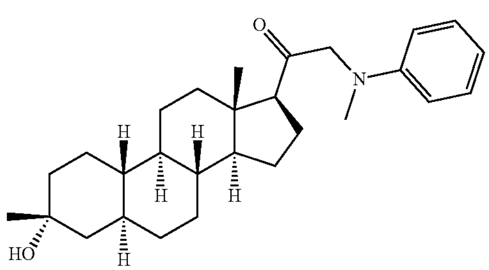 | 63 | D |
| 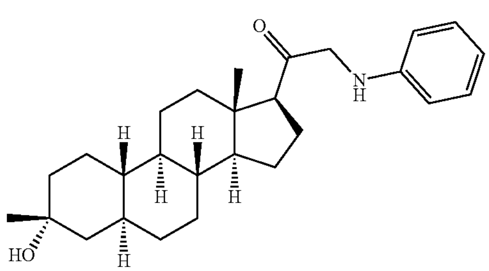 | 64 | C |

TABLE 2-continued

TBPS Data

| Compound structure | Compound number | TBPS IC$_{50}$ (nM) |
|---|---|---|
| 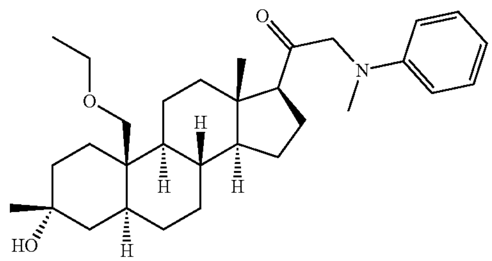 | 65 | D |
| 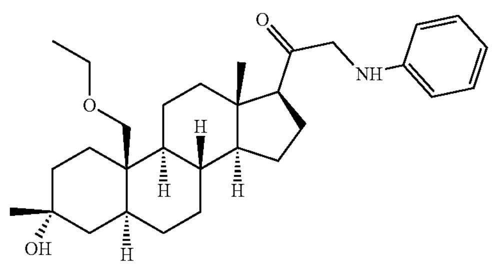 | 66 | C |
| 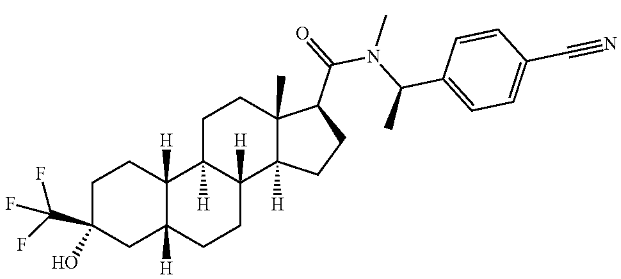 | 69 | D |
| 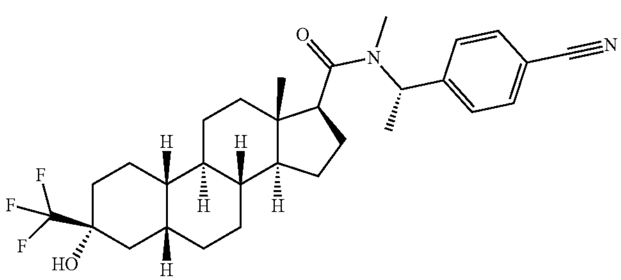 | 70 | D |
| 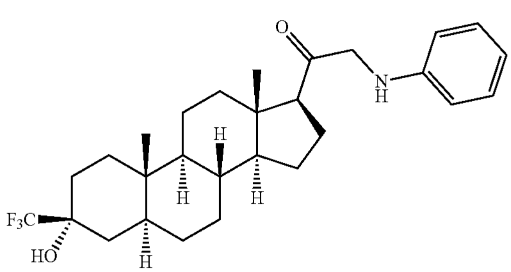 | 73 | C |

TABLE 2-continued

TBPS Data

| Compound structure | Compound number | TBPS IC$_{50}$ (nM) |
|---|---|---|
| 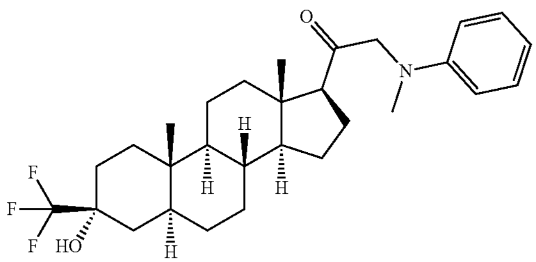 | 74 | E |
| 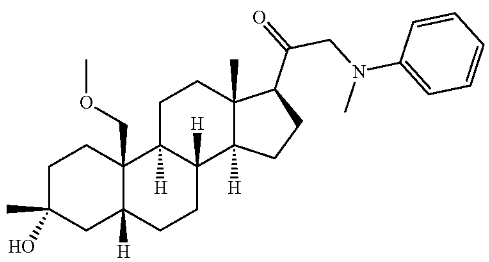 | 75 | B |
| 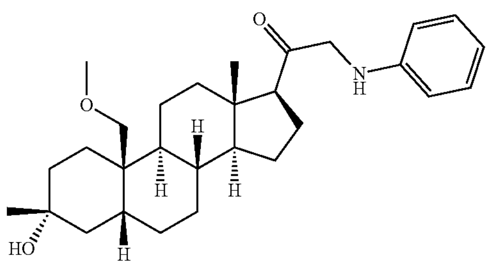 | 76 | A |
| 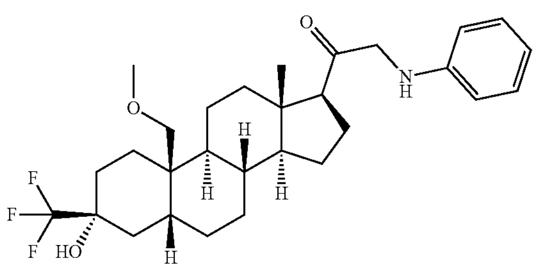 | 77 | B |
| 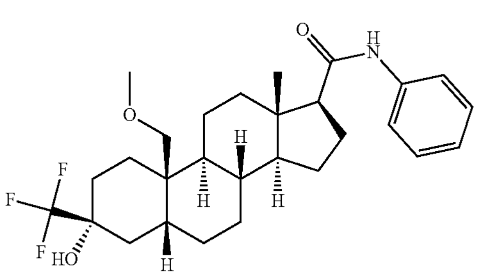 | 78 | C |

TABLE 2-continued

TBPS Data

| Compound structure | Compound number | TBPS IC$_{50}$ (nM) |
|---|---|---|
| 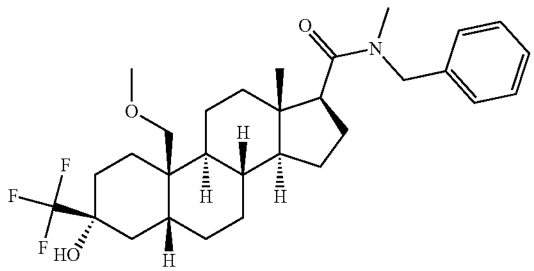 | 79 | D |
| 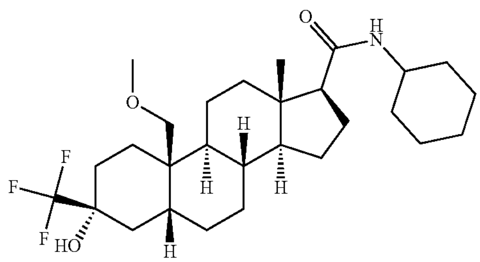 | 80 | E |
| 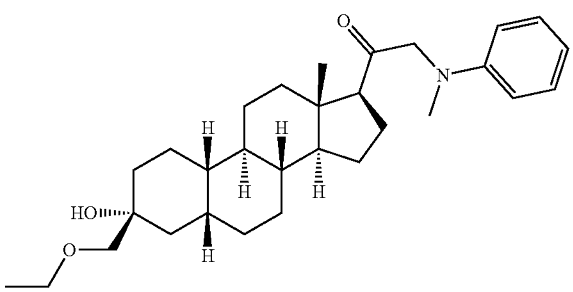 | 83 | D |
| 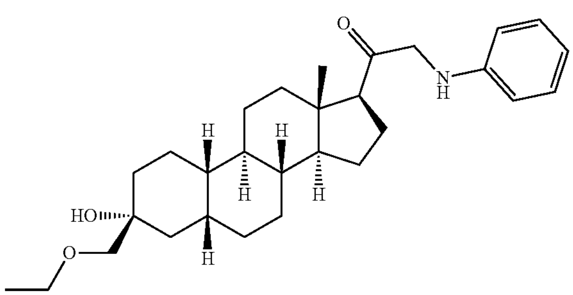 | 84 | B |
| 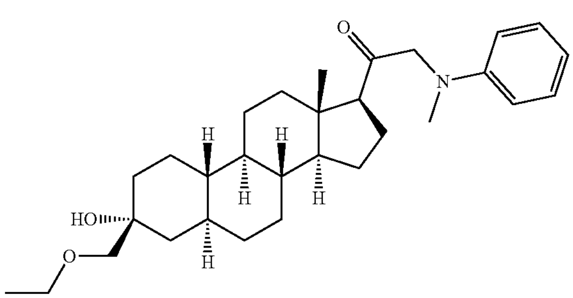 | 85 | E |

TABLE 2-continued
TBPS Data
| Compound structure | Compound number | TBPS IC$_{50}$ (nM) |
|---|---|---|
| 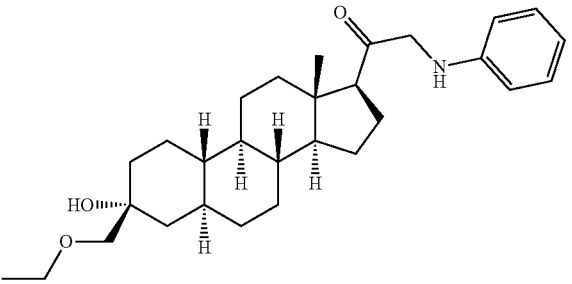 | 86 | D |
| 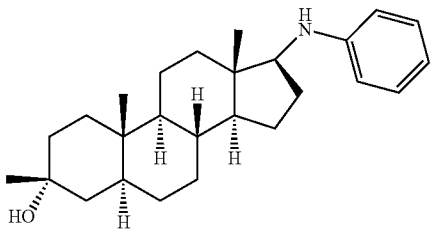 | 87 | D |
| 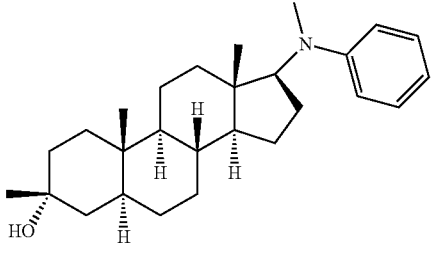 | 88 | E |
| 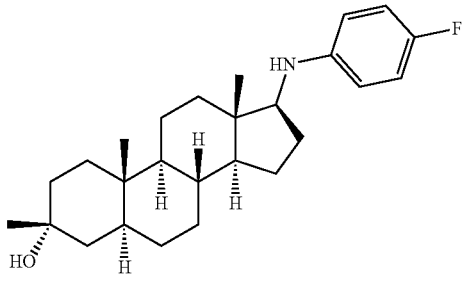 | 89 | D |
| 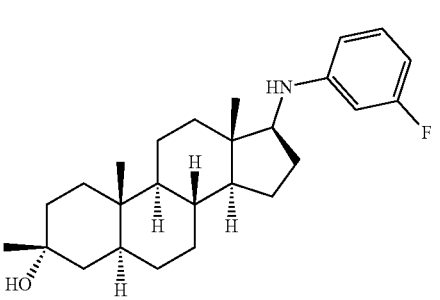 | 90 | D |

TABLE 2-continued

TBPS Data

| Compound structure | Compound number | TBPS IC$_{50}$ (nM) |
|---|---|---|
| 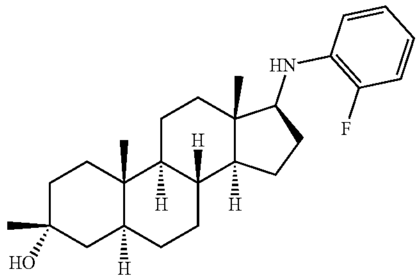 | 91 | E |
| 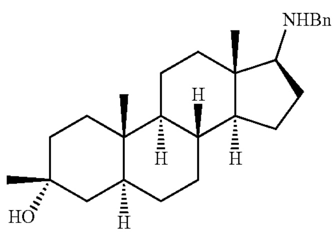 | 92 | E |
| 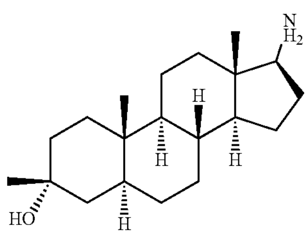 | 93 | E |
| 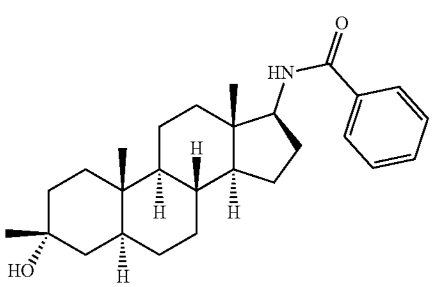 | 94 | E |
| 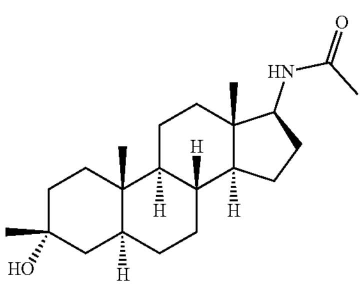 | 95 | E |

TABLE 2-continued

TBPS Data

| Compound structure | Compound number | TBPS IC$_{50}$ (nM) |
|---|---|---|
| (steroid with 17-N(Me)SO$_2$Ph, 3α-OH, 5α-H) | 96 | E |
| (steroid with 17-NHSO$_2$Me, 3α-OH, 5α-H) | 97 | E |
| (steroid with 17-N(Me)SO$_2$Me, 3α-OH, 5α-H) | 98 | E |
| (steroid with 17-N(Me)C(O)OMe, 3α-OH, 5α-H) | 99 | E |
| (steroid with 17-OH, 17-Ph, 3α-OH, 5β-H) | 100 | E |

TABLE 2-continued

TBPS Data

| Compound structure | Compound number | TBPS IC$_{50}$ (nM) |
|---|---|---|
| 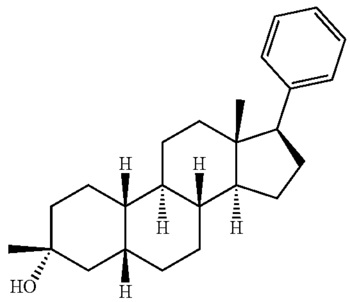 | 101 | D |
| 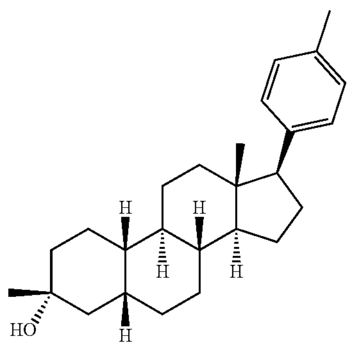 | 102 | D |
| 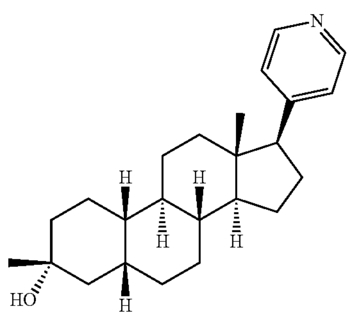 | 103 | B |
| 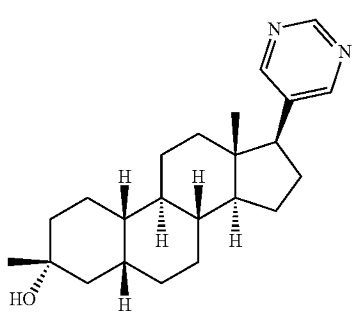 | 104 | C |

TABLE 2-continued

TBPS Data

| Compound structure | Compound number | TBPS IC$_{50}$ (nM) |
|---|---|---|
| 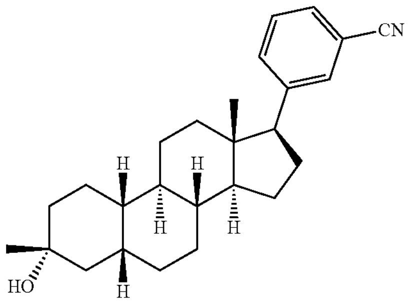 | 105 | B |
| 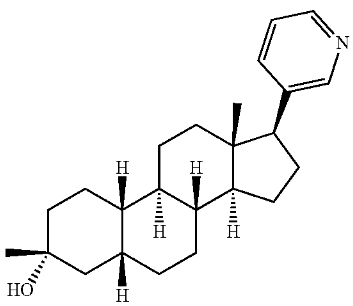 | 106 | B |
| 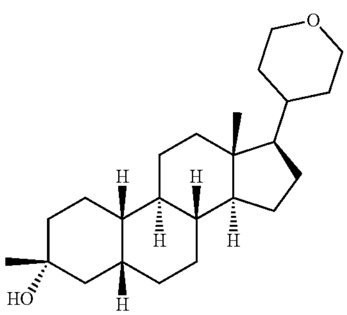 | 107 | E |
| 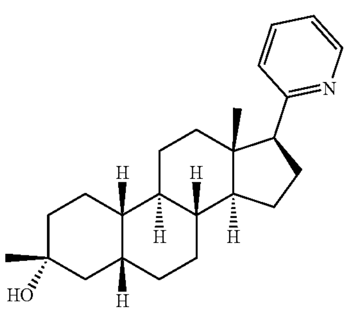 | 108 | D |
| 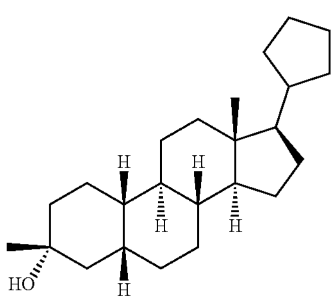 | 109 | E |

TABLE 2-continued
TBPS Data
| Compound structure | Compound number | TBPS IC$_{50}$ (nM) |
|---|---|---|
| 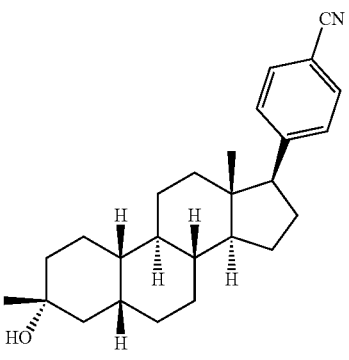 | 110 | B |
| 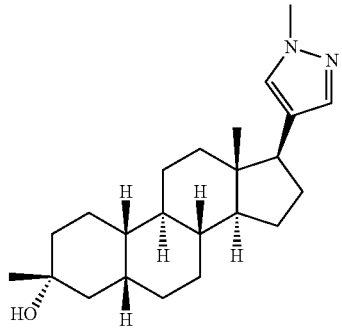 | 111 | C |
| 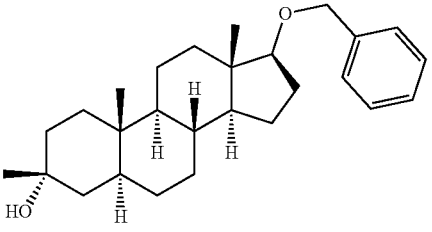 | 112 | E |
| 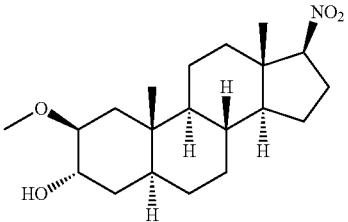 | 118 | B |
| 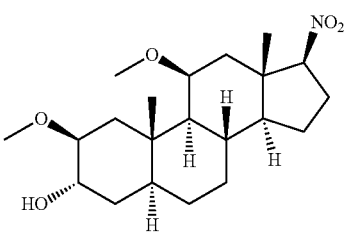 | 119 | B |

TABLE 2-continued

| TBPS Data | | |
|---|---|---|
| Compound structure | Compound number | TBPS IC$_{50}$ (nM) |
| [steroid structure with 2β-OMe, 3α-OH, 11β-OH, 17-NO$_2$, 5α-H] | 120 | D |
| [steroid structure with 2β-OMe, 3α-OH, 11-oxo, 17-NO$_2$, 5α-H] | 121 | D |
| [steroid structure with 2β-OEt, 3α-OH, 11β-OH, 17-NO$_2$, 5α-H] | 122 | D |
| [steroid structure with 2β-OEt, 3α-OH, 11-oxo, 17-NO$_2$, 5α-H] | 123 | C |
| [steroid structure with 2β-Me, 3α-OH, 17β-OMe, 5α-H] | 125 | B |
| [steroid structure with 2α-Me, 3α-OH, 11β-OMe, 17β-OMe, 5α-H] | 125 | D |

TABLE 2-continued

TBPS Data

| Compound structure | Compound number | TBPS IC$_{50}$ (nM) |
|---|---|---|
| (steroid structure with OH and HO groups) | 126 | E |

For Table 2: TBPS: "A" indicates an IC$_{50}$ <10 nM, "B" indicates an IC$_{50}$ 10 to <50 nM, "C" indicates an IC$_{50}$ 50 nM to <100 nM, "D" indicates an IC$_{50}$ 100 nM to <500 nM, and "E" indicates IC$_{50}$ greater than or equal to 500 nM.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (1-A):

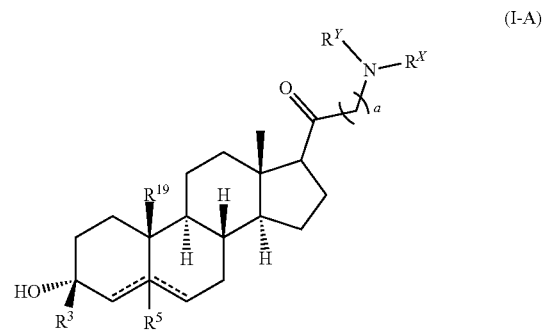

(I-A)

or a pharmaceutically acceptable salt thereof, wherein:
a) the compound of Formula (1-A) is a compound of Formula (1-A-1)

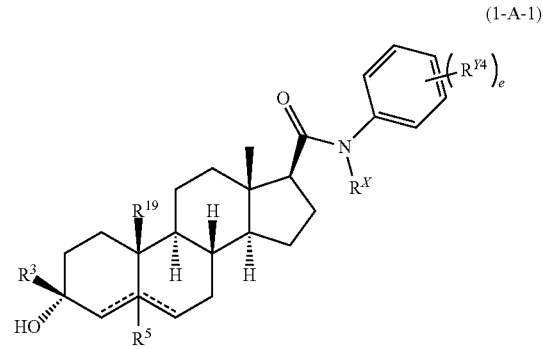

(1-A-1)

wherein each instance of $R^{Y4}$ is independently alkyl, cyano, or halo; and e is 0, 1, 2, 3, 4, or 5; or b) the compound of Formula (1-A) is a compound of Formula (1-A-3)

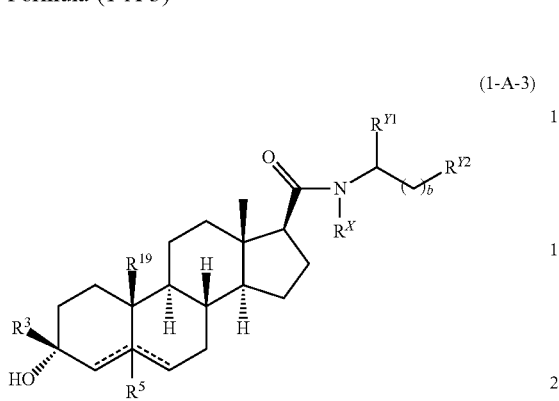

(1-A-3)

wherein $R^{Y1}$ is hydrogen, —CH$_3$, —CH$_2$CH$_3$, —CH(CH$_3$)$_2$, or cycloalkyl; $R^{Y2}$ is alkyl, cycloalkyl, heterocycyl, aryl, or heteroaryl; and b is 0, 1, 2, or 3; or c) the compound of Formula (1-A) is a compound of Formula (1-A-5)

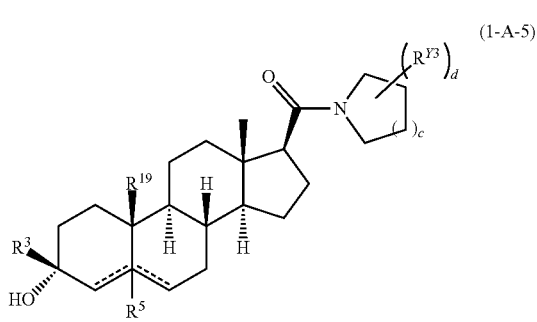

(1-A-5)

wherein each occurrence of $R^{Y3}$ is aryl or heteroaryl; two $R^{Y3}$ groups are joined together to form a 6-10 membered ring; c is 0, 1, 2, or 3; and d is 0, 1, 2, or 3, and wherein $R^3$ is —CH$_3$, —CF$_3$, —CH$_2$OCH$_3$, —CH$_2$OCH$_2$CH$_3$;

each of $R^X$ and $R^Y$ is independently hydrogen, aryl, or alkyl; or $R^X$ and $R^Y$ are joined together to form a 3-10 membered heterocyclic ring;

$R^{19}$ is hydrogen or alkyl;

$R^5$ is absent or hydrogen;

a is 0; and

--- represents a single or double bond, wherein when one --- is a double bond, the other --- is a single bond and $R^5$ is absent.

2. The compound of claim 1, wherein the compound is a compound of Formula (1-A-2)

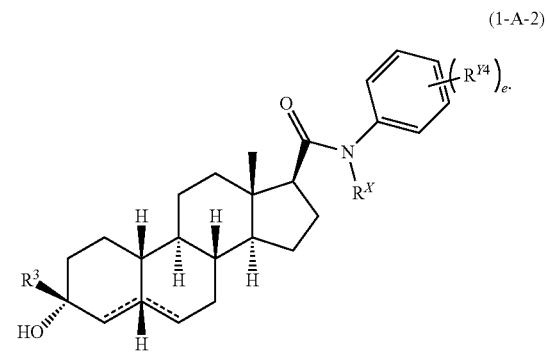

(1-A-2)

3. The compound of claim 2, wherein each instance of $R^{Y4}$ is independently —CH$_3$, —CN, or —F.

4. The compound of claim 2, wherein $R^X$ is hydrogen.

5. The compound of claim 1, wherein the compound is a compound of Formula (1-A-4)

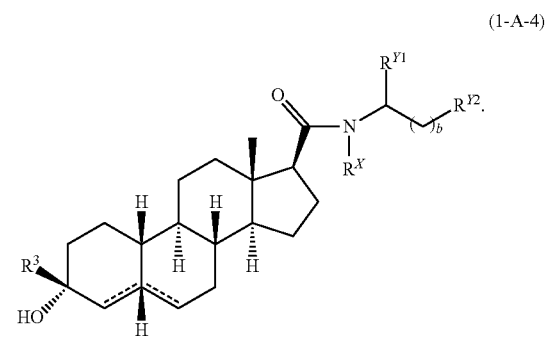

(1-A-4)

6. The compound of claim 5, wherein $R^{Y2}$ is heterocyclyl, aryl, or heteroaryl.

7. A compound selected from the group consisting of:

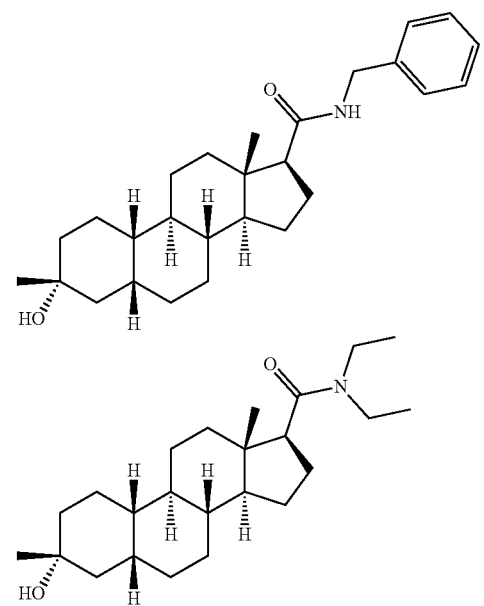

299
-continued
300
-continued
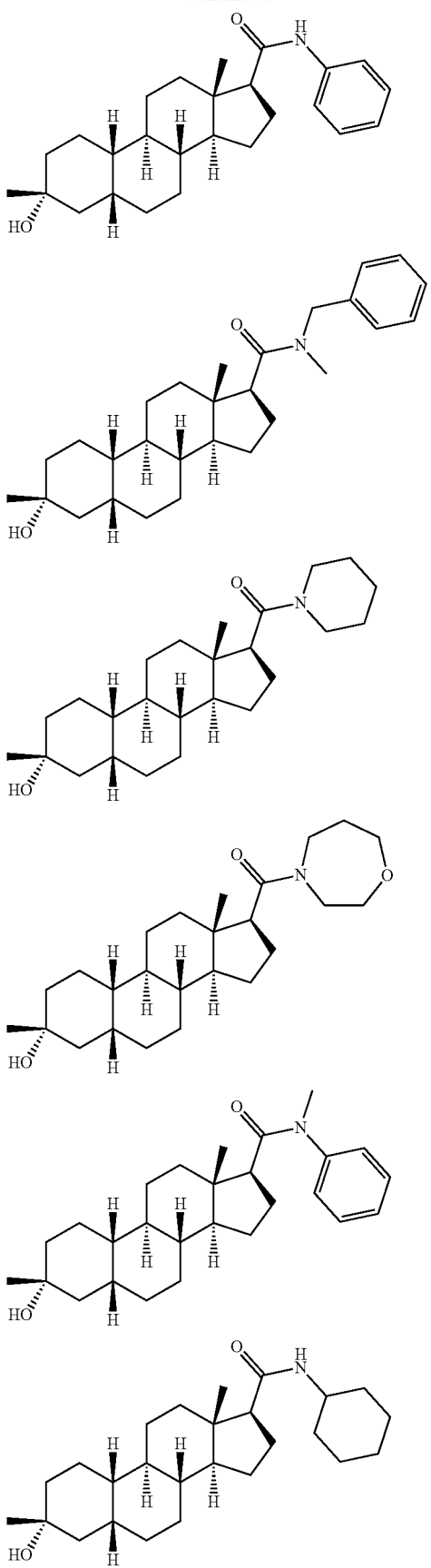
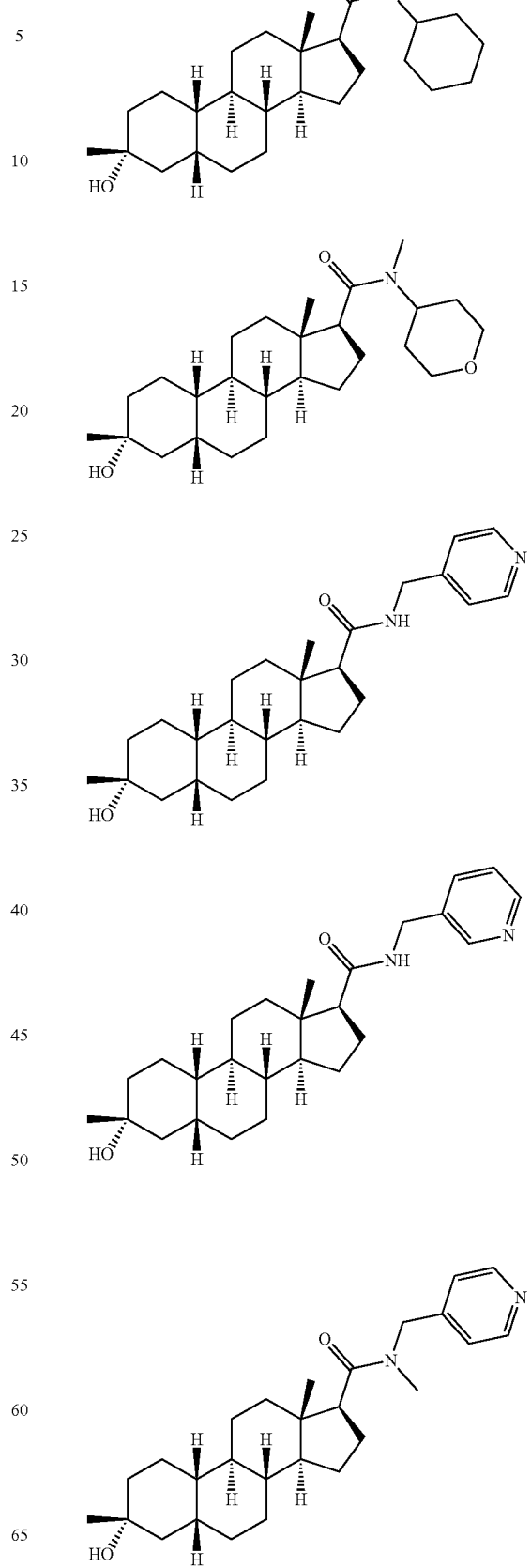

301
-continued
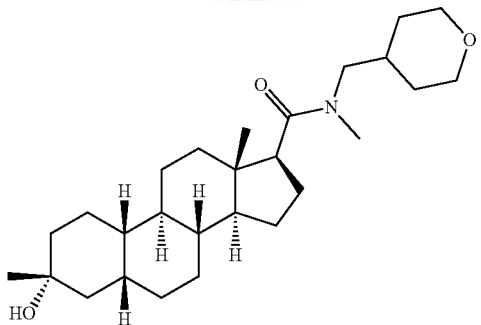
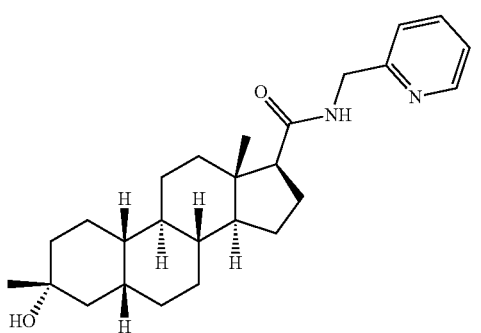
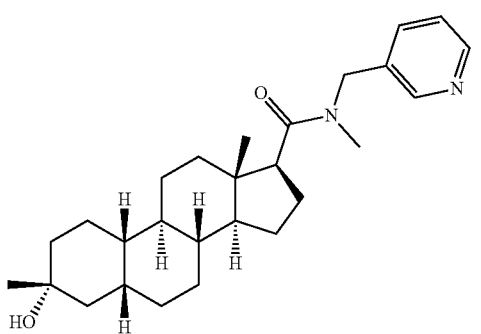
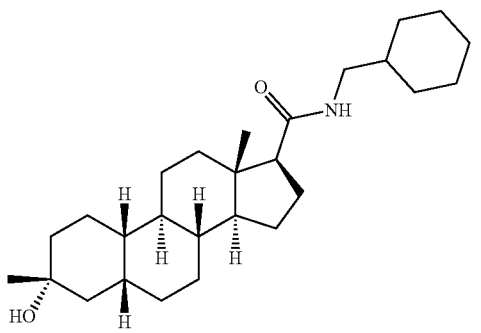
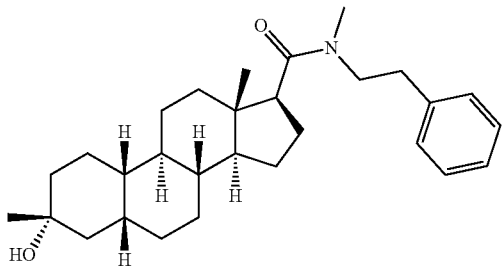
302
-continued
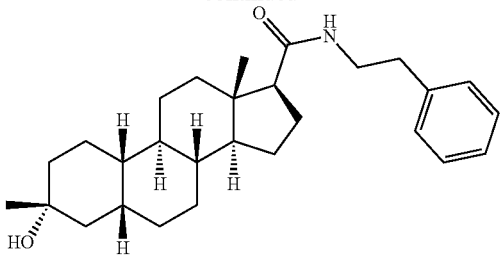
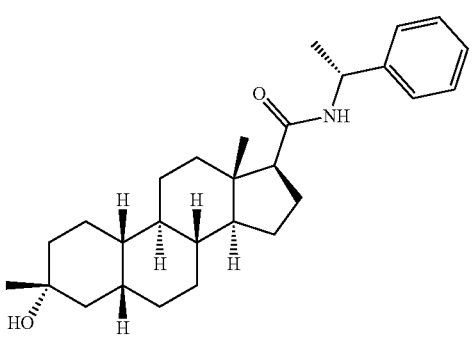
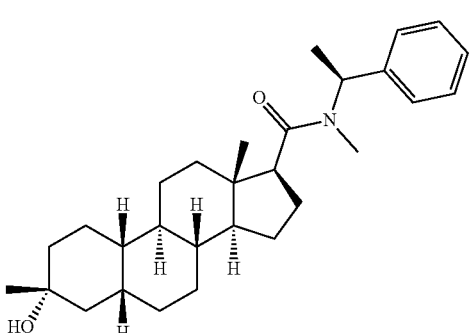
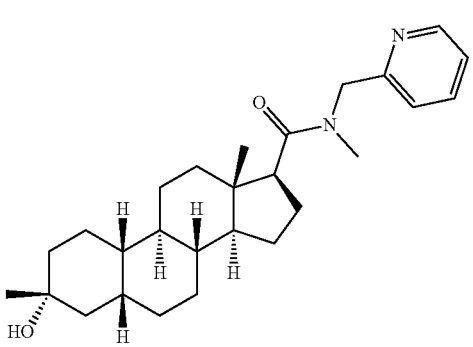
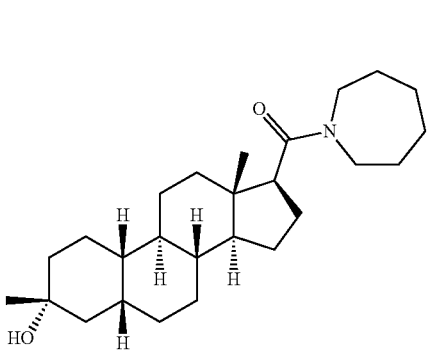

303
-continued
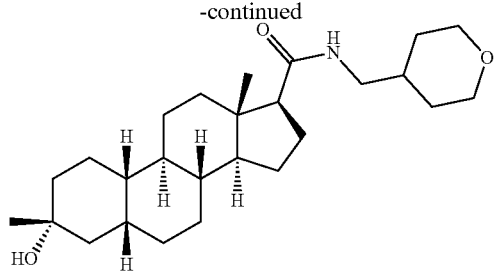
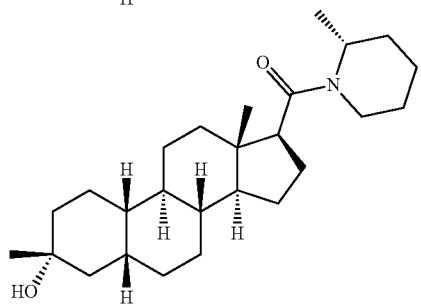
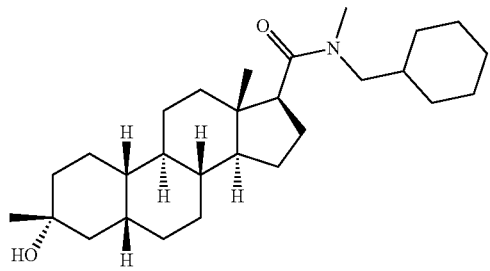
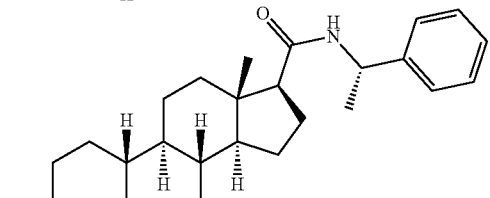
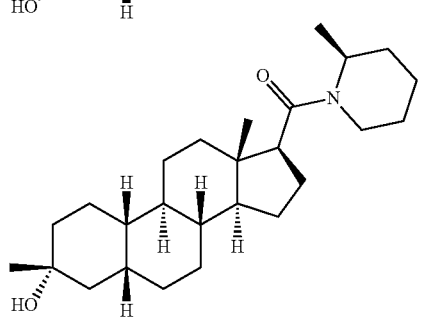
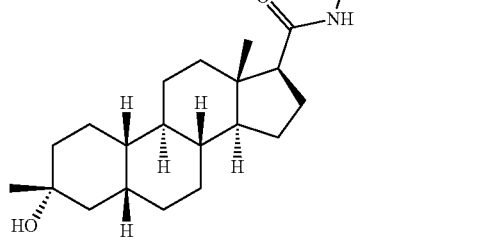
304
-continued
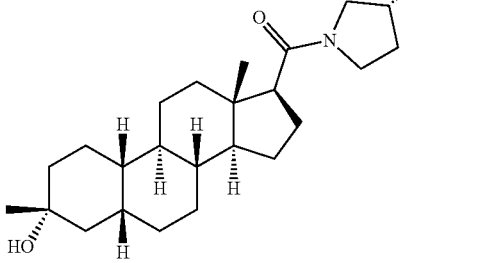
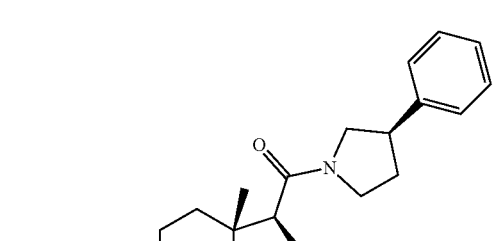
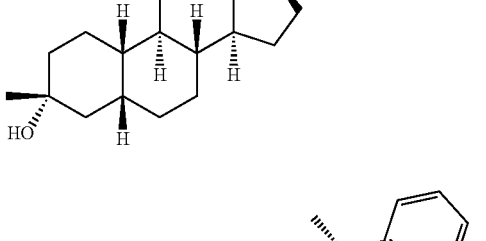
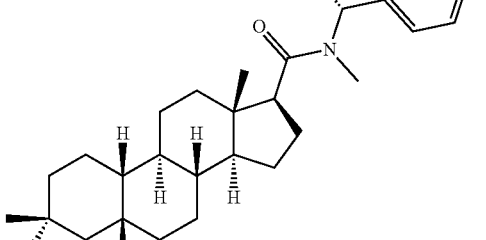
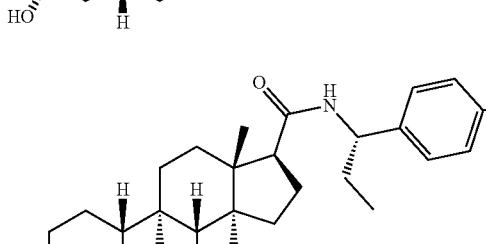
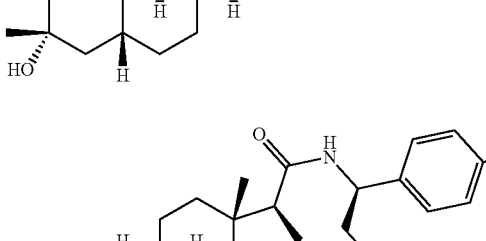

305
-continued
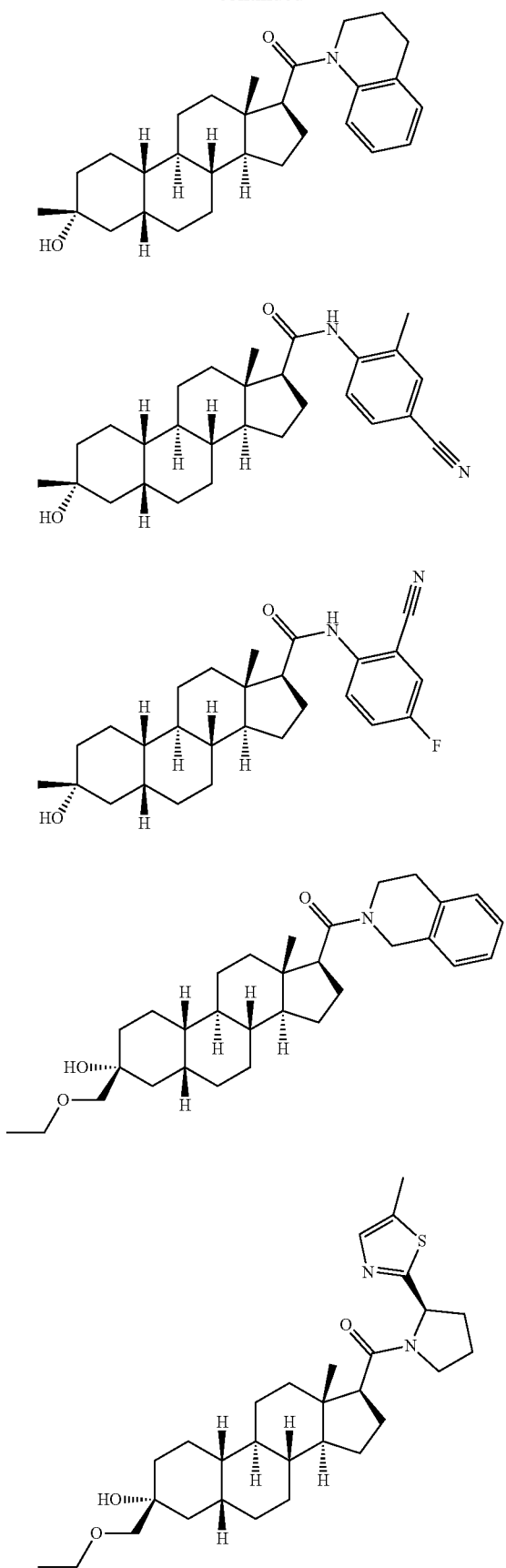
306
-continued
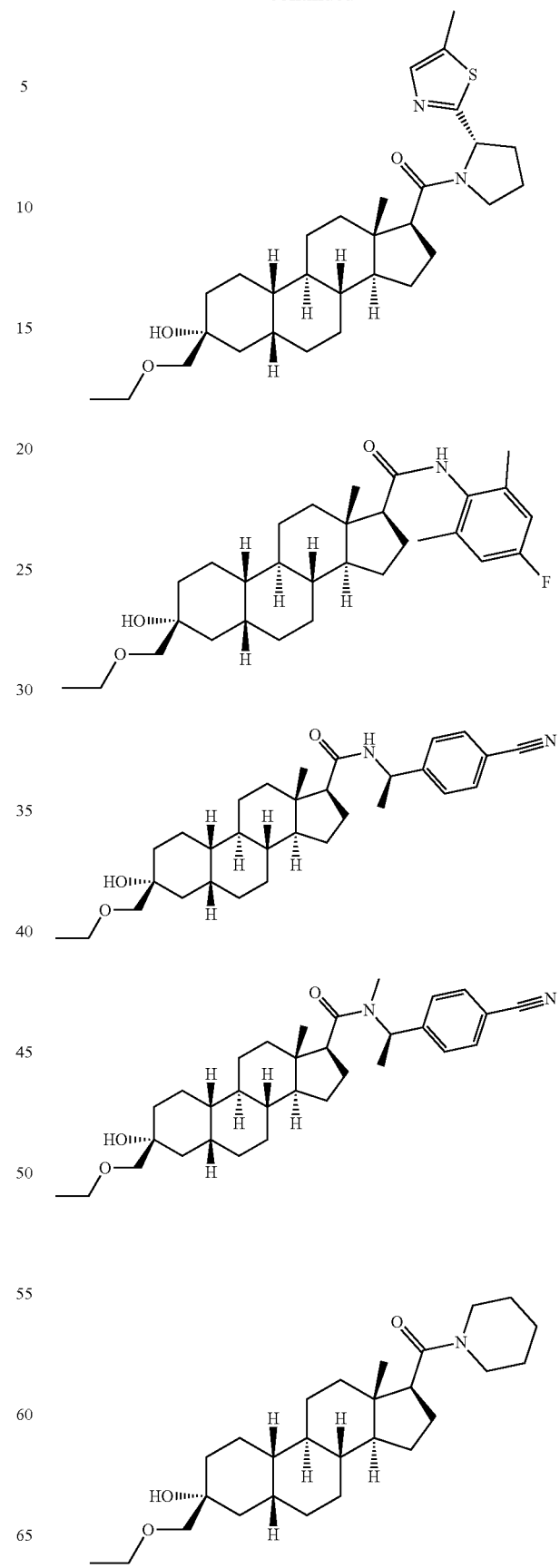

307
-continued
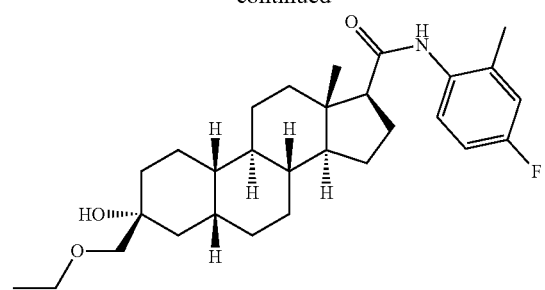
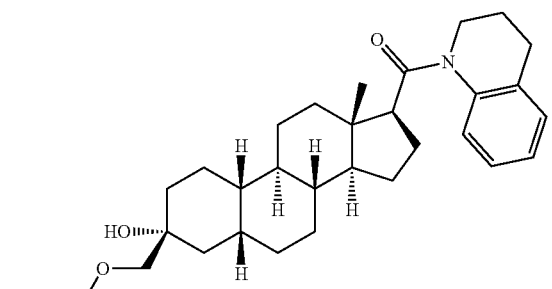
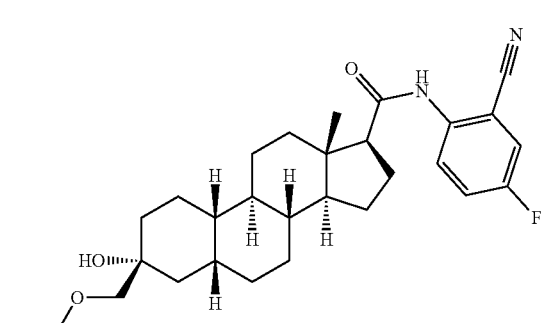
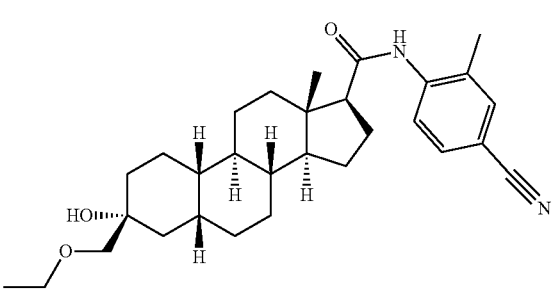
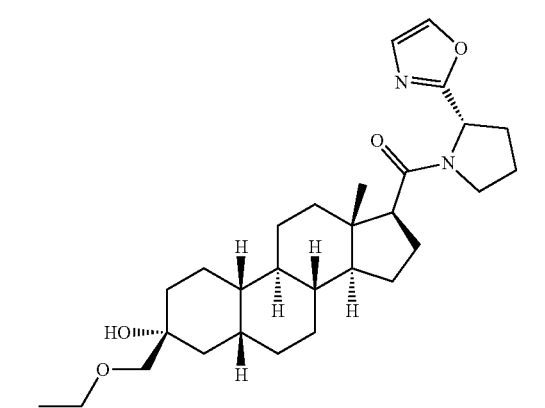
308
-continued
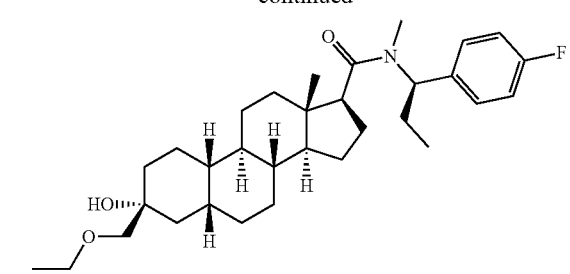
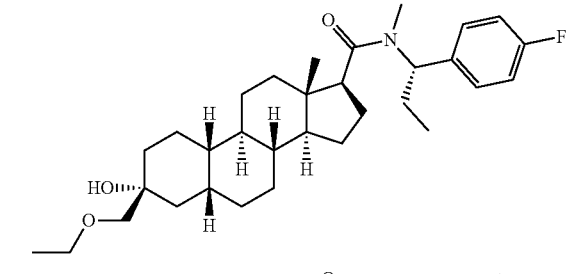
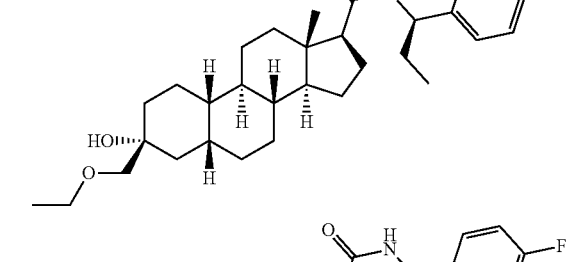
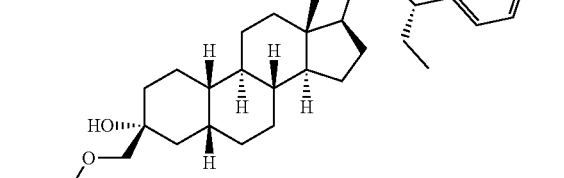
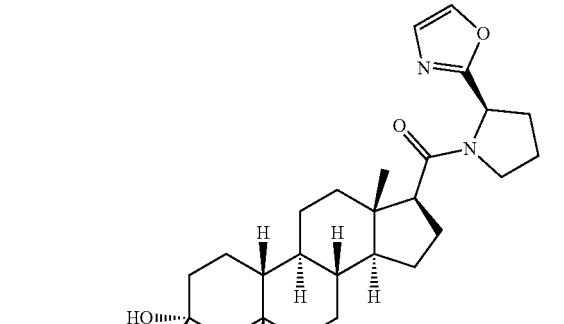
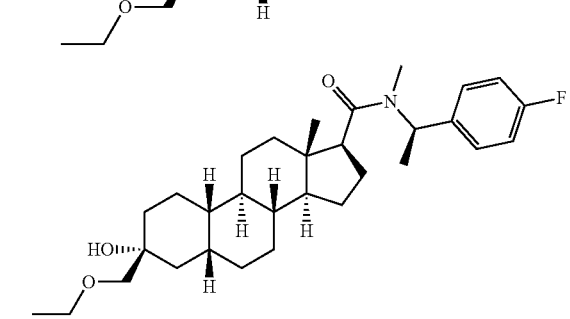

-continued

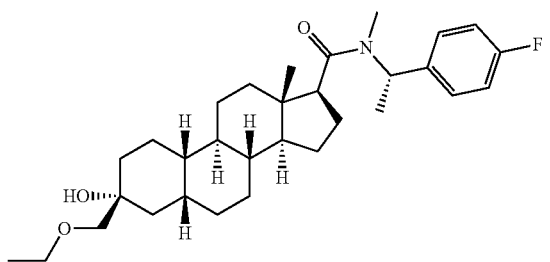

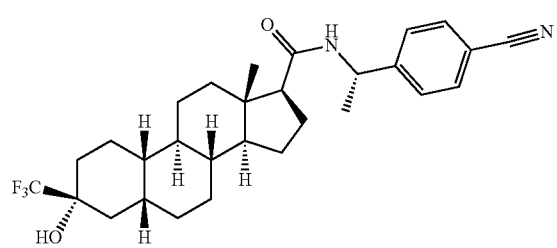

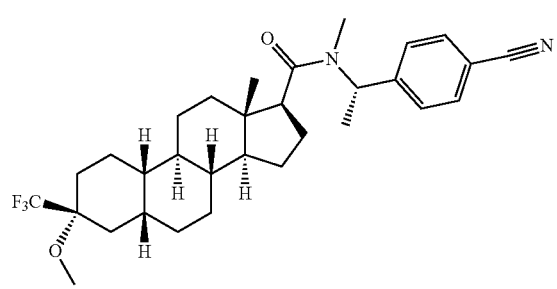

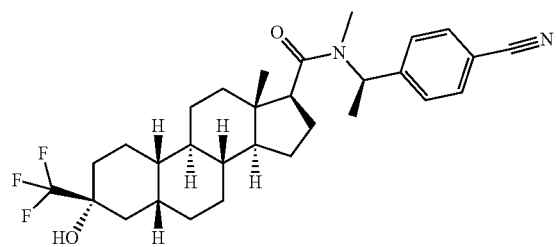

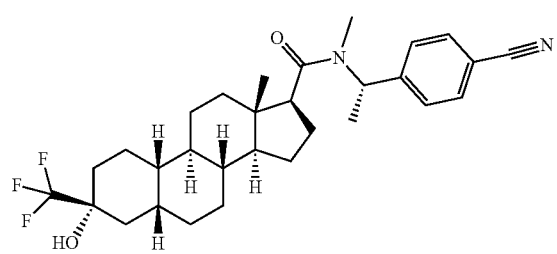

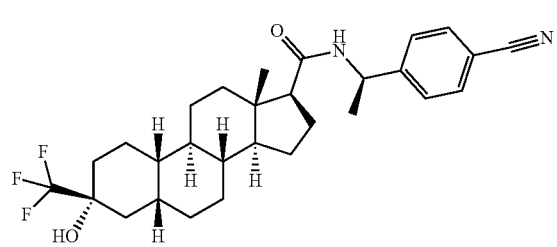

-continued

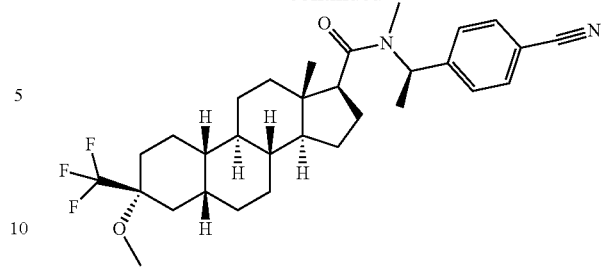

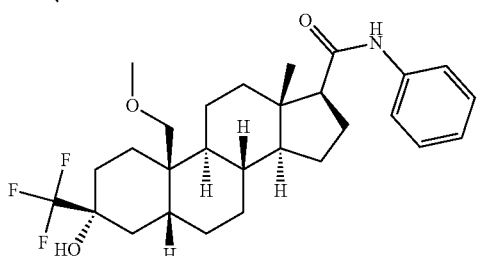

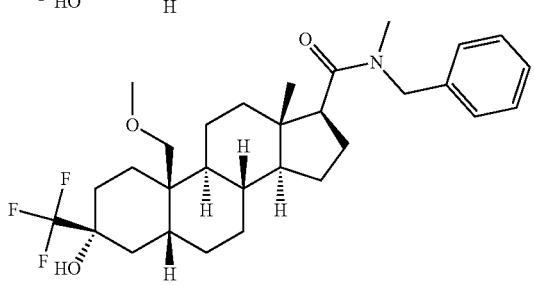

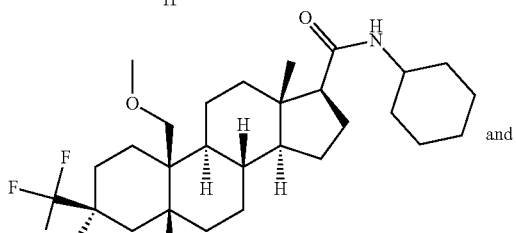

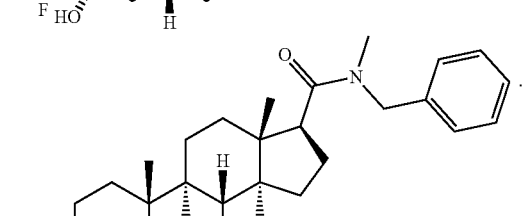

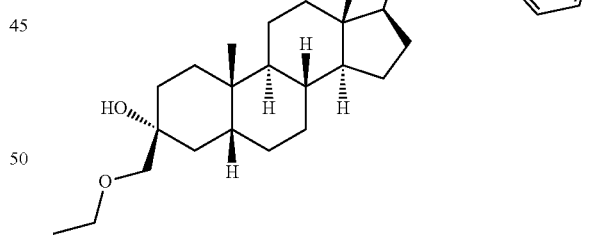

8. A pharmaceutical composition comprising a compound of claim 1 and a pharmaceutically acceptable excipient.

9. A method for reducing the severity or retarding or slowing the progression of a CNS-related disorder in a subject in need thereof, comprising administering to the subject an effective amount of a compound of claim 1, wherein the CNS-related disorder is sleep disorder, mood disorder, anxiety disorder, epilepsy, essential tremor, tremor, status epilepticus, fragile X syndrome, pain, alcohol dependence, traumatic brain injury, bipolar disorder, morphine withdrawal, major depressive disorder, tinnitus, postnatal depression, schizophrenia, or autism.

10. A kit comprising a solid composition comprising a compound of claim 1 and a sterile diluent.

11. The method of claim 9, wherein the CNS-related disorder is a bipolar I disorder, bipolar II disorder, generalized anxiety disorder, social anxiety disorder, depression, postnatal depression, or major depressive disorder.

12. A pharmaceutical composition comprising a compound of claim 7 and a pharmaceutically acceptable excipient.

13. A method for reducing the severity or retarding or slowing the progression of a CNS-related disorder in a subject in need thereof, comprising administering to the subject an effective amount of a compound of claim 7, wherein the CNS-related disorder is sleep disorder, mood disorder, anxiety disorder, essential tremor, tremor, epilepsy, status epilepticus, fragile X syndrome, pain, alcohol dependence, traumatic brain injury, bipolar disorder, morphine withdrawal, major depressive disorder, tinnitus, postnatal depression, schizophrenia, or autism.

14. The method of claim 13, wherein the CNS-related disorder is a bipolar I disorder, bipolar II disorder, generalized anxiety disorder, social anxiety disorder, depression, postnatal depression, or major depressive disorder.

15. A kit comprising a solid composition comprising a compound of claim 7 and a sterile diluent.

* * * * *